US012559527B2

(12) United States Patent
Saunders et al.

(10) Patent No.: US 12,559,527 B2
(45) Date of Patent: Feb. 24, 2026

(54) COMPOSITIONS COMPRISING V2 OPT HIV ENVELOPES

(71) Applicants: Duke University, Durham, NC (US); Triad National Security, LLC, Los Alamos, NM (US); The Trustees of The University of Pennsylvania, Philadelphia, PA (US)

(72) Inventors: Kevin O. Saunders, Durham, NC (US); Barton F. Haynes, Durham, NC (US); Bette T. Korber, Los Alamos, NM (US); Kshitij G. Wagh, Los Alamos, NM (US); Beatrice H. Hahn, Philadelphia, PA (US); Ronnie M. Russell, Philadelphia, PA (US)

(73) Assignees: Duke University, Durham, NC (US); Triad National Security, LLC, Los Alamos, NM (US); The Trustees of The University of Pennsylvania, Philadelphia, PA (US)

( * ) Notice: Subject to any disclaimer, the term of this patent is extended or adjusted under 35 U.S.C. 154(b) by 976 days.

(21) Appl. No.: 17/771,349

(22) PCT Filed: Oct. 23, 2020

(86) PCT No.: PCT/US2020/057205
§ 371 (c)(1),
(2) Date: Apr. 22, 2022

(87) PCT Pub. No.: WO2021/081437
PCT Pub. Date: Apr. 29, 2021

(65) Prior Publication Data
US 2022/0380412 A1 Dec. 1, 2022

Related U.S. Application Data

(60) Provisional application No. 62/925,173, filed on Oct. 23, 2019.

(51) Int. Cl.
| | |
|---|---|
| *A61K 39/00* | (2006.01) |
| *A61K 39/12* | (2006.01) |
| *A61K 39/21* | (2006.01) |
| *A61P 31/18* | (2006.01) |
| *C07K 14/005* | (2006.01) |
| *C07K 14/16* | (2006.01) |

(52) U.S. Cl.
CPC ............ *C07K 14/005* (2013.01); *A61K 39/12* (2013.01); *A61P 31/18* (2018.01); *C12N 2740/16022* (2013.01); *C12N 2740/16034* (2013.01); *C12N 2740/16134* (2013.01)

(58) Field of Classification Search
CPC .... C07K 14/005; C07K 14/162; C07K 14/16; C07K 2319/00; C12N 2740/16134
See application file for complete search history.

(56) References Cited

U.S. PATENT DOCUMENTS

| | | | |
|---|---|---|---|
| 7,951,377 | B2 | 5/2011 | Korber et al. |
| 9,012,219 | B2 | 4/2015 | Kariko et al. |
| 9,371,511 | B2 | 6/2016 | Kariko et al. |
| 10,004,800 | B2 | 6/2018 | Haynes et al. |
| 10,006,007 | B2 | 6/2018 | Kariko et al. |
| 2009/0286852 | A1 | 11/2009 | Kariko et al. |
| 2013/0111615 | A1 | 5/2013 | Kariko et al. |
| 2013/0197068 | A1 | 8/2013 | Kariko et al. |
| 2013/0261172 | A1 | 10/2013 | Kariko et al. |
| 2015/0038558 | A1 | 2/2015 | Kariko et al. |
| 2016/0032316 | A1 | 2/2016 | Weissman et al. |
| 2017/0043037 | A1 | 2/2017 | Kariko et al. |
| 2017/0327842 | A1 | 11/2017 | Weissman et al. |
| 2018/0028645 | A1 | 2/2018 | Ciaramella et al. |
| 2018/0265848 | A1 | 9/2018 | Kariko et al. |
| 2018/0344838 | A1 | 12/2018 | Ciaramella et al. |

FOREIGN PATENT DOCUMENTS

| | | | |
|---|---|---|---|
| WO | WO-2013/006688 | A2 | 1/2013 |
| WO | WO-2014/042669 | A1 | 3/2014 |
| WO | WO-2015/127108 | A1 | 8/2015 |
| WO | WO-2016/176330 | A1 | 11/2016 |
| WO | WO-2017/151801 | A1 | 9/2017 |
| WO | WO-2017/182524 | A1 | 10/2017 |
| WO | WO-2018/005558 | A1 | 1/2018 |
| WO | WO-2018/075559 | A1 | 4/2018 |
| WO | WO-2018/081638 | A1 | 5/2018 |
| WO | WO-2018/218225 | A1 | 11/2018 |
| WO | WO-2020/072169 | A1 | 4/2020 |
| WO | WO-2021/081437 | A2 | 4/2021 |

OTHER PUBLICATIONS

Andrabi, R., et al., "The Chimpanzee SIV Envelope Trimer: Structure and Deployment as an HIV Vaccine Template," Cell Reports, vol. 27, No. 8, pp. 2426-2441 and e1-e6—23 total pages (May 21, 2019).

Arnaoty, A., et al., "Reliability of the nanopheres-DNA immunization technology to produce polyclonal antibodies directed against human neogenic proteins," Mol. Genet. Genomics, vol. 288, pp. 347-363, 17 total pages (published online Jun. 7, 2013).

Arnaoty, A., et al., "Novel approach for the development of new antibodies directed against transposase-derived proteins encoded by human neogenes," Yves Bigot (ed.), Mobile Genetic Elements: Protocols and Genomic Applications, Methods in Molecular Biology, vol. 859, pp. 293-305, 13 total pages (2012).

Bamrungsap, S., et al., "Nanotechnology in therapeutics: a focus on nanoparticles as a drug delivery system," Nanomedicine, vol. 7, No. 8, pp. 1253-1271, 19 total pages (2012).

(Continued)

*Primary Examiner* — Barry A Chestnut
(74) *Attorney, Agent, or Firm* — Baker Donelson

(57) ABSTRACT

In certain aspects the invention provides HIV-1 immunogens, including HIV-1 envelopes with optimized V2 loop for antibody induction.

36 Claims, 49 Drawing Sheets

Specification includes a Sequence Listing.

(56)           References Cited

OTHER PUBLICATIONS

Barouch, D. H., et al., "Mosaic HIV-1 vaccines expand the breadth and depth of cellular immune responses in rhesus monkeys," Nature Medicine, vol. 16, No. 3, pp. 319-323 (2010)—Author Manuscript available in PMC Sep. 1, 2010 (15 total pages).

Batista, F. D., et al., "B cells extract and present immobilized antigen: implications for affinity discrimination," The EMBO Journal, vol. 19, No. 4, pp. 513-520, 8 total pages (2000).

Batista, F.D., et.al., "Affinity dependence of the B cell response to antigen: a threshold, a ceiling, and the importance of off-rate," Immunity 8: pp. 751-759, 9 total pages (1998).

Binley, James M., et al., "Enhancing the Proteolytic Maturation of Human Immunodeficiency Virus Type 1 Envelope Glycoproteins," Journal of Virology, vol. 76, No. 6, pp. 2606-2616 (Mar. 2002).

Bonsignori, M., et al., "Staged induction of HIV-1 glycan-dependent boradly neutralizing antibodies," Sci Transl Med., vol. 9, No. 381: doi: 10.1126/scitranslmed.aai7514, pp. 1-26 (Mar. 15, 2017)—Author Manuscript available in PMC Aug. 18, 2017 (26 total pages).

Bosch, Valerie, et al., "Mutational Analysis of the Human Immunodeficiency Virus Type 1 env Gene Product Proteolytic Cleavage Site," Journal of Virology, vol. 64, No. 5, pp. 2337-2344, 8 total pages (May 1990).

Bricault, CH.A., et al., "HIV-1 Neutralizing Antibody Signatures and Applicaton to Epitope-Trgeted Vaccine Design," Cell Host Microbe, vol. 25, pp. 59-72 and e1-e8, 23 total pages (Jan. 9, 2019).

Cany, J., et al., "AFP-specific immunotherapy impairs growth of autochthonous hepatocellular carcinoma in mice," Journal of Hepatology, vol. 54, pp. 115-121, 7 total pages (available online Aug. 26, 2010).

Center, R.J., et al., "Oligomeric structure of the human immunodeficiency virus type 1 envelope protein on the virion surface," Journal of Virology, vol. 76, No. 15, pp. 7863-7867, 5 total pages (Aug. 2002).

Chakrabarti, B. K., et al., "Modifications of the Human Immunodeficiency Virus Envelope Glycoprotein Enhance Immunogenicity for Genetic Immunization," Journal of Virology, vol. 76, No. 11, pp. 5357-5368, 12 total pages (Jun. 2002).

Chen, C., et al., "The site and stage of anti-DNA B-cell deletion," Nature, vol. 373, pp. 252-255, 4 total pages (Jan. 19, 1995).

De Taeye, S. W., et al., "Immunogenicity of stabilized HIV-1 envelope trimers with reduced exposure of non-neutralizing epitopes," Cell., vol. 163, No. 7, pp. 1702-1715 (Dec. 17, 2015)—Author Manuscript available in PMC Jan. 29, 2016 (25 total pages).

Gao, F., et al., "Antigenicity and Immunogenicity of a Synthetic Human Immunodeficiency Virus Type 1 Group M Consensus Envelope Glycoprotein," Journal of Virology, vol. 79, No. 2, pp. 1154-1163, 10 total pages (Jan. 2005).

Gorman, J., et al., "Structures of HIV-1 Env V1V2 with broadly neutralizing antibodies reveal commonalities that enable vaccine design," Nature Structural and Molecular Biology, vol. 23, No. 1, pp. 81-90 (Jan. 2016)—Author Manuscript available in PMC Jun. 21, 2016 (34 total pages).

Graham, B.S., et al., "DNA Vaccine Delivered by a Needle-Free Injection Device Improves Potency of Priming for Antibody and CD8+ T-Cell Responses after rAd5 Boost in a Randomized Clinical Trial," Public Library of Science ONE, vol. 8, No. 4, e59340, pp. 1-11, 11 total pages (Apr. 2013).

Guo, H.-G., et al., "Characterization of an HIV-1 Point Mutant Blocked in Envelope Glycoprotein Cleavage," Virology, vol. 174, pp. 217-224, 8 total pages (accepted Sep. 29, 1989).

Haynes, B. F., et al., "B-cell-lineage immunogen design in vaccine development with HIV-1 as a case study," Nat. Biotechnol., vol. 30, No. 5, pp. 423-433 (2012)—Author Manuscript available in PMC May 7, 2013 (30 total pages).

He, L., et al., "Presenting native-like trimeric HIV-1 antigens with self-assembling nanoparticles," Nature Communications, vol. 7, No. 12041, pp. 1-15, 15 total pages (Jun. 28, 2016).

International Search Report and Written Opinion mailed Apr. 21, 2021 by U.S Patent and Trademark Office in International Patent Application No. PCT/US2020/057205 (16 total pages).

Julien, J-P., et al., "Design and structure of two HIV-1 clade C SOSIP.664 trimers that increase the arsenal of native-like Env immunogens," Proceedings of the National Academy of Sciences of the United States of America, vol. 112, No. 38, pp. 11947-11952, 6 total pages (Sep. 22, 2015).

Kepler, T.B., et al., "Somatic Hypermutation in B Cells: an Optimal Cootrol Treatment," Journal of Theoretical Biology, vol. 164, pp. 37-64, 28 total pages (accepted Jan. 14, 1993).

Kibler, K. V., et al., "Improved NYVAC-based vaccine vectors," Public Library of Science ONE, vol. 6, No. 11: e25674, pp. 1-13, 13 total pages (Nov. 9, 2011).

Kwon, Y. D., et al., "Crystal structure, conformational fixation and entry-related interactions of mature ligand-free HIV-1 Env," Nature Structural & Molecular Biology, vol. 22, No. 7, pp. 522-531, 10 total pages (Jul. 2015)—Author Manuscript available in PMC Jan. 8, 2016 (30 total pages).

Li, Y., et al., "Control of Expression, Glycosylation, and Secretion of HIV-1 gp120 by Homologous and Heterologous Signal Sequences," Virology, vol. 204, No. 1, pp. 266-278, 13 total pages (accepted Jun. 23, 1994).

Li, Y., et al., "Effects of inefficient cleavage of the signal sequence of HIV-1 gp120 on its association with calnexin, folding, and intracellular transport," Proceedings of the National Academy of Sciences of the United States of America, vol. 93, pp. 9606-9611, 6 total pages (Sep. 1996).

Liao, H. X., et al., "A group M consensus envelope glycoportein induces antibodies that neutralize subsets of subtype B and C HIV-1 primary viruses," Virology 2006, vol. 353, pp. 268-282, 15 total pages (available online Jul. 7, 2006).

Liao, H.X, et al., "Antigenicity and immunogenicity of transmitted/founder, consensus, and chronic envelope glycoproteins of human immunodeficiency virus type 1," Journal of Virology, vol. 87, No. 8, pp. 4185-4201, 17 total pages (Apr. 2013).

Liao, H.X., et al., "Co-evolution of a broadly neutralizing HIV-1 antibody and founder virus," Nature, vol. 496, No. 7446, pp. 469-476 (Apr. 25, 2013)—Author Manuscript available in PMC Oct. 25, 2017 (25 total pages).

Liu, M., et al., "Polyreactivity and autoreactivity among HIV-1 antibodies," Journal of Virology, vol. 89, No. 1, pp. 784-798, 15 total pages (Jan. 2015).

Mascola, J. R., et al., "HIV-1 neutralizing antibodies: understanding nature's pathways," Immunological Reviews, vol. 254, No. 1, pp. 225-244 (2013)—Manuscript available in PMC Jul. 1, 2014 (29 total pages).

McCune, J.M., et al., "Endoproteolytic Cleavage of gp160 Is Required for the Activation of Human Immunodeficiency Virus," Cell, vol. 53, pp. 55-67, 13 total pages (Apr. 8, 1988).

Meffre, E., et al., "Immunoglobulin heavy chain expression shapes the B cell receptor repertoire in human B cell development," The Journal of Clinical Investigation, vol. 108, No. 6, pp. 879-886, 8 total pages (Sep. 2001).

Moody, M.A., et al., "Toll-Like Receptor 7/8 (TLR7 /8) and TLR9 Agonists Cooperate To Enhance HIV-I Envelope Antibody Responses in Rhesus Macaques," Journal of Virology, vol. 88, No. 6, pp. 3329-3339, 11 total pages (Mar. 2014).

Parren, P.W.H.I., et al., "Antibody Neutralization-Resistant Primary Isolates of Human Immunodeficiency Virus Type 1," Journal of Virology, vol. 72, No. 12, pp. 10270-10274, 5 total pages (Dec. 1998).

Perreau, M., et al., "DNA/NYVAC Vaccine Regimen Induces HIV-Specific CD4 and CD8 T-Cell Responses in Intestinal Mucosa," Journal of Virology, vol. 85, No. 19, pp. 9854-9862, 9 total pages (Oct. 2011).

Poignard, P., et al., "Heterogeneity of envelope molecules expressed on primary human immunodeficiency virus type 1 particles as probed by the binding of neutralizing and nonneutralizing antibodies. ," Journal of Virology, vol. 77, No. 1, pp. 353-365, 13 total pages (Jan. 2003).

(56)                    References Cited

OTHER PUBLICATIONS

Proft, T., "Sortase-mediated protein ligation: an emerging biotechnology tool for protein modification and immobilisation," Biotechnology Letters, vol. 32, pp. 1-10, 11 total pages (published online Sep. 1, 2009).

Ringe PR., et al., 2015, Influences on the design and purification of soluble, recombinant native-like HIV-1 envelope glycoprotein trimers, J Virol, vol. 89, No. 23 pp. 12189-12210. doi: 10.1128/JVI. 01768-15, 22 total pages (Dec. 2015).

Sanders, R.W., et al., "A Next-Generation Cleaved, Soluble HIV-1 Env Trimer, BGSOS SOSIP.664 gp140, Expresses Multiple Epitopes for Broadly Neutralizing but Not Non-Neutralizing Antibodies," Public Library of Science Pathogens, vol. 9, No. 9, e1003618 20 total pages, (Sep. 2013).

Santra, S., et al., "Mosaic Vaccines Elicit CD8+ T lymphocyte Responses in Monkeys that Confer Enhanced Immune Coverage of Diverse HIV Strains," Nature Medicine, vol. 16, No. 3, pp. 324-328 (Mar. 2010)—Manuscript available in PMC Sep. 1, 2010 (13 total pages).

Sarzotti-Kelsoe M., et al., "Optimization and Validation of the TZM-bl Assay for Standardized Assessments of Neutralizing Antibodies Against HIV-1," J. Immunol Methods, pp. 131-146, doi:10. 1016/j.jim.2013.11.022 (Jul. 2014)—Author Manuscript available in PMC Jul. 1, 2015 (37 total pages).

Saunders, K.O., et al.,"Vaccine Induction of Heterologous Tier 2 HIV-1 Neutralizing Antibodies in Animal Models," Cell Reports, vol. 21, pp. 3681-3690, 11 total pages (Dec. 26, 2017).

Schmohl, L., et al., "Sortase-mediated ligations for the site-specific modification of proteins," Current Opinion in Chemical Biology, vol. 22, pp. 122-128, 7 total pages (available online Oct. 6, 2014).

Shiokawa, S., et al., "IgM Heavy Chain Complementarity-Determining Region 3 Diversity Is Constrained by Genetic and Somatic Mechanisms Until Two Months After Birth," Journal of Immunology, vol. 162, pp. 6060-6070, 11 total pages (accepted for publication Mar. 1, 1999).

Sliepen, K., et al., "Presenting native-like HIV-1 envelope trimers on ferritin nanoparticles improves their immunogenicity," Retrovirology, vol. 12, No. 82, pp. 1-5, 5 total pages (2015).

Tabata, A., et al., "Development of a Sortase A-mediated Peptide-labeled Liposome Applicable to Drug-delivery Systems," Anticancer Research, vol. 35, pp. 4411-4417, 7 total pages (accepted May 12, 2015).

Tsukiji, S., et al., "Sortase-Mediated Ligation: A Gift from Gram-Positive Bacteria to Protein Engineering," ChemBioChem, vol. 10, pp. 787-798, 12 total pages (published online on Feb. 6, 2009).

Verkoczy, L., et al., "Autoreactivity in an HIV-1 broadly reactive neutralizing antibody variable region heavy chain induces immunologic tolerance," Proceedings of the National Academy of Sciences of the United States of America, vol. 107, No. 1, pp. 181-186, 6 total pages (Jan. 5, 2010).

Verkoczy, L., et al., "Rescue of HIV-1 Broad Neutralizing Antibody-Expressing B Cells in 2F5 VH X VL Knockin Mice Reveals Multiple Tolerance Controls," Journal of Immunology, vol. 187, pp. 3785-3797, 13 total pages (accepted for publication Aug. 1, 2011).

Wiehe, K., et al., "Funcitonal Relevance of Imporbable Antibody Mutations for HIV Broadly Neutralizing Antibody Development," Cell Host & Microbe, vol. 23, No. 6, pp. 759-765, 19 pages, (June 13, 20182018).

Yang. X., et al., "Antibody binding is a dominant determinant of the efficiency of human immunodeficiency virus type 1 neutralization," Journal of Virology, vol. 80, No. 22, pp. 11404-11408, 5 total pages (Nov. 2006).

Yu, J.S., et al., "Recombinant Mycobacterium bovis Bacillus Calmette-Guérin Elicits Human Immunodeficiency Virus Type 1 Envelope-Specific T Lymphocytes at Mucosal Sites," Clinical and Vaccine Immunology, vol. 14, No. 7, pp. 886-893, 8 total pages (Jul. 2007).

Zhang, J., et al., "Optimality of Mutation and Selection in Germinal Centers," Public Library of Science Computational Biology, vol. 6, No. 6, pp. 1-9, e1000800, pp. 1-9 , 9 total pages (Jun. 2010).

Crooks, Emma T., et al. "Engineering well-expressed, V2-immunofocusing HIV-1 envelope glycoprotein membrane trimers for use in heterologous prime-boost vaccine regimens." PLoS Pathogens 17.10 (2021): e1009807, 67 pages.

Nerrienet, Eric, et al. "Simian immunodeficiency virus infection in wild-caught chimpanzees from Cameroon." Journal of virology 79.2 (2005): 1312-1319.

Figure 2

Natural proteins for reference.
>CH0505.TF baseline natural immunogen
MRV-M---GIQRNYPQWWIWSMLGFWMLMI-CNG---MWVTVYYGVPVWKEAKTTLFCAS
DAKAYEKEVHNVWATHACVPTDPNPQEMVLKNVTENFNMWKNDMVDQMHEDVISLWDQSL
KPCVKLTPLCVTLNCTNATAS----------NSSIIEGMKNCSFNITTELRDKREKKNALF
YKLDIVQLDGN--------SSQYRLINCNTSVITQACPKVSFDPIPIHYCAPAGYAILKC
NNKTFTGTGPCNNVSTVQCTHGIKPVVSTQLLLNGSLAEGEIIIRSENITNNVKTIIVHL
NESVKIECTRPNNKTRTSIRI---GPGQAFYATGQVIGDIREAYCNINESKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN--
-TETFRPGGGNMKDNWRSELYKYKVVEVKPLGVAPTNARRRVVEREKR--AVGMGAVFLG
FLGAAGSTMGAASITLTVQARQLLSGIVQQQSNLLKAIEAQQHMLKLTVWGIKQLQARVL
ALERYLKDQQLLGMWGCSGKLICTTNVYWNSSWSNKTYGDIWDNMTWMQWEREISNYTEI
IYELLEESQNQQEKNEQDLLALDPWNSLWNWFNITNWLWYIKIFIMIVGGLIGLRIIFAV
LSLVNRVRQGYSPLSLQTLIPSPRGPDRPGGIEEEGGEQDRNPSTRLVSGFLALVWDDLR
SLCLFIYHRLRDFILIAARAGELLGRSSLKGLRPGWEALKYLGSLVQYWGLELKRSAISL
LDTLAIAVGEGTDRILEFVLGICRAIRNIPTRIRQGFETALL*

>HXB2 reference strain
MRVKE---KYQHLWRWGWRWGTMLLG-MLMICSATEKLWVTVYYGVPVWKEATTTLFCAS
DAKAYDTEVHNVWATHACVPTDPNPQEVVLVNVTENFNMWKNDMVEQMHEDIISLWDQSL
KPCVKLTPLCVSLKCTDLKNDTNTNSSSGRMIMEKGEIKNCSFNISTSIRGKVQKEYAFF
YKLDIIPIDN--------DTTSYKLTSCNTSVITQACPKVSFEPIPIHYCAPAGFAILKC
NNKTFNGTGPCTNVSTVQCTHGIRPVVSTQLLLNGSLAEEEVVIRSVNFTDNAKTIIVQL
NTSVEINCTRPNNNTRKRIRIQRGPGRAFVTIGK--IGNMRQAHCNISRAKWNNTLKQIAS
KLREQFGNNKTIIFKQSSGGDPEIVTHSFNCGGEFFYCNSTQLFNSTWFNSTW---STEG
SNNTEGSDTITLPCRIKQIINMWQKVGKAMYAPPISGQIRCSSNITGLLLTRDGGNSN-N
ESEIFRPGGGDMRDNWRSELYKYKVVKIEPLGVAPTKAKRRVVQREKR--AVGIGALFLG
FLGAAGSTMGAASMTLTVQARQLLSGIVQQQNNLLRAIEAQQHLLQLTVWGIKQLQARIL
AVERYLKDQQLLGIWGCSGKLICTTAVPWNASWSNKSLEQIWNHTTWMEWDREINNYTSL
IHSLIEESQNQQEKNEQELLELDKWASLWNWFNITNWLWYIKLFIMIVGGLVGLRIVFAV
LSIVNRVRQGYSPLSFQTHLPTPRGPDRPEGIEEEGGERDRDRSIRLVNGSLALIWDDLR
SLCLFSYHRLRDLLLIVTRIVELLGR-------RGWEALKYWWNLLQYWSQELKNSAVSL
LNATAIAVAEGTDRVIEVVQGACRAIRHIPRRIRQGLERILL*

>T250-4 natural V2 apex sensitive protein, V1V2 contributions
MRVMGIQRNYPPL----WRWGTMIFW-MMMLCSA-EKLWVTVYYGVPVWREADTTLFCAS
DAKGYDTEAHNVWATHACVPTDPRPQEMYLENVTENFNMWKNSMVEQMHTDIISLWDESL
KPCVKLTPLCVTLDCQAFNSSSH------TNSSIAMQEMKNCSFNVTTELRDKKKKEYSFF
YKTDIEQINK--------NGRQYRLINCNTSAITQACPKVSFEPIPIHFCAPAGFAILKC
NEKHFNGKGPCKNVSTVQCTHGIKPVVSTQLLLNGSLAEEEVVIRVENTIDNAKTIIVQL
AKPVKINCTRPNNNTRKSIRI---GPGQTFYATGDIIGNIRKAYCNVSKREWNNTLQQVAA
QLSKSFNNTK-IVFEKHSGGDLEVITHSFVCGGEFFYCNTSGLFNSTWTNSTWTN-STTG
SNGTESNDTITLQCEIKQFINMWQRVGRAMYAPPIPGVIRCESDITGLLLTRDGPNST--
QNETFRPGGGDMRDNWRSELYKYKVVQIEPLGVAPTHAKRRVVEREKR--AVGLGAVFFG
FLGAAGSTMGAASITLTVQARQLLSGIVQQQSNLLKAIEAQQQLLRLTVWGIKQLQARVL
ALERYLKDQQLLGIWGCSGKLICTTTVPWNSSWSNKNYTDIWDNMTWLQWDREISNYTDE
IYPLIEQSQNQQEKNEQDLLALDKWASLWNWFDITNWLWYIKIFIMIVGGLIGLRIIFTV
LNVINRVRQGYSPLSFQTLTHHQREPDRPERIEEGGGEQDRDRSVRLVSGFLALAWDDLR
SLCLFSFHRLRDLVLIAARGVELLGHSSLKGLRLGWEALKLLGNLLSYWGQELKNSAINL
LDAVAIAVANWTDRVIKIGQRAGRAILNIPIRIRQGLERALL*

>ZM233.6 natural V2 apex sensitive protein, V1V2 contributions
MRVRGIMRNWQQW----WIWGSLGFW-MLIICNVMGSLWVTVYYGVPVWREAKTTLFCAS
DAKAYETEAHSVWATHACVPTDPNPQEMVLENVTENFNMWKNDMVDQMHEDVISIWDQSL
KPCVKLTPLCVTLDCSTYNKT-----------HNISKEMKICSFNMTTELRDKKRKVNVLF
YKLDLVPLTNSS-------NTTNYRLISCNTSTITQACPKVSFDPIPIHYCAPAGYAILKC

Figure 3A

```
NNKTFNGTGPCNNVSTVQCTHGIKPVVSTQLLLNGSLAEEEIIIRFENLTDNVKIIIVQL
NETINITCTRPNNNTRKSIRI--GPGQSFYATGEIVGNIREAHCNISASKWNKTLERVRT
KLKEHFPNKT-IEFEPSSGGDLEITTHSFNCGGEFFYCNTSGLFNSAINGT---------
------LTSNVTLPCRIKQIINMWQEVGRAMYAPPIAGNITCKSNITGLLLTRDGGENSSS
TTETFRPTGGDMKNNWRSELYKYKVVEIKPLGIAPTEAKRPVVEREKR--AVGIGAVFLG
FLGAAGSTMGAASMTLTVQARQLLSGIVQQQSNLLKAIEAQQHMLQLTVWGIKQLQARVL
AIERYLKDQQLLGLWGCSGKLICTTNVPWNASWSNKSKNDIWDNMTWMQWDREISNHTDT
IYRLLEDSQNQQEKNEKDLLALDSWKNLWNWFSITKWLWYIKIFIMIVGGLIGLRIIFAV
LSIVNRVRQGYSPLSFQTLTPNPRGPDRLGGIEEEGGEQDKNKSRRLVTGFLPVVWDDLR
SLCLFSYHLLRDFILIVARTVELLGR-------RGWEALKYLGGLVQYWGLELKKSTISL
LDTIAIVVAEGTDRIIEVLQRIGRAIYNIPRRIRQGFETALL*
```

>BG505.T332N used for gp41 stable SOSIP expression
```
MPVMGIQRNCQHL-----FRWGTMILG-MIIICSAAENLWVTVYYGVPVWKDAETTLFCAS
DAKAYETEKHNVWATHACVPTDPNPQEIHLENVTEEFNMWKNNMVEQMHTDIISLWDQSL
KPCVKLTPLCVTLQCTNVTNNITDDM--------RGELKNCSFNMTTELRDKKQKVYSLF
YRLDVVQINENQGNRSNNSNKEYRLINCNTSAITQACPKVSFEPIPIHYCAPAGFAILKC
KDKKFNGTGPCPSVSTVQCTHGIKPVVSTQLLLNGSLAEEEVMIRSENITNNAKNILVQF
NTPVQINCTRPNNNTRKSIRI--GPGQAFYATGDIIGDIRQAHCNVSKATWNETLGKVVK
QLRKHFGNNTIIRFANSSGGDLEVTTHSFNCGGEFFYCNTSGLFNSTWISNT----SVQG
SNSTGSNDSITLPCRIKQIINMWQRIGQAMYAPPIQGVIRCVSNITGLILTRDGGSTN-S
TTETFRPGGGDMRDNWRSELYKYKVVKIEPLGVAPTPAKRRVVGREKR--AVGIGAVFLG
FLGAAGSTMGAASMTLTVQARNLLSGIVQQQSNLLRAIEAQQHLLKLTVWGIKQLQARVL
AVERYLRDQQLLGIWGCSGKLICTTNVPWNSSWSNPNLSEIWDNMTWLQWDKEISNYTQI
IYGLLEESQNQQEKNEQDLLALDKWASLWNWFDISNWLWYIKIFIMIVGGLIGLRIVFAV
LSVIHRVRQGYSPLSFQTHTPNPRGLDRPERIEEEDGEQDRGRSTRLVSGFLALAWDDLR
SLCLFCYHRLRDFILIAARIVELLGHSSLKGLRLGWEGLKYLWNLLAYWGRELKISAINL
FDTIAIAVAEWTDRVIEIGQRLCRAFLHIPRRIRQGLERALL*
```

Figure 3A continued

CH505 Full length modified proteins.

>V2.SET.OPT
MPV--M----GIQRNYPQWWIWSMLGFWMLMI--CNG----MWVTVYYGVPVWKEAKTTLFCAS
DAKAYEKEVHNVWATHACVPTDPNPQEMVLKNVTENFNMWKNDMVDQMHEDVISLWDQSL
KPCVKLTPLCVTLHCSTYNNT---------HNISKGMKNCSFNATTELRDKKQKVNALF
YKLDIVQLNK--------NGRQYRLINCNTSVITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRTSIRI--GPGQTFYATGQVIGDIREAYCNINKSKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN--
-TETFRPGGGNMKDNWRSELYKYKVVEVKPLGVAPTNARRRVVEREKR--AVGMGAVFLG
FLGAAGSTMGAASITLTVQARQLLSGIVQQQSNLLKAIEAQQHMLKLTVWGIKQLQARVL
ALERYLKDQQLLGMWGCSGKLICTTNVYWNSSWSNKTYGDIWDNMTWMQWDREISNYTEI
IYRLLEESQNQQEKNEQDLLALDRWNSLWNWFNITNWLWYIKIFIMIVGGLIGLRIIFAV
LSLVNRVRQGYSPLSFQTLIPSPRGPDRPGGIEEEGGEQDPNRSTRLVSGFLALVWDDLR
SLCLFIYHRLRDFILIAARAGELLGRSSLKGLRRGWEALKYLGSLVQYWGLELKRSAISL
LDTLAIAVGEGTDRILEFVLGICRAIRNIPTRIRQGFETALL*

>V2.SET.OPT.N332
MRV--M----GIQRNYPQWWIWSMLGFWMLMI--CNG----MWVTVYYGVPVWKEAKTTLFCAS
DAKAYEKEVHNVWATHACVPTDPNPQEMVLKNVTENFNMWKNDMVDQMHEDVISLWDQSL
KPCVKLTPLCVTLHCSTYNNT---------HNISKGMKNCSFNATTELRDKKQKVNALF
YKLDIVQLNK--------NGRQYRLINCNTSVITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRTSIRI--GPGQTFYATGQVIGDIREAYCNISKSKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN--
-TETFRPGGGNMKDNWRSELYKYKVVEVKPLGVAPTNARRRVVEREKR--AVGMGAVFLG
FLGAAGSTMGAASITLTVQARQLLSGIVQQQSNLLKAIEAQQHMLKLTVWGIKQLQARVL
ALERYLKDQQLLGMWGCSGKLICTTNVYWNSSWSNKTYGDIWDNMTWMQWDREISNYTEI
IYRLLEESQNQQEKNEQDLLALDRWNSLWNWFNITNWLWYIKIFIMIVGGLIGLRIIFAV
LSLVNRVRQGYSPLSFQTLIPSPRGPDRPGGIEEEGGEQDPNRSTRLVSGFLALVWDDLR
SLCLFIYHRLRDFILIAARAGELLGRSSLKGLRRGWEALKYLGSLVQYWGLELKRSAISL
LDTLAIAVGEGTDRILEFVLGICRAIRNIPTRIRQGFETALL*

>V2.UCA.OPT1
MPV--M----GIQRNYPQWWIWSMLGFWMLMI--CNG----MWVTVYYGVPVWKEAKTTLFCAS
DAKAYEKEVHNVWATHACVPTDPNPQEMVLKNVTENFNMWKNDMVDQMHEDVISLWDQSL
KPCVKLTPLCVTLHCSTYNNT---------HNISKGMKNCSFNMTTELRDKKQKVNALF
YKLDIVQLNK--------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRKSIRI--GPGQTFYATGDVIGDIREAYCNINKSKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN--
-TETFRPGGGNMKDNWRSELYKYKVVEVKPLGVAPTNARRRVVEREKR--AVGMGAVFLG
FLGAAGSTMGAASITLTVQARQLLSGIVQQQSNLLKAIEAQQHMLKLTVWGIKQLQARVL
ALERYLKDQQLLGMWGCSGKLICTTNVYWNSSWSNKTYGDIWDNMTWMQWDREISNYTEI
IYRLLEESQNQQEKNEQDLLALDRWNSLWNWFNITNWLWYIKIFIMIVGGLIGLRIIFAV
LSLVNRVRQGYSPLSFQTLIPSPRGPDRPGRIEEEGGEQDPNRSTRLVSGFLALVWDDLR
SLCLFIYHRLRDFILIAARAGELLGRSSLKGLRRGWEALKYLGSLVQYWGLELKRSAISL
LDTLAIAVGEGTDRILEFVLGICRAIRNIPTRIRQGFETALL*

>V2.UCA.OPT1.N332
MRV--M----GIQRNYPQWWIWSMLGFWMLMI--CNG----MWVTVYYGVPVWKEAKTTLFCAS
DAKAYEKEVHNVWATHACVPTDPNPQEMVLKNVTENFNMWKNDMVDQMHEDVISLWDQSL
KPCVKLTPLCVTLHCSTYNNT---------HNISKGMKNCSFNMTTELRDKKQKVNALF

Figure 3B

```
YKLDIVQLNK---------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRKSIRI--GPGQTFYATGDVIGDIREAYCNISKSKWNETLQRVSK
KLKEYFP-HKNITFQPSSGGDLEITTHSFNCGGEFFYCNTSSLFNRTYMANSTDMA----N
STETNSTRTITIHCRIKQIINMWQEVGRAMYAPPIAGNITCISNITGLLLTRDGGKNN--
-TETFRPGGGNMKDNWRSELYKYKVVEVKPLGVAPTNARRRVVEREKR--AVGMGAVFLG
FLGAAGSTMGAASITLTVQARQLLSGIVQQQSNLLKAIEAQQHMLKLTVWGIKQLQARVL
ALERYLKDQQLLGMWGCSGKLICTTNVYWNSSWSNKTYGDIWDNMTWMQWDREISNYTEI
IYRLLEESQNQQEKNEQDLLALDRWNSLWNWFNITNWLWYIKIFIMIVGGLIGLRIIFAV
LSLVNRVRQGYSPLSFQTLIPSPRGPDRPGRIEEEGGGEQDRNRSTRLVSGFLALVWDDLR
SLCLFIYHRLRDFILIAARAGELLGRSSLKGLRRGWEALKYLGSLVQYWGLELKRSAISL
LDTLAIAVGEGTDRILEFVLGICRAIRNIPTRIRQGFETALL*

>V2.UCA.OPT2
MRV-M----GIQRNYPQWWIWSMLGFWMLMI--CNG----MWVTVYYGVPVWKEAKTTLFCAS
DAKAYEKEVHNVWATHACVPTDPNPQEMVLKNVTENFNMWKNDMVDQMHEDVISLWDQSL
KPCVKLTPLCVTLHCSTYNNT-----------HNISKGMKNCSFNMTTELRDKKQKVNALF
YKLDIVQLNK---------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRKSIRI--GPGQTFYATGDVIGDIREAYCNINKSKWNETLQRVSK
KLKEYFP-HKNITFQPSSGGDLEITTHSFNCGGEFFYCNTSSLFNRTYMANSTDMA----N
STETNSTRTITIHCRIKQIINMWQEVGRAMYAPPIAGNITCISNITGLLLTRDGGKNN--
-TETFRPGGGNMKDNWRSELYKYKVVEVKPLGVAPTNARRRVVEREKR--AVGMGAVFLG
FLGAAGSTMGAASITLTVQARQLLSGIVQQQSNLLKAIEAQQHMLKLTVWGIKQLQARVL
ALERYLKDQQLLGMWGCSGKLICTTNVYWNSSWSNKTYGDIWDNMTWMQWDREISNYTEI
IYRLLEESQNQQEKNEQDLLALDRWNSLWNWFNITNWLWYIKIFIMIVGGLIGLRIIFAV
LSLVNRVRQGYSPLSFQTLIPSPRGPDRPGRIEEEGGGEQDRNRSTRLVSGFLALVWDDLR
SLCLFIYHRLRDFILIAARAGELLGRSSLKGLRRGWEALKYLGSLVQYWGLELKRSAISL
LDTLAIAVGEGTDRILEFVLGICRAIRHIPTRIRQGFETALL*

>V2.UCA.OPT2.N332
MRV-M----GIQRNYPQWWIWSMLGFWMLMI--CNG----MWVTVYYGVPVWKEAKTTLFCAS
DAKAYEKEVHNVWATHACVPTDPNPQEMVLKNVTENFNMWKNDMVDQMHEDVISLWDQSL
KPCVKLTPLCVTLHCSTYNNT----------HNISKGMKNCSFNMTTELRDKKQKVNALF
YKLDIVQLNK---------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRKSIRI--GPGQTFYATGDVIGDIREAYCNISKSKWNETLQRVSK
KLKEYFP-HKNITFQPSSGGDLEITTHSFNCGGEFFYCNTSSLFNRTYMANSTDMA----N
STETNSTRTITIHCRIKQIINMWQEVGRAMYAPPIAGNITCISNITGLLLTRDGGKNN--
-TETFRPGGGNMKDNWRSELYKYKVVEVKPLGVAPTNARRRVVEREKR--AVGMGAVFLG
FLGAAGSTMGAASITLTVQARQLLSGIVQQQSNLLKAIEAQQHMLKLTVWGIKQLQARVL
ALERYLKDQQLLGMWGCSGKLICTTNVYWNSSWSNKTYGDIWDNMTWMQWDREISNYTEI
IYRLLEESQNQQEKNEQDLLALDRWNSLWNWFNITNWLWYIKIFIMIVGGLIGLRIIFAV
LSLVNRVRQGYSPLSFQTLIPSPRGPDRPGRIEEEGGGEQDRNRSTRLVSGFLALVWDDLR
SLCLFIYHRLRDFILIAARAGELLGRSSLKGLRRGWEALKYLGSLVQYWGLELKRSAISL
LDTLAIAVGEGTDRILEFVLGICRAIRHIPTRIRQGFETALL*
>CH505.TF.chim.6R.SOSIP
MPM------GSLQPLATLYLL---GMLVAS--VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLNCTNATAS---------NSSIIEGMKNCSFNITTELRDKREKKNALF
YKLDIVQLDGN--------SSQYRLINCNTSVITQACPKVSFDPIPIHYCAPAGYAILKC
NNKTFTGTGPCNNVSTVQCTHGIKPVVSTQLLLNGSLAEGEIIIRSENITNNVKTIIVHL
NESVKIECTRPNNKTRTSIRI---GPGQWFYATGQVIGDIREAYCNINESKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN--
-TETFRPGGGNMKDNWRSELYKYKVVKIEPLGVAPTRCKRRVVGRRRRRRAVGIGAVFLG
FLGAAGSTMGAASMTLTVQARNLLSGIVQQQSNLLRAPEAQQHLLKLTVWGIKQLQARVL
AVERYLRDQQLLGIWGCSGKLICCTNVPWNSSWSNPNLSEIWDNMTWLQWDKEISNYTQI
IYGLLEESQNQQEKNEQDLLALD*
```

Figure 3B continued

Modified proteins revised for expression as SOSIP proteins.

```
>CH505TF_V2.SET.OPT_ch.SOSIPv4.1 (A)
MPM------GSLQPLATLYLL----GMLVAS---VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNATTELRDKKQKVNALF
YKLDIVQLNK--------NGRQYRLINCNTSVITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRTSIRI--GPGQTFYATGQVIGDIREAYCNINKSKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN---
-TETFRPGGGNMKDNWRSELYKYKVVKIEPLGVAPTRCKRRVVGRRRRRRAVGIGAVFLG
FLGAAGSTMGAASMTLTVQARNLLSGIVQQQSNLLPAPEAQQHLLKLTVWGIKQLQARVL
AVERYLRDQQLLGIWGCSGKLICCTNVPWNSSWSNPNLSEIWDNMTWLQWDKEISNYTQI
IYGLLEESQNQQEKNEQDLLALD*

>CH505TF_V2.SET.OPT.N332_ch.SOSIPv4.1 (B)
MPM------GSLQPLATLYLL----GMLVAS---VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNATTELRDKKQKVNALF
YKLDIVQLNK--------NGRQYRLINCNTSVITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRTSIRI--GPGQTFYATGQVIGDIREAYCNISKSKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN---
-TETFRPGGGNMKDNWRSELYKYKVVKIEPLGVAPTRCKRRVVGRRRRRRAVGIGAVFLG
FLGAAGSTMGAASMTLTVQARNLLSGIVQQQSNLLPAPEAQQHLLKLTVWGIKQLQARVL
AVERYLRDQQLLGIWGCSGKLICCTNVPWNSSWSNPNLSEIWDNMTWLQWDKEISNYTQI
IYGLLEESQNQQEKNEQDLLALD*

>CH505TF_V2.UCA.OPT1_ch.SOSIPv4.1 (C)
MPM------GSLQPLATLYLL----GMLVAS---VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNMTTELRDKKQKVNALF
YKLDIVQLNK--------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRKSIRI--GPGQTFYATGDVIGDIREAYCNINKSKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN---
-TETFRPGGGNMKDNWRSELYKYKVVKIEPLGVAPTRCKRRVVGRRRRRRAVGIGAVFLG
FLGAAGSTMGAASMTLTVQARNLLSGIVQQQSNLLPAPEAQQHLLKLTVWGIKQLQARVL
AVERYLRDQQLLGIWGCSGKLICCTNVPWNSSWSNPNLSEIWDNMTWLQWDKEISNYTQI
IYGLLEESQNQQEKNEQDLLALD*

>CH505TF_V2.UCA.OPT1.N332_ch.SOSIP.v4.1 (D)
MPM------GSLQPLATLYLL----GMLVAS---VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNMTTELRDKKQKVNALF
YKLDIVQLNK--------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTRKSIRI--GPGQTFYATGDVIGDIREAYCNISKSKWNETLQRVSK
KLKEYFP-HKNITFQPSSGGDLEITTHSFNCGGEFFYCNTSSLFNRTYMANSTDMA---N
STETNSTRTITIHCRIKQIINMWQEVGRAMYAPPIAGNITCISNITGLLLTRDGGKNN---
-TETFRPGGGNMKDNWRSELYKYKVVKIEPLGVAPTRCKRRVVGRRRRRRAVGIGAVFLG
FLGAAGSTMGAASMTLTVQARNLLSGIVQQQSNLLPAPEAQQHLLKLTVWGIKQLQARVL
AVERYLRDQQLLGIWGCSGKLICCTNVPWNSSWSNPNLSEIWDNMTWLQWDKEISNYTQI
IYGLLEESQNQQEKNEQDLLALD*
```

Figure 3C

```
>CH505TF_V2.UCA.OPT2_ch.SOSIPv4.1 (E)
MPM-----GSLQPLATLYLL---GMLVAS--VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNMTTELRDKKQKVNALF
YKLDIVQLNK--------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTPKSIRI--GPGQTFYATGDVIGDIREAYCNINKSKWNETLQRVSK
KLKEYFP-HKNITFQPSSGGDLEITTHSFNCGGEFFYCNTSSLFNRTYMANSTDMA----N
STETNSTRTITIHCRIKQIINMWQEVGRAMYAPPIAGNITCISNITGLLLTRDGGKNN--
-TETFRPGGGNMKDNWRSELYKYKVVKIEPLGVAPTRCKRRVVGRRRRRPAVGIGAVFLG
FLGAAGSTMGAASMTLTVQARNLLSGIVQQQSNLLPAPEAQQHLLKLTVWGIKQLQARVL
AVERYLRDQQLLGIWGCSGKLICCTNVPWNSSWSNRNLSEIWDNMTWLQWDKEISNYTQI
IYGLLEESQNQQEKNEQDLLALD*

>CH505TF_V2.UCA.OPT2.N332_ch.SOSIP.v4.1 (F)
MPM-----GSLQPLATLYLL---GMLVAS--VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNMTTELRDKKQKVNALF
YKLDIVQLNK--------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTPKSIRI--GPGQTFYATGDVIGDIREAYCNISKSKWNETLQRVSK
KLKEYFP-HKNITFQPSSGGDLEITTHSFNCGGEFFYCNTSSLFNRTYMANSTDMA----N
STETNSTRTITIHCRIKQIINMWQEVGRAMYAPPIAGNITCISNITGLLLTRDGGKNN--
-TETFRPGGGNMKDNWRSELYKYKVVKIEPLGVAPTRCKRRVVGRRRRRPAVGIGAVFLG
FLGAAGSTMGAASMTLTVQARNLLSGIVQQQSNLLPAPEAQQHLLKLTVWGIKQLQARVL
AVERYLRDQQLLGIWGCSGKLICCTNVPWNSSWSNRNLSEIWDNMTWLQWDKEISNYTQI
IYGLLEESQNQQEKNEQDLLALD*

>CH505TF_V2.UCA.OPT1.gp41mut_ch.SOSIP.v4.1 (G)
MPM-----GSLQPLATLYLL---GMLVAS--VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNMTTELRDKKQKVNALF
YKLDIVQLNK--------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTPKSIRI--GPGQTFYATGDVIGDIREAYCNINKSKWNETLQRVSK
KLKEYFP-HKNITFQPSSGGDLEITTHSFNCGGEFFYCNTSSLFNRTYMANSTDMA----N
STETNSTRTITIHCRIKQIINMWQEVGRAMYAPPIAGNITCISNITGLLLTRDGGKNN--
-TETFRPGGGNMKDNWRSELYKYKVVKIEPLGVAPTRCKRRVVGRRRRRPAVGIGAVFLG
FLGAAGSTMGAASITLTVQARNLLSGIVQQQSNLLPAPEAQQHLLKLTVWGIKQLQARVL
AVERYLKDQQLLGIWGCSGKLICCTNVPWNSSWSNRNLSEIWDNMTWLQWDKEISNYTQI
IYRLLEESQNQQEKNEQDLLALD*

>CH505TF_V2.UCA.OPT1.N332.gp41mut_ch.SOSIP.v4.1 (H)
MPM-----GSLQPLATLYLL---GMLVAS--VLAAENLWVTVYYGVPVWKEAKTTLFCAS
DAKAYEKKVHNVWATHACVPTDPNPQEMVLKNVTENFNMWKNDMVDQMHEDVISLWDQSL
KPCVKLTPLCVTLHCSTYNNT----------HNISKGMKNCSFNMTTELRDKKQKVNALF
YKLDIVQLNK--------NGRQYRLINCNTSAITQACPKVSFDPIPIHYCAPAGYAILKC
NNKTFNGTGPCNNVSTVQCTHGIKPVVSTQLLLNGSLAEGEIIIRSENITNNVKTIIVHL
NESVKIECTRPNNKTPKSIRI--GPGQTFYATGDVIGDIREAYCNISKSKWNETLQRVSK
KLKEYFP-HKNITFQPSSGGDLEITTHSFNCGGEFFYCNTSSLFNRTYMANSTDMA----N
STETNSTRTITIHCRIKQIINMWQEVGRAMYAPPIAGNITCISNITGLLLTRDGGKNN--
-TETFRPGGGNMKDNWRSELYKYKVVKIEPLGVAPTRCKRRVVGRRRRRPAVGIGAVFLG
FLGAAGSTMGAASITLTVQARNLLSGIVQQQSNLLPAPEAQQHLLKLTVWGIKQLQARVL
AVERYLKDQQLLGIWGCSGKLICCTNVPWNSSWSNRNLSEIWDNMTWLQWDKEISNYTQI
IYRLLEESQNQQEKNEQDLLALD*
```

Figure 3C continued

| Gene number | Protein name |
|---|---|
| HV1301908 | CH505TF_V2.UCA.OPT1.gp41mut_ch.SOSIP.v4.1 |
| HV1301909 | CH505TF_V2.UCA.OPT1.N332.gp41mut_ch.SOSIP.v4.1 |
| HV1301910 | CH505TF_V2.SET.OPT_ch.SOSIPv4.1 |
| HV1301911 | CH505TF_V2.SET.OPT.N332_ch.SOSIPv4.1 |
| HV1301912 | CH505TF_V2.UCA.OPT1_ch.SOSIPv4.1 |
| HV1301913 | CH505TF_V2.UCA.OPT1.N332_ch.SOSIP.v4.1 |

Nucleic Acid sequences

>HV1301908 (CH505TF_V2.UCA.OPT1.gp41mut_ch.SOSIP.v4.1)

<u>GTCGAC</u>GCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGTGCCAGCGACGCCAAGGCCTACGAGAAGAAAGTGCACAACGTGTGGGCCACTCACGCCTGCG
TTCCCACCGATCCTAATCCTCAAGAGATGGTGCTGAAGAACGTGACCGAGAACTTCAACATGTGGAAGAACG
ACATGGTGGACCAGATGCACGAGGACGTGATCAGCCTGTGGGACCAGAGCCTGAAGCCTTGCGTGAAGCTG
ACCCCTCTGTGTGTGACCCTGCACTGCAGCACCTACAACAACACCCACAACATCAGCAAGGGCATGAAGAACT
GCAGCTTCAATATGACCACCGAGCTGCGGGACAAGAAGCAGAAAGTCAACGCCCTGTTCTACAAGCTGGACA
TCGTGCAGCTGAACAAGAACGGCCGGCAGTACCGGCTGATCAACTGCAACACAAGCGCCATCACACAGGCTT
GCCCCAAGGTGTCCTTCGATCCCATTCCTATCCACTACTGTGCCCCTGCCGGCTACGCCATCCTGAAGTGCAAC
AACAAGACCTTCAACGGCACAGGCCCCTGCAACAACGTGTCCACCGTGCAGTGTACCCACGGCATCAAGCCAG
TGGTGTCTACCCAGCTGCTGCTGAATGGATCTCTGGCCGAGGGCGAGATCATCATCAGAAGCGAGAACATCA
CCAACAACGTCAAGACCATCATCGTCCACCTGAACGAGAGCGTGAAGATCGAGTGCACCCGGCCTAACAACA
AAACCAGAAAGAGCATCCGGATCGGCCCTGGCCAGACCTTTTATGCTACTGGCGACGTGATCGGCGACATCA
GAGAGGCCTACTGCAACATCAACAAGAGCAAGTGGAACGAGACACTGCAGCGGGTGTCCAAGAAACTGAAA
GAGTACTTCCCGCACAAGAATATCACCTTCCAGCCTAGCTCTGGCGGCGACCTGGAAATCACCACACACAGCT
TTAACTGTGGCGGCGAGTTCTTCTACTGCAATACCAGCAGCCTGTTCAACCGGACCTACATGGCCAACTCCACC
GATATGGCCAACAGCACCGAGACAAACAGCACCCGGACCATCACCATCCACTGCCGGATCAAGCAGATCATC
AATATGTGGCAAGAAGTCGGCAGGGCTATGTACGCCCCTCCTATCGCCGGCAACATCACCTGTATCAGCAATA
TCACCGGCCTGCTGCTCACCAGAGATGGCGGCAAGAACAACACCGAAACCTTCAGACCCGGCGGAGGCAACA
TGAAGGACAATTGGAGAAGCGAGCTGTACAAGTACAAGGTGGTCAAGATCGAGCCCCTGGGCGTCGCACCA
ACACGGTGCAAGAGAAGAGTCGTGGGCCGTCGTAGAAGGCGGAGAGCCGTTGGAATTGGCGCCGTGTTCCT
GGGCTTTCTGGGAGCCGCTGGATCTACAATGGGCGCTGCCAGCATCACCCTGACAGTGCAGGCTAGAAATCT
GCTGAGCGGCATTGTGCAGCAGCAGAGCAACCTGCTGAGAGCCCCTGAAGCTCAGCAGCACCT

*Figure 4A*

CCTGAAACTGACCGTGTGGGGAATCAAGCAGCTGCAGGCAAGAGTGCTGGCAGTGGAAAGATACCTGAAGG
ACCAGCAGCTCCTCGGAATCTGGGGCTGTTCTGGCAAGCTGATCTGCTGCACCAACGTGCCCTGGAACAGCTC
CTGGTCCAACAGAAACCTGAGCGAGATCTGGGACAACATGACCTGGCTGCAGTGGGACAAAGAGATCAGCA
ACTACACCCAGATCATCTACCGGCTGCTGGAAGAGAGCCAGAACCAGCAAGAGAAAAACGAGCAGGACCTGC
TGGCCCTGGACTGATAA<u>GGATCC</u>

>HV1301909 (CH505TF_V2.UCA.OPT1.N332.gp41mut_ch.SOSIP.v4.1)

<u>GTCGAC</u>GCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGTGCCAGCGACGCCAAGGCCTACGAGAAGAAAGTGCACAACGTGTGGGCCACTCACGCCTGCG
TTCCCACCGATCCTAATCCTCAAGAGATGGTGCTGAAGAACGTGACCGAGAACTTCAACATGTGGAAGAACG
ACATGGTGGACCAGATGCACGAGGACGTGATCAGCCTGTGGGACCAGAGCCTGAAGCCTTGCGTGAAGCTG
ACCCCTCTGTGTGTGACCCTGCACTGCAGCACCTACAACAACACCCACAACATCAGCAAGGGCATGAAGAACT
GCAGCTTCAATATGACCACCGAGCTGCGGGACAAGAAGCAGAAAGTCAACGCCCTGTTCTACAAGCTGGACA
TCGTGCAGCTGAACAAGAACGGCCGGCAGTACCGGCTGATCAACTGCAACACAAGCGCCATCACACAGGCTT
GCCCCAAGGTGTCCTTCGATCCCATTCCTATCCACTACTGTGCCCCTGCCGGCTACGCCATCCTGAAGTGCAAC
AACAAGACCTTCAACGGCACAGGCCCCTGCAACAACGTGTCCACCGTGCAGTGTACCCACGGCATCAAGCCAG
TGGTGTCTACCCAGCTGCTGCTGAATGGATCTCTGGCCGAGGGCGAGATCATCATCAGAAGCGAGAACATCA
CCAACAACGTCAAGACCATCATCGTCCACCTGAACGAGAGCGTGAAGATCGAGTGCACCCGGCCTAACAACA
AAACCAGAAAGAGCATCCGGATCGGCCCTGGCCAGACCTTTTATGCTACTGGCGACGTGATCGGCGACATCA
GAGAGGCCTACTGCAACATCTCCAAGAGCAAGTGGAACGAGACACTGCAGCGGGTGTCCAAGAAACTGAAA
GAGTACTTCCCGCACAAGAATATCACCTTCCAGCCTAGCTCTGGCGGCGACCTGGAAATCACCACACACAGCT
TTAACTGTGGCGGCGAGTTCTTCTACTGCAATACCAGCAGCCTGTTCAACCGGACCTACATGGCCAACTCCACC
GATATGGCCAACAGCACCGAGACAAACAGCACCCGGACCATCACCATCCACTGCCGGATCAAGCAGATCATC
AATATGTGGCAAGAAGTCGGCAGGGCTATGTACGCCCCTCCTATCGCCGGCAACATCACCTGTATCAGCAATA
TCACCGGCCTGCTGCTCACCAGAGATGGCGGCAAGAACAACACCGAAACCTTCAGACCCGGCGGAGGCAACA
TGAAGGACAATTGGAGAAGCGAGCTGTACAAGTACAAGGTGGTCAAGATCGAGCCCCTGGGCGTCGCACCA
ACACGGTGCAAGAGAAGAGTCGTGGGCCGTCGTAGAAGGCGGAGAGCCGTTGGAATTGGCGCCGTGTTCCT
GGGCTTTCTGGGAGCCGCTGGATCTACAATGGGCGCTGCCAGCATCACCCTGACAGTGCAGGCTAGAAATCT
GCTGAGCGGCATTGTGCAGCAGCAGAGCAACCTGCTGAGAGCCCCTGAAGCTCAGCAGCACCTCCTGAAACT
GACCGTGTGGGGAATCAAGCAGCTGCAGGCAAGAGTGCTGGCAGTGGAAAGATACCTGAAGGACCAGCAGC
TCCTCGGAATCTGGGGCTGTTCTGGCAAGCTGATCTGCTGCACCAACGTGCCCTGGAACAGCTCCTGGTCCAA
CAGAAACCTGAGCGAGATCTGGGACAACATGACCTGGCTGCAGTGGGACAAAGAGATCAGCAACTACACCCA
GATCATCTACCGGCTGCTGGAAGAGAGCCAGAACCAGCAAGAGAAAAACGAGCAGGACCTGCTGGCCCTGG
ACTGATAA<u>GGATCC</u>

>HV1301910 (CH505TF_V2.SET.OPT_ch.SOSIPv4.1)

<u>GTCGAC</u>GCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGT

*Figure 4A continued*

TCTGTGCCAGCGACGCCAAGGCCTACGAGAAGAAAGTGCACAACGTGTGGGCCACTCACGCCTGCGTTCCCA
CCGATCCTAATCCTCAAGAGATGGTGCTGAAGAACGTGACCGAGAACTTCAACATGTGGAAGAACGACATGG
TGGACCAGATGCACGAGGACGTGATCAGCCTGTGGGACCAGAGCCTGAAGCCTTGCGTGAAGCTGACCCCTC
TGTGTGTGACCCTGCACTGCAGCACCTACAACAACACCCACAACATCAGCAAGGGCATGAAGAACTGCAGCTT
CAACGCCACCACCGAGCTGCGGGACAAGAAACAGAAAGTGAACGCCCTGTTCTACAAGCTGGACATCGTGCA
GCTGAACAAGAACGGCCGGCAGTACCGGCTGATCAACTGCAACACCAGCGTGATCACCCAGGCCTGTCCTAA
GGTGTCCTTCGATCCCATTCCTATCCACTACTGTGCCCCTGCCGGCTACGCCATCCTGAAGTGCAACAACAAGA
CCTTCAACGGCACAGGCCCCTGCAACAACGTGTCCACCGTGCAGTGTACCCACGGCATCAAGCCTGTGGTGTC
TACCCAGCTGCTGCTGAATGGATCTCTGGCCGAGGGCGAGATCATCATCAGAAGCGAGAACATCACCAACAA
CGTCAAGACCATCATCGTCCACCTGAACGAGAGCGTGAAGATCGAGTGCACCGGCCTAACAACAAAACCCG
GACCAGCATCAGAATCGGCCCTGGCCAGACCTTTTACGCCACCGGACAAGTGATCGGCGACATCAGAGAGGC
CTACTGCAACATCAACAAGAGCAAGTGGAACGAGACACTGCAGCGGGTGTCCAAGAAGCTGAAAGAGTACTT
CCCTCACAAGAATATCACCTTCCAGCCTAGCTCTGGCGGCGACCTGGAAATCACCACACACAGCTTCAATTGTG
GCGGCGAGTTCTTCTACTGCAATACCTCCAGCCTGTTCAACCGGACCTACATGGCCAACTCCACCGATATGGCC
AACAGCACCGAGACAAACAGCACCAGAACCATCACCATCCACTGCCGGATCAAGCAGATCATCAATATGTGGC
AAGAAGTCGGCAGGGCTATGTACGCCCCTCCTATCGCCGGCAACATCACCTGTATCAGCAATATCACCGGCCT
GCTGCTCACCAGAGATGGCGGCAAGAACAACACCGAAACCTTCAGACCCGGCGGAGGCAACATGAAGGACA
ATTGGAGAAGCGAGCTGTACAAGTACAAGGTGGTCAAGATCGAGCCCCTGGGCGTCGCACCCACCAGGTGCA
AAAGAAGAGTCGTCGGAAGAAGGCGGAGGCGGAGAGCCGTTGGAATTGGAGCAGTGTTCCTGGGCTTTCTG
GGAGCCGCCGGATCTACAATGGGAGCTGCCAGCATGACCCTGACCGTGCAGGCTAGAAATCTGCTGAGCGGC
ATTGTGCAGCAGCAGAGCAACCTGCTGAGAGCCCCTGAAGCTCAGCAGCACCTCCTGAAACTGACCGTGTGG
GGAATCAAGCAGCTGCAGGCAAGAGTGCTGGCAGTGGAAAGATACCTGCGGGACCAGCAGCTCCTCGGAAT
CTGGGGATGTAGCGGCAAGCTGATCTGCTGCACCAACGTGCCCTGGAACAGCTCCTGGTCCAACAGAAACCT
GAGCGAGATCTGGGACAACATGACCTGGCTGCAGTGGGACAAAGAGATCAGCAACTACACCCAGATCATCTA
CGGACTGCTGGAAGAGAGCCAGAACCAGCAAGAGAAGAACGAGCAGGACCTGCTGGCCCTGGACTGATAA<u>G</u>
<u>GATCC</u>

>HV1301911 (CH505TF_V2.SET.OPT.N332_ch.SOSIPv4.1)

<u>GTCGAC</u>GCCACCATGGCTATGGGATCTCTGCAGCCTCTGGCCACAGTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGTGCCAGCGACGCCAAGGCCTACGAGAAGAAAGTGCACAACGTGTGGGCCACTCACGCCTGCG
TTCCCACCGATCCTAATCCTCAAGAGATGGTGCTGAAGAACGTGACCGAGAACTTCAACATGTGGAAGAACG
ACATGGTGGACCAGATGCACGAGGACGTGATCAGCCTGTGGGACCAGAGCCTGAAGCCTTGCGTGAAGCTG
ACCCCTCTGTGTGTGACCCTGCACTGCAGCACCTACAACAACACCCACAACATCAGCAAGGGCATGAAGAACT
GCAGCTTCAACGCCACCACCGAGCTGCGGGACAAGAAACAGAAAGTGAACGCCCTGTTCTACAAGCTGGACA
TCGTGCAGCTGAACAAGAACGGCCGGCAGTACCGGCTGATCAACTGCAACACCAGCGTGATCACCCAGGCCT
GTCCTAAGGTGTCCTTCGATCCCATTCCTATCCACTACTGTGCCCCTGCCGGCTACGCCATCCTGAAGTGCAAC
AACAAGACCTTCAACGGCACAGGCCCCTGCAACAACGTGTCCACCGTGCAGTGTACCCACGGCATCAAGCCTG
TGGTGTCTACCCAGCTGCTGCTGAATGGATCTCTGGCCGAGGGCGAGATCATCATCAGAAGCGAGAACATCA
CCAACAACGTCAAGACCATCATCGTCCACCTGAACGAGAGCGTGAAGATCGAGTGCACCCGGCCTAACAACA
AAACCCGGACCAGCATCAGAATCGGCCCTGGCCAG

*Figure 4A continued*

ACCTTTTACGCCACCGGACAAGTGATCGGCGACATCAGAGAGGCCTACTGCAACATCTCCAAGAGCAAGTGG
AACGAGACACTGCAGCGGGTGTCCAAGAAGCTGAAAGAGTACTTCCCTCACAAGAATATCACCTTCCAGCCTA
GCTCTGGCGGCGACCTGGAAATCACCACACACAGCTTCAATTGTGGCGGCGAGTTCTTCTACTGCAATACCTC
CAGCCTGTTCAACCGGACCTACATGGCCAACTCCACCGATATGGCCAACAGCACCGAGACAAACAGCACCAGA
ACCATCACCATCCACTGCCGGATCAAGCAGATCATCAATATGTGGCAAGAAGTCGGCAGGGCTATGTACGCCC
CTCCTATCGCCGGCAACATCACCTGTATCAGCAATATCACCGGCCTGCTGCTCACCAGAGATGGCGGCAAGAA
CAACACCGAAACCTTCAGACCCGGCGGAGGCAACATGAAGGACAATTGGAGAAGCGAGCTGTACAAGTACA
AGGTGGTCAAGATCGAGCCCCTGGGCGTCGCACCCACCAGGTGCAAAAGAAGAGTCGTCGGAAGAAGGCGG
AGGCGGAGAGCCGTTGGAATTGGAGCAGTGTTCCTGGGCTTTCTGGGAGCCGCCGGATCTACAATGGGAGCT
GCCAGCATGACCCTGACCGTGCAGGCTAGAAATCTGCTGAGCGGCATTGTGCAGCAGCAGAGCAACCTGCTG
AGAGCCCCTGAAGCTCAGCAGCACCTCCTGAAACTGACCGTGTGGGGAATCAAGCAGCTGCAGGCAAGAGTG
CTGGCAGTGGAAAGATACCTGCGGGACCAGCAGCTCCTCGGAATCTGGGGATGTAGCGGCAAGCTGATCTGC
TGCACCAACGTGCCCTGGAACAGCTCCTGGTCCAACAGAAACCTGAGCGAGATCTGGGACAACATGACCTGG
CTGCAGTGGGACAAAGAGATCAGCAACTACACCCAGATCATCTACGGACTGCTGGAAGAGAGCCAGAACCAG
CAAGAGAAGAACGAGCAGGACCTGCTGGCCCTGGACTGATAAGGATCC

>HV1301912 (CH505TF_V2.UCA.OPT1_ch.SOSIPv4.1)

GTCGACGCCACCATGCCTATGGGATCTCTGCAGCCTCTGGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGTGCCAGCGACGCCAAGGCCTACGAGAAGAAAGTGCACAACGTGTGGGCCACTCACGCCTGCG
TTCCCACCGATCCTAATCCTCAAGAGATGGTGCTGAAGAACGTGACCGAGAACTTCAACATGTGGAAGAACG
ACATGGTGGACCAGATGCACGAGGACGTGATCAGCCTGTGGGACCAGAGCCTGAAGCCTTGCGTGAAGCTG
ACCCCTCTGTGTGTGACCCTGCACTGCAGCACCTACAACAACACCCACAACATCAGCAAGGGCATGAAGAACT
GCAGCTTCAATATGACCACCGAGCTGCGGGACAAGAAGCAGAAAGTCAACGCCCTGTTCTACAAGCTGGACA
TCGTGCAGCTGAACAAGAACGGCCGGCAGTACCGGCTGATCAACTGCAACACAAGCGCCATCACACAGGCTT
GCCCCAAGGTGTCCTTCGATCCCATTCCTATCCACTACTGTGCCCCTGCCGGCTACGCCATCCTGAAGTGCAAC
AACAAGACCTTCAACGGCACAGGCCCCTGCAACAACGTGTCCACCGTGCAGTGTACCCACGGCATCAAGCCAG
TGGTGTCTACCCAGCTGCTGCTGAATGGATCTCTGGCCGAGGGCGAGATCATCATCAGAAGCGAGAACATCA
CCAACAACGTCAAGACCATCATCGTCCACCTGAACGAGAGCGTGAAGATCGAGTGCACCCGGCCTAACAACA
AAACCAGAAAGAGCATCCGGATCGGCCCTGGCCAGACCTTTTATGCTACTGGCGACGTGATCGGCGACATCA
GAGAGGCCTACTGCAACATCAACAAGAGCAAGTGGAACGAGACACTGCAGCGGGTGTCCAAGAAACTGAAA
GAGTACTTCCCGCACAAGAATATCACCTTCCAGCCTAGCTCTGGCGGCGACCTGGAAATCACCACACACAGCT
TTAACTGTGGCGGCGAGTTCTTCTACTGCAATACCAGCAGCCTGTTCAACCGGACCTACATGGCCAACTCCACC
GATATGGCCAACAGCACCGAGACAAACAGCACCCGGACCATCACCATCCACTGCCGGATCAAGCAGATCATC
AATATGTGGCAAGAAGTCGGCAGGGCTATGTACGCCCCTCCTATCGCCGGCAACATCACCTGTATCAGCAATA
TCACCGGCCTGCTGCTCACCAGAGATGGCGGCAAGAACAACACCGAAACCTTCAGACCCGGCGGAGGCAACA
TGAAGGACAATTGGAGAAGCGAGCTGTACAAGTACAAGGTGGTCAAGATCGAGCCCCTGGGCGTCGCACCC
ACCAGGTGCAAAAGAAGAGTCGTCGGAAGAAGGCGGAGGCGGAGAGCCGTTGGAATTGGAGCTGTGTTCCT
GGGCTTTCTGGGAGCCGCCGGATCTACAATGGGAGCTGCCAGCATGACCCTGACCGTGC

Figure 4A continued

AGGCTAGAAATCTGCTGAGCGGCATTGTGCAGCAGCAGAGCAACCTGCTGAGAGCCCCTGAAGCTCAGCAGC
ACCTCCTGAAACTGACCGTGTGGGGAATCAAGCAGCTGCAGGCAAGAGTGCTGGCAGTGGAAAGATACCTGC
GGGACCAGCAGCTCCTCGGAATCTGGGGATGTAGCGGCAAGCTGATCTGCTGCACCAACGTGCCCTGGAACA
GCTCCTGGTCCAACAGAAACCTGAGCGAGATCTGGGACAACATGACCTGGCTGCAGTGGGACAAAGAGATCA
GCAACTACACCCAGATCATCTACGGACTGCTGGAAGAGAGCCAGAACCAGCAAGAGAAGAACGAGCAGGAC
CTGCTGGCCCTGGACTGATAAGGATCC

>HV1301913 (CH505TF_V2.UCA.OPT1.N332_ch.SOSIP.v4.1)

GTCGACGCCACCATGGCCTATGGGATCTCTGCAGCCTCTGCCACACTGTACCTGCTGGGAATGCTGGTGGCTT
CTGTGCTGGCCGCCGAGAATCTGTGGGTCACAGTGTACTATGGCGTGCCCGTGTGGAAAGAGGCCAAGACCA
CACTGTTCTGTGCCAGCGACGCCAAGGCCTACGAGAAGAAAGTGCACAACGTGTGGGCCACTCACGCCTGCG
TTCCCACCGATCCTAATCCTCAAGAGATGGTGCTGAAGAACGTGACCGAGAACTTCAACATGTGGAAGAACG
ACATGGTGGACCAGATGCACGAGGACGTGATCAGCCTGTGGGACCAGAGCCTGAAGCCTTGCGTGAAGCTG
ACCCCTCTGTGTGTGACCCTGCACTGCAGCACCTACAACAACACCCACAACATCAGCAAGGGCATGAAGAACT
GCAGCTTCAATATGACCACCGAGCTGCGGGACAAGAAGCAGAAAGTCAACGCCCTGTTCTACAAGCTGGACA
TCGTGCAGCTGAACAAGAACGGCCGGCAGTACCGGCTGATCAACTGCAACACAAGCGCCATCACACAGGCTT
GCCCCAAGGTGTCCTTCGATCCCATTCCTATCCACTACTGTGCCCCTGCCGGCTACGCCATCCTGAAGTGCAAC
AACAAGACCTTCAACGGCACAGGCCCCTGCAACAACGTGTCCACCGTGCAGTGTACCCACGGCATCAAGCCAG
TGGTGTCTACCCAGCTGCTGCTGAATGGATCTCTGGCCGAGGGCGAGATCATCATCAGAAGCGAGAACATCA
CCAACAACGTCAAGACCATCATCGTCCACCTGAACGAGAGCGTGAAGATCGAGTGCACCCGGCCTAACAACA
AAACCAGAAAGAGCATCCGGATCGGCCCTGGCCAGACCTTTTATGCTACTGGCGACGTGATCGGCGACATCA
GAGAGGCCTACTGCAACATCTCCAAGAGCAAGTGGAACGAGACACTGCAGCGGGGTGTCCAAGAAACTGAAA
GAGTACTTCCCGCACAAGAATATCACCTTCCAGCCTAGCTCTGGCGGCGACCTGGAAATCACCACACACAGCT
TTAACTGTGGCGGCGAGTTCTTCTACTGCAATACCAGCAGCCTGTTCAACCGGACCTACATGGCCAACTCCACC
GATATGGCCAACAGCACCGAGACAAACAGCACCCGGACCATCACCATCCACTGCCGGATCAAGCAGATCATC
AATATGTGGCAAGAAGTCGGCAGGGCTATGTACGCCCCTCCTATCGCCGGCAACATCACCTGTATCAGCAATA
TCACCGGCCTGCTGCTCACCAGAGATGGCGGCAAGAACAACACCGAAACCTTCAGACCCGGCGGAGGCAACA
TGAAGGACAATTGGAGAAGCGAGCTGTACAAGTACAAGGTGGTCAAGATCGAGCCCCTGGGCGTCGCACCC
ACCAGGTGCAAAAGAAGAGTCGTCGGAAGAAGGCGGAGGCGGAGAGCCGTTGGAATTGGAGCTGTGTTCCT
GGGCTTTCTGGGAGCCGCCGGATCTACAATGGGAGCTGCCAGCATGACCCTGACCGTGCAGGCTAGAAATCT
GCTGAGCGGCATTGTGCAGCAGCAGAGCAACCTGCTGAGAGCCCCTGAAGCTCAGCAGCACCTCCTGAAACT
GACCGTGTGGGGAATCAAGCAGCTGCAGGCAAGAGTGCTGGCAGTGGAAAGATACCTGCGGGACCAGCAGC
TCCTCGGAATCTGGGGATGTAGCGGCAAGCTGATCTGCTGCACCAACGTGCCCTGGAACAGCTCCTGGTCCAA
CAGAAACCTGAGCGAGATCTGGGACAACATGACCTGGCTGCAGTGGGACAAAGAGATCAGCAACTACACCCA
GATCATCTACGGACTGCTGGAAGAGAGCCAGAACCAGCAAGAGAAGAACGAGCAGGACCTGCTGGCCCTGG
ACTGATAAGGATCC

Figure 4A continued

Amino Acid sequences

>HV1301908 (CH505TF_V2.UCA.OPT1.gp41mut_ch.SOSIP.v4.1)

VDATMPMGSLQPLATLYLLGMLVASVLAAENLWVTVYYGVPVWKEAKTTLFCASDAKAYEKKVHNVWATHACV
PTDPNPQEMVLKNVTENFNMWKNDMVDQMHEDVISLWDQSLKPCVKLTPLCVTLHCSTYNNTHNISKGMKNC
SFNMTTELRDKKQKVNALFYKLDIVQLNKNGRQYRLINCNTSAITQACPKVSFDPIPIHYCAPAGYAILKCNNKTFNG
TGPCNNVSTVQCTHGIKPVVSTQLLLNGSLAEGEIIRSENITNNVKTIIVHLNESVKIECTRPNNKTRKSIRIGPGQTFY
ATGDVIGDIREAYCNINKSKWNETLQRVSKKLKEYFPHKNITFQPSSGGDLEITTHSFNCGGEFFYCNTSSLFNRTYM
ANSTDMANSTETNSTRTITIHCRIKQIINMWQEVGRAMYAPPIAGNITCISNITGLLLTRDGGKNNTETFRPGGGN
MKDNWRSELYKYKVVKIEPLGVAPTRCKRRVVGRRRRRRAVGIGAVFLGFLGAAGSTMGAASITLTVQARNLLSGI
VQQQSNLLRAPEAQQHLLKLTVWGIKQLQARVLAVERYLKDQQLLGIWGCSGKLICCTNVPWNSSWSNRNLSEI
WDNMTWLQWDKEISNYTQIIYRLLEESQNQQEKNEQDLLALD

>HV1301909 (CH505TF_V2.UCA.OPT1.N332.gp41mut_ch.SOSIP.v4.1)

VDATMPMGSLQPLATLYLLGMLVASVLAAENLWVTVYYGVPVWKEAKTTLFCASDAKAYEKKVHNVWATHACV
PTDPNPQEMVLKNVTENFNMWKNDMVDQMHEDVISLWDQSLKPCVKLTPLCVTLHCSTYNNTHNISKGMKNC
SFNMTTELRDKKQKVNALFYKLDIVQLNKNGRQYRLINCNTSAITQACPKVSFDPIPIHYCAPAGYAILKCNNKTFNG
TGPCNNVSTVQCTHGIKPVVSTQLLLNGSLAEGEIIRSENITNNVKTIIVHLNESVKIECTRPNNKTRKSIRIGPGQTFY
ATGDVIGDIREAYCNISKSKWNETLQRVSKKLKEYFPHKNITFQPSSGGDLEITTHSFNCGGEFFYCNTSSLFNRTYM
ANSTDMANSTETNSTRTITIHCRIKQIINMWQEVGRAMYAPPIAGNITCISNITGLLLTRDGGKNNTETFRPGGGN
MKDNWRSELYKYKVVKIEPLGVAPTRCKRRVVGRRRRRRAVGIGAVFLGFLGAAGSTMGAASITLTVQARNLLSGI
VQQQSNLLRAPEAQQHLLKLTVWGIKQLQARVLAVERYLKDQQLLGIWGCSGKLICCTNVPWNSSWSNRNLSEI
WDNMTWLQWDKEISNYTQIIYRLLEESQNQQEKNEQDLLALD

>HV1301910 (CH505TF_V2.SET.OPT_ch.SOSIPv4.1)

VDATMPMGSLQPLATLYLLGMLVASVLAAENLWVTVYYGVPVWKEAKTTLFCASDAKAYEKKVHNVWATHACV
PTDPNPQEMVLKNVTENFNMWKNDMVDQMHEDVISLWDQSLKPCVKLTPLCVTLHCSTYNNTHNISKGMKNC
SFNATTELRDKKQKVNALFYKLDIVQLNKNGRQYRLINCNTSVITQACPKVSFDPIPIHYCAPAGYAILKCNNKTFNG
TGPCNNVSTVQCTHGIKPVVSTQLLLNGSLAEGEIIRSENITNNVKTIIVHLNESVKIECTRPNNKTRTSIRIGPGQTFY
ATGQVIGDIREAYCNINKSKWNETLQRVSKKLKEYFPHKNITFQPSSGGDLEITTHSFNCGGEFFYCNTSSLFNRTYM
ANSTDMANSTETNSTRTITIHCRIKQIINMWQEVGRAMYAPPIAGNITCISNITGLLLTRDGGKNNTETFRPGGGN
MKDNWRSELYKYKVVKIEPLGVAPTRCKRRVVGRRRRRRAVGIGAVFLGFLGAAGSTMGAASMTLTVQARNLLS
GIVQQQSNLLRAPEAQQHLLKLTVWGIKQLQARVLAVERYLRDQQLLGIWGCSGKLICCTNVPWNSSWSNRNLS
EIWDNMTWLQWDKEISNYTQIIYGLLEESQNQQEKNEQDLLALD

Figure 4B

>HV1301911 (CH505TF_V2.SET.OPT.N332_ch.SOSIPv4.1)

VDATMPMGSLQPLATLYLLGMLVASVLAAENLWVTVYYGVPVWKEAKTTLFCASDAKAYEKKVHNVWATHACV
PTDPNPQEMVLKNVTENFNMWKNDMVDQMHEDVISLWDQSLKPCVKLTPLCVTLHCSTYNNTHNISKGMKNC
SFNATTELRDKKQKVNALFYKLDIVQLNKNGRQYRLINCNTSVITQACPKVSFDPIPIHYCAPAGYAILKCNNKTFNG
TGPCNNVSTVQCTHGIKPVVSTQLLLNGSLAEGEIIRSENITNNVKTIIVHLNESVKIECTRPNNKTRTSIRIGPGQTFY
ATGQVIGDIREAYCNISKSKWNETLQRVSKKLKEYFPHKNITFQPSSGGDLEITTHSFNCGGEFFYCNTSSLFNRTYM
ANSTDMANSTETNSTRTITIHCRIKQIINMWQEVGRAMYAPPIAGNITCISNITGLLLTRDGGKNNTETFRPGGGN
MKDNWRSELYKYKVVKIEPLGVAPTRCKRRVVGRRRRRRAVGIGAVFLGFLGAAGSTMGAASMTLTVQARNLLS
GIVQQQSNLLRAPEAQQHLLKLTVWGIKQLQARVLAVERYLRDQQLLGIWGCSGKLICCTNVPWNSSWSNRNLS
EIWDNMTWLQWDKEISNYTQIIYGLLEESQNQQEKNEQDLLALD

>HV1301912 (CH505TF_V2.UCA.OPT1_ch.SOSIPv4.1)

VDATMPMGSLQPLATLYLLGMLVASVLAAENLWVTVYYGVPVWKEAKTTLFCASDAKAYEKKVHNVWATHACV
PTDPNPQEMVLKNVTENFNMWKNDMVDQMHEDVISLWDQSLKPCVKLTPLCVTLHCSTYNNTHNISKGMKNC
SFNMTTELRDKKQKVNALFYKLDIVQLNKNGRQYRLINCNTSAITQACPKVSFDPIPIHYCAPAGYAILKCNNKTFNG
TGPCNNVSTVQCTHGIKPVVSTQLLLNGSLAEGEIIRSENITNNVKTIIVHLNESVKIECTRPNNKTRKSIRIGPGQTFY
ATGDVIGDIREAYCNINKSKWNETLQRVSKKLKEYFPHKNITFQPSSGGDLEITTHSFNCGGEFFYCNTSSLFNRTYM
ANSTDMANSTETNSTRTITIHCRIKQIINMWQEVGRAMYAPPIAGNITCISNITGLLLTRDGGKNNTETFRPGGGN
MKDNWRSELYKYKVVKIEPLGVAPTRCKRRVVGRRRRRRAVGIGAVFLGFLGAAGSTMGAASMTLTVQARNLLS
GIVQQQSNLLRAPEAQQHLLKLTVWGIKQLQARVLAVERYLRDQQLLGIWGCSGKLICCTNVPWNSSWSNRNLS
EIWDNMTWLQWDKEISNYTQIIYGLLEESQNQQEKNEQDLLALD

>HV1301913 (CH505TF_V2.UCA.OPT1.N332_ch.SOSIP.v4.1)

VDATMPMGSLQPLATLYLLGMLVASVLAAENLWVTVYYGVPVWKEAKTTLFCASDAKAYEKKVHNVWATHACV
PTDPNPQEMVLKNVTENFNMWKNDMVDQMHEDVISLWDQSLKPCVKLTPLCVTLHCSTYNNTHNISKGMKNC
SFNMTTELRDKKQKVNALFYKLDIVQLNKNGRQYRLINCNTSAITQACPKVSFDPIPIHYCAPAGYAILKCNNKTFNG
TGPCNNVSTVQCTHGIKPVVSTQLLLNGSLAEGEIIRSENITNNVKTIIVHLNESVKIECTRPNNKTRKSIRIGPGQTFY
ATGDVIGDIREAYCNISKSKWNETLQRVSKKLKEYFPHKNITFQPSSGGDLEITTHSFNCGGEFFYCNTSSLFNRTYM
ANSTDMANSTETNSTRTITIHCRIKQIINMWQEVGRAMYAPPIAGNITCISNITGLLLTRDGGKNNTETFRPGGGN
MKDNWRSELYKYKVVKIEPLGVAPTRCKRRVVGRRRRRRAVGIGAVFLGFLGAAGSTMGAASMTLTVQARNLLS
GIVQQQSNLLRAPEAQQHLLKLTVWGIKQLQARVLAVERYLRDQQLLGIWGCSGKLICCTNVPWNSSWSNRNLS
EIWDNMTWLQWDKEISNYTQIIYGLLEESQNQQEKNEQDLLALD

Figure 4B continued

>CH505TF chimera SOSIP.664.v4.1 C-SORTA (HV1301189_C_SORTAv2)

```
ATGCCCATGGGCAGCCTGCAGCCCCTGGCCACCCTGTACCTGCTGGGCATGCTGGTGGCTAGCGTGCTGGC
CGCCGAGAACCTGTGGGTGACCGTCTACTATGGCGTGCCCGTCTGGAAGGAAGCCAAAACCACACTGTTCT
GCGCTAGCGACGCTAAGGCATACGAGAAAAAAGTGCACAATGTCTGGGCTACTCATGCATGCGTGCCTAC
CGATCCAAATCCCCAGGAGATGGTGCTGAAGAACGTCACAGAAAACTTTAATATGTGGAAGAACGACATG
GTGGATCAGATGCACGAGGACGTGATCAGCCTGTGGGATCAGTCCCTGAAGCCATGCGTGAAACTGACTC
CCCTGTGCGTCACCCTGAACTGTACTAATGCCACCGCTTCCAACAGCTCCATCATTGAGGGGATGAAGAACT
GTTCTTTCAATATCACTACCGAGCTGCGCGACAAGCGAGAAAAGAAAAATGCCCTGTTTTACAAACTGGAC
ATCGTGCAGCTGGATGGCAACTCTAGTCAGTATAGACTGATTAACTGCAATACAAGCGTGATCACTCAGGC
ATGTCCAAAGGTCAGTTTCGATCCTATTCCAATCCACTACTGCGCACCCGCCGGATATGCTATCCTGAAGTG
TAACAACAAGACCTTCACCGGCACTGGGCCTTGCAACAACGTGAGCACCGTCCAGTGTACACATGGCATTA
AGCCAGTGGTCAGCACCCAGCTGCTGCTGAACGGCAGCCTGGCAGAGGGCGAAATCATTATCCGCAGCGA
GAACATCACAAATAATGTGAAGACTATCATCGTCCACCTGAACGAGAGCGTGAAGATTGAATGCACACGGC
CCAACAACAAGACCAGGACATCCATTCGCATCGGACCTGGCCAGTGGTTCTACGCTACTGGCCAGGTCATC
GGGGACATCAGAGAGGCCTATTGTAACATCAATGAGTCAAAGTGGAATGAAACTCTGCAGAGGGTGAGCA
AGAAACTGAAGGAATACTTCCCTCACAAAAACATCACCTTTCAGCCATCAAGCGGCGGGGACCTGGAGATT
ACAACTCATTCTTTCAATTGCGGAGGCGAATTCTTTTACTGTAACACCTCCTCTCTGTTTAATCGCACATATAT
GGCTAACAGTACTGATATGGCAAACTCTACTGAGACCAATAGTACACGAACTATTACCATCCATTGCCGGAT
CAAGCAGATTATCAACATGTGGCAGGAAGTGGGGCGGGCCATGTATGCTCCCCCTATTGCAGGAAATATTA
CCTGTATCAGCAACATTACCGGCCTGCTGCTGACAAGAGACGGGGGAAAGAACAATACAGAGACTTTTAG
GCCTGGCGGGGGAAACATGAAAGATAATTGGCGCTCCGAGCTGTACAAGTATAAAGTGGTCAAGATCGAA
CCACTGGGAGTGGCACCTACCCGATGTAAACGGAGAGTGGTCGGAAGGCGCCGACGGAGAAGGGCAGTG
GGAATCGGAGCCGTCTTCCTGGGCTTTCTGGGAGCAGCTGGCAGCACAATGGGAGCAGCCTCTATGACCCT
GACAGTGCAGGCTCGAAATCTGCTGAGTGGGATCGTGCAGCAGCAGTCAAACCTGCTGCGAGCACCAGAG
GCACAGCAGCATCTGCTGAAGCTGACCGTGTGGGGCATCAAGCAGCTGCAGGCCAGAGTGCTGGCTGTCG
AACGGTACCTGAGAGATCAGCAGCTGCTGGGAATCTGGGGATGCAGCGGAAAGCTGATTTGCTGTACAAA
CGTGCCCTGGAATAGTTCATGGTCAAACAGGAATCTGAGCGAGATCTGGGACAATATGACCTGGCTGCAG
TGGGATAAGGAAATCAGTAACTACACACAGATCATCTATGGCCTGCTGGAGGAATCACAGAACCAGCAGG
AGAAAAATGAACAGGACCTGCTGGCCCTGGATCTGCCTAGCACCGGATGATGA
```

Figure 5A

>CH505TF.6R.SOSIP.664.v4.1_N_SORTA (HV1301189_N-SORTA)

ATGCCCATGGGCAGCCTGCAGCCCCTGGCCACCCTGTACCTGCTGGGCATGCTGGTGGCTAGCGTGCTGGCCGGCGG
GGGCGGGGGCGGCGGGGGCGGGGGCGGCGGGGGCGGGGGCGCCGAGAACCTGTGGGTGACCGTCTACTATGGC
GTGCCCGTCTGGAAGGAAGCCAAAACCACACTGTTCTGCGCTAGCGACGCTAAGGCATACGAGAAAAAAGTGCACA
ATGTCTGGGCTACTCATGCATGCGTGCCTACCGATCCAAATCCCCAGGAGATGGTGCTGAAGAACGTCACAGAAAAC
TTTAATATGTGGAAGAACGACATGGTGGATCAGATGCACGAGGACGTGATCAGCCTGTGGGATCAGTCCCTGAAGCC
ATGCGTGAAACTGACTCCCCTGTGCGTCACCCTGAACTGTACTAATGCCACCGCTTCCAACAGCTCCATCATTGAGGG
GATGAAGAACTGTTCTTTCAATATCACTACCGAGCTGCGCGACAAGCGAGAAAAGAAAAATGCCCTGTTTTACAAACT
GGACATCGTGCAGCTGGATGGCAACTCTAGTCAGTATAGACTGATTAACTGCAATACAAGCGTGATCACTCAGGCAT
GTCCAAAGGTCAGTTTCGATCCTATTCCAATCCACTACTGCGCACCCGCCGGATATGCTATCCTGAAGTGTAACAACAA
GACCTTCACCGGCACTGGGCCTTGCAACAACGTGAGCACCGTCCAGTGTACACATGGCATTAAGCCAGTGGTCAGCA
CCCAGCTGCTGCTGAACGGCAGCCTGGCAGAGGGCGAAATCATTATCCGCAGCGAGAACATCACAAATAATGTGAA
GACTATCATCGTCCACCTGAACGAGAGCGTGAAGATTGAATGCACACGGCCCAACAACAAGACCAGGACATCCATTC
GCATCGGACCTGGCCAGTGGTTCTACGCTACTGGCCAGGTCATCGGGGACATCAGAGAGGCCTATTGTAACATCAAT
GAGTCAAAGTGGAATGAAACTCTGCAGAGGGTGAGCAAGAAACTGAAGGAATACTTCCCTCACAAAAACATCACCTT
TCAGCCATCAAGCGGCGGGGACCTGGAGATTACAACTCATTCTTTCAATTGCGGAGGCGAATTCTTTTACTGTAACAC
CTCCTCTCTGTTTAATCGCACATATATGGCTAACAGTACTGATATGGCAAACTCTACTGAGACCAATAGTACACGAACT
ATTACCATCCATTGCCGGATCAAGCAGATTATCAACATGTGGCAGGAAGTGGGGCGGGCCATGTATGCTCCCCCTATT
GCAGGAAATATTACCTGTATCAGCAACATTACCGGCCTGCTGCTGACAAGAGACGGGGGAAAGAACAATACAGAGA
CTTTTAGGCCTGGCGGGGGAAACATGAAAGATAATTGGCGCTCCGAGCTGTACAAGTATAAAGTGGTCAAGATCGAA
CCACTGGGAGTGGCACCTACCCGATGTAAACGGAGAGTGGTCGGAAGGCGCCGACGGAGAAGGGCAGTGGGAATC
GGAGCCGTCTTCCTGGGCTTTCTGGGAGCAGCTGGCAGCACAATGGGAGCAGCCTCTATGACCCTGACAGTGCAGGC
TCGAAATCTGCTGAGTGGGATCGTGCAGCAGCAGTCAAACCTGCTGCGAGCACCAGAGGCACAGCAGCATCTGCTGA
AGCTGACCGTGTGGGGCATCAAGCAGCTGCAGGCCAGAGTGCTGGCTGTCGAACGGTACCTGAGAGATCAGCAGCT
GCTGGGAATCTGGGGATGCAGCGGAAAGCTGATTTGCTGTACAAACGTGCCCTGGAATAGTTCATGGTCAAACAGG
AATCTGAGCGAGATCTGGGACAATATGACCTGGCTGCAGTGGGATAAGGAAATCAGTAACTACACACAGATCATCTA
TGGCCTGCTGGAGGAATCACAGAACCAGCAGGAGAAAAATGAACAGGACCTGCTGGCCCTGGATTGATGA

Figure 5B

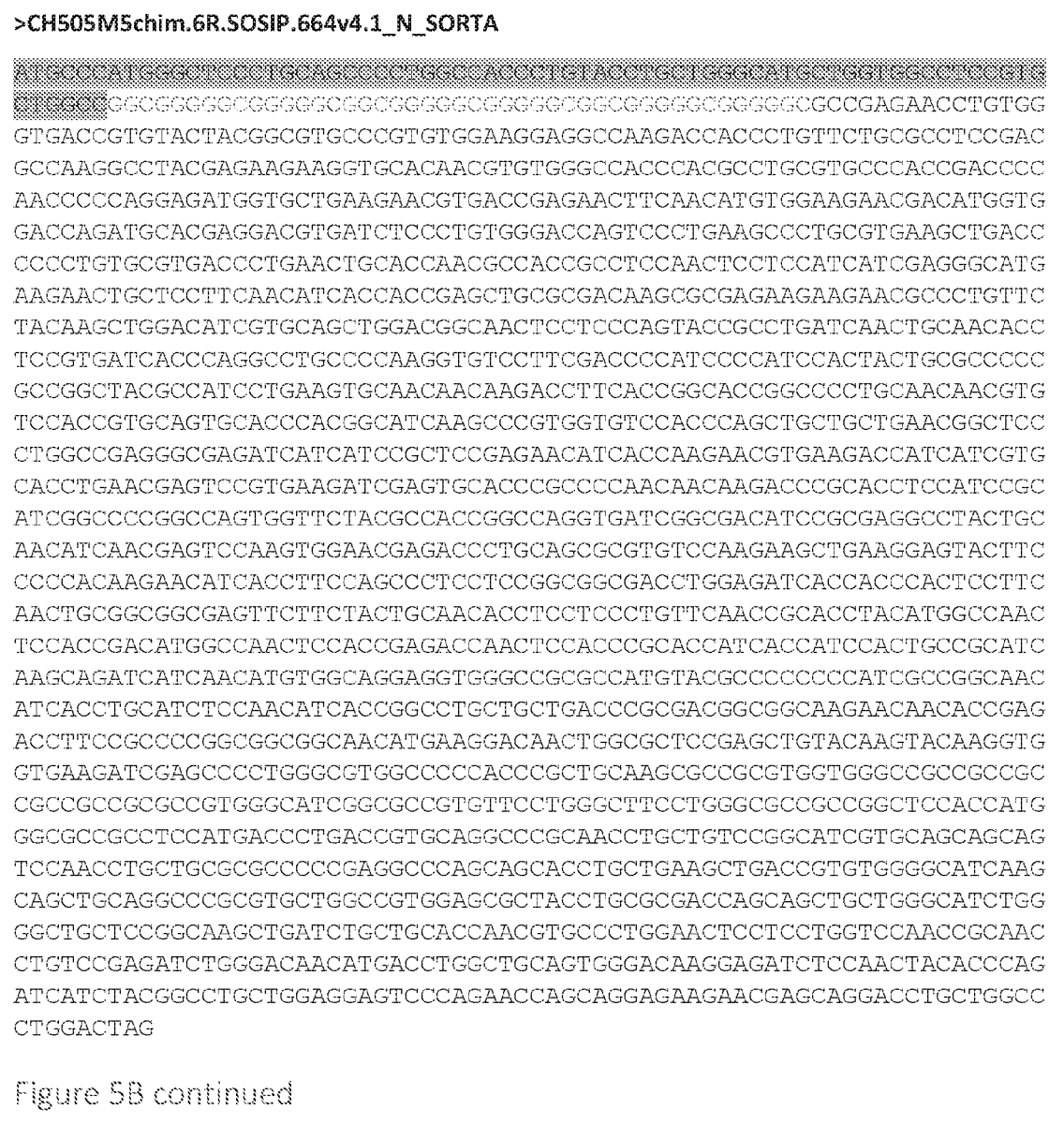

>CH505M5chim.6R.SOSIP.664v4.1_N_SORTA

ATGGCCATGGGCTCCCTGCAGCCCCTGGCCACCTTGTACCTGCTGGGCATGCTGGTCGCCTCCGTG
CTGGCGGGGGGCGGGGGCGGCGGGGGCGGGGGCGGCGGGGGCGGGGGCGCCGAGAACCTGTGG
GTGACCGTGTACTACGGCGTGCCCGTGTGGAAGGAGGCCAAGACCACCCTGTTCTGCGCCTCCGAC
GCCAAGGCCTACGAGAAGAAGGTGCACAACGTGTGGGCCACCCACGCCTGCGTGCCCACCGACCCC
AACCCCCAGGAGATGGTGCTGAAGAACGTGACCGAGAACTTCAACATGTGGAAGAACGACATGGTG
GACCAGATGCACGAGGACGTGATCTCCCTGTGGGACCAGTCCCTGAAGCCCTGCGTGAAGCTGACC
CCCCTGTGCGTGACCCTGAACTGCACCAACGCCACCGCCTCCAACTCCTCCATCATCGAGGGCATG
AAGAACTGCTCCTTCAACATCACCACCGAGCTGCGCGACAAGCGCGAGAAGAAGAACGCCCTGTTC
TACAAGCTGGACATCGTGCAGCTGGACGGCAACTCCTCCCAGTACCGCCTGATCAACTGCAACACC
TCCGTGATCACCCAGGCCTGCCCCAAGGTGTCCTTCGACCCCATCCCCATCCACTACTGCGCCCCC
GCCGGCTACGCCATCCTGAAGTGCAACAACAAGACCTTCACCGGCACCGGCCCCTGCAACAACGTG
TCCACCGTGCAGTGCACCCACGGCATCAAGCCCGTGGTGTCCACCCAGCTGCTGCTGAACGGCTCC
CTGGCCGAGGGCGAGATCATCATCCGCTCCGAGAACATCACCAAGAACGTGAAGACCATCATCGTG
CACCTGAACGAGTCCGTGAAGATCGAGTGCACCCGCCCCAACAACAAGACCCGCACCTCCATCCGC
ATCGGCCCCGGCCAGTGGTTCTACGCCACCGGCCAGGTGATCGGCGACATCCGCGAGGCCTACTGC
AACATCAACGAGTCCAAGTGGAACGAGACCCTGCAGCGCGTGTCCAAGAAGCTGAAGGAGTACTTC
CCCCACAAGAACATCACCTTCCAGCCCTCCTCCGGCGGCGACCTGGAGATCACCACCCACTCCTTC
AACTGCGGCGGCGAGTTCTTCTACTGCAACACCTCCTCCCTGTTCAACCGCACCTACATGGCCAAC
TCCACCGACATGGCCAACTCCACCGAGACCAACTCCACCCGCACCATCACCATCCACTGCCGCATC
AAGCAGATCATCAACATGTGGCAGGAGGTGGGCCGCGCCATGTACGCCCCCCCCATCGCCGGCAAC
ATCACCTGCATCTCCAACATCACCGGCCTGCTGCTGACCCGCGACGGCGGCAAGAACAACACCGAG
ACCTTCCGCCCCGGCGGCGGCAACATGAAGGACAACTGGCGCTCCGAGCTGTACAAGTACAAGGTG
GTGAAGATCGAGCCCCTGGGCGTGGCCCCCACCCGCTGCAAGCGCCGCGTGGTGGGCCGCCGCCGC
CGCCGCCGCGCCGTGGGCATCGGCGCCGTGTTCCTGGGCTTCCTGGGCGCCGCCGGCTCCACCATG
GGCGCCGCCTCCATGACCCTGACCGTGCAGGCCCGCAACCTGCTGTCCGGCATCGTGCAGCAGCAG
TCCAACCTGCTGCGCGCCCCCGAGGCCCAGCAGCACCTGCTGAAGCTGACCGTGTGGGGCATCAAG
CAGCTGCAGGCCCGCGTGCTGGCCGTGGAGCGCTACCTGCGCGACCAGCAGCTGCTGGGCATCTGG
GGCTGCTCCGGCAAGCTGATCTGCTGCACCAACGTGCCCTGGAACTCCTCCTGGTCCAACCGCAAC
CTGTCCGAGATCTGGGACAACATGACCTGGCTGCAGTGGGACAAGGAGATCTCCAACTACACCCAG
ATCATCTACGGCCTGCTGGAGGAGTCCCAGAACCAGCAGGAGAAGAACGAGCAGGACCTGCTGGCC
CTGGACTAG

Figure 5B continued

>CH505M5chim.6R.SOSIP.664v4.1_N_SORTA

MRVKGSLQPLATLYLLGMLVASVLAGGGGGGGGGGGGGGGGAENLWVTVYYGVPVWKEAKTTLFCASD
AKAYEKKVHNVWATHACVPTDPNPQEMVLKNVTENFNMWKNDMVDQMHEDVISLWDQSLKPCVKLT
PLCVTLNCTNATASNSSIIEGMKNCSFNITTELRDKREKKNALFYKLDIVQLDGNSSQYRLINCNT
SVITQACPKVSFDPIPIHYCAPAGYAILKCNNKTFTGTGPCNNVSTVQCTHGIKPVVSTQLLLNGS
LAEGEIIIRSENITKNVKTIIVHLNESVKIECTRPNNKTRTSIRIGPGQWFYATGQVIGDIREAYC
NINESKWNETLQRVSKKLKEYFPHKNITFQPSSGGDLEITTHSFNCGGEFFYCNTSSLFNRTYMAN
STDMANSTETNSTRTITIHCRIKQIINMWQEVGRAMYAPPIAGNITCISNITGLLLTRDGGKNNTE
TFRPGGGNMKDNWRSELYKYKVVKIEPLGVAPTRCKRRVVGRRRRRRAVGIGAVFLGFLGAAGSTM
GAASMTLTVQARNLLSGIVQQQSNLLRAPEAQQHLLKLTVWGIKQLQARVLAVERYLRDQQLLGIW
GCSGKLICCTNVPWNSSWSNRNLSEIWDNMTWLQWDKEISNYTQIIYGLLEESQNQQEKNEQDLLA
LD*

>CH505M5chim.6R.SOSIP.664v4.1_C_SORTA

ATGCGCGTGAAGGGCTCCCTGCAGCCCCTGGCCACCCTGTACCTGCTGGGCATGCTGGTGGCCTCCGTG
CTGGCCGAGAACCTGTGGGTGACCGTGTACTACGGCGTGCCCGTGTGGAAGGAGGCCAAGACC
ACCCTGTTCTGCGCCTCCGACGCCAAGGCCTACGAGAAGAAGGTGCACAACGTGTGGGCCACCCAC
GCCTGCGTGCCCACCGACCCCAACCCCCAGGAGATGGTGCTGAAGAACGTGACCGAGAACTTCAAC
ATGTGGAAGAACGACATGGTGGACCAGATGCACGAGGACGTGATCTCCCTGTGGGACCAGTCCCTG
AAGCCCTGCGTGAAGCTGACCCCCCTGTGCGTGACCCTGAACTGCACCAACGCCACCGCCTCCAAC
TCCTCCATCATCGAGGGCATGAAGAACTGCTCCTTCAACATCACCACCGAGCTGCGCGACAAGCGC
GAGAAGAAGAACGCCCTGTTCTACAAGCTGGACATCGTGCAGCTGGACGGCAACTCCTCCCAGTAC
CGCCTGATCAACTGCAACACCTCCGTGATCACCCAGGCCTGCCCCAAGGTGTCCTTCGACCCCATC
CCCATCCACTACTGCGCCCCCGCCGGCTACGCCATCCTGAAGTGCAACAACAAGACCTTCACCGGC
ACCGGCCCCTGCAACAACGTGTCCACCGTGCAGTGCACCCACGGCATCAAGCCCGTGGTGTCCACC
CAGCTGCTGCTGAACGGCTCCCTGGCCGAGGGCGAGATCATCATCCGCTCCGAGAACATCACCAAG
AACGTGAAGACCATCATCGTGCACCTGAACGAGTCCGTGAAGATCGAGTGCACCCGCCCCAACAAC
AAGACCCGCACCTCCATCCGCATCGGCCCCGGCCAGTGGTTCTACGCCACCGGCCAGGTGATCGGC
GACATCCGCGAGGCCTACTGCAACATCAACGAGTCCAAGTGGAACGAGACCCTGCAGCGCGTGTCC
AAGAAGCTGAAGGAGTACTTCCCCCACAAGAACATCACCTTCCAGCCCTCCTCCGGCGGCGACCTG
GAGATCACCACCCACTCCTTCAACTGCGGCGGCGAGTTCTTCTACTGCAACACCTCCTCCCTGTTC
AACCGCACCTACATGGCCAACTCCACCGACATGGCCAACTCCACCGAGACCAACTCCACCCGCACC
ATCACCATCCACTGCCGCATCAAGCAGATCATCAACATGTGGCAGGAGGTGGGCCGCGCCATGTAC
GCCCCCCCCATCGCCGGCAACATCACCTGCATCTCCAACATCACCGGCCTGCTGCTGACCCGCGAC
GGCGGCAAGAACAACACCGAGACCTTCCGCCCCGGCGGCGGCAACATGAAGGACAACTGGCGCTCC
GAGCTGTACAAGTACAAGGTGGTGAAGATCGAGCCCCTGGGCGTGGCCCCCACCCGCTGCAAGCGC
CGCGTGGTGGGCCGCCGCCGCCGCCGCCGCCGTGGGCATCGGCGCCGTGTTCCTGGGCTTCCTG
GGCGCCGCCGGCTCCACCATGGGCGCCGCCTCCATGACCCTGACCGTGCAGGCCCGCAACCTGCTG
TCCGGCATCGTGCAGCAGCAGTCCAACCTGCTGCGCGCCCCCGAGGCCCAGCAGCACCTGCTGAAG
CTGACCGTGTGGGGCATCAAGCAGCTGCAGGCCCGCGTGCTGGCCGTGGAGCGCTACCTGCGCGAC
CAGCAGCTGCTGGGCATCTGGGGCTGCTCCGGCAAGCTGATCTGCTGCACCAACGTGCCCTGGAAC
TCCTCCTGGTCCAACCGCAACCTGTCCGAGATCTGGGACAACATGACCTGGCTGCAGTGGGACAAG
GAGATCTCCAACTACACCCAGATCATCTACGGCCTGCTGGAGGAGTCCCAGAACCAGCAGGAGAAG
AACGAGCAGGACCTGCTGGCCCTGGACCTGCCTAGCACCGGATAG

Figure 5B continued

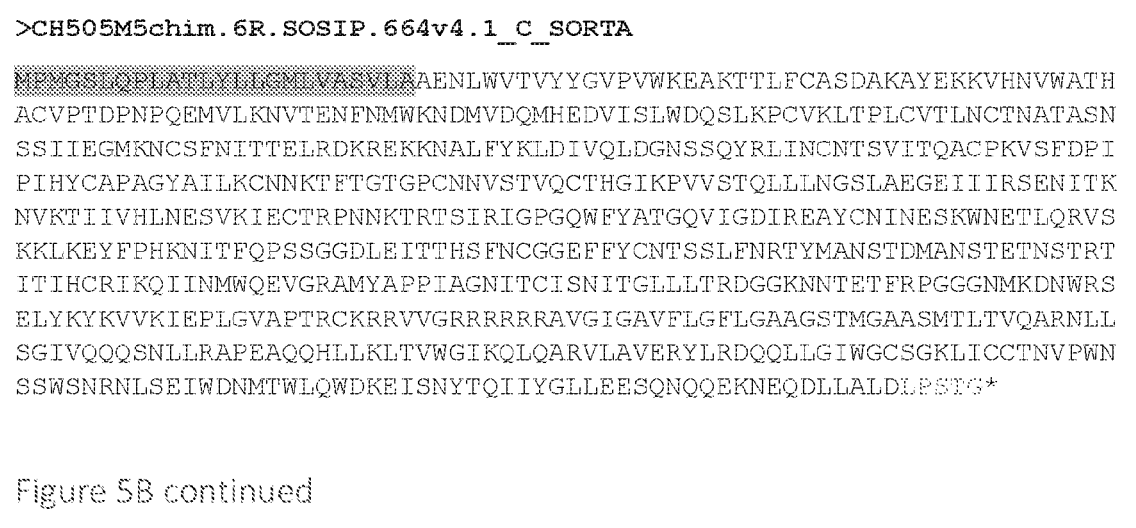

>CH505M5chim.6R.SOSIP.664v4.1_C_SORTA

MRVKGSXQPIAXXVIXGMXVASVIRAENLWVTVYYGVPVWKEAKTTLFCASDAKAYEKKVHNVWATH
ACVPTDPNPQEMVLKNVTENFNMWKNDMVDQMHEDVISLWDQSLKPCVKLTPLCVTLNCTNATASN
SSIIEGMKNCSFNITTELRDKREKKNALFYKLDIVQLDGNSSQYRLINCNTSVITQACPKVSFDPI
PIHYCAPAGYAILKCNNKTFTGTGPCNNVSTVQCTHGIKPVVSTQLLLNGSLAEGEIIIRSENITK
NVKTIIVHLNESVKIECTRPNNKTRTSIRIGPGQWFYATGQVIGDIREAYCNINESKWNETLQRVS
KKLKEYFPHKNITFQPSSGGDLEITTHSFNCGGEFFYCNTSSLFNRTYMANSTDMANSTETNSTRT
ITIHCRIKQIINMWQEVGRAMYAPPIAGNITCISNITGLLLTRDGGKNNTETFRPGGGNMKDNWRS
ELYKYKVVKIEPLGVAPTRCKRRVVGRRRRRRAVGIGAVFLGFLGAAGSTMGAASMTLTVQARNLL
SGIVQQQSNLLRAPEAQQHLLKLTVWGIKQLQARVLAVERYLRDQQLLGIWGCSGKLICCTNVPWN
SSWSNRNLSEIWDNMTWLQWDKEISNYTQIIYGLLEESQNQQEKNEQDLLALDLPSTG*

Figure 5B continued

N-terminal modification of SOSIP trimer

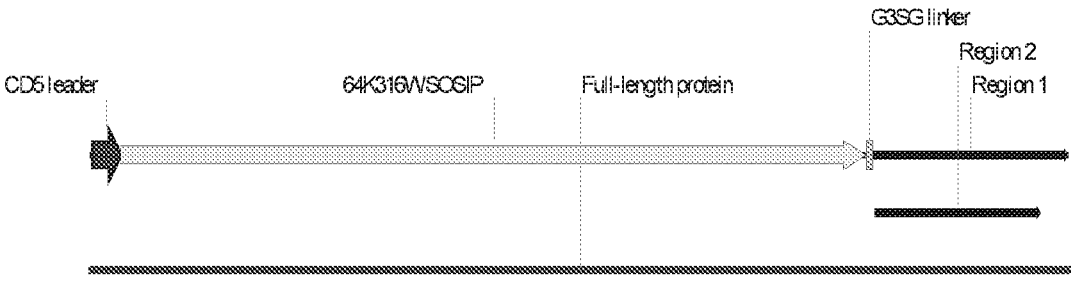

CH505TFchimv4.1-ferritin 815 aa

>CH505TFchimv4.1-ferritin (signal peptide; ferritin, glycine linker)

```
MPMGSLQPLA TLYLLGMLVA SVLAAENLWV TVYYGVPVWK EAKTTLFCAS
DAKAYEKKVH NVWATHACVP TDPNPQEMVL KNVTENFNMW KNDMVDQMHE
DVISLWDQSL KPCVKLTPLC VTLNCTNATA SNSSIIEGMK NCSFNITTEL
RDKREKKNAL FYKLDIVQLD GNSSQYRLIN CNTSVITQAC PKVSFDPIPI
HYCAPAGYAI LKCNNKTFTG TGPCNNVSTV QCTHGIKPVV STQLLLNGSL
AEGEIIIRSE NITNNVKTII VHLNESVKIE CTRPNNKTRT SIRIGPGQWF
YATGQVIGDI REAYCNINES KWNETLQRVS KKLKEYFPHK NITFQPSSGG
DLEITTHSFN CGGEFFYCNT SSLFNRTYMA NSTDMANSTE TNSTRTITIH
CRIKQIINMW QEVGRAMYAP PIAGNITCIS NITGLLLTRD GGKNNTETFR
PGGGNMKDNW RSELYKYKVV KIEPLGVAPT RCKRRVVGRR RRRRAVGIGA
VFLGFLGAAG STMGAASMTL TVQARNLLSG IVQQQSNLLR APEAQQHLLK
LTVWGIKQLQ ARVLAVERYL RDQQLLGIWG CSGKLICCTN VPWNSSWSNR
NLSEIWDNMT WLQWDKEISN YTQIIYGLLE ESQNQQEKNE QDLLALDGGG
SGDIIKLLNE QVNKEMNSSN LYMSMSSWCY THSLDGAGLF LFDHAAEEYE
HAKKLIIFLN ENNVPVQLTS ISAPEHKFEG LTQIFQKAYE HEQHISESIN
NIVDHAIKSK DHATFNFLQW YVAEQHEEEV LFKDILDKIE LIGNENHGLY
LADQYVKGIA KSRKS**
```

>CH505TFchimv4.1-ferritin(HV1301350)

```
ATGCCCATGGGCTCCCTGCAGCCCCTGGCCACCCTGTACCTGCTGGGCATGCTGGTGGCCTC
CGTGCTGGCCGCCGAGAACCTGTGGGTGACCGTGTACTACGGCGTGCCCGTGTGGAAGGAGG
CCAAGACCACCCTGTTCTGCGCCTCCGACGCCAAGGCCTACGAGAAGAAGGTGCACAACGTG
TGGGCCACCCACGCCTGCGTGCCCACCGACCCCAACCCCCAGGAGATGGTGCTGAAGAACGT
GACCGAGAACTTCAACATGTGGAAGAACGACATGGTGGACCAGATGCACGAGGACGTGATCT
CCCTGTGGGACCAGTCCCTGAAGCCCTGCGTGAAGCTGACCCCCCTGTGCGTGACCCTGAAC
TGCACCAACGCC
```

Figure 5E

ACCGCCTCCAACTCCTCCATCATCGAGGGCATGAAGAACTGCTCCTTCAACATCACCACCGA
GCTGCGCGACAAGCGCGAGAAGAAGAACGCCCTGTTCTACAAGCTGGACATCGTGCAGCTGG
ACGGCAACTCCTCCCAGTACCGCCTGATCAACTGCAACACCTCCGTGATCACCCAGGCCTGC
CCCAAGGTGTCCTTCGACCCCATCCCCATCCACTACTGCGCCCCCGCCGGCTACGCCATCCT
GAAGTGCAACAACAAGACCTTCACCGGCACCGGCCCCTGCAACAACGTGTCCACCGTGCAGT
GCACCCACGGCATCAAGCCCGTGGTGTCCACCCAGCTGCTGCTGAACGGCTCCCTGGCCGAG
GGCGAGATCATCATCCGCTCCGAGAACATCACCAACAACGTGAAGACCATCATCGTGCACCT
GAACGAGTCCGTGAAGATCGAGTGCACCCGCCCCAACAACAAGACCCGCACCTCCATCCGCA
TCGGCCCCGGCCAGTGGTTCTACGCCACCGGCCAGGTGATCGGCGACATCCGCGAGGCCTAC
TGCAACATCAACGAGTCCAAGTGGAACGAGACCCTGCAGCGCGTGTCCAAGAAGCTGAAGGA
GTACTTCCCCCACAAGAACATCACCTTCCAGCCCTCCTCCGGCGGCGACCTGGAGATCACCA
CCCACTCCTTCAACTGCGGCGGCGAGTTCTTCTACTGCAACACCTCCTCCCTGTTCAACCGC
ACCTACATGGCCAACTCCACCGACATGGCCAACTCCACCGAGACCAACTCCACCCGCACCAT
CACCATCCACTGCCGCATCAAGCAGATCATCAACATGTGGCAGGAGGTGGGCCGCGCCATGT
ACGCCCCCCCCATCGCCGGCAACATCACCTGCATCTCCAACATCACCGGCCTGCTGCTGACC
CGCGACGGCGGCAAGAACAACACCGAGACCTTCCGCCCCGGCGGCGGCAACATGAAGGACAA
CTGGCGCTCCGAGCTGTACAAGTACAAGGTGGTGAAGATCGAGCCCCTGGGCGTGGCCCCCA
CCCGCTGCAAGCGCCGCGTGGTGGGCCGCCGCCGCCGCCGCGCCGTGGGCATCGGCGCC
GTGTTCCTGGGCTTCCTGGGCGCCGCCGGCTCCACCATGGGCGCCGCCTCCATGACCCTGAC
CGTGCAGGCCCGCAACCTGCTGTCCGGCATCGTGCAGCAGCAGTCCAACCTGCTGCGCGCCC
CCGAGGCCCAGCAGCACCTGCTGAAGCTGACCGTGTGGGGCATCAAGCAGCTGCAGGCCCGC
GTGCTGGCCGTGGAGCGCTACCTGCGCGACCAGCAGCTGCTGGGCATCTGGGGCTGCTCCGG
CAAGCTGATCTGCTGCACCAACGTGCCCTGGAACTCCTCCTGGTCCAACCGCAACCTGTCCG
AGATCTGGGACAACATGACCTGGCTGCAGTGGGACAAGGAGATCTCCAACTACACCCAGATC
ATCTACGGCCTGCTGGAGGAGTCCCAGAACCAGCAGGAGAAGAACGAGCAGGACCTGCTGGC
CCTGGACGGCGGCGGCTCCGGCGACATCATCAAGCTGCTGAACGAGCAGGTGAACAAGGAGA
TGAACTCCTCCAACCTGTACATGTCCATGTCCTCCTGGTGCTACACCCACTCCCTGGACGGC
GCCGGCCTGTTCCTGTTCGACCACGCCGCCGAGGAGTACGAGCACGCCAAGAAGCTGATCAT
CTTCCTGAACGAGAACAACGTGCCCGTGCAGCTGACCTCCATCTCCGCCCCCGAGCACAAGT
TCGAGGGCCTGACCCAGATCTTCCAGAAGGCCTACGAGCACGAGCAGCACATCTCCGAGTCC
ATCAACAACATCGTGGACCACGCCATCAAGTCCAAGGACCACGCCACCTTCAACTTCCTGCA
GTGGTACGTGGCCGAGCAGCACGAGGAGGAGGTGCTGTTCAAGGACATCCTGGACAAGATCG
AGCTGATCGGCAACGAGAACCACGGCCTGTACCTGGCCGACCAGTACGTGAAGGGCATCGCC
AAGTCCCGCAAGTCCTGATAA

>CH505M5chimv4.1-ferritin (signal peptide; ferritin, glycine linker)

MPMGSLQPLATLTLLGMLVASVLAAENLWVTVYYGVPVWKEAKTTLFCASDAKAYEKKVH
NVWATHACVPTDPNPQEMVLKNVTENFNMWKNDMVDQMHEDVISLWDQSLKPCVKLTPLC
VTLNCTNATASNSSIIEGMKNCSFNITTELRDKREKKNALFYKLDIVQLDGNSSQYRLIN
CNTSVITQACPKVSFDPIPIHYCAPAGYAILKCNNKTFTGTGPCNNVSTVQCTHGIKPVV

Figure 5E continued

STQLLLNGSLAEGEIIIRSENITKNVKTIIVHLNESVKIECTRPNNKTRTSIRIGPGQWF
YATGQVIGDIREAYCNINESKWNETLQRVSKKLKEYFPHKNITFQPSSGGDLEITTHSFN
CGGEFFYCNTSSLFNRTYMANSTDMANSTETNSTRTITIHCRIKQIINMWQEVGRAMYAP
PIAGNITCISNITGLLLTRDGGKNNTETFRPGGGNMKDNWRSELYKYKVVKIEPLGVAPT
RCKRRVVGRRRRRRAVGIGAVFLGFLGAAGSTMGAASMTLTVQARNLLSGIVQQQSNLLR
APEAQQHLLKLTVWGIKQLQARVLAVERYLRDQQLLGIWGCSGKLICCTNVPWNSSWSNR
NLSEIWDNMTWLQWDKEISNYTQIIYGLLEESQNQQEKNEQDLLALDꞰWꞰGSGDIIKLLNE
QVNKEMNSSNLYMSMSSWCYTHSLDGAGLFLFDHAAEEYEHAKKLIIFLNENNVPVQLTS
ISAPEHKFEGLTQIFQKAYEHEQHISESINNIVDHAIKSKDHATFNFLQWYVAEQHEEEV
LFKDILDKIELIGNENHGLYLADQYVKGIAKSRKS**

>CH505M5chimv4.1-ferritin(HV1301349)

ATGGCCATGGGACTGCCTGCAGCCACCTGGCCCACCCTGTACCTGCTGGGCATGCTGGTGGCCCCGCTGCTGCTGCCGCCGAGAACCTGTGGGTGACCGTGTACTACGGCGTGCCCGTGTGGAAGGAGG
CCAAGACCACCCTGTTCTGCGCCTCCGACGCCAAGGCCTACGAGAAGAAGGTGCACAACGTG
TGGGCCACCCACGCCTGCGTGCCCACCGACCCCAACCCCCAGGAGATGGTGCTGAAGAACGT
GACCGAGAACTTCAACATGTGGAAGAACGACATGGTGGACCAGATGCACGAGGACGTGATCT
CCCTGTGGGACCAGTCCCTGAAGCCCTGCGTGAAGCTGACCCCCCTGTGCGTGACCCTGAAC
TGCACCAACGCCACCGCCTCCAACTCCTCCATCATCGAGGGCATGAAGAACTGCTCCTTCAA
CATCACCACCGAGCTGCGCGACAAGCGCGAGAAGAAGAACGCCCTGTTCTACAAGCTGGACA
TCGTGCAGCTGGACGGCAACTCCTCCCAGTACCGCCTGATCAACTGCAACACCTCCGTGATC
ACCCAGGCCTGCCCCAAGGTGTCCTTCGACCCCATCCCCATCCACTACTGCGCCCCCGCCGG
CTACGCCATCCTGAAGTGCAACAACAAGACCTTCACCGGCACCGGCCCCTGCAACAACGTGT
CCACCGTGCAGTGCACCCACGGCATCAAGCCCGTGGTGTCCACCCAGCTGCTGCTGAACGGC
TCCCTGGCCGAGGGCGAGATCATCATCCGCTCCGAGAACATCACCAAGAACGTGAAGACCAT
CATCGTGCACCTGAACGAGTCCGTGAAGATCGAGTGCACCCGCCCCAACAACAAGACCCGCA
CCTCCATCCGCATCGGCCCCGGCCAGTGGTTCTACGCCACCGGCCAGGTGATCGGCGACATC
CGCGAGGCCTACTGCAACATCAACGAGTCCAAGTGGAACGAGACCCTGCAGCGCGTGTCCAA
GAAGCTGAAGGAGTACTTCCCCCACAAGAACATCACCTTCCAGCCCTCCTCCGGCGGCGACC
TGGAGATCACCACCCACTCCTTCAACTGCGGCGGCGAGTTCTTCTACTGCAACACCTCCTCC
CTGTTCAACCGCACCTACATGGCCAACTCCACCGACATGGCCAACTCCACCGAGACCAACTC
CACCCGCACCATCACCATCCACTGCCGCATCAAGCAGATCATCAACATGTGGCAGGAGGTGG
GCCGCGCCATGTACGCCCCCCCCATCGCCGGCAACATCACCTGCATCTCCAACATCACCGGC
CTGCTGCTGACCCGCGACGGCGGCAAGAACAACACCGAGACCTTCCGCCCCGGCGGCGGCAA
CATGAAGGACAACTGGCGCTCCGAGCTGTACAAGTACAAGGTGGTGAAGATCGAGCCCCTGG
GCGTGGCCCCCACCCGCTGCAAGCGCCGCGTGGTGGGCCGCCGCCGCCGCCGCGCCGTG
GGCATCGGCGCCGTGTTCCTGGGCTTCCTGGGCGCCGCCGGCTCCACCATGGGCGCCGCCTC
CATGACCCTGACCGTGCAGGCCCGCAACCTGCTGTCCGGCATCGTGCAGCAGCAGTCCAACC
TGCTGCGCGCCCCCGAGGCCCAGCAGCACCTGCTGAAGCTGACCGTGTGGGG

Figure 5E continued

CATCAAGCAGCTGCAGGCCCGCGTGCTGGCCGTGGAGCGCTACCTGCGCGACCAGCAGCTGC
TGGGCATCTGGGGCTGCTCCGGCAAGCTGATCTGCTGCACCAACGTGCCCTGGAACTCCTCC
TGGTCCAACCGCAACCTGTCCGAGATCTGGGACAACATGACCTGGCTGCAGTGGGACAAGGA
GATCTCCAACTACACCCAGATCATCTACGGCCTGCTGGAGGAGTCCCAGAACCAGCAGGAGA
AGAACGAGCAGGACCTGCTGGCCCTGGACGGCGGCGGCTCCGGCGACATCATCAAGCTGCTG
AACGAGCAGGTGAACAAGGAGATGAACTCCTCCAACCTGTACATGTCCATGTCCTCCTGGTG
CTACACCCACTCCCTGGACGGCGCCGGCCTGTTCCTGTTCGACCACGCCGCCGAGGAGTACG
AGCACGCCAAGAAGCTGATCATCTTCCTGAACGAGAACAACGTGCCCGTGCAGCTGACCTCC
ATCTCCGCCCCCGAGCACAAGTTCGAGGGCCTGACCCAGATCTTCCAGAAGGCCTACGAGCA
CGAGCAGCACATCTCCGAGTCCATCAACAACATCGTGGACCACGCCATCAAGTCCAAGGACC
ACGCCACCTTCAACTTCCTGCAGTGGTACGTGGCCGAGCAGCACGAGGAGGAGGTGCTGTTC
AAGGACATCCTGGACAAGATCGAGCTGATCGGCAACGAGAACCACGGCCTGTACCTGGCCGA
CCAGTACGTGAAGGGCATCGCCAAGTCCCGCAAGTCCTAGTAA

*Figure 5E continued*

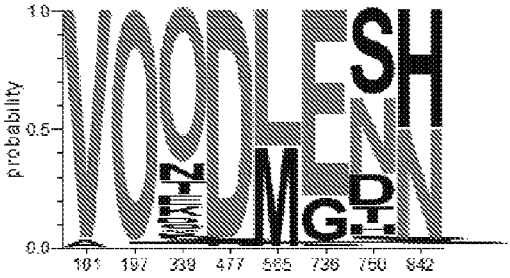
CAP256 IA4 Signatures
CH505 TF / Mature OPT    V O O D M E S N
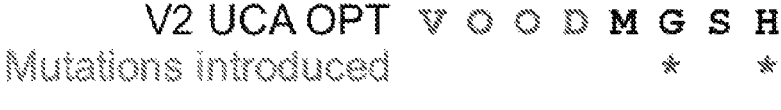
V2 UCA OPT    V O O D M G S H
Mutations introduced    *    *
Sensitivity signature    Resistance signature
Figure 6

|  | HYP V1: | HYP V2: |
|---|---|---|
| CH505.TF | TNATASNSSIIE | DGNSSQ |
| ZM233.6 | STYNNTHNISK | TNSSNTIN |
| T250-4 | QAFNSSSHTNSSIAMQ | NKNGRQ |
| Designed constructs | STYNNTHNISK | NKNGRQ |

Figure 8A

PG9
PGDM1400
PGT145
VRC26.25

Figure 11E

| Ab | WT | SET OPT | UCA OPT |
|---|---|---|---|
| CAP256.25 | 1.36 | 0.002 | 0.002 |
| CH01 | 9.25 | 7.82 | 0.480 |
| PG9 | 1.15 | 0.009 | 0.004 |
| PG16 | 0.369 | 0.037 | 0.007 |
| PCT64-35S | 8.06 | 0.086 | 0.030 |
|  |  |  |  |
| VRC26.25 UCA | >250 | >50 | >250 |
| CH01 RUA3 | >50 | 3.19 | 0.170 |
| PG9 RUA | >50 | >50 | >50 |
| PG16 RUA | >50 | >50 | >50 |
| PCT64 LMCA | >250 | >50 | 105 |

Figure 12

V2.UCA.OPT1.N332.gp41mut_ch.SOSIP.v4.1

VRC26.25

--◆-- CH505 TF          --◆-- CH505 V2 SET          --◆-- CH505 UCA OPT 1

--◇-- CH505 V2 SET + N332--◇-- CH505 UCA OPT 1 + N332

CH01

PG9

PG16

PCT64-35S

PGT121

VRC26 UCA

CH505 TF

CH505 V2 SET          CH505 UCA OPT 1

CH505 V2 SET + N332    CH505 UCA OPT 1 + N332    CH505 UCA OPT 2 + N332

CH01 RUA3

SEQUENCE LISTING

<160> NUMBER OF SEQ ID NOS: 61

<210> SEQ ID NO 1
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Asp Ala Thr
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Glu Lys Arg
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Val Val Glu Arg Glu Lys Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Arg Val Val Glu Arg Glu Lys Glu
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Glu Lys Ser
1

<210> SEQ ID NO 6
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Arg Val Met Gly Ile Gln Arg Asn Tyr Pro Gln Trp Trp Ile Trp
```

-continued

```
1               5                   10                  15

Ser Met Leu Gly Phe Trp Met Leu Met Ile Cys Asn Gly Met Trp Val
                20                  25                  30

Thr Val Tyr Tyr Gly Val Pro Val Trp Lys Glu Ala Lys Thr Thr Leu
            35                  40                  45

Phe Cys Ala Ser Asp Ala Lys Ala Tyr Glu Lys Glu Val His Asn Val
        50                  55                  60

Trp Ala Thr His Ala Cys Val Pro Thr Asp Pro Asn Pro Gln Glu
65                  70                  75
```

```
<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Pro Met Gly Ser Leu Gln Pro Leu Ala Thr Leu Tyr Leu Leu Gly
1               5                   10                  15

Met Leu Val Ala Ser Val Leu Ala
            20
```

```
<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 8

Leu Pro Xaa Thr Gly
1               5
```

```
<210> SEQ ID NO 9
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
                20                  25                  30

Thr Val Tyr Tyr Gly Val Pro Val Trp Lys Glu Ala Lys Thr Thr Leu
            35                  40                  45

Phe Cys Ala Ser Asp Ala Lys Ala Tyr Glu Lys Glu Val His Asn Val
        50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
```

```
                    100                 105                 110
Lys Pro Cys Val Lys Leu Thr Pro Leu Cys Val Thr Leu Asn Cys Thr
                115                 120                 125

Asn Ala Thr Ala Ser Asn Ser Ser Ile Ile Glu Gly Met Lys Asn Cys
        130                 135                 140

Ser Phe Asn Ile Thr Thr Glu Leu Arg Asp Lys Arg Glu Lys Lys Asn
145                 150                 155                 160

Ala Leu Phe Tyr Lys Leu Asp Ile Val Gln Leu Asp Gly Asn Ser Ser
                165                 170                 175

Gln Tyr Arg Leu Ile Asn Cys Asn Thr Ser Val Ile Thr Gln Ala Cys
                180                 185                 190

Pro Lys Val Ser Phe Asp Pro Ile Pro Ile His Tyr Cys Ala Pro Ala
                195                 200                 205

Gly Tyr Ala Ile Leu Lys Cys Asn Asn Lys Thr Phe Thr Gly Thr Gly
        210                 215                 220

Pro Cys Asn Asn Val Ser Thr Val Gln Cys Thr His Gly Ile Lys Pro
225                 230                 235                 240

Val Val Ser Thr Gln Leu Leu Leu Asn Gly Ser Leu Ala Glu Gly Glu
                245                 250                 255

Ile Ile Ile Arg Ser Glu Asn Ile Thr Asn Asn Val Lys Thr Ile Ile
                260                 265                 270

Val His Leu Asn Glu Ser Val Lys Ile Glu Cys Thr Arg Pro Asn Asn
        275                 280                 285

Lys Thr Arg Thr Ser Ile Arg Ile Gly Pro Gly Gln Ala Phe Tyr Ala
        290                 295                 300

Thr Gly Gln Val Ile Gly Asp Ile Arg Glu Ala Tyr Cys Asn Ile Asn
305                 310                 315                 320

Glu Ser Lys Trp Asn Glu Thr Leu Gln Arg Val Ser Lys Lys Leu Lys
                325                 330                 335

Glu Tyr Phe Pro His Lys Asn Ile Thr Phe Gln Pro Ser Ser Gly Gly
                340                 345                 350

Asp Leu Glu Ile Thr Thr His Ser Phe Asn Cys Gly Gly Glu Phe Phe
        355                 360                 365

Tyr Cys Asn Thr Ser Ser Leu Phe Asn Arg Thr Tyr Met Ala Asn Ser
        370                 375                 380

Thr Asp Met Ala Asn Ser Thr Glu Thr Asn Ser Thr Arg Thr Ile Thr
385                 390                 395                 400

Ile His Cys Arg Ile Lys Gln Ile Ile Asn Met Trp Gln Glu Val Gly
                405                 410                 415

Arg Ala Met Tyr Ala Pro Pro Ile Ala Gly Asn Ile Thr Cys Ile Ser
                420                 425                 430

Asn Ile Thr Gly Leu Leu Leu Thr Arg Asp Gly Gly Lys Asn Asn Thr
                435                 440                 445

Glu Thr Phe Arg Pro Gly Gly Gly Asn Met Lys Asp Asn Trp Arg Ser
        450                 455                 460

Glu Leu Tyr Lys Tyr Lys Val Val Glu Val Lys Pro Leu Gly Val Ala
465                 470                 475                 480

Pro Thr Asn Ala Arg Arg Arg Val Val Glu Arg Glu Lys Arg Ala Val
                485                 490                 495

Gly Met Gly Ala Val Phe Leu Gly Phe Leu Gly Ala Ala Gly Ser Thr
                500                 505                 510

Met Gly Ala Ala Ser Ile Thr Leu Thr Val Gln Ala Arg Gln Leu Leu
                515                 520                 525
```

-continued

```
Ser Gly Ile Val Gln Gln Gln Ser Asn Leu Leu Lys Ala Ile Glu Ala
    530                 535                 540

Gln Gln His Met Leu Lys Leu Thr Val Trp Gly Ile Lys Gln Leu Gln
545                 550                 555                 560

Ala Arg Val Leu Ala Leu Glu Arg Tyr Leu Lys Asp Gln Gln Leu Leu
                565                 570                 575

Gly Met Trp Gly Cys Ser Gly Lys Leu Ile Cys Thr Thr Asn Val Tyr
                580                 585                 590

Trp Asn Ser Ser Trp Ser Asn Lys Thr Tyr Gly Asp Ile Trp Asp Asn
                595                 600                 605

Met Thr Trp Met Gln Trp Glu Arg Glu Ile Ser Asn Tyr Thr Glu Ile
    610                 615                 620

Ile Tyr Glu Leu Leu Glu Glu Ser Gln Asn Gln Gln Glu Lys Asn Glu
625                 630                 635                 640

Gln Asp Leu Leu Ala Leu Asp Arg Trp Asn Ser Leu Trp Asn Trp Phe
                645                 650                 655

Asn Ile Thr Asn Trp Leu Trp Tyr Ile Lys Ile Phe Ile Met Ile Val
                660                 665                 670

Gly Gly Leu Ile Gly Leu Arg Ile Ile Phe Ala Val Leu Ser Leu Val
                675                 680                 685

Asn Arg Val Arg Gln Gly Tyr Ser Pro Leu Ser Leu Gln Thr Leu Ile
    690                 695                 700

Pro Ser Pro Arg Gly Pro Asp Arg Pro Gly Gly Ile Glu Glu Glu Gly
705                 710                 715                 720

Gly Glu Gln Asp Arg Asn Arg Ser Thr Arg Leu Val Ser Gly Phe Leu
                725                 730                 735

Ala Leu Val Trp Asp Asp Leu Arg Ser Leu Cys Leu Phe Ile Tyr His
                740                 745                 750

Arg Leu Arg Asp Phe Ile Leu Ile Ala Ala Arg Ala Gly Glu Leu Leu
                755                 760                 765

Gly Arg Ser Ser Leu Lys Gly Leu Arg Arg Gly Trp Glu Ala Leu Lys
    770                 775                 780

Tyr Leu Gly Ser Leu Val Gln Tyr Trp Gly Leu Glu Leu Lys Arg Ser
785                 790                 795                 800

Ala Ile Ser Leu Leu Asp Thr Leu Ala Ile Ala Val Gly Glu Gly Thr
                805                 810                 815

Asp Arg Ile Leu Glu Phe Val Leu Gly Ile Cys Arg Ala Ile Arg Asn
                820                 825                 830

Ile Pro Thr Arg Ile Arg Gln Gly Phe Glu Thr Ala Leu Leu
    835                 840                 845
```

```
<210> SEQ ID NO 10
<211> LENGTH: 856
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

```
Met Arg Val Lys Glu Lys Tyr Gln His Leu Trp Arg Trp Gly Trp Arg
1                   5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
```

-continued

```
              35                    40                    45
Thr Thr Thr Leu Phe Cys Ala Ser Asp Ala Lys Ala Tyr Asp Thr Glu
    50                    55                    60

Val His Asn Val Trp Ala Thr His Ala Cys Val Pro Thr Asp Pro Asn
65                    70                    75                    80

Pro Gln Glu Val Val Leu Val Asn Val Thr Glu Asn Phe Asn Met Trp
                    85                    90                    95

Lys Asn Asp Met Val Glu Gln Met His Glu Asp Ile Ile Ser Leu Trp
                100                   105                   110

Asp Gln Ser Leu Lys Pro Cys Val Lys Leu Thr Pro Leu Cys Val Ser
                115                   120                   125

Leu Lys Cys Thr Asp Leu Lys Asn Asp Thr Asn Thr Asn Ser Ser Ser
    130                   135                   140

Gly Arg Met Ile Met Glu Lys Gly Glu Ile Lys Asn Cys Ser Phe Asn
145                   150                   155                   160

Ile Ser Thr Ser Ile Arg Gly Lys Val Gln Lys Glu Tyr Ala Phe Phe
                165                   170                   175

Tyr Lys Leu Asp Ile Ile Pro Ile Asp Asn Asp Thr Thr Ser Tyr Lys
                180                   185                   190

Leu Thr Ser Cys Asn Thr Ser Val Ile Thr Gln Ala Cys Pro Lys Val
                195                   200                   205

Ser Phe Glu Pro Ile Pro Ile His Tyr Cys Ala Pro Ala Gly Phe Ala
    210                   215                   220

Ile Leu Lys Cys Asn Asn Lys Thr Phe Asn Gly Thr Gly Pro Cys Thr
225                   230                   235                   240

Asn Val Ser Thr Val Gln Cys Thr His Gly Ile Arg Pro Val Val Ser
                245                   250                   255

Thr Gln Leu Leu Leu Asn Gly Ser Leu Ala Glu Glu Glu Val Val Ile
                260                   265                   270

Arg Ser Val Asn Phe Thr Asp Asn Ala Lys Thr Ile Ile Val Gln Leu
                275                   280                   285

Asn Thr Ser Val Glu Ile Asn Cys Thr Arg Pro Asn Asn Asn Thr Arg
    290                   295                   300

Lys Arg Ile Arg Ile Gln Arg Gly Pro Gly Arg Ala Phe Val Thr Ile
305                   310                   315                   320

Gly Lys Ile Gly Asn Met Arg Gln Ala His Cys Asn Ile Ser Arg Ala
                325                   330                   335

Lys Trp Asn Asn Thr Leu Lys Gln Ile Ala Ser Lys Leu Arg Glu Gln
                340                   345                   350

Phe Gly Asn Asn Lys Thr Ile Ile Phe Lys Gln Ser Ser Gly Gly Asp
                355                   360                   365

Pro Glu Ile Val Thr His Ser Phe Asn Cys Gly Gly Glu Phe Phe Tyr
    370                   375                   380

Cys Asn Ser Thr Gln Leu Phe Asn Ser Thr Trp Phe Asn Ser Thr Trp
385                   390                   395                   400

Ser Thr Glu Gly Ser Asn Asn Thr Glu Gly Ser Asp Thr Ile Thr Leu
                405                   410                   415

Pro Cys Arg Ile Lys Gln Ile Ile Asn Met Trp Gln Lys Val Gly Lys
                420                   425                   430

Ala Met Tyr Ala Pro Pro Ile Ser Gly Gln Ile Arg Cys Ser Ser Asn
                435                   440                   445

Ile Thr Gly Leu Leu Leu Thr Arg Asp Gly Gly Asn Ser Asn Asn Glu
    450                   455                   460
```

-continued

```
Ser Glu Ile Phe Arg Pro Gly Gly Gly Asp Met Arg Asp Asn Trp Arg
465                 470             475              480

Ser Glu Leu Tyr Lys Tyr Lys Val Val Lys Ile Glu Pro Leu Gly Val
                485             490             495

Ala Pro Thr Lys Ala Lys Arg Arg Val Val Gln Arg Glu Lys Arg Ala
            500             505             510

Val Gly Ile Gly Ala Leu Phe Leu Gly Phe Leu Gly Ala Ala Gly Ser
            515             520             525

Thr Met Gly Ala Ala Ser Met Thr Leu Thr Val Gln Ala Arg Gln Leu
    530             535             540

Leu Ser Gly Ile Val Gln Gln Gln Asn Asn Leu Leu Arg Ala Ile Glu
545             550             555             560

Ala Gln Gln His Leu Leu Gln Leu Thr Val Trp Gly Ile Lys Gln Leu
                565             570             575

Gln Ala Arg Ile Leu Ala Val Glu Arg Tyr Leu Lys Asp Gln Gln Leu
            580             585             590

Leu Gly Ile Trp Gly Cys Ser Gly Lys Leu Ile Cys Thr Thr Ala Val
            595             600             605

Pro Trp Asn Ala Ser Trp Ser Asn Lys Ser Leu Glu Gln Ile Trp Asn
    610             615             620

His Thr Thr Trp Met Glu Trp Asp Arg Glu Ile Asn Asn Tyr Thr Ser
625             630             635             640

Leu Ile His Ser Leu Ile Glu Glu Ser Gln Asn Gln Gln Glu Lys Asn
            645             650             655

Glu Gln Glu Leu Leu Glu Leu Asp Lys Trp Ala Ser Leu Trp Asn Trp
            660             665             670

Phe Asn Ile Thr Asn Trp Leu Trp Tyr Ile Lys Leu Phe Ile Met Ile
            675             680             685

Val Gly Gly Leu Val Gly Leu Arg Ile Val Phe Ala Val Leu Ser Ile
    690             695             700

Val Asn Arg Val Arg Gln Gly Tyr Ser Pro Leu Ser Phe Gln Thr His
705             710             715             720

Leu Pro Thr Pro Arg Gly Pro Asp Arg Pro Glu Gly Ile Glu Glu Glu
            725             730             735

Gly Gly Glu Arg Asp Arg Asp Arg Ser Ile Arg Leu Val Asn Gly Ser
            740             745             750

Leu Ala Leu Ile Trp Asp Asp Leu Arg Ser Leu Cys Leu Phe Ser Tyr
            755             760             765

His Arg Leu Arg Asp Leu Leu Leu Ile Val Thr Arg Ile Val Glu Leu
    770             775             780

Leu Gly Arg Arg Gly Trp Glu Ala Leu Lys Tyr Trp Trp Asn Leu Leu
785             790             795             800

Gln Tyr Trp Ser Gln Glu Leu Lys Asn Ser Ala Val Ser Leu Leu Asn
                805             810             815

Ala Thr Ala Ile Ala Val Ala Glu Gly Thr Asp Arg Val Ile Glu Val
            820             825             830

Val Gln Gly Ala Cys Arg Ala Ile Arg His Ile Pro Arg Arg Ile Arg
            835             840             845

Gln Gly Leu Glu Arg Ile Leu Leu
    850             855
```

```
<210> SEQ ID NO 11
<211> LENGTH: 855
```

-continued

<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 11

```
Met Arg Val Met Gly Ile Gln Arg Asn Tyr Pro Pro Leu Trp Arg Trp
1               5                   10                  15

Gly Thr Met Ile Phe Trp Met Met Met Leu Cys Ser Ala Glu Lys Leu
            20                  25                  30

Trp Val Thr Val Tyr Tyr Gly Val Pro Val Trp Arg Glu Ala Asp Thr
            35                  40                  45

Thr Leu Phe Cys Ala Ser Asp Ala Lys Gly Tyr Asp Thr Glu Ala His
        50                  55                  60

Asn Val Trp Ala Thr His Ala Cys Val Pro Thr Asp Pro Arg Pro Gln
65                  70                  75                  80

Glu Met Tyr Leu Glu Asn Val Thr Glu Asn Phe Asn Met Trp Lys Asn
                85                  90                  95

Ser Met Val Glu Gln Met His Thr Asp Ile Ile Ser Leu Trp Asp Glu
            100                 105                 110

Ser Leu Lys Pro Cys Val Lys Leu Thr Pro Leu Cys Val Thr Leu Asp
            115                 120                 125

Cys Gln Ala Phe Asn Ser Ser Ser His Thr Asn Ser Ser Ile Ala Met
        130                 135                 140

Gln Glu Met Lys Asn Cys Ser Phe Asn Val Thr Thr Glu Leu Arg Asp
145                 150                 155                 160

Lys Lys Lys Lys Glu Tyr Ser Phe Phe Tyr Lys Thr Asp Ile Glu Gln
                165                 170                 175

Ile Asn Lys Asn Gly Arg Gln Tyr Arg Leu Ile Asn Cys Asn Thr Ser
            180                 185                 190

Ala Ile Thr Gln Ala Cys Pro Lys Val Ser Phe Glu Pro Ile Pro Ile
            195                 200                 205

His Phe Cys Ala Pro Ala Gly Phe Ala Ile Leu Lys Cys Asn Glu Lys
        210                 215                 220

His Phe Asn Gly Lys Gly Pro Cys Lys Asn Val Ser Thr Val Gln Cys
225                 230                 235                 240

Thr His Gly Ile Lys Pro Val Val Ser Thr Gln Leu Leu Leu Asn Gly
                245                 250                 255

Ser Leu Ala Glu Glu Glu Val Val Ile Arg Val Glu Asn Thr Ile Asp
            260                 265                 270

Asn Ala Lys Thr Ile Ile Val Gln Leu Ala Lys Pro Val Lys Ile Asn
            275                 280                 285

Cys Thr Arg Pro Asn Asn Asn Thr Arg Lys Ser Ile Arg Ile Gly Pro
        290                 295                 300

Gly Gln Thr Phe Tyr Ala Thr Gly Asp Ile Ile Gly Asn Ile Arg Lys
305                 310                 315                 320

Ala Tyr Cys Asn Val Ser Lys Arg Glu Trp Asn Asn Thr Leu Gln Gln
                325                 330                 335

Val Ala Ala Gln Leu Ser Lys Ser Phe Asn Asn Thr Lys Ile Val Phe
            340                 345                 350

Glu Lys His Ser Gly Gly Asp Leu Glu Val Ile Thr His Ser Phe Val
            355                 360                 365

Cys Gly Gly Glu Phe Phe Tyr Cys Asn Thr Ser Gly Leu Phe Asn Ser
        370                 375                 380
```

-continued

```
Thr Trp Thr Asn Ser Thr Trp Thr Asn Ser Thr Thr Gly Ser Asn Gly
385                 390                 395                 400

Thr Glu Ser Asn Asp Thr Ile Thr Leu Gln Cys Glu Ile Lys Gln Phe
                405                 410                 415

Ile Asn Met Trp Gln Arg Val Gly Arg Ala Met Tyr Ala Pro Pro Ile
            420                 425                 430

Pro Gly Val Ile Arg Cys Glu Ser Asp Ile Thr Gly Leu Leu Leu Thr
            435                 440                 445

Arg Asp Gly Pro Asn Ser Thr Gln Asn Glu Thr Phe Arg Pro Gly Gly
        450                 455                 460

Gly Asp Met Arg Asp Asn Trp Arg Ser Glu Leu Tyr Lys Tyr Lys Val
465                 470                 475                 480

Val Gln Ile Glu Pro Leu Gly Val Ala Pro Thr His Ala Lys Arg Arg
                485                 490                 495

Val Val Glu Arg Glu Lys Arg Ala Val Gly Leu Gly Ala Val Phe Phe
            500                 505                 510

Gly Phe Leu Gly Ala Ala Gly Ser Thr Met Gly Ala Ala Ser Ile Thr
            515                 520                 525

Leu Thr Val Gln Ala Arg Gln Leu Leu Ser Gly Ile Val Gln Gln Gln
        530                 535                 540

Ser Asn Leu Leu Lys Ala Ile Glu Ala Gln Gln Gln Leu Leu Arg Leu
545                 550                 555                 560

Thr Val Trp Gly Ile Lys Gln Leu Gln Ala Arg Val Leu Ala Leu Glu
            565                 570                 575

Arg Tyr Leu Lys Asp Gln Gln Leu Leu Gly Ile Trp Gly Cys Ser Gly
            580                 585                 590

Lys Leu Ile Cys Thr Thr Thr Val Pro Trp Asn Ser Ser Trp Ser Asn
            595                 600                 605

Lys Asn Tyr Thr Asp Ile Trp Asp Asn Met Thr Trp Leu Gln Trp Asp
        610                 615                 620

Arg Glu Ile Ser Asn Tyr Thr Asp Glu Ile Tyr Arg Leu Ile Glu Gln
625                 630                 635                 640

Ser Gln Asn Gln Gln Glu Lys Asn Glu Gln Asp Leu Leu Ala Leu Asp
                645                 650                 655

Lys Trp Ala Ser Leu Trp Asn Trp Phe Asp Ile Thr Asn Trp Leu Trp
            660                 665                 670

Tyr Ile Lys Ile Phe Ile Met Ile Val Gly Gly Leu Ile Gly Leu Arg
            675                 680                 685

Ile Ile Phe Thr Val Leu Asn Val Ile Asn Arg Val Arg Gln Gly Tyr
        690                 695                 700

Ser Pro Leu Ser Phe Gln Thr Leu Thr His His Gln Arg Glu Pro Asp
705                 710                 715                 720

Arg Pro Glu Arg Ile Glu Glu Gly Gly Gly Glu Gln Asp Arg Asp Arg
                725                 730                 735

Ser Val Arg Leu Val Ser Gly Phe Leu Ala Leu Ala Trp Asp Asp Leu
            740                 745                 750

Arg Ser Leu Cys Leu Phe Ser Phe His Arg Leu Arg Asp Leu Val Leu
            755                 760                 765

Ile Ala Ala Arg Gly Val Glu Leu Leu Gly His Ser Ser Leu Lys Gly
        770                 775                 780

Leu Arg Leu Gly Trp Glu Ala Leu Lys Leu Leu Gly Asn Leu Leu Ser
785                 790                 795                 800
```

-continued

```
Tyr Trp Gly Gln Glu Leu Lys Asn Ser Ala Ile Asn Leu Leu Asp Ala
                805              810              815

Val Ala Ile Ala Val Ala Asn Trp Thr Asp Arg Val Ile Lys Ile Gly
        820              825              830

Gln Arg Ala Gly Arg Ala Ile Leu Asn Ile Pro Ile Arg Ile Arg Gln
        835              840              845

Gly Leu Glu Arg Ala Leu Leu
    850              855

<210> SEQ ID NO 12
<211> LENGTH: 835
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Val Arg Gly Ile Met Arg Asn Trp Gln Gln Trp Trp Ile Trp
1               5                   10                  15

Gly Ser Leu Gly Phe Trp Met Leu Ile Ile Cys Asn Val Met Gly Ser
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Glu Thr Glu Ala
    50                  55                  60

His Ser Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Val Ile Ser Ile Trp Asp
            100                 105                 110

Gln Ser Leu Lys Pro Cys Val Lys Leu Thr Pro Leu Cys Val Thr Leu
        115                 120                 125

Asp Cys Ser Thr Tyr Asn Asn Thr His Asn Ile Ser Lys Glu Met Lys
    130                 135                 140

Ile Cys Ser Phe Asn Met Thr Thr Glu Leu Arg Asp Lys Lys Arg Lys
145                 150                 155                 160

Val Asn Val Leu Phe Tyr Lys Leu Asp Leu Val Pro Leu Thr Asn Ser
                165                 170                 175

Ser Asn Thr Thr Asn Tyr Arg Leu Ile Ser Cys Asn Thr Ser Thr Ile
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
    210                 215                 220

Asn Gly Thr Gly Pro Cys Asn Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Glu Glu Ile Ile Ile Arg Phe Glu Asn Leu Thr Asp Asn Val
            260                 265                 270

Lys Ile Ile Ile Val Gln Leu Asn Glu Thr Ile Asn Ile Thr Cys Thr
        275                 280                 285

Arg Pro Asn Asn Asn Thr Arg Lys Ser Ile Arg Ile Gly Pro Gly Gln
    290                 295                 300
```

-continued

```
Ser Phe Tyr Ala Thr Gly Glu Ile Val Gly Asn Ile Arg Glu Ala His
305                 310                 315                 320

Cys Asn Ile Ser Ala Ser Lys Trp Asn Lys Thr Leu Glu Arg Val Arg
                325                 330                 335

Thr Lys Leu Lys Glu His Phe Pro Asn Lys Thr Ile Glu Phe Glu Pro
            340                 345                 350

Ser Ser Gly Gly Asp Leu Glu Ile Thr Thr His Ser Phe Asn Cys Gly
            355                 360                 365

Gly Glu Phe Phe Tyr Cys Asn Thr Ser Gly Leu Phe Asn Ser Ala Ile
            370                 375                 380

Asn Gly Thr Leu Thr Ser Asn Val Thr Leu Pro Cys Arg Ile Lys Gln
385                 390                 395                 400

Ile Ile Asn Met Trp Gln Glu Val Gly Arg Ala Met Tyr Ala Pro Pro
                    405                 410                 415

Ile Ala Gly Asn Ile Thr Cys Lys Ser Asn Ile Thr Gly Leu Leu Leu
                420                 425                 430

Thr Arg Asp Gly Gly Glu Asn Ser Ser Ser Thr Thr Glu Thr Phe Arg
            435                 440                 445

Pro Thr Gly Gly Asp Met Lys Asn Asn Trp Arg Ser Glu Leu Tyr Lys
        450                 455                 460

Tyr Lys Val Val Glu Ile Lys Pro Leu Gly Ile Ala Pro Thr Glu Ala
465                 470                 475                 480

Lys Arg Arg Val Val Glu Arg Glu Lys Arg Ala Val Gly Ile Gly Ala
                485                 490                 495

Val Phe Leu Gly Phe Leu Gly Ala Ala Gly Ser Thr Met Gly Ala Ala
            500                 505                 510

Ser Met Thr Leu Thr Val Gln Ala Arg Gln Leu Leu Ser Gly Ile Val
            515                 520                 525

Gln Gln Gln Ser Asn Leu Leu Lys Ala Ile Glu Ala Gln Gln His Met
        530                 535                 540

Leu Gln Leu Thr Val Trp Gly Ile Lys Gln Leu Gln Ala Arg Val Leu
545                 550                 555                 560

Ala Ile Glu Arg Tyr Leu Lys Asp Gln Gln Leu Leu Gly Leu Trp Gly
                565                 570                 575

Cys Ser Gly Lys Leu Ile Cys Thr Thr Asn Val Pro Trp Asn Ala Ser
            580                 585                 590

Trp Ser Asn Lys Ser Lys Asn Asp Ile Trp Asp Asn Met Thr Trp Met
            595                 600                 605

Gln Trp Asp Arg Glu Ile Ser Asn His Thr Asp Thr Ile Tyr Arg Leu
        610                 615                 620

Leu Glu Asp Ser Gln Asn Gln Gln Glu Lys Asn Glu Lys Asp Leu Leu
625                 630                 635                 640

Ala Leu Asp Ser Trp Lys Asn Leu Trp Asn Trp Phe Ser Ile Thr Lys
                645                 650                 655

Trp Leu Trp Tyr Ile Lys Ile Phe Ile Met Ile Val Gly Gly Leu Ile
            660                 665                 670

Gly Leu Arg Ile Ile Phe Ala Val Leu Ser Ile Val Asn Arg Val Arg
            675                 680                 685

Gln Gly Tyr Ser Pro Leu Ser Phe Gln Thr Leu Thr Pro Asn Pro Arg
        690                 695                 700

Gly Pro Asp Arg Leu Gly Gly Ile Glu Glu Glu Gly Gly Glu Gln Asp
705                 710                 715                 720
```

-continued

```
Lys Asn Lys Ser Arg Arg Leu Val Thr Gly Phe Leu Pro Val Val Trp
            725                 730                 735

Asp Asp Leu Arg Ser Leu Cys Leu Phe Ser Tyr His Leu Leu Arg Asp
            740                 745                 750

Phe Ile Leu Ile Val Ala Arg Thr Val Glu Leu Leu Gly Arg Arg Gly
            755                 760                 765

Trp Glu Ala Leu Lys Tyr Leu Gly Gly Leu Val Gln Tyr Trp Gly Leu
        770                 775                 780

Glu Leu Lys Lys Ser Thr Ile Ser Leu Leu Asp Thr Ile Ala Ile Val
785                 790                 795                 800

Val Ala Glu Gly Thr Asp Arg Ile Ile Glu Val Leu Gln Arg Ile Gly
                805                 810                 815

Arg Ala Ile Tyr Asn Ile Pro Arg Arg Ile Arg Gln Gly Phe Glu Thr
                820                 825                 830

Ala Leu Leu
        835

<210> SEQ ID NO 13
<211> LENGTH: 860
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Arg Val Met Gly Ile Gln Arg Asn Cys Gln His Leu Phe Arg Trp
1               5                   10                  15

Gly Thr Met Ile Leu Gly Met Ile Ile Ile Cys Ser Ala Ala Glu Asn
            20                  25                  30

Leu Trp Val Thr Val Tyr Tyr Gly Val Pro Val Trp Lys Asp Ala Glu
            35                  40                  45

Thr Thr Leu Phe Cys Ala Ser Asp Ala Lys Ala Tyr Glu Thr Glu Lys
        50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
        130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
        210                 215                 220

Leu Lys Cys Lys Asp Lys Lys Phe Asn Gly Thr Gly Pro Cys Pro Ser
225                 230                 235                 240
```

-continued

```
Val Ser Thr Val Gln Cys Thr His Gly Ile Lys Pro Val Val Ser Thr
            245                 250                 255

Gln Leu Leu Leu Asn Gly Ser Leu Ala Glu Glu Glu Val Met Ile Arg
            260                 265                 270

Ser Glu Asn Ile Thr Asn Asn Ala Lys Asn Ile Leu Val Gln Phe Asn
            275                 280                 285

Thr Pro Val Gln Ile Asn Cys Thr Arg Pro Asn Asn Asn Thr Arg Lys
        290                 295                 300

Ser Ile Arg Ile Gly Pro Gly Gln Ala Phe Tyr Ala Thr Gly Asp Ile
305                 310                 315                 320

Ile Gly Asp Ile Arg Gln Ala His Cys Asn Val Ser Lys Ala Thr Trp
                325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
            355                 360                 365

Val Thr Thr His Ser Phe Asn Cys Gly Gly Glu Phe Phe Tyr Cys Asn
        370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
                405                 410                 415

Ile Lys Gln Ile Ile Asn Met Trp Gln Arg Ile Gly Gln Ala Met Tyr
                420                 425                 430

Ala Pro Pro Ile Gln Gly Val Ile Arg Cys Val Ser Asn Ile Thr Gly
            435                 440                 445

Leu Ile Leu Thr Arg Asp Gly Gly Ser Thr Asn Ser Thr Thr Glu Thr
        450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Arg Ala Lys Arg Arg Val Val Gly Arg Glu Lys Arg Ala Val Gly Ile
            500                 505                 510

Gly Ala Val Phe Leu Gly Phe Leu Gly Ala Ala Gly Ser Thr Met Gly
            515                 520                 525

Ala Ala Ser Met Thr Leu Thr Val Gln Ala Arg Asn Leu Leu Ser Gly
        530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Asn Val Pro Trp Asn
            595                 600                 605

Ser Ser Trp Ser Asn Arg Asn Leu Ser Glu Ile Trp Asp Asn Met Thr
        610                 615                 620

Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Lys Asn Glu Gln Asp
                645                 650                 655
```

```
Leu Leu Ala Leu Asp Lys Trp Ala Ser Leu Trp Asn Trp Phe Asp Ile
            660                 665                 670

Ser Asn Trp Leu Trp Tyr Ile Lys Ile Phe Ile Met Ile Val Gly Gly
        675                 680                 685

Leu Ile Gly Leu Arg Ile Val Phe Ala Val Leu Ser Val Ile His Arg
    690                 695                 700

Val Arg Gln Gly Tyr Ser Pro Leu Ser Phe Gln Thr His Thr Pro Asn
705                 710                 715                 720

Pro Arg Gly Leu Asp Arg Pro Glu Arg Ile Glu Glu Glu Asp Gly Glu
                725                 730                 735

Gln Asp Arg Gly Arg Ser Thr Arg Leu Val Ser Gly Phe Leu Ala Leu
            740                 745                 750

Ala Trp Asp Asp Leu Arg Ser Leu Cys Leu Phe Cys Tyr His Arg Leu
            755                 760                 765

Arg Asp Phe Ile Leu Ile Ala Ala Arg Ile Val Glu Leu Leu Gly His
    770                 775                 780

Ser Ser Leu Lys Gly Leu Arg Leu Gly Trp Glu Gly Leu Lys Tyr Leu
785                 790                 795                 800

Trp Asn Leu Leu Ala Tyr Trp Gly Arg Glu Leu Lys Ile Ser Ala Ile
                805                 810                 815

Asn Leu Phe Asp Thr Ile Ala Ile Ala Val Ala Glu Trp Thr Asp Arg
            820                 825                 830

Val Ile Glu Ile Gly Gln Arg Leu Cys Arg Ala Phe Leu His Ile Pro
            835                 840                 845

Arg Arg Ile Arg Gln Gly Leu Glu Arg Ala Leu Leu
    850                 855                 860
```

<210> SEQ ID NO 14
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu His Cys Ser
        115                 120                 125

Thr Tyr Asn Asn Thr His Asn Ile Ser Lys Gly Met Lys Asn Cys Ser
    130                 135                 140

Phe Asn Ala Thr Thr Glu Leu Arg Asp Lys Lys Gln Lys Val Asn Ala
145                 150                 155                 160
```

-continued

```
Leu Phe Tyr Lys Leu Asp Ile Val Gln Leu Asn Lys Asn Gly Arg Gln
            165                 170                 175

Tyr Arg Leu Ile Asn Cys Asn Thr Ser Val Ile Thr Gln Ala Cys Pro
            180                 185                 190

Lys Val Ser Phe Asp Pro Ile Pro Ile His Tyr Cys Ala Pro Ala Gly
            195                 200                 205

Tyr Ala Ile Leu Lys Cys Asn Asn Lys Thr Phe Asn Gly Thr Gly Pro
        210                 215                 220

Cys Asn Asn Val Ser Thr Val Gln Cys Thr His Gly Ile Lys Pro Val
225                 230                 235                 240

Val Ser Thr Gln Leu Leu Leu Asn Gly Ser Leu Ala Glu Gly Glu Ile
                245                 250                 255

Ile Ile Arg Ser Glu Asn Ile Thr Asn Asn Val Lys Thr Ile Ile Val
            260                 265                 270

His Leu Asn Glu Ser Val Lys Ile Glu Cys Thr Arg Pro Asn Asn Lys
            275                 280                 285

Thr Arg Thr Ser Ile Arg Ile Gly Pro Gly Gln Thr Phe Tyr Ala Thr
        290                 295                 300

Gly Gln Val Ile Gly Asp Ile Arg Glu Ala Tyr Cys Asn Ile Asn Lys
305                 310                 315                 320

Ser Lys Trp Asn Glu Thr Leu Gln Arg Val Ser Lys Lys Leu Lys Glu
                325                 330                 335

Tyr Phe Pro His Lys Asn Ile Thr Phe Gln Pro Ser Ser Gly Gly Asp
            340                 345                 350

Leu Glu Ile Thr Thr His Ser Phe Asn Cys Gly Gly Glu Phe Phe Tyr
            355                 360                 365

Cys Asn Thr Ser Ser Leu Phe Asn Arg Thr Tyr Met Ala Asn Ser Thr
        370                 375                 380

Asp Met Ala Asn Ser Thr Glu Thr Asn Ser Thr Arg Thr Ile Thr Ile
385                 390                 395                 400

His Cys Arg Ile Lys Gln Ile Ile Asn Met Trp Gln Glu Val Gly Arg
                405                 410                 415

Ala Met Tyr Ala Pro Pro Ile Ala Gly Asn Ile Thr Cys Ile Ser Asn
            420                 425                 430

Ile Thr Gly Leu Leu Leu Thr Arg Asp Gly Gly Lys Asn Asn Thr Glu
            435                 440                 445

Thr Phe Arg Pro Gly Gly Gly Asn Met Lys Asp Asn Trp Arg Ser Glu
        450                 455                 460

Leu Tyr Lys Tyr Lys Val Val Glu Val Lys Pro Leu Gly Val Ala Pro
465                 470                 475                 480

Thr Asn Ala Arg Arg Arg Val Val Glu Arg Glu Lys Arg Ala Val Gly
                485                 490                 495

Met Gly Ala Val Phe Leu Gly Phe Leu Gly Ala Ala Gly Ser Thr Met
            500                 505                 510

Gly Ala Ala Ser Ile Thr Leu Thr Val Gln Ala Arg Gln Leu Leu Ser
            515                 520                 525

Gly Ile Val Gln Gln Gln Ser Asn Leu Leu Lys Ala Ile Glu Ala Gln
        530                 535                 540

Gln His Met Leu Lys Leu Thr Val Trp Gly Ile Lys Gln Leu Gln Ala
545                 550                 555                 560

Arg Val Leu Ala Leu Glu Arg Tyr Leu Lys Asp Gln Gln Leu Leu Gly
                565                 570                 575
```

```
Met Trp Gly Cys Ser Gly Lys Leu Ile Cys Thr Thr Asn Val Tyr Trp
            580                 585                 590

Asn Ser Ser Trp Ser Asn Lys Thr Tyr Gly Asp Ile Trp Asp Asn Met
            595                 600                 605

Thr Trp Met Gln Trp Asp Arg Glu Ile Ser Asn Tyr Thr Glu Ile Ile
    610                 615                 620

Tyr Arg Leu Leu Glu Glu Ser Gln Asn Gln Gln Glu Lys Asn Glu Gln
625                 630                 635                 640

Asp Leu Leu Ala Leu Asp Arg Trp Asn Ser Leu Trp Asn Trp Phe Asn
                645                 650                 655

Ile Thr Asn Trp Leu Trp Tyr Ile Lys Ile Phe Ile Met Ile Val Gly
            660                 665                 670

Gly Leu Ile Gly Leu Arg Ile Ile Phe Ala Val Leu Ser Leu Val Asn
            675                 680                 685

Arg Val Arg Gln Gly Tyr Ser Pro Leu Ser Phe Gln Thr Leu Ile Pro
    690                 695                 700

Ser Pro Arg Gly Pro Asp Arg Pro Gly Gly Ile Glu Glu Glu Gly Gly
705                 710                 715                 720

Glu Gln Asp Arg Asn Arg Ser Thr Arg Leu Val Ser Gly Phe Leu Ala
                725                 730                 735

Leu Val Trp Asp Asp Leu Arg Ser Leu Cys Leu Phe Ile Tyr His Arg
                740                 745                 750

Leu Arg Asp Phe Ile Leu Ile Ala Ala Arg Ala Gly Glu Leu Leu Gly
            755                 760                 765

Arg Ser Ser Leu Lys Gly Leu Arg Arg Gly Trp Glu Ala Leu Lys Tyr
    770                 775                 780

Leu Gly Ser Leu Val Gln Tyr Trp Gly Leu Glu Leu Lys Arg Ser Ala
785                 790                 795                 800

Ile Ser Leu Leu Asp Thr Leu Ala Ile Ala Val Gly Glu Gly Thr Asp
                805                 810                 815

Arg Ile Leu Glu Phe Val Leu Gly Ile Cys Arg Ala Ile Arg Asn Ile
            820                 825                 830

Pro Thr Arg Ile Arg Gln Gly Phe Glu Thr Ala Leu Leu
            835                 840                 845
```

```
<210> SEQ ID NO 15
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15
```

```
Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95
```

-continued

```
Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu His Cys Ser
            115                 120                 125

Thr Tyr Asn Asn Thr His Asn Ile Ser Lys Gly Met Lys Asn Cys Ser
            130                 135                 140

Phe Asn Ala Thr Thr Glu Leu Arg Asp Lys Lys Gln Lys Val Asn Ala
145                 150                 155                 160

Leu Phe Tyr Lys Leu Asp Ile Val Gln Leu Asn Lys Asn Gly Arg Gln
                165                 170                 175

Tyr Arg Leu Ile Asn Cys Asn Thr Ser Val Ile Thr Gln Ala Cys Pro
                180                 185                 190

Lys Val Ser Phe Asp Pro Ile Pro Ile His Tyr Cys Ala Pro Ala Gly
                195                 200                 205

Tyr Ala Ile Leu Lys Cys Asn Asn Lys Thr Phe Asn Gly Thr Gly Pro
    210                 215                 220

Cys Asn Asn Val Ser Thr Val Gln Cys Thr His Gly Ile Lys Pro Val
225                 230                 235                 240

Val Ser Thr Gln Leu Leu Leu Asn Gly Ser Leu Ala Glu Gly Glu Ile
                245                 250                 255

Ile Ile Arg Ser Glu Asn Ile Thr Asn Asn Val Lys Thr Ile Ile Val
                260                 265                 270

His Leu Asn Glu Ser Val Lys Ile Glu Cys Thr Arg Pro Asn Asn Lys
                275                 280                 285

Thr Arg Thr Ser Ile Arg Ile Gly Pro Gly Gln Thr Phe Tyr Ala Thr
    290                 295                 300

Gly Gln Val Ile Gly Asp Ile Arg Glu Ala Tyr Cys Asn Ile Ser Lys
305                 310                 315                 320

Ser Lys Trp Asn Glu Thr Leu Gln Arg Val Ser Lys Lys Leu Lys Glu
                325                 330                 335

Tyr Phe Pro His Lys Asn Ile Thr Phe Gln Pro Ser Ser Gly Gly Asp
                340                 345                 350

Leu Glu Ile Thr Thr His Ser Phe Asn Cys Gly Gly Glu Phe Phe Tyr
                355                 360                 365

Cys Asn Thr Ser Ser Leu Phe Asn Arg Thr Tyr Met Ala Asn Ser Thr
    370                 375                 380

Asp Met Ala Asn Ser Thr Glu Thr Asn Ser Thr Arg Thr Ile Thr Ile
385                 390                 395                 400

His Cys Arg Ile Lys Gln Ile Ile Asn Met Trp Gln Glu Val Gly Arg
                405                 410                 415

Ala Met Tyr Ala Pro Pro Ile Ala Gly Asn Ile Thr Cys Ile Ser Asn
                420                 425                 430

Ile Thr Gly Leu Leu Leu Thr Arg Asp Gly Gly Lys Asn Asn Thr Glu
                435                 440                 445

Thr Phe Arg Pro Gly Gly Gly Asn Met Lys Asp Asn Trp Arg Ser Glu
    450                 455                 460

Leu Tyr Lys Tyr Lys Val Val Glu Val Lys Pro Leu Gly Val Ala Pro
465                 470                 475                 480

Thr Asn Ala Arg Arg Arg Val Val Glu Arg Glu Lys Arg Ala Val Gly
                485                 490                 495

Met Gly Ala Val Phe Leu Gly Phe Leu Gly Ala Ala Gly Ser Thr Met
                500                 505                 510
```

-continued

```
Gly Ala Ala Ser Ile Thr Leu Thr Val Gln Ala Arg Gln Leu Leu Ser
        515                 520                 525

Gly Ile Val Gln Gln Gln Ser Asn Leu Leu Lys Ala Ile Glu Ala Gln
        530                 535                 540

Gln His Met Leu Lys Leu Thr Val Trp Gly Ile Lys Gln Leu Gln Ala
545                 550                 555                 560

Arg Val Leu Ala Leu Glu Arg Tyr Leu Lys Asp Gln Gln Leu Leu Gly
                565                 570                 575

Met Trp Gly Cys Ser Gly Lys Leu Ile Cys Thr Thr Asn Val Tyr Trp
                580                 585                 590

Asn Ser Ser Trp Ser Asn Lys Thr Tyr Gly Asp Ile Trp Asp Asn Met
        595                 600                 605

Thr Trp Met Gln Trp Asp Arg Glu Ile Ser Asn Tyr Thr Glu Ile Ile
        610                 615                 620

Tyr Arg Leu Leu Glu Glu Ser Gln Asn Gln Gln Glu Lys Asn Glu Gln
625                 630                 635                 640

Asp Leu Leu Ala Leu Asp Arg Trp Asn Ser Leu Trp Asn Trp Phe Asn
                645                 650                 655

Ile Thr Asn Trp Leu Trp Tyr Ile Lys Ile Phe Ile Met Ile Val Gly
                660                 665                 670

Gly Leu Ile Gly Leu Arg Ile Ile Phe Ala Val Leu Ser Leu Val Asn
        675                 680                 685

Arg Val Arg Gln Gly Tyr Ser Pro Leu Ser Phe Gln Thr Leu Ile Pro
        690                 695                 700

Ser Pro Arg Gly Pro Asp Arg Pro Gly Gly Ile Glu Glu Glu Gly Gly
705                 710                 715                 720

Glu Gln Asp Arg Asn Arg Ser Thr Arg Leu Val Ser Gly Phe Leu Ala
                725                 730                 735

Leu Val Trp Asp Asp Leu Arg Ser Leu Cys Leu Phe Ile Tyr His Arg
                740                 745                 750

Leu Arg Asp Phe Ile Leu Ile Ala Ala Arg Ala Gly Glu Leu Leu Gly
        755                 760                 765

Arg Ser Ser Leu Lys Gly Leu Arg Arg Gly Trp Glu Ala Leu Lys Tyr
        770                 775                 780

Leu Gly Ser Leu Val Gln Tyr Trp Gly Leu Glu Leu Lys Arg Ser Ala
785                 790                 795                 800

Ile Ser Leu Leu Asp Thr Leu Ala Ile Ala Val Gly Glu Gly Thr Asp
                805                 810                 815

Arg Ile Leu Glu Phe Val Leu Gly Ile Cys Arg Ala Ile Arg Asn Ile
        820                 825                 830

Pro Thr Arg Ile Arg Gln Gly Phe Glu Thr Ala Leu Leu
        835                 840                 845
```

```
<210> SEQ ID NO 16
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
        20                  25                  30
```

-continued

```
Thr Val Tyr Tyr Gly Val Pro Val Trp Lys Glu Ala Lys Thr Thr Leu
        35              40              45

Phe Cys Ala Ser Asp Ala Lys Ala Tyr Glu Lys Glu Val His Asn Val
    50              55              60

Trp Ala Thr His Ala Cys Val Pro Thr Asp Pro Asn Pro Gln Glu Met
65              70              75              80

Val Leu Lys Asn Val Thr Glu Asn Phe Asn Met Trp Lys Asn Asp Met
            85              90              95

Val Asp Gln Met His Glu Asp Val Ile Ser Leu Trp Asp Gln Ser Leu
            100             105             110

Lys Pro Cys Val Lys Leu Thr Pro Leu Cys Val Thr Leu His Cys Ser
        115             120             125

Thr Tyr Asn Asn Thr His Asn Ile Ser Lys Gly Met Lys Asn Cys Ser
    130             135             140

Phe Asn Met Thr Thr Glu Leu Arg Asp Lys Lys Gln Lys Val Asn Ala
145             150             155             160

Leu Phe Tyr Lys Leu Asp Ile Val Gln Leu Asn Lys Asn Gly Arg Gln
            165             170             175

Tyr Arg Leu Ile Asn Cys Asn Thr Ser Ala Ile Thr Gln Ala Cys Pro
        180             185             190

Lys Val Ser Phe Asp Pro Ile Pro Ile His Tyr Cys Ala Pro Ala Gly
        195             200             205

Tyr Ala Ile Leu Lys Cys Asn Asn Lys Thr Phe Asn Gly Thr Gly Pro
    210             215             220

Cys Asn Asn Val Ser Thr Val Gln Cys Thr His Gly Ile Lys Pro Val
225             230             235             240

Val Ser Thr Gln Leu Leu Leu Asn Gly Ser Leu Ala Glu Gly Glu Ile
            245             250             255

Ile Ile Arg Ser Glu Asn Ile Thr Asn Asn Val Lys Thr Ile Ile Val
            260             265             270

His Leu Asn Glu Ser Val Lys Ile Glu Cys Thr Arg Pro Asn Asn Lys
        275             280             285

Thr Arg Lys Ser Ile Arg Ile Gly Pro Gly Gln Thr Phe Tyr Ala Thr
    290             295             300

Gly Asp Val Ile Gly Asp Ile Arg Glu Ala Tyr Cys Asn Ile Asn Lys
305             310             315             320

Ser Lys Trp Asn Glu Thr Leu Gln Arg Val Ser Lys Lys Leu Lys Glu
            325             330             335

Tyr Phe Pro His Lys Asn Ile Thr Phe Gln Pro Ser Ser Gly Gly Asp
            340             345             350

Leu Glu Ile Thr Thr His Ser Phe Asn Cys Gly Gly Glu Phe Phe Tyr
            355             360             365

Cys Asn Thr Ser Ser Leu Phe Asn Arg Thr Tyr Met Ala Asn Ser Thr
    370             375             380

Asp Met Ala Asn Ser Thr Glu Thr Asn Ser Thr Arg Thr Ile Thr Ile
385             390             395             400

His Cys Arg Ile Lys Gln Ile Ile Asn Met Trp Gln Glu Val Gly Arg
            405             410             415

Ala Met Tyr Ala Pro Pro Ile Ala Gly Asn Ile Thr Cys Ile Ser Asn
            420             425             430

Ile Thr Gly Leu Leu Leu Thr Arg Asp Gly Gly Lys Asn Asn Thr Glu
        435             440             445
```

-continued

```
Thr Phe Arg Pro Gly Gly Gly Asn Met Lys Asp Asn Trp Arg Ser Glu
    450             455                 460

Leu Tyr Lys Tyr Lys Val Val Glu Val Lys Pro Leu Gly Val Ala Pro
465             470                 475                 480

Thr Asn Ala Arg Arg Arg Val Val Glu Arg Glu Lys Arg Ala Val Gly
                485             490                 495

Met Gly Ala Val Phe Leu Gly Phe Leu Gly Ala Ala Gly Ser Thr Met
            500             505                 510

Gly Ala Ala Ser Ile Thr Leu Thr Val Gln Ala Arg Gln Leu Leu Ser
            515             520                 525

Gly Ile Val Gln Gln Gln Ser Asn Leu Leu Lys Ala Ile Glu Ala Gln
        530             535                 540

Gln His Met Leu Lys Leu Thr Val Trp Gly Ile Lys Gln Leu Gln Ala
545             550                 555                 560

Arg Val Leu Ala Leu Glu Arg Tyr Leu Lys Asp Gln Gln Leu Leu Gly
                565             570                 575

Met Trp Gly Cys Ser Gly Lys Leu Ile Cys Thr Thr Asn Val Tyr Trp
            580             585                 590

Asn Ser Ser Trp Ser Asn Lys Thr Tyr Gly Asp Ile Trp Asp Asn Met
            595             600                 605

Thr Trp Met Gln Trp Asp Arg Glu Ile Ser Asn Tyr Thr Glu Ile Ile
    610             615                 620

Tyr Arg Leu Leu Glu Glu Ser Gln Asn Gln Gln Glu Lys Asn Glu Gln
625             630                 635                 640

Asp Leu Leu Ala Leu Asp Arg Trp Asn Ser Leu Trp Asn Trp Phe Asn
                645             650                 655

Ile Thr Asn Trp Leu Trp Tyr Ile Lys Ile Phe Ile Met Ile Val Gly
            660             665                 670

Gly Leu Ile Gly Leu Arg Ile Ile Phe Ala Val Leu Ser Leu Val Asn
            675             680                 685

Arg Val Arg Gln Gly Tyr Ser Pro Leu Ser Phe Gln Thr Leu Ile Pro
    690             695                 700

Ser Pro Arg Gly Pro Asp Arg Pro Gly Arg Ile Glu Glu Glu Gly Gly
705             710                 715                 720

Glu Gln Asp Arg Asn Arg Ser Thr Arg Leu Val Ser Gly Phe Leu Ala
                725             730                 735

Leu Val Trp Asp Asp Leu Arg Ser Leu Cys Leu Phe Ile Tyr His Arg
            740             745                 750

Leu Arg Asp Phe Ile Leu Ile Ala Ala Arg Ala Gly Glu Leu Leu Gly
            755             760                 765

Arg Ser Ser Leu Lys Gly Leu Arg Arg Gly Trp Glu Ala Leu Lys Tyr
    770             775                 780

Leu Gly Ser Leu Val Gln Tyr Trp Gly Leu Glu Leu Lys Arg Ser Ala
785             790                 795                 800

Ile Ser Leu Leu Asp Thr Leu Ala Ile Ala Val Gly Glu Gly Thr Asp
                805             810                 815

Arg Ile Leu Glu Phe Val Leu Gly Ile Cys Arg Ala Ile Arg Asn Ile
            820             825                 830

Pro Thr Arg Ile Arg Gln Gly Phe Glu Thr Ala Leu Leu
            835             840                 845
```

<210> SEQ ID NO 17
<211> LENGTH: 845
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 17

Met Arg Val Met Gly Ile Gln Arg Asn Tyr Pro Gln Trp Trp Ile Trp
1               5                   10                  15

Ser Met Leu Gly Phe Trp Met Leu Met Ile Cys Asn Gly Met Trp Val
            20                  25                  30

Thr Val Tyr Tyr Gly Val Pro Val Trp Lys Glu Ala Lys Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Met
65                  70                  75                  80

Val Leu Lys Asn Val Thr Glu Asn Phe Asn Met Trp Lys Asn Asp Met
                85                  90                  95

Val Asp Gln Met His Glu Asp Val Ile Ser Leu Trp Asp Gln Ser Leu
            100                 105                 110

Lys Pro Cys Val Lys Leu Thr Pro Leu Cys Val Thr Leu His Cys Ser
        115                 120                 125

Thr Tyr Asn Asn Thr His Asn Ile Ser Lys Gly Met Lys Asn Cys Ser
    130                 135                 140

Phe Asn Met Thr Thr Glu Leu Arg Asp Lys Lys Gln Lys Val Asn Ala
145                 150                 155                 160

Leu Phe Tyr Lys Leu Asp Ile Val Gln Leu Asn Lys Asn Gly Arg Gln
                165                 170                 175

Tyr Arg Leu Ile Asn Cys Asn Thr Ser Ala Ile Thr Gln Ala Cys Pro
            180                 185                 190

Lys Val Ser Phe Asp Pro Ile Pro Ile His Tyr Cys Ala Pro Ala Gly
        195                 200                 205

Tyr Ala Ile Leu Lys Cys Asn Asn Lys Thr Phe Asn Gly Thr Gly Pro
    210                 215                 220

Cys Asn Asn Val Ser Thr Val Gln Cys Thr His Gly Ile Lys Pro Val
225                 230                 235                 240

Val Ser Thr Gln Leu Leu Leu Asn Gly Ser Leu Ala Glu Gly Glu Ile
                245                 250                 255

Ile Ile Arg Ser Glu Asn Ile Thr Asn Asn Val Lys Thr Ile Ile Val
            260                 265                 270

His Leu Asn Glu Ser Val Lys Ile Glu Cys Thr Arg Pro Asn Asn Lys
        275                 280                 285

Thr Arg Lys Ser Ile Arg Ile Gly Pro Gly Gln Thr Phe Tyr Ala Thr
    290                 295                 300

Gly Asp Val Ile Gly Asp Ile Arg Glu Ala Tyr Cys Asn Ile Ser Lys
305                 310                 315                 320

Ser Lys Trp Asn Glu Thr Leu Gln Arg Val Ser Lys Lys Leu Lys Glu
                325                 330                 335

Tyr Phe Pro His Lys Asn Ile Thr Phe Gln Pro Ser Ser Gly Gly Asp
            340                 345                 350

Leu Glu Ile Thr Thr His Ser Phe Asn Cys Gly Gly Glu Phe Phe Tyr
        355                 360                 365

Cys Asn Thr Ser Ser Leu Phe Asn Arg Thr Tyr Met Ala Asn Ser Thr
    370                 375                 380
```

-continued

```
Asp Met Ala Asn Ser Thr Glu Thr Asn Ser Thr Arg Thr Ile Thr Ile
385                 390                 395                 400

His Cys Arg Ile Lys Gln Ile Ile Asn Met Trp Gln Glu Val Gly Arg
                405                 410                 415

Ala Met Tyr Ala Pro Pro Ile Ala Gly Asn Ile Thr Cys Ile Ser Asn
                420                 425                 430

Ile Thr Gly Leu Leu Leu Thr Arg Asp Gly Gly Lys Asn Asn Thr Glu
            435                 440                 445

Thr Phe Arg Pro Gly Gly Gly Asn Met Lys Asp Asn Trp Arg Ser Glu
        450                 455                 460

Leu Tyr Lys Tyr Lys Val Val Glu Val Lys Pro Leu Gly Val Ala Pro
465                 470                 475                 480

Thr Asn Ala Arg Arg Arg Val Val Glu Arg Glu Lys Arg Ala Val Gly
                485                 490                 495

Met Gly Ala Val Phe Leu Gly Phe Leu Gly Ala Ala Gly Ser Thr Met
                500                 505                 510

Gly Ala Ala Ser Ile Thr Leu Thr Val Gln Ala Arg Gln Leu Leu Ser
            515                 520                 525

Gly Ile Val Gln Gln Gln Ser Asn Leu Leu Lys Ala Ile Glu Ala Gln
        530                 535                 540

Gln His Met Leu Lys Leu Thr Val Trp Gly Ile Lys Gln Leu Gln Ala
545                 550                 555                 560

Arg Val Leu Ala Leu Glu Arg Tyr Leu Lys Asp Gln Gln Leu Leu Gly
                565                 570                 575

Met Trp Gly Cys Ser Gly Lys Leu Ile Cys Thr Thr Asn Val Tyr Trp
                580                 585                 590

Asn Ser Ser Trp Ser Asn Lys Thr Tyr Gly Asp Ile Trp Asp Asn Met
            595                 600                 605

Thr Trp Met Gln Trp Asp Arg Glu Ile Ser Asn Tyr Thr Glu Ile Ile
        610                 615                 620

Tyr Arg Leu Leu Glu Glu Ser Gln Asn Gln Glu Lys Asn Glu Gln
625                 630                 635                 640

Asp Leu Leu Ala Leu Asp Arg Trp Asn Ser Leu Trp Asn Trp Phe Asn
                645                 650                 655

Ile Thr Asn Trp Leu Trp Tyr Ile Lys Ile Phe Ile Met Ile Val Gly
            660                 665                 670

Gly Leu Ile Gly Leu Arg Ile Ile Phe Ala Val Leu Ser Leu Val Asn
        675                 680                 685

Arg Val Arg Gln Gly Tyr Ser Pro Leu Ser Phe Gln Thr Leu Ile Pro
        690                 695                 700

Ser Pro Arg Gly Pro Asp Arg Pro Gly Arg Ile Glu Glu Glu Gly Gly
705                 710                 715                 720

Glu Gln Asp Arg Asn Arg Ser Thr Arg Leu Val Ser Gly Phe Leu Ala
                725                 730                 735

Leu Val Trp Asp Asp Leu Arg Ser Leu Cys Leu Phe Ile Tyr His Arg
                740                 745                 750

Leu Arg Asp Phe Ile Leu Ile Ala Ala Arg Ala Gly Glu Leu Leu Gly
            755                 760                 765

Arg Ser Ser Leu Lys Gly Leu Arg Arg Gly Trp Glu Ala Leu Lys Tyr
        770                 775                 780

Leu Gly Ser Leu Val Gln Tyr Trp Gly Leu Glu Leu Lys Arg Ser Ala
785                 790                 795                 800

Ile Ser Leu Leu Asp Thr Leu Ala Ile Ala Val Gly Glu Gly Thr Asp
```

```
                        805                810                815

Arg Ile Leu Glu Phe Val Leu Gly Ile Cys Arg Ala Ile Arg Asn Ile
                820                825                830

Pro Thr Arg Ile Arg Gln Gly Phe Glu Thr Ala Leu Leu
        835                840                845

<210> SEQ ID NO 18
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Arg Val Met Gly Ile Gln Arg Asn Tyr Pro Gln Trp Trp Ile Trp
1                5                10                15

Ser Met Leu Gly Phe Trp Met Leu Met Ile Cys Asn Gly Met Trp Val
                20                25                30

Thr Val Tyr Tyr Gly Val Pro Val Trp Lys Glu Ala Lys Thr Thr Leu
                35                40                45

Phe Cys Ala Ser Asp Ala Lys Ala Tyr Glu Lys Glu Val His Asn Val
        50                55                60

Trp Ala Thr His Ala Cys Val Pro Thr Asp Pro Asn Pro Gln Glu Met
65                70                75                80

Val Leu Lys Asn Val Thr Glu Asn Phe Asn Met Trp Lys Asn Asp Met
                85                90                95

Val Asp Gln Met His Glu Asp Val Ile Ser Leu Trp Asp Gln Ser Leu
                100                105                110

Lys Pro Cys Val Lys Leu Thr Pro Leu Cys Val Thr Leu His Cys Ser
        115                120                125

Thr Tyr Asn Asn Thr His Asn Ile Ser Lys Gly Met Lys Asn Cys Ser
        130                135                140

Phe Asn Met Thr Thr Glu Leu Arg Asp Lys Lys Gln Lys Val Asn Ala
145                150                155                160

Leu Phe Tyr Lys Leu Asp Ile Val Gln Leu Asn Lys Asn Gly Arg Gln
                165                170                175

Tyr Arg Leu Ile Asn Cys Asn Thr Ser Ala Ile Thr Gln Ala Cys Pro
                180                185                190

Lys Val Ser Phe Asp Pro Ile Pro Ile His Tyr Cys Ala Pro Ala Gly
        195                200                205

Tyr Ala Ile Leu Lys Cys Asn Asn Lys Thr Phe Asn Gly Thr Gly Pro
        210                215                220

Cys Asn Asn Val Ser Thr Val Gln Cys Thr His Gly Ile Lys Pro Val
225                230                235                240

Val Ser Thr Gln Leu Leu Leu Asn Gly Ser Leu Ala Glu Gly Glu Ile
                245                250                255

Ile Ile Arg Ser Glu Asn Ile Thr Asn Asn Val Lys Thr Ile Ile Val
                260                265                270

His Leu Asn Glu Ser Val Lys Ile Glu Cys Thr Arg Pro Asn Asn Lys
        275                280                285

Thr Arg Lys Ser Ile Arg Ile Gly Pro Gly Gln Thr Phe Tyr Ala Thr
        290                295                300

Gly Asp Val Ile Gly Asp Ile Arg Glu Ala Tyr Cys Asn Ile Asn Lys
305                310                315                320
```

-continued

Ser Lys Trp Asn Glu Thr Leu Gln Arg Val Ser Lys Lys Leu Lys Glu
                325                 330                 335

Tyr Phe Pro His Lys Asn Ile Thr Phe Gln Pro Ser Ser Gly Gly Asp
            340                 345                 350

Leu Glu Ile Thr Thr His Ser Phe Asn Cys Gly Gly Glu Phe Phe Tyr
            355                 360                 365

Cys Asn Thr Ser Ser Leu Phe Asn Arg Thr Tyr Met Ala Asn Ser Thr
370                 375                 380

Asp Met Ala Asn Ser Thr Glu Thr Asn Ser Thr Arg Thr Ile Thr Ile
385                 390                 395                 400

His Cys Arg Ile Lys Gln Ile Ile Asn Met Trp Gln Glu Val Gly Arg
                405                 410                 415

Ala Met Tyr Ala Pro Pro Ile Ala Gly Asn Ile Thr Cys Ile Ser Asn
            420                 425                 430

Ile Thr Gly Leu Leu Leu Thr Arg Asp Gly Gly Lys Asn Asn Thr Glu
            435                 440                 445

Thr Phe Arg Pro Gly Gly Gly Asn Met Lys Asp Asn Trp Arg Ser Glu
        450                 455                 460

Leu Tyr Lys Tyr Lys Val Val Glu Val Lys Pro Leu Gly Val Ala Pro
465                 470                 475                 480

Thr Asn Ala Arg Arg Arg Val Val Glu Arg Glu Lys Arg Ala Val Gly
                485                 490                 495

Met Gly Ala Val Phe Leu Gly Phe Leu Gly Ala Ala Gly Ser Thr Met
            500                 505                 510

Gly Ala Ala Ser Ile Thr Leu Thr Val Gln Ala Arg Gln Leu Leu Ser
            515                 520                 525

Gly Ile Val Gln Gln Gln Ser Asn Leu Leu Lys Ala Ile Glu Ala Gln
        530                 535                 540

Gln His Met Leu Lys Leu Thr Val Trp Gly Ile Lys Gln Leu Gln Ala
545                 550                 555                 560

Arg Val Leu Ala Leu Glu Arg Tyr Leu Lys Asp Gln Gln Leu Leu Gly
                565                 570                 575

Met Trp Gly Cys Ser Gly Lys Leu Ile Cys Thr Thr Asn Val Tyr Trp
            580                 585                 590

Asn Ser Ser Trp Ser Asn Lys Thr Tyr Gly Asp Ile Trp Asp Asn Met
        595                 600                 605

Thr Trp Met Gln Trp Asp Arg Glu Ile Ser Asn Tyr Thr Glu Ile Ile
        610                 615                 620

Tyr Arg Leu Leu Glu Glu Ser Gln Asn Gln Glu Lys Asn Glu Gln
625                 630                 635                 640

Asp Leu Leu Ala Leu Asp Arg Trp Asn Ser Leu Trp Asn Trp Phe Asn
            645                 650                 655

Ile Thr Asn Trp Leu Trp Tyr Ile Lys Ile Phe Ile Met Ile Val Gly
            660                 665                 670

Gly Leu Ile Gly Leu Arg Ile Ile Phe Ala Val Leu Ser Leu Val Asn
            675                 680                 685

Arg Val Arg Gln Gly Tyr Ser Pro Leu Ser Phe Gln Thr Leu Ile Pro
        690                 695                 700

Ser Pro Arg Gly Pro Asp Arg Pro Gly Arg Ile Glu Glu Gly Gly Gly
705                 710                 715                 720

Glu Gln Asp Arg Asn Arg Ser Thr Arg Leu Val Ser Gly Phe Leu Ala
                725                 730                 735

Leu Val Trp Asp Asp Leu Arg Ser Leu Cys Leu Phe Ile Tyr His Arg

-continued

```
                340              345              350

Leu Arg Asp Phe Ile Leu Ile Ala Ala Arg Ala Gly Glu Leu Leu Gly
            755              760              765

Arg Ser Ser Leu Lys Gly Leu Arg Arg Gly Trp Glu Ala Leu Lys Tyr
        770              775              780

Leu Gly Ser Leu Val Gln Tyr Trp Gly Leu Glu Leu Lys Arg Ser Ala
785              790              795              800

Ile Ser Leu Leu Asp Thr Leu Ala Ile Ala Val Gly Glu Gly Thr Asp
                805              810              815

Arg Ile Leu Glu Phe Val Leu Gly Ile Cys Arg Ala Ile Arg His Ile
            820              825              830

Pro Thr Arg Ile Arg Gln Gly Phe Glu Thr Ala Leu Leu
        835              840              845
```

<210> SEQ ID NO 19
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Arg Val Met Gly Ile Gln Arg Asn Tyr Pro Gln Trp Trp Ile Trp
1               5               10               15

Ser Met Leu Gly Phe Trp Met Leu Met Ile Cys Asn Gly Met Trp Val
            20               25               30

Thr Val Tyr Tyr Gly Val Pro Val Trp Lys Glu Ala Lys Thr Thr Leu
        35               40               45

Phe Cys Ala Ser Asp Ala Lys Ala Tyr Glu Lys Glu Val His Asn Val
    50               55               60

Trp Ala Thr His Ala Cys Val Pro Thr Asp Pro Asn Pro Gln Glu Met
65               70               75               80

Val Leu Lys Asn Val Thr Glu Asn Phe Asn Met Trp Lys Asn Asp Met
                85               90               95

Val Asp Gln Met His Glu Asp Val Ile Ser Leu Trp Asp Gln Ser Leu
            100              105              110

Lys Pro Cys Val Lys Leu Thr Pro Leu Cys Val Thr Leu His Cys Ser
        115              120              125

Thr Tyr Asn Asn Thr His Asn Ile Ser Lys Gly Met Lys Asn Cys Ser
    130              135              140

Phe Asn Met Thr Thr Glu Leu Arg Asp Lys Lys Gln Lys Val Asn Ala
145              150              155              160

Leu Phe Tyr Lys Leu Asp Ile Val Gln Leu Asn Lys Asn Gly Arg Gln
                165              170              175

Tyr Arg Leu Ile Asn Cys Asn Thr Ser Ala Ile Thr Gln Ala Cys Pro
            180              185              190

Lys Val Ser Phe Asp Pro Ile Pro Ile His Tyr Cys Ala Pro Ala Gly
        195              200              205

Tyr Ala Ile Leu Lys Cys Asn Asn Lys Thr Phe Asn Gly Thr Gly Pro
    210              215              220

Cys Asn Asn Val Ser Thr Val Gln Cys Thr His Gly Ile Lys Pro Val
225              230              235              240

Val Ser Thr Gln Leu Leu Leu Asn Gly Ser Leu Ala Glu Gly Glu Ile
                245              250              255
```

-continued

```
Ile Ile Arg Ser Glu Asn Ile Thr Asn Asn Val Lys Thr Ile Ile Val
        260                 265                 270

His Leu Asn Glu Ser Val Lys Ile Glu Cys Thr Arg Pro Asn Asn Lys
        275                 280                 285

Thr Arg Lys Ser Ile Arg Ile Gly Pro Gly Gln Thr Phe Tyr Ala Thr
        290                 295                 300

Gly Asp Val Ile Gly Asp Ile Arg Glu Ala Tyr Cys Asn Ile Ser Lys
305                 310                 315                 320

Ser Lys Trp Asn Glu Thr Leu Gln Arg Val Ser Lys Lys Leu Lys Glu
                325                 330                 335

Tyr Phe Pro His Lys Asn Ile Thr Phe Gln Pro Ser Ser Gly Gly Asp
                340                 345                 350

Leu Glu Ile Thr Thr His Ser Phe Asn Cys Gly Gly Glu Phe Phe Tyr
                355                 360                 365

Cys Asn Thr Ser Ser Leu Phe Asn Arg Thr Tyr Met Ala Asn Ser Thr
        370                 375                 380

Asp Met Ala Asn Ser Thr Glu Thr Asn Ser Thr Arg Thr Ile Thr Ile
385                 390                 395                 400

His Cys Arg Ile Lys Gln Ile Ile Asn Met Trp Gln Glu Val Gly Arg
                405                 410                 415

Ala Met Tyr Ala Pro Pro Ile Ala Gly Asn Ile Thr Cys Ile Ser Asn
                420                 425                 430

Ile Thr Gly Leu Leu Leu Thr Arg Asp Gly Gly Lys Asn Asn Thr Glu
                435                 440                 445

Thr Phe Arg Pro Gly Gly Gly Asn Met Lys Asp Asn Trp Arg Ser Glu
        450                 455                 460

Leu Tyr Lys Tyr Lys Val Val Glu Val Lys Pro Leu Gly Val Ala Pro
465                 470                 475                 480

Thr Asn Ala Arg Arg Arg Val Val Glu Arg Glu Lys Arg Ala Val Gly
                485                 490                 495

Met Gly Ala Val Phe Leu Gly Phe Leu Gly Ala Ala Gly Ser Thr Met
                500                 505                 510

Gly Ala Ala Ser Ile Thr Leu Thr Val Gln Ala Arg Gln Leu Leu Ser
        515                 520                 525

Gly Ile Val Gln Gln Gln Ser Asn Leu Leu Lys Ala Ile Glu Ala Gln
        530                 535                 540

Gln His Met Leu Lys Leu Thr Val Trp Gly Ile Lys Gln Leu Gln Ala
545                 550                 555                 560

Arg Val Leu Ala Leu Glu Arg Tyr Leu Lys Asp Gln Gln Leu Leu Gly
                565                 570                 575

Met Trp Gly Cys Ser Gly Lys Leu Ile Cys Thr Thr Asn Val Tyr Trp
                580                 585                 590

Asn Ser Ser Trp Ser Asn Lys Thr Tyr Gly Asp Ile Trp Asp Asn Met
        595                 600                 605

Thr Trp Met Gln Trp Asp Arg Glu Ile Ser Asn Tyr Thr Glu Ile Ile
        610                 615                 620

Tyr Arg Leu Leu Glu Glu Ser Gln Asn Gln Gln Glu Lys Asn Glu Gln
625                 630                 635                 640

Asp Leu Leu Ala Leu Asp Arg Trp Asn Ser Leu Trp Asn Trp Phe Asn
                645                 650                 655

Ile Thr Asn Trp Leu Trp Tyr Ile Lys Ile Phe Ile Met Ile Val Gly
                660                 665                 670

Gly Leu Ile Gly Leu Arg Ile Ile Phe Ala Val Leu Ser Leu Val Asn
```

```
              675                 680                 685
Arg Val Arg Gln Gly Tyr Ser Pro Leu Ser Phe Gln Thr Leu Ile Pro
      690                 695                 700

Ser Pro Arg Gly Pro Asp Arg Pro Gly Arg Ile Glu Glu Gly Gly Gly
705                 710                 715                 720

Glu Gln Asp Arg Asn Arg Ser Thr Arg Leu Val Ser Gly Phe Leu Ala
                  725                 730                 735

Leu Val Trp Asp Asp Leu Arg Ser Leu Cys Leu Phe Ile Tyr His Arg
                  740                 745                 750

Leu Arg Asp Phe Ile Leu Ile Ala Ala Arg Ala Gly Glu Leu Leu Gly
                  755                 760                 765

Arg Ser Ser Leu Lys Gly Leu Arg Arg Gly Trp Glu Ala Leu Lys Tyr
      770                 775                 780

Leu Gly Ser Leu Val Gln Tyr Trp Gly Leu Glu Leu Lys Arg Ser Ala
785                 790                 795                 800

Ile Ser Leu Leu Asp Thr Leu Ala Ile Ala Val Gly Glu Gly Thr Asp
                  805                 810                 815

Arg Ile Leu Glu Phe Val Leu Gly Ile Cys Arg Ala Ile Arg His Ile
                  820                 825                 830

Pro Thr Arg Ile Arg Gln Gly Phe Glu Thr Ala Leu Leu
          835                 840                 845
```

<210> SEQ ID NO 20
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                  20                  25                  30

Tyr Tyr Gly Val Pro Val Trp Lys Glu Ala Lys Thr Thr Leu Phe Cys
          35                  40                  45

Ala Ser Asp Ala Lys Ala Tyr Glu Lys Lys Val His Asn Val Trp Ala
      50                  55                  60

Thr His Ala Cys Val Pro Thr Asp Pro Asn Pro Gln Glu Met Val Leu
65                  70                  75                  80

Lys Asn Val Thr Glu Asn Phe Asn Met Trp Lys Asn Asp Met Val Asp
                  85                  90                  95

Gln Met His Glu Asp Val Ile Ser Leu Trp Asp Gln Ser Leu Lys Pro
                  100                 105                 110

Cys Val Lys Leu Thr Pro Leu Cys Val Thr Leu Asn Cys Thr Asn Ala
          115                 120                 125

Thr Ala Ser Asn Ser Ser Ile Ile Glu Gly Met Lys Asn Cys Ser Phe
      130                 135                 140

Asn Ile Thr Thr Glu Leu Arg Asp Lys Arg Glu Lys Lys Asn Ala Leu
145                 150                 155                 160

Phe Tyr Lys Leu Asp Ile Val Gln Leu Asp Gly Asn Ser Ser Gln Tyr
                  165                 170                 175

Arg Leu Ile Asn Cys Asn Thr Ser Val Ile Thr Gln Ala Cys Pro Lys
                  180                 185                 190
```

```
Val Ser Phe Asp Pro Ile Pro Ile His Tyr Cys Ala Pro Ala Gly Tyr
        195             200             205
Ala Ile Leu Lys Cys Asn Asn Lys Thr Phe Thr Gly Thr Gly Pro Cys
        210             215             220
Asn Asn Val Ser Thr Val Gln Cys Thr His Gly Ile Lys Pro Val Val
225             230             235             240
Ser Thr Gln Leu Leu Leu Asn Gly Ser Leu Ala Glu Gly Glu Ile Ile
            245             250             255
Ile Arg Ser Glu Asn Ile Thr Asn Asn Val Lys Thr Ile Ile Val His
            260             265             270
Leu Asn Glu Ser Val Lys Ile Glu Cys Thr Arg Pro Asn Asn Lys Thr
            275             280             285
Arg Thr Ser Ile Arg Ile Gly Pro Gly Gln Trp Phe Tyr Ala Thr Gly
        290             295             300
Gln Val Ile Gly Asp Ile Arg Glu Ala Tyr Cys Asn Ile Asn Glu Ser
305             310             315             320
Lys Trp Asn Glu Thr Leu Gln Arg Val Ser Lys Lys Leu Lys Glu Tyr
            325             330             335
Phe Pro His Lys Asn Ile Thr Phe Gln Pro Ser Ser Gly Gly Asp Leu
            340             345             350
Glu Ile Thr Thr His Ser Phe Asn Cys Gly Gly Glu Phe Phe Tyr Cys
            355             360             365
Asn Thr Ser Ser Leu Phe Asn Arg Thr Tyr Met Ala Asn Ser Thr Asp
        370             375             380
Met Ala Asn Ser Thr Glu Thr Asn Ser Thr Arg Thr Ile Thr Ile His
385             390             395             400
Cys Arg Ile Lys Gln Ile Ile Asn Met Trp Gln Glu Val Gly Arg Ala
            405             410             415
Met Tyr Ala Pro Pro Ile Ala Gly Asn Ile Thr Cys Ile Ser Asn Ile
            420             425             430
Thr Gly Leu Leu Leu Thr Arg Asp Gly Gly Lys Asn Asn Thr Glu Thr
            435             440             445
Phe Arg Pro Gly Gly Gly Asn Met Lys Asp Asn Trp Arg Ser Glu Leu
        450             455             460
Tyr Lys Tyr Lys Val Val Lys Ile Glu Pro Leu Gly Val Ala Pro Thr
465             470             475             480
Arg Cys Lys Arg Arg Val Val Gly Arg Arg Arg Arg Arg Arg Ala Val
            485             490             495
Gly Ile Gly Ala Val Phe Leu Gly Phe Leu Gly Ala Ala Gly Ser Thr
            500             505             510
Met Gly Ala Ala Ser Met Thr Leu Thr Val Gln Ala Arg Asn Leu Leu
            515             520             525
Ser Gly Ile Val Gln Gln Ser Asn Leu Leu Arg Ala Pro Glu Ala
        530             535             540
Gln Gln His Leu Leu Lys Leu Thr Val Trp Gly Ile Lys Gln Leu Gln
545             550             555             560
Ala Arg Val Leu Ala Val Glu Arg Tyr Leu Arg Asp Gln Gln Leu Leu
            565             570             575
Gly Ile Trp Gly Cys Ser Gly Lys Leu Ile Cys Cys Thr Asn Val Pro
            580             585             590
Trp Asn Ser Ser Trp Ser Asn Arg Asn Leu Ser Glu Ile Trp Asp Asn
            595             600             605
Met Thr Trp Leu Gln Trp Asp Lys Glu Ile Ser Asn Tyr Thr Gln Ile
```

-continued

```
             610              615              620
Ile Tyr Gly Leu Leu Glu Glu Ser Gln Asn Gln Gln Glu Lys Asn Glu
625              630              635              640

Gln Asp Leu Leu Ala Leu Asp
             645

<210> SEQ ID NO 21
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Pro Met Gly Ser Leu Gln Pro Leu Ala Thr Leu Tyr Leu Leu Gly
1               5                10               15

Met Leu Val Ala Ser Val Leu Ala Ala Glu Asn Leu Trp Val Thr Val
             20               25               30

Tyr Tyr Gly Val Pro Val Trp Lys Glu Ala Lys Thr Thr Leu Phe Cys
             35               40               45

Ala Ser Asp Ala Lys Ala Tyr Glu Lys Lys Val His Asn Val Trp Ala
             50               55               60

Thr His Ala Cys Val Pro Thr Asp Pro Asn Pro Gln Glu Met Val Leu
65               70               75               80

Lys Asn Val Thr Glu Asn Phe Asn Met Trp Lys Asn Asp Met Val Asp
             85               90               95

Gln Met His Glu Asp Val Ile Ser Leu Trp Asp Gln Ser Leu Lys Pro
             100              105              110

Cys Val Lys Leu Thr Pro Leu Cys Val Thr Leu His Cys Ser Thr Tyr
             115              120              125

Asn Asn Thr His Asn Ile Ser Lys Gly Met Lys Asn Cys Ser Phe Asn
             130              135              140

Ala Thr Thr Glu Leu Arg Asp Lys Lys Gln Lys Val Asn Ala Leu Phe
145              150              155              160

Tyr Lys Leu Asp Ile Val Gln Leu Asn Lys Asn Gly Arg Gln Tyr Arg
             165              170              175

Leu Ile Asn Cys Asn Thr Ser Val Ile Thr Gln Ala Cys Pro Lys Val
             180              185              190

Ser Phe Asp Pro Ile Pro Ile His Tyr Cys Ala Pro Ala Gly Tyr Ala
             195              200              205

Ile Leu Lys Cys Asn Asn Lys Thr Phe Asn Gly Thr Gly Pro Cys Asn
             210              215              220

Asn Val Ser Thr Val Gln Cys Thr His Gly Ile Lys Pro Val Val Ser
225              230              235              240

Thr Gln Leu Leu Leu Asn Gly Ser Leu Ala Glu Gly Glu Ile Ile Ile
             245              250              255

Arg Ser Glu Asn Ile Thr Asn Asn Val Lys Thr Ile Ile Val His Leu
             260              265              270

Asn Glu Ser Val Lys Ile Glu Cys Thr Arg Pro Asn Asn Lys Thr Arg
             275              280              285

Thr Ser Ile Arg Ile Gly Pro Gly Gln Thr Phe Tyr Ala Thr Gly Gln
             290              295              300

Val Ile Gly Asp Ile Arg Glu Ala Tyr Cys Asn Ile Asn Lys Ser Lys
305              310              315              320
```

-continued

```
Trp Asn Glu Thr Leu Gln Arg Val Ser Lys Lys Leu Lys Glu Tyr Phe
                325                 330                 335

Pro His Lys Asn Ile Thr Phe Gln Pro Ser Ser Gly Gly Asp Leu Glu
            340                 345                 350

Ile Thr Thr His Ser Phe Asn Cys Gly Gly Glu Phe Phe Tyr Cys Asn
            355                 360                 365

Thr Ser Ser Leu Phe Asn Arg Thr Tyr Met Ala Asn Ser Thr Asp Met
        370                 375                 380

Ala Asn Ser Thr Glu Thr Asn Ser Thr Arg Thr Ile Thr Ile His Cys
385                 390                 395                 400

Arg Ile Lys Gln Ile Ile Asn Met Trp Gln Glu Val Gly Arg Ala Met
                405                 410                 415

Tyr Ala Pro Pro Ile Ala Gly Asn Ile Thr Cys Ile Ser Asn Ile Thr
            420                 425                 430

Gly Leu Leu Leu Thr Arg Asp Gly Gly Lys Asn Asn Thr Glu Thr Phe
            435                 440                 445

Arg Pro Gly Gly Gly Asn Met Lys Asp Asn Trp Arg Ser Glu Leu Tyr
        450                 455                 460

Lys Tyr Lys Val Val Lys Ile Glu Pro Leu Gly Val Ala Pro Thr Arg
465                 470                 475                 480

Cys Lys Arg Arg Val Val Gly Arg Arg Arg Arg Arg Ala Val Gly
                485                 490                 495

Ile Gly Ala Val Phe Leu Gly Phe Leu Gly Ala Ala Gly Ser Thr Met
            500                 505                 510

Gly Ala Ala Ser Met Thr Leu Thr Val Gln Ala Arg Asn Leu Leu Ser
            515                 520                 525

Gly Ile Val Gln Gln Gln Ser Asn Leu Leu Arg Ala Pro Glu Ala Gln
        530                 535                 540

Gln His Leu Leu Lys Leu Thr Val Trp Gly Ile Lys Gln Leu Gln Ala
545                 550                 555                 560

Arg Val Leu Ala Val Glu Arg Tyr Leu Arg Asp Gln Gln Leu Leu Gly
                565                 570                 575

Ile Trp Gly Cys Ser Gly Lys Leu Ile Cys Cys Thr Asn Val Pro Trp
            580                 585                 590

Asn Ser Ser Trp Ser Asn Arg Asn Leu Ser Glu Ile Trp Asp Asn Met
            595                 600                 605

Thr Trp Leu Gln Trp Asp Lys Glu Ile Ser Asn Tyr Thr Gln Ile Ile
        610                 615                 620

Tyr Gly Leu Leu Glu Glu Ser Gln Asn Gln Gln Glu Lys Asn Glu Gln
625                 630                 635                 640

Asp Leu Leu Ala Leu Asp
                645
```

```
<210> SEQ ID NO 22
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30
```

-continued

```
Tyr Tyr Gly Val Pro Val Trp Lys Glu Ala Lys Thr Thr Leu Phe Cys
        35              40              45

Ala Ser Asp Ala Lys Ala Tyr Glu Lys Lys Val His Asn Val Trp Ala
    50              55              60

Thr His Ala Cys Val Pro Thr Asp Pro Asn Pro Gln Glu Met Val Leu
65              70              75              80

Lys Asn Val Thr Glu Asn Phe Asn Met Trp Lys Asn Asp Met Val Asp
                85              90              95

Gln Met His Glu Asp Val Ile Ser Leu Trp Asp Gln Ser Leu Lys Pro
            100             105             110

Cys Val Lys Leu Thr Pro Leu Cys Val Thr Leu His Cys Ser Thr Tyr
        115             120             125

Asn Asn Thr His Asn Ile Ser Lys Gly Met Lys Asn Cys Ser Phe Asn
    130             135             140

Ala Thr Thr Glu Leu Arg Asp Lys Lys Gln Lys Val Asn Ala Leu Phe
145             150             155             160

Tyr Lys Leu Asp Ile Val Gln Leu Asn Lys Asn Gly Arg Gln Tyr Arg
                165             170             175

Leu Ile Asn Cys Asn Thr Ser Val Ile Thr Gln Ala Cys Pro Lys Val
            180             185             190

Ser Phe Asp Pro Ile Pro Ile His Tyr Cys Ala Pro Ala Gly Tyr Ala
        195             200             205

Ile Leu Lys Cys Asn Asn Lys Thr Phe Asn Gly Thr Gly Pro Cys Asn
    210             215             220

Asn Val Ser Thr Val Gln Cys Thr His Gly Ile Lys Pro Val Val Ser
225             230             235             240

Thr Gln Leu Leu Leu Asn Gly Ser Leu Ala Glu Gly Glu Ile Ile Ile
                245             250             255

Arg Ser Glu Asn Ile Thr Asn Asn Val Lys Thr Ile Ile Val His Leu
            260             265             270

Asn Glu Ser Val Lys Ile Glu Cys Thr Arg Pro Asn Asn Lys Thr Arg
        275             280             285

Thr Ser Ile Arg Ile Gly Pro Gly Gln Thr Phe Tyr Ala Thr Gly Gln
    290             295             300

Val Ile Gly Asp Ile Arg Glu Ala Tyr Cys Asn Ile Ser Lys Ser Lys
305             310             315             320

Trp Asn Glu Thr Leu Gln Arg Val Ser Lys Lys Leu Lys Glu Tyr Phe
                325             330             335

Pro His Lys Asn Ile Thr Phe Gln Pro Ser Ser Gly Gly Asp Leu Glu
            340             345             350

Ile Thr Thr His Ser Phe Asn Cys Gly Gly Glu Phe Phe Tyr Cys Asn
        355             360             365

Thr Ser Ser Leu Phe Asn Arg Thr Tyr Met Ala Asn Ser Thr Asp Met
    370             375             380

Ala Asn Ser Thr Glu Thr Asn Ser Thr Arg Thr Ile Thr Ile His Cys
385             390             395             400

Arg Ile Lys Gln Ile Ile Asn Met Trp Gln Glu Val Gly Arg Ala Met
                405             410             415

Tyr Ala Pro Pro Ile Ala Gly Asn Ile Thr Cys Ile Ser Asn Ile Thr
            420             425             430

Gly Leu Leu Leu Thr Arg Asp Gly Gly Lys Asn Asn Thr Glu Thr Phe
        435             440             445
```

```
Arg Pro Gly Gly Gly Asn Met Lys Asp Asn Trp Arg Ser Glu Leu Tyr
    450                 455                 460

Lys Tyr Lys Val Val Lys Ile Glu Pro Leu Gly Val Ala Pro Thr Arg
465                 470                 475                 480

Cys Lys Arg Arg Val Val Gly Arg Arg Arg Arg Arg Ala Val Gly
                485                 490                 495

Ile Gly Ala Val Phe Leu Gly Phe Leu Gly Ala Ala Gly Ser Thr Met
                500                 505                 510

Gly Ala Ala Ser Met Thr Leu Thr Val Gln Ala Arg Asn Leu Leu Ser
                515                 520                 525

Gly Ile Val Gln Gln Gln Ser Asn Leu Leu Arg Ala Pro Glu Ala Gln
                530                 535                 540

Gln His Leu Leu Lys Leu Thr Val Trp Gly Ile Lys Gln Leu Gln Ala
545                 550                 555                 560

Arg Val Leu Ala Val Glu Arg Tyr Leu Arg Asp Gln Gln Leu Leu Gly
                565                 570                 575

Ile Trp Gly Cys Ser Gly Lys Leu Ile Cys Cys Thr Asn Val Pro Trp
                580                 585                 590

Asn Ser Ser Trp Ser Asn Arg Asn Leu Ser Glu Ile Trp Asp Asn Met
                595                 600                 605

Thr Trp Leu Gln Trp Asp Lys Glu Ile Ser Asn Tyr Thr Gln Ile Ile
                610                 615                 620

Tyr Gly Leu Leu Glu Glu Ser Gln Asn Gln Gln Glu Lys Asn Glu Gln
625                 630                 635                 640

Asp Leu Leu Ala Leu Asp
                645

<210> SEQ ID NO 23
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Lys Val His Asn Val Trp Ala
        50                  55                  60

Thr His Ala Cys Val Pro Thr Asp Pro Asn Pro Gln Glu Met Val Leu
65                  70                  75                  80

Lys Asn Val Thr Glu Asn Phe Asn Met Trp Lys Asn Asp Met Val Asp
                85                  90                  95

Gln Met His Glu Asp Val Ile Ser Leu Trp Asp Gln Ser Leu Lys Pro
                100                 105                 110

Cys Val Lys Leu Thr Pro Leu Cys Val Thr Leu His Cys Ser Thr Tyr
            115                 120                 125

Asn Asn Thr His Asn Ile Ser Lys Gly Met Lys Asn Cys Ser Phe Asn
        130                 135                 140

Met Thr Thr Glu Leu Arg Asp Lys Lys Gln Lys Val Asn Ala Leu Phe
145                 150                 155                 160
```

-continued

```
Tyr Lys Leu Asp Ile Val Gln Leu Asn Lys Asn Gly Arg Gln Tyr Arg
                165                 170                 175

Leu Ile Asn Cys Asn Thr Ser Ala Ile Thr Gln Ala Cys Pro Lys Val
            180                 185                 190

Ser Phe Asp Pro Ile Pro Ile His Tyr Cys Ala Pro Ala Gly Tyr Ala
        195                 200                 205

Ile Leu Lys Cys Asn Asn Lys Thr Phe Asn Gly Thr Gly Pro Cys Asn
    210                 215                 220

Asn Val Ser Thr Val Gln Cys Thr His Gly Ile Lys Pro Val Val Ser
225                 230                 235                 240

Thr Gln Leu Leu Leu Asn Gly Ser Leu Ala Glu Gly Glu Ile Ile Ile
                245                 250                 255

Arg Ser Glu Asn Ile Thr Asn Asn Val Lys Thr Ile Ile Val His Leu
            260                 265                 270

Asn Glu Ser Val Lys Ile Glu Cys Thr Arg Pro Asn Asn Lys Thr Arg
        275                 280                 285

Lys Ser Ile Arg Ile Gly Pro Gly Gln Thr Phe Tyr Ala Thr Gly Asp
    290                 295                 300

Val Ile Gly Asp Ile Arg Glu Ala Tyr Cys Asn Ile Asn Lys Ser Lys
305                 310                 315                 320

Trp Asn Glu Thr Leu Gln Arg Val Ser Lys Lys Leu Lys Glu Tyr Phe
                325                 330                 335

Pro His Lys Asn Ile Thr Phe Gln Pro Ser Ser Gly Gly Asp Leu Glu
            340                 345                 350

Ile Thr Thr His Ser Phe Asn Cys Gly Gly Glu Phe Phe Tyr Cys Asn
        355                 360                 365

Thr Ser Ser Leu Phe Asn Arg Thr Tyr Met Ala Asn Ser Thr Asp Met
    370                 375                 380

Ala Asn Ser Thr Glu Thr Asn Ser Thr Arg Thr Ile Thr Ile His Cys
385                 390                 395                 400

Arg Ile Lys Gln Ile Ile Asn Met Trp Gln Glu Val Gly Arg Ala Met
                405                 410                 415

Tyr Ala Pro Pro Ile Ala Gly Asn Ile Thr Cys Ile Ser Asn Ile Thr
            420                 425                 430

Gly Leu Leu Leu Thr Arg Asp Gly Gly Lys Asn Asn Thr Glu Thr Phe
        435                 440                 445

Arg Pro Gly Gly Gly Asn Met Lys Asp Asn Trp Arg Ser Glu Leu Tyr
    450                 455                 460

Lys Tyr Lys Val Val Lys Ile Glu Pro Leu Gly Val Ala Pro Thr Arg
465                 470                 475                 480

Cys Lys Arg Arg Val Val Gly Arg Arg Arg Arg Arg Ala Val Gly
            485                 490                 495

Ile Gly Ala Val Phe Leu Gly Phe Leu Gly Ala Ala Gly Ser Thr Met
        500                 505                 510

Gly Ala Ala Ser Met Thr Leu Thr Val Gln Ala Arg Asn Leu Leu Ser
        515                 520                 525

Gly Ile Val Gln Gln Gln Ser Asn Leu Leu Arg Ala Pro Glu Ala Gln
    530                 535                 540

Gln His Leu Leu Lys Leu Thr Val Trp Gly Ile Lys Gln Leu Gln Ala
545                 550                 555                 560

Arg Val Leu Ala Val Glu Arg Tyr Leu Arg Asp Gln Gln Leu Leu Gly
                565                 570                 575
```

```
Ile Trp Gly Cys Ser Gly Lys Leu Ile Cys Cys Thr Asn Val Pro Trp
            580                 585                 590

Asn Ser Ser Trp Ser Asn Arg Asn Leu Ser Glu Ile Trp Asp Asn Met
            595                 600                 605

Thr Trp Leu Gln Trp Asp Lys Glu Ile Ser Asn Tyr Thr Gln Ile Ile
        610                 615                 620

Tyr Gly Leu Leu Glu Glu Ser Gln Asn Gln Gln Glu Lys Asn Glu Gln
625                 630                 635                 640

Asp Leu Leu Ala Leu Asp
                645

<210> SEQ ID NO 24
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Pro Met Gly Ser Leu Gln Pro Leu Ala Thr Leu Tyr Leu Leu Gly
1                   5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Lys Val His Asn Val Trp Ala
        50                  55                  60

Thr His Ala Cys Val Pro Thr Asp Pro Asn Pro Gln Glu Met Val Leu
65                  70                  75                  80

Lys Asn Val Thr Glu Asn Phe Asn Met Trp Lys Asn Asp Met Val Asp
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu His Cys Ser Thr Tyr
            115                 120                 125

Asn Asn Thr His Asn Ile Ser Lys Gly Met Lys Asn Cys Ser Phe Asn
        130                 135                 140

Met Thr Thr Glu Leu Arg Asp Lys Lys Gln Lys Val Asn Ala Leu Phe
145                 150                 155                 160

Tyr Lys Leu Asp Ile Val Gln Leu Asn Lys Asn Gly Arg Gln Tyr Arg
                165                 170                 175

Leu Ile Asn Cys Asn Thr Ser Ala Ile Thr Gln Ala Cys Pro Lys Val
            180                 185                 190

Ser Phe Asp Pro Ile Pro Ile His Tyr Cys Ala Pro Ala Gly Tyr Ala
            195                 200                 205

Ile Leu Lys Cys Asn Asn Lys Thr Phe Asn Gly Thr Gly Pro Cys Asn
        210                 215                 220

Asn Val Ser Thr Val Gln Cys Thr His Gly Ile Lys Pro Val Val Ser
225                 230                 235                 240

Thr Gln Leu Leu Leu Asn Gly Ser Leu Ala Glu Gly Glu Ile Ile Ile
                245                 250                 255

Arg Ser Glu Asn Ile Thr Asn Asn Val Lys Thr Ile Ile Val His Leu
            260                 265                 270

Asn Glu Ser Val Lys Ile Glu Cys Thr Arg Pro Asn Asn Lys Thr Arg
            275                 280                 285
```

-continued

```
Lys Ser Ile Arg Ile Gly Pro Gly Gln Thr Phe Tyr Ala Thr Gly Asp
    290                 295                 300

Val Ile Gly Asp Ile Arg Glu Ala Tyr Cys Asn Ile Ser Lys Ser Lys
305                 310                 315                 320

Trp Asn Glu Thr Leu Gln Arg Val Ser Lys Lys Leu Lys Glu Tyr Phe
                325                 330                 335

Pro His Lys Asn Ile Thr Phe Gln Pro Ser Ser Gly Gly Asp Leu Glu
                340                 345                 350

Ile Thr Thr His Ser Phe Asn Cys Gly Gly Glu Phe Phe Tyr Cys Asn
                355                 360                 365

Thr Ser Ser Leu Phe Asn Arg Thr Tyr Met Ala Asn Ser Thr Asp Met
    370                 375                 380

Ala Asn Ser Thr Glu Thr Asn Ser Thr Arg Thr Ile Thr Ile His Cys
385                 390                 395                 400

Arg Ile Lys Gln Ile Ile Asn Met Trp Gln Glu Val Gly Arg Ala Met
                405                 410                 415

Tyr Ala Pro Pro Ile Ala Gly Asn Ile Thr Cys Ile Ser Asn Ile Thr
                420                 425                 430

Gly Leu Leu Leu Thr Arg Asp Gly Gly Lys Asn Asn Thr Glu Thr Phe
                435                 440                 445

Arg Pro Gly Gly Gly Asn Met Lys Asp Asn Trp Arg Ser Glu Leu Tyr
    450                 455                 460

Lys Tyr Lys Val Val Lys Ile Glu Pro Leu Gly Val Ala Pro Thr Arg
465                 470                 475                 480

Cys Lys Arg Arg Val Val Gly Arg Arg Arg Arg Arg Ala Val Gly
                485                 490                 495

Ile Gly Ala Val Phe Leu Gly Phe Leu Gly Ala Ala Gly Ser Thr Met
                500                 505                 510

Gly Ala Ala Ser Met Thr Leu Thr Val Gln Ala Arg Asn Leu Leu Ser
                515                 520                 525

Gly Ile Val Gln Gln Gln Ser Asn Leu Leu Arg Ala Pro Glu Ala Gln
    530                 535                 540

Gln His Leu Leu Lys Leu Thr Val Trp Gly Ile Lys Gln Leu Gln Ala
545                 550                 555                 560

Arg Val Leu Ala Val Glu Arg Tyr Leu Arg Asp Gln Gln Leu Leu Gly
                565                 570                 575

Ile Trp Gly Cys Ser Gly Lys Leu Ile Cys Cys Thr Asn Val Pro Trp
                580                 585                 590

Asn Ser Ser Trp Ser Asn Arg Asn Leu Ser Glu Ile Trp Asp Asn Met
                595                 600                 605

Thr Trp Leu Gln Trp Asp Lys Glu Ile Ser Asn Tyr Thr Gln Ile Ile
    610                 615                 620

Tyr Gly Leu Leu Glu Glu Ser Gln Asn Gln Gln Glu Lys Asn Glu Gln
625                 630                 635                 640

Asp Leu Leu Ala Leu Asp
                645
```

```
<210> SEQ ID NO 25
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 25

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Lys Val His Asn Val Trp Ala
    50                  55                  60

Thr His Ala Cys Val Pro Thr Asp Pro Asn Pro Gln Glu Met Val Leu
65                  70                  75                  80

Lys Asn Val Thr Glu Asn Phe Asn Met Trp Lys Asn Asp Met Val Asp
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu His Cys Ser Thr Tyr
            115                 120                 125

Asn Asn Thr His Asn Ile Ser Lys Gly Met Lys Asn Cys Ser Phe Asn
    130                 135                 140

Met Thr Thr Glu Leu Arg Asp Lys Lys Gln Lys Val Asn Ala Leu Phe
145                 150                 155                 160

Tyr Lys Leu Asp Ile Val Gln Leu Asn Lys Asn Gly Arg Gln Tyr Arg
                165                 170                 175

Leu Ile Asn Cys Asn Thr Ser Ala Ile Thr Gln Ala Cys Pro Lys Val
            180                 185                 190

Ser Phe Asp Pro Ile Pro Ile His Tyr Cys Ala Pro Ala Gly Tyr Ala
            195                 200                 205

Ile Leu Lys Cys Asn Asn Lys Thr Phe Asn Gly Thr Gly Pro Cys Asn
    210                 215                 220

Asn Val Ser Thr Val Gln Cys Thr His Gly Ile Lys Pro Val Val Ser
225                 230                 235                 240

Thr Gln Leu Leu Leu Asn Gly Ser Leu Ala Glu Gly Glu Ile Ile Ile
            245                 250                 255

Arg Ser Glu Asn Ile Thr Asn Asn Val Lys Thr Ile Ile Val His Leu
            260                 265                 270

Asn Glu Ser Val Lys Ile Glu Cys Thr Arg Pro Asn Asn Lys Thr Arg
            275                 280                 285

Lys Ser Ile Arg Ile Gly Pro Gly Gln Thr Phe Tyr Ala Thr Gly Asp
    290                 295                 300

Val Ile Gly Asp Ile Arg Glu Ala Tyr Cys Asn Ile Asn Lys Ser Lys
305                 310                 315                 320

Trp Asn Glu Thr Leu Gln Arg Val Ser Lys Lys Leu Lys Glu Tyr Phe
            325                 330                 335

Pro His Lys Asn Ile Thr Phe Gln Pro Ser Ser Gly Gly Asp Leu Glu
            340                 345                 350

Ile Thr Thr His Ser Phe Asn Cys Gly Gly Glu Phe Phe Tyr Cys Asn
        355                 360                 365

Thr Ser Ser Leu Phe Asn Arg Thr Tyr Met Ala Asn Ser Thr Asp Met
    370                 375                 380

Ala Asn Ser Thr Glu Thr Asn Ser Thr Arg Thr Ile Thr Ile His Cys
385                 390                 395                 400

Arg Ile Lys Gln Ile Ile Asn Met Trp Gln Glu Val Gly Arg Ala Met
            405                 410                 415
```

```
Tyr Ala Pro Pro Ile Ala Gly Asn Ile Thr Cys Ile Ser Asn Ile Thr
            420                 425                 430

Gly Leu Leu Leu Thr Arg Asp Gly Gly Lys Asn Asn Thr Glu Thr Phe
            435                 440                 445

Arg Pro Gly Gly Gly Asn Met Lys Asp Asn Trp Arg Ser Glu Leu Tyr
            450                 455                 460

Lys Tyr Lys Val Val Lys Ile Glu Pro Leu Gly Val Ala Pro Thr Arg
465                 470                 475                 480

Cys Lys Arg Arg Val Val Gly Arg Arg Arg Arg Arg Ala Val Gly
                485                 490                 495

Ile Gly Ala Val Phe Leu Gly Phe Leu Gly Ala Ala Gly Ser Thr Met
            500                 505                 510

Gly Ala Ala Ser Ile Thr Leu Thr Val Gln Ala Arg Asn Leu Leu Ser
            515                 520                 525

Gly Ile Val Gln Gln Gln Ser Asn Leu Leu Arg Ala Pro Glu Ala Gln
            530                 535                 540

Gln His Leu Leu Lys Leu Thr Val Trp Gly Ile Lys Gln Leu Gln Ala
545                 550                 555                 560

Arg Val Leu Ala Val Glu Arg Tyr Leu Lys Asp Gln Gln Leu Leu Gly
                565                 570                 575

Ile Trp Gly Cys Ser Gly Lys Leu Ile Cys Cys Thr Asn Val Pro Trp
            580                 585                 590

Asn Ser Ser Trp Ser Asn Arg Asn Leu Ser Glu Ile Trp Asp Asn Met
            595                 600                 605

Thr Trp Leu Gln Trp Asp Lys Glu Ile Ser Asn Tyr Thr Gln Ile Ile
            610                 615                 620

Tyr Arg Leu Leu Glu Glu Ser Gln Asn Gln Gln Glu Lys Asn Glu Gln
625                 630                 635                 640

Asp Leu Leu Ala Leu Asp
                645
```

<210> SEQ ID NO 26
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Lys Val His Asn Val Trp Ala
            50                  55                  60

Thr His Ala Cys Val Pro Thr Asp Pro Asn Pro Gln Glu Met Val Leu
65                  70                  75                  80

Lys Asn Val Thr Glu Asn Phe Asn Met Trp Lys Asn Asp Met Val Asp
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu His Cys Ser Thr Tyr
```

-continued

```
        115                 120                 125

Asn Asn Thr His Asn Ile Ser Lys Gly Met Lys Asn Cys Ser Phe Asn
    130                 135                 140

Met Thr Thr Glu Leu Arg Asp Lys Lys Gln Lys Val Asn Ala Leu Phe
145                 150                 155                 160

Tyr Lys Leu Asp Ile Val Gln Leu Asn Lys Asn Gly Arg Gln Tyr Arg
                165                 170                 175

Leu Ile Asn Cys Asn Thr Ser Ala Ile Thr Gln Ala Cys Pro Lys Val
                180                 185                 190

Ser Phe Asp Pro Ile Pro Ile His Tyr Cys Ala Pro Ala Gly Tyr Ala
                195                 200                 205

Ile Leu Lys Cys Asn Asn Lys Thr Phe Asn Gly Thr Gly Pro Cys Asn
    210                 215                 220

Asn Val Ser Thr Val Gln Cys Thr His Gly Ile Lys Pro Val Val Ser
225                 230                 235                 240

Thr Gln Leu Leu Leu Asn Gly Ser Leu Ala Glu Gly Glu Ile Ile Ile
                245                 250                 255

Arg Ser Glu Asn Ile Thr Asn Asn Val Lys Thr Ile Ile Val His Leu
                260                 265                 270

Asn Glu Ser Val Lys Ile Glu Cys Thr Arg Pro Asn Asn Lys Thr Arg
                275                 280                 285

Lys Ser Ile Arg Ile Gly Pro Gly Gln Thr Phe Tyr Ala Thr Gly Asp
    290                 295                 300

Val Ile Gly Asp Ile Arg Glu Ala Tyr Cys Asn Ile Ser Lys Ser Lys
305                 310                 315                 320

Trp Asn Glu Thr Leu Gln Arg Val Ser Lys Lys Leu Lys Glu Tyr Phe
                325                 330                 335

Pro His Lys Asn Ile Thr Phe Gln Pro Ser Ser Gly Gly Asp Leu Glu
                340                 345                 350

Ile Thr Thr His Ser Phe Asn Cys Gly Gly Glu Phe Phe Tyr Cys Asn
                355                 360                 365

Thr Ser Ser Leu Phe Asn Arg Thr Tyr Met Ala Asn Ser Thr Asp Met
    370                 375                 380

Ala Asn Ser Thr Glu Thr Asn Ser Thr Arg Thr Ile Thr Ile His Cys
385                 390                 395                 400

Arg Ile Lys Gln Ile Ile Asn Met Trp Gln Glu Val Gly Arg Ala Met
                405                 410                 415

Tyr Ala Pro Pro Ile Ala Gly Asn Ile Thr Cys Ile Ser Asn Ile Thr
                420                 425                 430

Gly Leu Leu Leu Thr Arg Asp Gly Gly Lys Asn Asn Thr Glu Thr Phe
    435                 440                 445

Arg Pro Gly Gly Gly Asn Met Lys Asp Asn Trp Arg Ser Glu Leu Tyr
    450                 455                 460

Lys Tyr Lys Val Val Lys Ile Glu Pro Leu Gly Val Ala Pro Thr Arg
465                 470                 475                 480

Cys Lys Arg Arg Val Val Gly Arg Arg Arg Arg Arg Ala Val Gly
                485                 490                 495

Ile Gly Ala Val Phe Leu Gly Phe Leu Gly Ala Ala Gly Ser Thr Met
                500                 505                 510

Gly Ala Ala Ser Ile Thr Leu Thr Val Gln Ala Arg Asn Leu Leu Ser
    515                 520                 525

Gly Ile Val Gln Gln Gln Ser Asn Leu Leu Arg Ala Pro Glu Ala Gln
    530                 535                 540
```

```
Gln His Leu Leu Lys Leu Thr Val Trp Gly Ile Lys Gln Leu Gln Ala
545                 550                 555                 560

Arg Val Leu Ala Val Glu Arg Tyr Leu Lys Asp Gln Gln Leu Leu Gly
                565                 570                 575

Ile Trp Gly Cys Ser Gly Lys Leu Ile Cys Cys Thr Asn Val Pro Trp
                580                 585                 590

Asn Ser Ser Trp Ser Asn Arg Asn Leu Ser Glu Ile Trp Asp Asn Met
            595                 600                 605

Thr Trp Leu Gln Trp Asp Lys Glu Ile Ser Asn Tyr Thr Gln Ile Ile
        610                 615                 620

Tyr Arg Leu Leu Glu Glu Ser Gln Asn Gln Gln Glu Lys Asn Glu Gln
625                 630                 635                 640

Asp Leu Leu Ala Leu Asp
                645
```

```
<210> SEQ ID NO 27
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga agaggccaa gaccacactg ttctgtgcca gcgacgccaa ggcctacgag      180
aagaaagtgc acaacgtgtg ggccactcac gcctgcgttc ccaccgatcc taatcctcaa     240
gagatggtgc tgaagaacgt gaccgagaac ttcaacatgt ggaagaacga catggtggac     300
cagatgcacg aggacgtgat cagcctgtgg gaccagagcc tgaagccttg cgtgaagctg     360
acccctctgt gtgtgaccct gcactgcagc acctacaaca cacccacaa catcagcaag      420 ggcatgaaga actgcagctt caatatgacc accgagctgc gggacaagaa gcagaaagtc     480
aacgccctgt tctacaagct ggacatcgtg cagctgaaca gaacggccg gcagtaccgg      540 ctgatcaact gcaacacaag cgccatcaca caggcttgcc ccaaggtgtc cttcgatccc     600
attcctatcc actactgtgc ccctgccggc tacgccatcc tgaagtgcaa caacaagacc     660
ttcaacggca caggcccctg caacaacgtg tccaccgtgc agtgtaccca cggcatcaag     720
ccagtggtgt ctacccagct gctgctgaat ggatctctgg ccgagggcga gatcatcatc     780
agaagcgaga acatcaccaa caacgtcaag accatcatcg tccacctgaa cgagagcgtg     840
aagatcgagt gcaccggcc taacaacaaa accagaaaga gcatccggat cggccctggc     900 cagaccttt atgctactgg cgacgtgatc ggcgacatca gagaggccta ctgcaacatc      960
aacaagagca gtggaacga gacactgcag cgggtgtcca gaaaactgaa agagtacttc     1020
ccgcacaaga atatcaccctt ccagcctagc tctggcggcg acctggaaat caccacacac    1080
agctttaact gtggcggcga gttcttctac tgcaatacca gcagcctgtt caaccggacc    1140
tacatggcca actccaccga tatggccaac agcaccgaga caaacagcac ccggaccatc    1200
accatccact gccggatcaa gcagatcatc aatatgtggc aagaagtcgg cagggctatg    1260
tacgcccctc ctatcgccgg caacatcacc tgtatcagca atatcaccgg cctgctgctc    1320
accagagatg gcggcaagaa caacaccgaa accttcagac ccggcggagg caacatgaag    1380
```

```
gacaattgga gaagcgagct gtacaagtac aaggtggtca agatcgagcc cctgggcgtc   1440
gcaccaacac ggtgcaagag aagagtcgtg ggccgtcgta gaaggcggag agccgttgga   1500
attggcgccg tgttcctggg ctttctggga gccgctggat ctacaatggg cgctgccagc   1560
atcaccctga cagtgcaggc tagaaatctg ctgagcggca ttgtgcagca gcagagcaac   1620
ctgctgagag cccctgaagc tcagcagcac ctcctgaaac tgaccgtgtg gggaatcaag   1680
cagctgcagg caagagtgct ggcagtggaa agatacctga aggaccagca gctcctcgga   1740
atctggggct gttctggcaa gctgatctgc tgcaccaacg tgccctggaa cagctcctgg   1800
tccaacagaa acctgagcga gatctgggac aacatgacct ggctgcagtg ggacaaagag   1860
atcagcaact acacccagat catctaccgg ctgctggaag agagccagaa ccagcaagag   1920
aaaaacgagc aggacctgct ggccctggac tgataaggat cc                       1962
```

```
<210> SEQ ID NO 28
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
```

```
gtcgacgcca ccatgcctat gggatctctg cagcctctgg ccacactgta cctgctggga     60
atgctggtgg cttctgtgct ggccgccgag aatctgtggg tcacagtgta ctatggcgtg    120
cccgtgtgga aagaggccaa gaccacactg ttctgtgcca gcgacgccaa ggcctacgag    180
aagaaagtgc acaacgtgtg ggccactcac gcctgcgttc ccaccgatcc taatcctcaa    240
gagatggtgc tgaagaacgt gaccgagaac ttcaacatgt ggaagaacga catggtggac    300
cagatgcacg aggacgtgat cagcctgtgg gaccagagcc tgaagccttg cgtgaagctg    360
acccctctgt gtgtgaccct gcactgcagc acctacaaca acacccacaa catcagcaag    420
ggcatgaaga actgcagctt caatatgacc accgagctgc gggacaagaa gcagaaagtc    480
aacgccctgt tctacaagct ggacatcgtg cagctgaaca agaacggccg gcagtaccgg    540
ctgatcaact gcaacacaag cgccatcaca caggcttgcc ccaaggtgtc cttcgatccc    600
attcctatcc actactgtgc ccctgccggc tacgccatcc tgaagtgcaa caacaagacc    660
ttcaacggca caggcccctg caacaacgtg tccaccgtgc agtgtaccca cggcatcaag    720
ccagtggtgt ctacccagct gctgctgaat ggatctctgg ccgagggcga gatcatcatc    780
agaagcgaga acatcaccaa caacgtcaag accatcatcg tccacctgaa cgagagcgtg    840
aagatcgagt gcacccggcc taacaacaaa accagaaaga gcatccggat cggccctggc    900
cagacctttt atgctactgg cgacgtgatc ggcgacatca gagaggccta ctgcaacatc    960
tccaagagca gtggaacgga cactgcag cgggtgtcca agaaactgaa agagtacttc   1020
ccgcacaaga atatcacctt ccagcctagc tctggcggcg acctggaaat caccacacac   1080
agctttaact gtggcggcga gttcttctac tgcaatacca gcagcctgtt caaccggacc   1140
tacatggcca actccaccga tatggccaac agcaccgaga caaacagcac ccggaccatc   1200
accatccact gccggatcaa gcagatcatc aatatgtggc aagaagtcgg cagggctatg   1260
tacgcccctc ctatcgccgg caacatcacc tgtatcagca atatcaccgg cctgctgctc   1320
accagagatg gcggcaagaa caacaccgaa accttcagac ccggcggagg caacatgaag   1380
gacaattgga gaagcgagct gtacaagtac aaggtggtca agatcgagcc cctgggcgtc   1440
```

-continued

```
gcaccaacac ggtgcaagag aagagtcgtg ggccgtcgta gaaggcggag agccgttgga    1500
attggcgccg tgttcctggg ctttctggga gccgctggat ctacaatggg cgctgccagc    1560
atcaccctga cagtgcaggc tagaaatctg ctgagcggca ttgtgcagca gcagagcaac    1620
ctgctgagag cccctgaagc tcagcagcac ctcctgaaac tgaccgtgtg gggaatcaag    1680
cagctgcagg caagagtgct ggcagtggaa agatacctga aggaccagca gctcctcgga    1740 atctgggget gttctggcaa gctgatctgc tgcaccaacg tgccctggaa cagctcctgg    1800
tccaacagaa acctgagcga gatctgggac aacatgacct ggctgcagtg ggacaaagag    1860
atcagcaact acacccagat catctaccgg ctgctggaag agagccagaa ccagcaagag    1920
aaaaacgagc aggacctgct ggccctggac tgataaggat cc                       1962
```

<210> SEQ ID NO 29
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gtcgacgcca ccatgcctat gggatctctg cagcctctgg ccacactgta cctgctggga     60
atgctggtgg cttctgtgct ggccgccgag aatctgtggg tcacagtgta ctatggcgtg    120
cccgtgtgga agaggccaa gaccacactg ttctgtgcca gcgacgccaa ggcctacgag    180
aagaaagtgc acaacgtgtg ggccactcac gcctgcgttc ccaccgatcc taatcctcaa    240
gagatggtgc tgaagaacgt gaccgagaac ttcaacatgt ggaagaacga catggtggac    300
cagatgcacg aggacgtgat cagcctgtgg gaccagagcc tgaagccttg cgtgaagctg    360
acccctctgt gtgtgaccct gcactgcagc acctacaaca cacccacaa catcagcaag    420 ggcatgaaga actgcagctt caacgccacc accgagctgc gggacaagaa acagaaagtg    480
aacgccctgt tctacaagct ggacatcgtg cagctgaaca gaacggccg gcagtaccgg    540 ctgatcaact gcaacaccag cgtgatcacc caggcctgtc ctaaggtgtc cttcgatccc    600
attcctatcc actactgtgc ccctgccggc tacgccatcc tgaagtgcaa caacaagacc    660
ttcaacggca caggcccctg caacaacgtg tccaccgtgc agtgtaccca cggcatcaag    720
cctgtggtgt ctacccagct gctgctgaat ggatctctgg ccgagggcga gatcatcatc    780
agaagcgaga acatcaccaa caacgtcaag accatcatcg tccacctgaa cgagagcgtg    840
aagatcgagt gcaccggcc taacaacaaa acccggacca gcatcagaat cggccctggc    900
cagacctttt acgccaccgg acaagtgatc ggcgacatca gagaggccta ctgcaacatc    960
aacaagagca gtggaacga gacactgcag cgggtgtcca agaagctgaa agagtacttc   1020
cctcacaaga atatcacctt ccagcctagc tctggcggcg acctggaaat caccacacac   1080
agcttcaatt gtggcggcga gttcttctac tgcaatacct ccagcctgtt caaccggacc   1140
tacatggcca actccaccga tatggccaac agcaccgaga caaacagcac cagaaccatc   1200
accatccact gccggatcaa gcagatcatc aatatgtggc aagaagtcgg cagggctatg   1260
tacgcccctc ctatcgccgg caacatcacc tgtatcagca atatcaccgg cctgctgctc   1320
accagagatg gcggcaagaa caacaccgaa accttcagac ccggcggagg caacatgaag   1380
gacaattgga gaagcgagct gtacaagtac aaggtggtca gatcgagcc cctgggcgtc   1440 gcacccacca ggtgcaaaag aagagtcgtc ggaagaaggc ggaggcggag agccgttgga   1500
```

-continued

```
attggagcag tgttcctggg ctttctggga gccgccggat ctacaatggg agctgccagc      1560
atgaccctga ccgtgcaggc tagaaatctg ctgagcggca ttgtgcagca gcagagcaac      1620
ctgctgagag cccctgaagc tcagcagcac ctcctgaaac tgaccgtgtg gggaatcaag      1680
cagctgcagg caagagtgct ggcagtggaa agatacctgc gggaccagca gctcctcgga      1740
atctggggat gtagcggcaa gctgatctgc tgcaccaacg tgccctggaa cagctcctgg      1800
tccaacagaa acctgagcga gatctgggac aacatgacct ggctgcagtg ggacaaagag      1860
atcagcaact acacccagat catctacgga ctgctggaag agagccagaa ccagcaagag      1920
aagaacgagc aggacctgct ggccctggac tgataaggat cc                        1962
```

<210> SEQ ID NO 30
<211> LENGTH: 1962
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 30

```
gtcgacgcca ccatgcctat gggatctctg cagcctctgg ccacactgta cctgctggga        60
atgctggtgg cttctgtgct ggccgccgag aatctgtggg tcacagtgta ctatggcgtg       120
cccgtgtgga agaggccaa gaccacactg ttctgtgcca gcgacgccaa ggcctacgag        180
aagaaagtgc acaacgtgtg ggccactcac gcctgcgttc ccaccgatcc taatcctcaa       240
gagatggtgc tgaagaacgt gaccgagaac ttcaacatgt ggaagaacga catggtggac       300
cagatgcacg aggacgtgat cagcctgtgg gaccagagcc tgaagccttg cgtgaagctg       360
acccctctgt gtgtgaccct gcactgcagc acctacaaca cacccacaa catcagcaag       420 ggcatgaaga actgcagctt caacgccacc accgagctgc gggacaagaa acagaaagtg       480
aacgccctgt tctacaagct ggacatcgtg cagctgaaca agaacggccg gcagtaccgg       540
ctgatcaact gcaacaccag cgtgatcacc caggcctgtc ctaaggtgtc cttcgatccc       600
attcctatcc actactgtgc ccctgccggc tacgccatcc tgaagtgcaa caacaagacc       660
ttcaacggca caggcccctg caacaacgtg tccaccgtgc agtgtaccca cggcatcaag       720
cctgtggtgt ctacccagct gctgctgaat ggatctctgg ccgagggcga tcatcatc       780 agaagcgaga acatcaccaa caacgtcaag accatcatcg tccacctgaa cgagagcgtg       840
aagatcgagt gcacccggcc taacaacaaa acccggacca gcatcagaat cggccctggc       900
cagacctttt acgccaccgg acaagtgatc ggcgacatca gagaggccta ctgcaacatc       960
tccaagagca gtggaacga gacactgcag cgggtgtcca agaagctgaa agagtacttc      1020
cctcacaaga atatcacctt ccagcctagc tctggcggcg acctggaaat caccacacac      1080
agcttcaatt gtggcggcga gttcttctac tgcaatacct ccagcctgtt caaccggacc      1140
tacatggcca actccaccga tatggccaac agcaccgaga caaacagcac cagaaccatc      1200
accatccact gccggatcaa gcagatcatc aatatgtggc aagaagtcgg cagggctatg      1260
tacgcccctc ctatcgccgg caacatcacc tgtatcagca atatcaccgg cctgctgctc      1320
accagagatg cggcaagaa caacaccgaa accttcagac ccggcggagg caacatgaag      1380
gacaattgga gaagcgagct gtacaagtac aaggtggtca agatcgagcc cctgggcgtc      1440
gcacccacca ggtgcaaaag aagagtcgtc ggaagaaggc ggaggcggag agccgttgga      1500
attggagcag tgttcctggg ctttctggga gccgccggat ctacaatggg agctgccagc      1560
```

```
atgaccctga ccgtgcaggc tagaaatctg ctgagcggca ttgtgcagca gcagagcaac    1620
ctgctgagag cccctgaagc tcagcagcac ctcctgaaac tgaccgtgtg gggaatcaag    1680
cagctgcagg caagagtgct ggcagtggaa agatacctgc gggaccagca gctcctcgga    1740
atctggggat gtagcggcaa gctgatctgc tgcaccaacg tgccctggaa cagctcctgg    1800
tccaacagaa acctgagcga gatctgggac aacatgacct ggctgcagtg ggacaaagag    1860
atcagcaact acacccagat catctacgga ctgctggaag agagccagaa ccagcaagag    1920
aagaacgagc aggacctgct ggccctggac tgataaggat cc                       1962
```

<210> SEQ ID NO 31
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga aagaggccaa gaccacactg ttctgtgcca gcgacgccaa ggcctacgag     180
aagaaagtgc acaacgtgtg ggccactcac gcctgcgttc ccaccgatcc taatcctcaa     240
gagatggtgc tgaagaacgt gaccgagaac ttcaacatgt ggaagaacga catggtggac     300
cagatgcacg aggacgtgat cagcctgtgg gaccagagcc tgaagccttg cgtgaagctg     360
acccctctgt gtgtgaccct gcactgcagc acctacaaca cacccacaa catcagcaag     420 ggcatgaaga actgcagctt caatatgacc accgagctgc gggacaagaa gcagaaagtc     480
aacgccctgt tctacaagct ggacatcgtg cagctgaaca gaaacggccg gcagtaccgg     540
ctgatcaact gcaacacaag cgccatcaca caggcttgcc ccaaggtgtc cttcgatccc     600
attcctatcc actactgtgc ccctgccggc tacgccatcc tgaagtgcaa caacaagacc     660
ttcaacggca caggcccctg caacaacgtg tccaccgtgc agtgtaccca cggcatcaag     720
ccagtggtgt ctacccagct gctgctgaat ggatctctgg ccgagggcga gatcatcatc     780
agaagcgaga acatcaccaa caacgtcaag accatcatcg tccacctgaa cgagagcgtg     840
aagatcgagt gcacccggcc taacaacaaa accagaaaga gcatccggat cggccctggc     900
cagacctttt atgctactgg cgacgtgatc ggcgacatca gagaggccta ctgcaacatc     960
aacaagagca gtggaacga gacactgcag cgggtgtcca agaaactgaa agagtacttc    1020
ccgcacaaga atatcacctt ccagcctagc tctggcggcg acctggaaat caccacacac    1080
agctttaact gtggcggcga gttcttctac tgcaatacca gcagcctgtt caaccggacc    1140
tacatggcca actccaccga tatggccaac agcaccgaga caaacagcac ccggaccatc    1200
accatccact gccggatcaa gcagatcatc aatatgtggc aagaagtcgg cagggctatg    1260
tacgcccctc ctatcgccgg caacatcacc tgtatcagca atatcaccgg cctgctgctc    1320
accagagatg cggcaagaa caacaccgaa accttcagac ccggcggagg caacatgaag    1380
gacaattgga gagcgagct gtacaagtac aaggtggtca gatcgagcc cctgggcgtc    1440 gcacccacca ggtgcaaaag aagagtcgtc ggaagaaggc ggaggcggag agccgttgga    1500
attggagctg tgttcctggg ctttctggga gccgccggat ctacaatggg agctgccagc    1560
atgaccctga ccgtgcaggc tagaaatctg ctgagcggca ttgtgcagca gcagagcaac    1620
```

```
ctgctgagag cccctgaagc tcagcagcac ctcctgaaac tgaccgtgtg gggaatcaag    1680
cagctgcagg caagagtgct ggcagtggaa agatacctgc gggaccagca gctcctcgga    1740
atctggggat gtagcggcaa gctgatctgc tgcaccaacg tgccctggaa cagctcctgg    1800
tccaacagaa acctgagcga gatctgggac aacatgacct ggctgcagtg ggacaaagag    1860
atcagcaact acacccagat catctacgga ctgctggaag agagccagaa ccagcaagag    1920
aagaacgagc aggacctgct ggccctggac tgataaggat cc                       1962
```

```
<210> SEQ ID NO 32
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
```

```
gtcgacgcca ccatgcctat gggatctctg cagcctctgg ccacactgta cctgctggga      60
atgctggtgg cttctgtgct ggccgccgag aatctgtggg tcacagtgta ctatggcgtg     120
cccgtgtgga agaggccaa gaccacactg ttctgtgcca cgacgccaa ggcctacgag     180 aagaaagtgc acaacgtgtg ggccactcac gcctgcgttc ccaccgatcc taatcctcaa     240
gagatggtgc tgaagaacgt gaccgagaac ttcaacatgt ggaagaacga catggtggac     300
cagatgcacg aggacgtgat cagcctgtgg gaccagagcc tgaagccttg cgtgaagctg     360
acccctctgt gtgtgaccct gcactgcagc acctacaaca acacccacaa catcagcaag     420
ggcatgaaga actgcagctt caatatgacc accgagctgc gggacaagaa gcagaaagtc     480
aacgccctgt tctacaagct ggacatcgtg cagctgaaca agaacggccg gcagtaccgg     540
ctgatcaact gcaacacaag cgccatcaca caggcttgcc ccaaggtgtc cttcgatccc     600
attcctatcc actactgtgc ccctgccggc tacgccatcc tgaagtgcaa caacaagacc     660
ttcaacggca caggcccctg caacaacgtg tccaccgtgc agtgtaccca cggcatcaag     720
ccagtggtgt ctacccagct gctgctgaat ggatctctgg ccgagggcga gatcatcatc     780
agaagcgaga acatcaccaa caacgtcaag accatcatcg tccacctgaa cgagagcgtg     840
aagatcgagt gcacccggcc taacaacaaa accagaaaga gcatccggat cggccctggc     900
cagacctttt atgctactgg cgacgtgatc ggcgacatca gagaggccta ctgcaacatc     960
tccaagagca gtggaacga gacactgcag cgggtgtcca agaaactgaa agagtacttc    1020
ccgcacaaga atatcacctt ccagcctagc tctggcggcg acctggaaat caccacacac    1080
agctttaact gtggcggcga gttcttctac tgcaatacca gcagcctgtt caaccggacc    1140
tacatggcca actccaccga tatggccaac agcaccgaga caacagcac ccggaccatc    1200 accatccact gccggatcaa gcagatcatc aatatgtggc aagaagtcgg cagggctatg    1260
tacgcccctc ctatcgccgg caacatcacc tgtatcagca atatcaccgg cctgctgctc    1320
accagagatg gcggcaagaa caacaccgaa accttcagac ccggcggagg caacatgaag    1380
gacaattgga gaagcgagct gtacaagtac aaggtggtca gatcgagcc cctgggcgtc    1440 gcacccacca ggtgcaaaag aagagtcgtc ggaagaaggc ggaggcggag agccgttgga    1500
attggagctg tgttcctggg ctttctggga gccgccggat ctacaatggg agctgccagc    1560
atgaccctga ccgtgcaggc tagaaatctg ctgagcggca ttgtgcagca gcagagcaac    1620
ctgctgagag cccctgaagc tcagcagcac ctcctgaaac tgaccgtgtg gggaatcaag    1680
```

```
cagctgcagg caagagtgct ggcagtggaa agatacctgc gggaccagca gctcctcgga    1740 atctgggggat gtagcggcaa gctgatctgc tgcaccaacg tgccctggaa cagctcctgg    1800
tccaacagaa acctgagcga gatctgggac aacatgacct ggctgcagtg ggacaaagag    1860
atcagcaact acacccagat catctacgga ctgctggaag agagccagaa ccagcaagag    1920
aagaacgagc aggacctgct ggccctggac tgataaggat cc                       1962
```

```
<210> SEQ ID NO 33
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Val Asp Ala Thr Met Pro Met Gly Ser Leu Gln Pro Leu Ala Thr Leu
1               5                   10                  15

Tyr Leu Leu Gly Met Leu Val Ala Ser Val Leu Ala Ala Glu Asn Leu
            20                  25                  30

Trp Val Thr Val Tyr Tyr Gly Val Pro Val Trp Lys Glu Ala Lys Thr
            35                  40                  45

Thr Leu Phe Cys Ala Ser Asp Ala Lys Ala Tyr Glu Lys Lys Val His
        50                  55                  60

Asn Val Trp Ala Thr His Ala Cys Val Pro Thr Asp Pro Asn Pro Gln
65                  70                  75                  80

Glu Met Val Leu Lys Asn Val Thr Glu Asn Phe Asn Met Trp Lys Asn
                85                  90                  95

Asp Met Val Asp Gln Met His Glu Asp Val Ile Ser Leu Trp Asp Gln
            100                 105                 110

Ser Leu Lys Pro Cys Val Lys Leu Thr Pro Leu Cys Val Thr Leu His
            115                 120                 125

Cys Ser Thr Tyr Asn Asn Thr His Asn Ile Ser Lys Gly Met Lys Asn
        130                 135                 140

Cys Ser Phe Asn Met Thr Thr Glu Leu Arg Asp Lys Lys Gln Lys Val
145                 150                 155                 160

Asn Ala Leu Phe Tyr Lys Leu Asp Ile Val Gln Leu Asn Lys Asn Gly
                165                 170                 175

Arg Gln Tyr Arg Leu Ile Asn Cys Asn Thr Ser Ala Ile Thr Gln Ala
                180                 185                 190

Cys Pro Lys Val Ser Phe Asp Pro Ile Pro Ile His Tyr Cys Ala Pro
            195                 200                 205

Ala Gly Tyr Ala Ile Leu Lys Cys Asn Asn Lys Thr Phe Asn Gly Thr
        210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Gly
                245                 250                 255

Glu Ile Ile Ile Arg Ser Glu Asn Ile Thr Asn Asn Val Lys Thr Ile
                260                 265                 270

Ile Val His Leu Asn Glu Ser Val Lys Ile Glu Cys Thr Arg Pro Asn
            275                 280                 285

Asn Lys Thr Arg Lys Ser Ile Arg Ile Gly Pro Gly Gln Thr Phe Tyr
        290                 295                 300

Ala Thr Gly Asp Val Ile Gly Asp Ile Arg Glu Ala Tyr Cys Asn Ile
```

-continued

```
305                 310                 315                 320

Asn Lys Ser Lys Trp Asn Glu Thr Leu Gln Arg Val Ser Lys Lys Leu
                325                 330                 335

Lys Glu Tyr Phe Pro His Lys Asn Ile Thr Phe Gln Pro Ser Ser Gly
                340                 345                 350

Gly Asp Leu Glu Ile Thr Thr His Ser Phe Asn Cys Gly Gly Glu Phe
                355                 360                 365

Phe Tyr Cys Asn Thr Ser Ser Leu Phe Asn Arg Thr Tyr Met Ala Asn
        370                 375                 380

Ser Thr Asp Met Ala Asn Ser Thr Glu Thr Asn Ser Thr Arg Thr Ile
385                 390                 395                 400

Thr Ile His Cys Arg Ile Lys Gln Ile Ile Asn Met Trp Gln Glu Val
                405                 410                 415

Gly Arg Ala Met Tyr Ala Pro Pro Ile Ala Gly Asn Ile Thr Cys Ile
                420                 425                 430

Ser Asn Ile Thr Gly Leu Leu Leu Thr Arg Asp Gly Gly Lys Asn Asn
                435                 440                 445

Thr Glu Thr Phe Arg Pro Gly Gly Gly Asn Met Lys Asp Asn Trp Arg
        450                 455                 460

Ser Glu Leu Tyr Lys Tyr Lys Val Val Lys Ile Glu Pro Leu Gly Val
465                 470                 475                 480

Ala Pro Thr Arg Cys Lys Arg Arg Val Val Gly Arg Arg Arg Arg
                485                 490                 495

Arg Ala Val Gly Ile Gly Ala Val Phe Leu Gly Phe Leu Gly Ala Ala
                500                 505                 510

Gly Ser Thr Met Gly Ala Ala Ser Ile Thr Leu Thr Val Gln Ala Arg
                515                 520                 525

Asn Leu Leu Ser Gly Ile Val Gln Gln Gln Ser Asn Leu Leu Arg Ala
        530                 535                 540

Pro Glu Ala Gln Gln His Leu Leu Lys Leu Thr Val Trp Gly Ile Lys
545                 550                 555                 560

Gln Leu Gln Ala Arg Val Leu Ala Val Glu Arg Tyr Leu Lys Asp Gln
                565                 570                 575

Gln Leu Leu Gly Ile Trp Gly Cys Ser Gly Lys Leu Ile Cys Cys Thr
                580                 585                 590

Asn Val Pro Trp Asn Ser Ser Trp Ser Asn Arg Asn Leu Ser Glu Ile
                595                 600                 605

Trp Asp Asn Met Thr Trp Leu Gln Trp Asp Lys Glu Ile Ser Asn Tyr
        610                 615                 620

Thr Gln Ile Ile Tyr Arg Leu Leu Glu Glu Ser Gln Asn Gln Gln Glu
625                 630                 635                 640

Lys Asn Glu Gln Asp Leu Leu Ala Leu Asp
                645                 650
```

```
<210> SEQ ID NO 34
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Val Asp Ala Thr Met Pro Met Gly Ser Leu Gln Pro Leu Ala Thr Leu
1               5                   10                  15
```

-continued

```
Tyr Leu Leu Gly Met Leu Val Ala Ser Val Leu Ala Ala Glu Asn Leu
            20                  25                  30

Trp Val Thr Val Tyr Tyr Gly Val Pro Val Trp Lys Glu Ala Lys Thr
            35                  40                  45

Thr Leu Phe Cys Ala Ser Asp Ala Lys Ala Tyr Glu Lys Lys Val His
        50                  55                  60

Asn Val Trp Ala Thr His Ala Cys Val Pro Thr Asp Pro Asn Pro Gln
65                  70                  75                  80

Glu Met Val Leu Lys Asn Val Thr Glu Asn Phe Asn Met Trp Lys Asn
                85                  90                  95

Asp Met Val Asp Gln Met His Glu Asp Val Ile Ser Leu Trp Asp Gln
            100                 105                 110

Ser Leu Lys Pro Cys Val Lys Leu Thr Pro Leu Cys Val Thr Leu His
            115                 120                 125

Cys Ser Thr Tyr Asn Asn Thr His Asn Ile Ser Lys Gly Met Lys Asn
        130                 135                 140

Cys Ser Phe Asn Met Thr Thr Glu Leu Arg Asp Lys Lys Gln Lys Val
145                 150                 155                 160

Asn Ala Leu Phe Tyr Lys Leu Asp Ile Val Gln Leu Asn Lys Asn Gly
                165                 170                 175

Arg Gln Tyr Arg Leu Ile Asn Cys Asn Thr Ser Ala Ile Thr Gln Ala
            180                 185                 190

Cys Pro Lys Val Ser Phe Asp Pro Ile Pro Ile His Tyr Cys Ala Pro
            195                 200                 205

Ala Gly Tyr Ala Ile Leu Lys Cys Asn Asn Lys Thr Phe Asn Gly Thr
        210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Gly
                245                 250                 255

Glu Ile Ile Ile Arg Ser Glu Asn Ile Thr Asn Asn Val Lys Thr Ile
            260                 265                 270

Ile Val His Leu Asn Glu Ser Val Lys Ile Glu Cys Thr Arg Pro Asn
        275                 280                 285

Asn Lys Thr Arg Lys Ser Ile Arg Ile Gly Pro Gly Gln Thr Phe Tyr
        290                 295                 300

Ala Thr Gly Asp Val Ile Gly Asp Ile Arg Glu Ala Tyr Cys Asn Ile
305                 310                 315                 320

Ser Lys Ser Lys Trp Asn Glu Thr Leu Gln Arg Val Ser Lys Lys Leu
                325                 330                 335

Lys Glu Tyr Phe Pro His Lys Asn Ile Thr Phe Gln Pro Ser Ser Gly
            340                 345                 350

Gly Asp Leu Glu Ile Thr Thr His Ser Phe Asn Cys Gly Gly Glu Phe
            355                 360                 365

Phe Tyr Cys Asn Thr Ser Ser Leu Phe Asn Arg Thr Tyr Met Ala Asn
        370                 375                 380

Ser Thr Asp Met Ala Asn Ser Thr Glu Thr Asn Ser Thr Arg Thr Ile
385                 390                 395                 400

Thr Ile His Cys Arg Ile Lys Gln Ile Ile Asn Met Trp Gln Glu Val
                405                 410                 415

Gly Arg Ala Met Tyr Ala Pro Pro Ile Ala Gly Asn Ile Thr Cys Ile
            420                 425                 430

Ser Asn Ile Thr Gly Leu Leu Leu Thr Arg Asp Gly Gly Lys Asn Asn
```

```
                435                     440                     445
Thr Glu Thr Phe Arg Pro Gly Gly Asn Met Lys Asp Asn Trp Arg
    450                     455                     460
Ser Glu Leu Tyr Lys Tyr Lys Val Val Lys Ile Glu Pro Leu Gly Val
465                     470                     475                     480
Ala Pro Thr Arg Cys Lys Arg Arg Val Val Gly Arg Arg Arg Arg
                485                     490                     495
Arg Ala Val Gly Ile Gly Ala Val Phe Leu Gly Phe Leu Gly Ala Ala
                500                     505                     510
Gly Ser Thr Met Gly Ala Ala Ser Ile Thr Leu Thr Val Gln Ala Arg
                515                     520                     525
Asn Leu Leu Ser Gly Ile Val Gln Gln Ser Asn Leu Leu Arg Ala
                530                     535                     540
Pro Glu Ala Gln Gln His Leu Leu Lys Leu Thr Val Trp Gly Ile Lys
545                     550                     555                     560
Gln Leu Gln Ala Arg Val Leu Ala Val Glu Arg Tyr Leu Lys Asp Gln
                565                     570                     575
Gln Leu Leu Gly Ile Trp Gly Cys Ser Gly Lys Leu Ile Cys Cys Thr
                580                     585                     590
Asn Val Pro Trp Asn Ser Ser Trp Ser Asn Arg Asn Leu Ser Glu Ile
                595                     600                     605
Trp Asp Asn Met Thr Trp Leu Gln Trp Asp Lys Glu Ile Ser Asn Tyr
                610                     615                     620
Thr Gln Ile Ile Tyr Arg Leu Leu Glu Glu Ser Gln Asn Gln Gln Glu
625                     630                     635                     640
Lys Asn Glu Gln Asp Leu Leu Ala Leu Asp
                645                     650
```

<210> SEQ ID NO 35
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Val Asp Ala Thr Met Pro Met Gly Ser Leu Gln Pro Leu Ala Thr Leu
1                   5                   10                  15
Tyr Leu Leu Gly Met Leu Val Ala Ser Val Leu Ala Ala Glu Asn Leu
                20                  25                  30
Trp Val Thr Val Tyr Tyr Gly Val Pro Val Trp Lys Glu Ala Lys Thr
                35                  40                  45
Thr Leu Phe Cys Ala Ser Asp Ala Lys Ala Tyr Glu Lys Lys Val His
    50                  55                  60
Asn Val Trp Ala Thr His Ala Cys Val Pro Thr Asp Pro Asn Pro Gln
65                  70                  75                  80
Glu Met Val Leu Lys Asn Val Thr Glu Asn Phe Asn Met Trp Lys Asn
                85                  90                  95
Asp Met Val Asp Gln Met His Glu Asp Val Ile Ser Leu Trp Asp Gln
                100                 105                 110
Ser Leu Lys Pro Cys Val Lys Leu Thr Pro Leu Cys Val Thr Leu His
        115                 120                 125
Cys Ser Thr Tyr Asn Asn Thr His Asn Ile Ser Lys Gly Met Lys Asn
        130                 135                 140
```

```
Cys Ser Phe Asn Ala Thr Thr Glu Leu Arg Asp Lys Lys Gln Lys Val
145                 150                 155                 160

Asn Ala Leu Phe Tyr Lys Leu Asp Ile Val Gln Leu Asn Lys Asn Gly
                165                 170                 175

Arg Gln Tyr Arg Leu Ile Asn Cys Asn Thr Ser Val Ile Thr Gln Ala
            180                 185                 190

Cys Pro Lys Val Ser Phe Asp Pro Ile Pro Ile His Tyr Cys Ala Pro
            195                 200                 205

Ala Gly Tyr Ala Ile Leu Lys Cys Asn Asn Lys Thr Phe Asn Gly Thr
        210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Gly
                245                 250                 255

Glu Ile Ile Ile Arg Ser Glu Asn Ile Thr Asn Asn Val Lys Thr Ile
            260                 265                 270

Ile Val His Leu Asn Glu Ser Val Lys Ile Glu Cys Thr Arg Pro Asn
        275                 280                 285

Asn Lys Thr Arg Thr Ser Ile Arg Ile Gly Pro Gly Gln Thr Phe Tyr
    290                 295                 300

Ala Thr Gly Gln Val Ile Gly Asp Ile Arg Glu Ala Tyr Cys Asn Ile
305                 310                 315                 320

Asn Lys Ser Lys Trp Asn Glu Thr Leu Gln Arg Val Ser Lys Lys Leu
                325                 330                 335

Lys Glu Tyr Phe Pro His Lys Asn Ile Thr Phe Gln Pro Ser Ser Gly
            340                 345                 350

Gly Asp Leu Glu Ile Thr Thr His Ser Phe Asn Cys Gly Gly Glu Phe
        355                 360                 365

Phe Tyr Cys Asn Thr Ser Ser Leu Phe Asn Arg Thr Tyr Met Ala Asn
    370                 375                 380

Ser Thr Asp Met Ala Asn Ser Thr Glu Thr Asn Ser Thr Arg Thr Ile
385                 390                 395                 400

Thr Ile His Cys Arg Ile Lys Gln Ile Ile Asn Met Trp Gln Glu Val
            405                 410                 415

Gly Arg Ala Met Tyr Ala Pro Pro Ile Ala Gly Asn Ile Thr Cys Ile
            420                 425                 430

Ser Asn Ile Thr Gly Leu Leu Leu Thr Arg Asp Gly Gly Lys Asn Asn
        435                 440                 445

Thr Glu Thr Phe Arg Pro Gly Gly Gly Asn Met Lys Asp Asn Trp Arg
    450                 455                 460

Ser Glu Leu Tyr Lys Tyr Lys Val Val Lys Ile Glu Pro Leu Gly Val
465                 470                 475                 480

Ala Pro Thr Arg Cys Lys Arg Arg Val Val Gly Arg Arg Arg Arg Arg
            485                 490                 495

Arg Ala Val Gly Ile Gly Ala Val Phe Leu Gly Phe Leu Gly Ala Ala
            500                 505                 510

Gly Ser Thr Met Gly Ala Ala Ser Met Thr Leu Thr Val Gln Ala Arg
            515                 520                 525

Asn Leu Leu Ser Gly Ile Val Gln Gln Gln Ser Asn Leu Leu Arg Ala
        530                 535                 540

Pro Glu Ala Gln Gln His Leu Leu Lys Leu Thr Val Trp Gly Ile Lys
545                 550                 555                 560

Gln Leu Gln Ala Arg Val Leu Ala Val Glu Arg Tyr Leu Arg Asp Gln
```

```
                       565                     570                     575

Gln Leu Leu Gly Ile Trp Gly Cys Ser Gly Lys Leu Ile Cys Cys Thr
              580                     585                     590

Asn Val Pro Trp Asn Ser Ser Trp Ser Asn Arg Asn Leu Ser Glu Ile
          595                     600                     605

Trp Asp Asn Met Thr Trp Leu Gln Trp Asp Lys Glu Ile Ser Asn Tyr
      610                     615                     620

Thr Gln Ile Ile Tyr Gly Leu Leu Glu Glu Ser Gln Asn Gln Gln Glu
625                     630                     635                     640

Lys Asn Glu Gln Asp Leu Leu Ala Leu Asp
              645                     650

<210> SEQ ID NO 36
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Val Asp Ala Thr Met Pro Met Gly Ser Leu Gln Pro Leu Ala Thr Leu
1                   5                   10                  15

Tyr Leu Leu Gly Met Leu Val Ala Ser Val Leu Ala Ala Glu Asn Leu
              20                  25                  30

Trp Val Thr Val Tyr Tyr Gly Val Pro Val Trp Lys Glu Ala Lys Thr
          35                  40                  45

Thr Leu Phe Cys Ala Ser Asp Ala Lys Ala Tyr Glu Lys Lys Val His
      50                  55                  60

Asn Val Trp Ala Thr His Ala Cys Val Pro Thr Asp Pro Asn Pro Gln
65                  70                  75                  80

Glu Met Val Leu Lys Asn Val Thr Glu Asn Phe Asn Met Trp Lys Asn
              85                  90                  95

Asp Met Val Asp Gln Met His Glu Asp Val Ile Ser Leu Trp Asp Gln
          100                 105                 110

Ser Leu Lys Pro Cys Val Lys Leu Thr Pro Leu Cys Val Thr Leu His
          115                 120                 125

Cys Ser Thr Tyr Asn Asn Thr His Asn Ile Ser Lys Gly Met Lys Asn
      130                 135                 140

Cys Ser Phe Asn Ala Thr Thr Glu Leu Arg Asp Lys Lys Gln Lys Val
145                 150                 155                 160

Asn Ala Leu Phe Tyr Lys Leu Asp Ile Val Gln Leu Asn Lys Asn Gly
              165                 170                 175

Arg Gln Tyr Arg Leu Ile Asn Cys Asn Thr Ser Val Ile Thr Gln Ala
          180                 185                 190

Cys Pro Lys Val Ser Phe Asp Pro Ile Pro Ile His Tyr Cys Ala Pro
          195                 200                 205

Ala Gly Tyr Ala Ile Leu Lys Cys Asn Asn Lys Thr Phe Asn Gly Thr
      210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Gly
              245                 250                 255

Glu Ile Ile Ile Arg Ser Glu Asn Ile Thr Asn Asn Val Lys Thr Ile
          260                 265                 270
```

-continued

```
Ile Val His Leu Asn Glu Ser Val Lys Ile Glu Cys Thr Arg Pro Asn
        275                 280                 285

Asn Lys Thr Arg Thr Ser Ile Arg Ile Gly Pro Gly Gln Thr Phe Tyr
        290                 295                 300

Ala Thr Gly Gln Val Ile Gly Asp Ile Arg Glu Ala Tyr Cys Asn Ile
305                 310                 315                 320

Ser Lys Ser Lys Trp Asn Glu Thr Leu Gln Arg Val Ser Lys Lys Leu
                325                 330                 335

Lys Glu Tyr Phe Pro His Lys Asn Ile Thr Phe Gln Pro Ser Ser Gly
                340                 345                 350

Gly Asp Leu Glu Ile Thr Thr His Ser Phe Asn Cys Gly Gly Glu Phe
                355                 360                 365

Phe Tyr Cys Asn Thr Ser Ser Leu Phe Asn Arg Thr Tyr Met Ala Asn
        370                 375                 380

Ser Thr Asp Met Ala Asn Ser Thr Glu Thr Asn Ser Thr Arg Thr Ile
385                 390                 395                 400

Thr Ile His Cys Arg Ile Lys Gln Ile Ile Asn Met Trp Gln Glu Val
                405                 410                 415

Gly Arg Ala Met Tyr Ala Pro Pro Ile Ala Gly Asn Ile Thr Cys Ile
                420                 425                 430

Ser Asn Ile Thr Gly Leu Leu Leu Thr Arg Asp Gly Gly Lys Asn Asn
                435                 440                 445

Thr Glu Thr Phe Arg Pro Gly Gly Gly Asn Met Lys Asp Asn Trp Arg
        450                 455                 460

Ser Glu Leu Tyr Lys Tyr Lys Val Val Lys Ile Glu Pro Leu Gly Val
465                 470                 475                 480

Ala Pro Thr Arg Cys Lys Arg Arg Val Val Gly Arg Arg Arg Arg
                485                 490                 495

Arg Ala Val Gly Ile Gly Ala Val Phe Leu Gly Phe Leu Gly Ala Ala
                500                 505                 510

Gly Ser Thr Met Gly Ala Ala Ser Met Thr Leu Thr Val Gln Ala Arg
                515                 520                 525

Asn Leu Leu Ser Gly Ile Val Gln Gln Gln Ser Asn Leu Leu Arg Ala
        530                 535                 540

Pro Glu Ala Gln Gln His Leu Leu Lys Leu Thr Val Trp Gly Ile Lys
545                 550                 555                 560

Gln Leu Gln Ala Arg Val Leu Ala Val Glu Arg Tyr Leu Arg Asp Gln
                565                 570                 575

Gln Leu Leu Gly Ile Trp Gly Cys Ser Gly Lys Leu Ile Cys Cys Thr
                580                 585                 590

Asn Val Pro Trp Asn Ser Ser Trp Ser Asn Arg Asn Leu Ser Glu Ile
        595                 600                 605

Trp Asp Asn Met Thr Trp Leu Gln Trp Asp Lys Glu Ile Ser Asn Tyr
        610                 615                 620

Thr Gln Ile Ile Tyr Gly Leu Leu Glu Glu Ser Gln Asn Gln Gln Glu
625                 630                 635                 640

Lys Asn Glu Gln Asp Leu Leu Ala Leu Asp
                645                 650
```

<210> SEQ ID NO 37
<211> LENGTH: 650
<212> TYPE: PRT
<213> ORGANISM: Artificial Sequence
<220> FEATURE:
<223> OTHER INFORMATION: Description of Artificial Sequence: Synthetic -continued

```
        polypeptide

<400> SEQUENCE: 37

Val Asp Ala Thr Met Pro Met Gly Ser Leu Gln Pro Leu Ala Thr Leu
1               5                   10                  15

Tyr Leu Leu Gly Met Leu Val Ala Ser Val Leu Ala Ala Glu Asn Leu
            20                  25                  30

Trp Val Thr Val Tyr Tyr Gly Val Pro Val Trp Lys Glu Ala Lys Thr
            35                  40                  45

Thr Leu Phe Cys Ala Ser Asp Ala Lys Ala Tyr Glu Lys Lys Val His
    50                  55                  60

Asn Val Trp Ala Thr His Ala Cys Val Pro Thr Asp Pro Asn Pro Gln
65                  70                  75                  80

Glu Met Val Leu Lys Asn Val Thr Glu Asn Phe Asn Met Trp Lys Asn
                85                  90                  95

Asp Met Val Asp Gln Met His Glu Asp Val Ile Ser Leu Trp Asp Gln
            100                 105                 110

Ser Leu Lys Pro Cys Val Lys Leu Thr Pro Leu Cys Val Thr Leu His
            115                 120                 125

Cys Ser Thr Tyr Asn Asn Thr His Asn Ile Ser Lys Gly Met Lys Asn
        130                 135                 140

Cys Ser Phe Asn Met Thr Thr Glu Leu Arg Asp Lys Lys Gln Lys Val
145                 150                 155                 160

Asn Ala Leu Phe Tyr Lys Leu Asp Ile Val Gln Leu Asn Lys Asn Gly
                165                 170                 175

Arg Gln Tyr Arg Leu Ile Asn Cys Asn Thr Ser Ala Ile Thr Gln Ala
            180                 185                 190

Cys Pro Lys Val Ser Phe Asp Pro Ile Pro Ile His Tyr Cys Ala Pro
            195                 200                 205

Ala Gly Tyr Ala Ile Leu Lys Cys Asn Asn Lys Thr Phe Asn Gly Thr
    210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Gly
                245                 250                 255

Glu Ile Ile Ile Arg Ser Glu Asn Ile Thr Asn Asn Val Lys Thr Ile
            260                 265                 270

Ile Val His Leu Asn Glu Ser Val Lys Ile Glu Cys Thr Arg Pro Asn
            275                 280                 285

Asn Lys Thr Arg Lys Ser Ile Arg Ile Gly Pro Gly Gln Thr Phe Tyr
    290                 295                 300

Ala Thr Gly Asp Val Ile Gly Asp Ile Arg Glu Ala Tyr Cys Asn Ile
305                 310                 315                 320

Asn Lys Ser Lys Trp Asn Glu Thr Leu Gln Arg Val Ser Lys Lys Leu
                325                 330                 335

Lys Glu Tyr Phe Pro His Lys Asn Ile Thr Phe Gln Pro Ser Ser Gly
            340                 345                 350

Gly Asp Leu Glu Ile Thr Thr His Ser Phe Asn Cys Gly Gly Glu Phe
            355                 360                 365

Phe Tyr Cys Asn Thr Ser Ser Leu Phe Asn Arg Thr Tyr Met Ala Asn
    370                 375                 380

Ser Thr Asp Met Ala Asn Ser Thr Glu Thr Asn Ser Thr Arg Thr Ile
385                 390                 395                 400
```

-continued

```
Thr Ile His Cys Arg Ile Lys Gln Ile Ile Asn Met Trp Gln Glu Val
                405             410             415

Gly Arg Ala Met Tyr Ala Pro Pro Ile Ala Gly Asn Ile Thr Cys Ile
                420             425             430

Ser Asn Ile Thr Gly Leu Leu Leu Thr Arg Asp Gly Gly Lys Asn Asn
                435             440             445

Thr Glu Thr Phe Arg Pro Gly Gly Gly Asn Met Lys Asp Asn Trp Arg
        450             455             460

Ser Glu Leu Tyr Lys Tyr Lys Val Val Lys Ile Glu Pro Leu Gly Val
465             470             475             480

Ala Pro Thr Arg Cys Lys Arg Arg Val Val Gly Arg Arg Arg Arg Arg
                485             490             495

Arg Ala Val Gly Ile Gly Ala Val Phe Leu Gly Phe Leu Gly Ala Ala
                500             505             510

Gly Ser Thr Met Gly Ala Ala Ser Met Thr Leu Thr Val Gln Ala Arg
                515             520             525

Asn Leu Leu Ser Gly Ile Val Gln Gln Gln Ser Asn Leu Leu Arg Ala
        530             535             540

Pro Glu Ala Gln Gln His Leu Leu Lys Leu Thr Val Trp Gly Ile Lys
545             550             555             560

Gln Leu Gln Ala Arg Val Leu Ala Val Glu Arg Tyr Leu Arg Asp Gln
                565             570             575

Gln Leu Leu Gly Ile Trp Gly Cys Ser Gly Lys Leu Ile Cys Cys Thr
                580             585             590

Asn Val Pro Trp Asn Ser Ser Trp Ser Asn Arg Asn Leu Ser Glu Ile
                595             600             605

Trp Asp Asn Met Thr Trp Leu Gln Trp Asp Lys Glu Ile Ser Asn Tyr
        610             615             620

Thr Gln Ile Ile Tyr Gly Leu Leu Glu Glu Ser Gln Asn Gln Gln Glu
625             630             635             640

Lys Asn Glu Gln Asp Leu Leu Ala Leu Asp
                645             650
```

```
<210> SEQ ID NO 38
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Val Asp Ala Thr Met Pro Met Gly Ser Leu Gln Pro Leu Ala Thr Leu
1               5               10              15

Tyr Leu Leu Gly Met Leu Val Ala Ser Val Leu Ala Ala Glu Asn Leu
                20              25              30

Trp Val Thr Val Tyr Tyr Gly Val Pro Val Trp Lys Glu Ala Lys Thr
                35              40              45

Thr Leu Phe Cys Ala Ser Asp Ala Lys Ala Tyr Glu Lys Lys Val His
        50              55              60

Asn Val Trp Ala Thr His Ala Cys Val Pro Thr Asp Pro Asn Pro Gln
65              70              75              80

Glu Met Val Leu Lys Asn Val Thr Glu Asn Phe Asn Met Trp Lys Asn
                85              90              95

Asp Met Val Asp Gln Met His Glu Asp Val Ile Ser Leu Trp Asp Gln
                100             105             110
```

-continued

```
Ser Leu Lys Pro Cys Val Lys Leu Thr Pro Leu Cys Val Thr Leu His
        115                 120                 125

Cys Ser Thr Tyr Asn Asn Thr His Asn Ile Ser Lys Gly Met Lys Asn
        130                 135                 140

Cys Ser Phe Asn Met Thr Thr Glu Leu Arg Asp Lys Lys Gln Lys Val
145                 150                 155                 160

Asn Ala Leu Phe Tyr Lys Leu Asp Ile Val Gln Leu Asn Lys Asn Gly
                165                 170                 175

Arg Gln Tyr Arg Leu Ile Asn Cys Asn Thr Ser Ala Ile Thr Gln Ala
                180                 185                 190

Cys Pro Lys Val Ser Phe Asp Pro Ile Pro Ile His Tyr Cys Ala Pro
        195                 200                 205

Ala Gly Tyr Ala Ile Leu Lys Cys Asn Asn Lys Thr Phe Asn Gly Thr
        210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Gly
                245                 250                 255

Glu Ile Ile Ile Arg Ser Glu Asn Ile Thr Asn Asn Val Lys Thr Ile
                260                 265                 270

Ile Val His Leu Asn Glu Ser Val Lys Ile Glu Cys Thr Arg Pro Asn
        275                 280                 285

Asn Lys Thr Arg Lys Ser Ile Arg Ile Gly Pro Gly Gln Thr Phe Tyr
        290                 295                 300

Ala Thr Gly Asp Val Ile Gly Asp Ile Arg Glu Ala Tyr Cys Asn Ile
305                 310                 315                 320

Ser Lys Ser Lys Trp Asn Glu Thr Leu Gln Arg Val Ser Lys Lys Leu
                325                 330                 335

Lys Glu Tyr Phe Pro His Lys Asn Ile Thr Phe Gln Pro Ser Ser Gly
                340                 345                 350

Gly Asp Leu Glu Ile Thr Thr His Ser Phe Asn Cys Gly Gly Glu Phe
        355                 360                 365

Phe Tyr Cys Asn Thr Ser Ser Leu Phe Asn Arg Thr Tyr Met Ala Asn
        370                 375                 380

Ser Thr Asp Met Ala Asn Ser Thr Glu Thr Asn Ser Thr Arg Thr Ile
385                 390                 395                 400

Thr Ile His Cys Arg Ile Lys Gln Ile Ile Asn Met Trp Gln Glu Val
                405                 410                 415

Gly Arg Ala Met Tyr Ala Pro Pro Ile Ala Gly Asn Ile Thr Cys Ile
                420                 425                 430

Ser Asn Ile Thr Gly Leu Leu Leu Thr Arg Asp Gly Gly Lys Asn Asn
        435                 440                 445

Thr Glu Thr Phe Arg Pro Gly Gly Gly Asn Met Lys Asp Asn Trp Arg
        450                 455                 460

Ser Glu Leu Tyr Lys Tyr Lys Val Val Lys Ile Glu Pro Leu Gly Val
465                 470                 475                 480

Ala Pro Thr Arg Cys Lys Arg Arg Val Val Gly Arg Arg Arg Arg
                485                 490                 495

Arg Ala Val Gly Ile Gly Ala Val Phe Leu Gly Phe Leu Gly Ala Ala
                500                 505                 510

Gly Ser Thr Met Gly Ala Ala Ser Met Thr Leu Thr Val Gln Ala Arg
        515                 520                 525
```

```
Asn Leu Leu Ser Gly Ile Val Gln Gln Gln Ser Asn Leu Leu Arg Ala
    530             535             540

Pro Glu Ala Gln Gln His Leu Leu Lys Leu Thr Val Trp Gly Ile Lys
545             550             555             560

Gln Leu Gln Ala Arg Val Leu Ala Val Glu Arg Tyr Leu Arg Asp Gln
            565             570             575

Gln Leu Leu Gly Ile Trp Gly Cys Ser Gly Lys Leu Ile Cys Cys Thr
            580             585             590

Asn Val Pro Trp Asn Ser Ser Trp Ser Asn Arg Asn Leu Ser Glu Ile
        595             600             605

Trp Asp Asn Met Thr Trp Leu Gln Trp Asp Lys Glu Ile Ser Asn Tyr
    610             615             620

Thr Gln Ile Ile Tyr Gly Leu Leu Glu Glu Ser Gln Asn Gln Gln Glu
625             630             635             640

Lys Asn Glu Gln Asp Leu Leu Ala Leu Asp
            645             650

<210> SEQ ID NO 39
<211> LENGTH: 1962
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atgcccatgg gcagcctgca gcccctggcc accctgtacc tgctgggcat gctggtggct      60
agcgtgctgg ccgccgagaa cctgtgggtg accgtctact atggcgtgcc cgtctggaag     120
gaagccaaaa ccacactgtt ctgcgctagc gacgctaagg catacgagaa aaaagtgcac     180
aatgtctggg ctactcatgc atgcgtgcct accgatccaa atccccagga gatggtgctg     240
aagaacgtca cagaaaactt taatatgtgg aagaacgaca tggtggatca gatgcacgag     300
gacgtgatca gcctgtggga tcagtccctg aagccatgcg tgaaactgac tccctgtgc     360 gtcaccctga actgtactaa tgccaccgct tccaacagct ccatcattga ggggatgaag     420
aactgttctt tcaatatcac taccgagctg cgcgacaagc gagaaaagaa aaatgccctg     480
ttttacaaac tggacatcgt gcagctggat ggcaactcta gtcagtatag actgattaac     540
tgcaatacaa gcgtgatcac tcaggcatgt ccaaaggtca gtttcgatcc tattccaatc     600
cactactgcg cacccgccgg atatgctatc ctgaagtgta caacaagac cttcaccggc     660 actgggcctt gcaacaacgt gagcaccgtc cagtgtacac atggcattaa gccagtggtc     720
agcacccagc tgctgctgaa cggcagcctg gcagagggcg aaatcattat ccgcagcgag     780
aacatcacaa ataatgtgaa gactatcatc gtccacctga cgagagcgt gaagattgaa     840 tgcacacggc ccaacaacaa gaccaggaca tccattcgca tcggacctgg ccagtggttc     900
tacgctactg gccaggtcat cggggacatc agagaggcct attgtaacat caatgagtca     960
aagtggaatg aaactctgca gagggtgagc aagaaactga aggaatactt ccctcacaaa    1020
aacatcacct ttcagccatc aagcggcggg gacctggaga ttacaactca ttctttcaat    1080
tgcggaggcg aattcttta ctgtaacacc tcctctctgt ttaatcgcac atatatggct    1140
aacagtactg atatggcaaa ctctactgag accaatagta cacgaactat taccatccat    1200
tgccggatca gcagattat caacatgtgg caggaagtgg ggcgggccat gtatgctccc    1260
cctattgcag gaaatattac ctgtatcagc aacattaccg gctgctgct gacaagagac    1320
```

-continued

```
gggggaaaga acaatacaga gacttttagg cctggcgggg gaaacatgaa agataattgg    1380
cgctccgagc tgtacaagta taaagtggtc aagatcgaac cactgggagt ggcacctacc    1440
cgatgtaaac ggagagtggt cggaaggcgc cgacggagaa gggcagtggg aatcggagcc    1500
gtcttcctgg gctttctggg agcagctggc agcacaatgg gagcagcctc tatgaccctg    1560
acagtgcagg ctcgaaatct gctgagtggg atcgtgcagc agcagtcaaa cctgctgcga    1620
gcaccagagg cacagcagca tctgctgaag ctgaccgtgt ggggcatcaa gcagctgcag    1680
gccagagtgc tggctgtcga acggtacctg agagatcagc agctgctggg aatctgggga    1740
tgcagcggaa agctgatttg ctgtacaaac gtgccctgga atagttcatg gtcaaacagg    1800
aatctgagcg agatctggga caatatgacc tggctgcagt gggataagga aatcagtaac    1860
tacacacaga tcatctatgg cctgctggag gaatcacaga accagcagga gaaaaatgaa    1920
caggacctgc tggccctgga tctgcctagc accggatgat ga                     1962
```

```
<210> SEQ ID NO 40
<211> LENGTH: 1992
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
```

```
atgcccatgg gcagcctgca gccctggcc acctgtacc tgctgggcat gctggtggct       60
agcgtgctgg ccggcggggg cggggccggc ggggcggggg gcggcggggg cggggggcgcc     120 gagaacctgt gggtgaccgt ctactatggc gtgcccgtct ggaaggaagc caaaaccaca     180
ctgttctgcg ctagcgacgc taaggcatac gagaaaaaag tgcacaatgt ctgggctact     240
catgcatgcg tgcctaccga tccaaatccc caggagatgg tgctgaagaa cgtcacagaa     300
aactttaata tgtggaagaa cgacatggtg gatcagatgc acgaggacgt gatcagcctg     360
tgggatcagt ccctgaagcc atgcgtgaaa ctgactcccc tgtgcgtcac cctgaactgt     420
actaatgcca ccgcttccaa cagctccatc attgagggga tgaagaactg ttctttcaat     480
atcactaccg agctgcgcga caagcgagaa aagaaaaatg ccctgtttta caaactggac     540
atcgtgcagc tggatggcaa ctctagtcag tatagactga ttaactgcaa tacaagcgtg     600
atcactcagg catgtccaaa ggtcagtttc gatcctattc caatccacta ctgcgcaccc     660
gccggatatg ctatcctgaa gtgtaacaac aagaccttca ccggcactgg gccttgcaac     720
aacgtgagca ccgtccagtg tacacatggc attaagccag tggtcagcac ccagctgctg     780
ctgaacggca gcctggcaga gggcgaaatc attatccgca gcgagaacat cacaaataat     840
gtgaagacta tcatcgtcca cctgaacgag agcgtgaaga ttgaatgcac acggcccaac     900
aacaagacca ggacatccat tcgcatcgga cctggccagt ggttctacgc tactggccag     960
gtcatcgggg acatcagaga ggcctattgt aacatcaatg agtcaaagtg gaatgaaact     1020
ctgcagaggg tgagcaagaa actgaaggaa tacttccctc acaaaaacat caccttttcag    1080 ccatcaagcg gcgggacct ggagattaca actcattctt tcaattgcgg aggcgaattc      1140 tttactgta acacctcctc tctgtttaat cgcacatata tggctaacag tactgatatg      1200
gcaaactcta ctgagaccaa tagtacacga actattacca tccattgccg gatcaagcag      1260
attatcaaca tgtggcagga gtggggcgg gccatgtatg ctccccctat tgcaggaaat       1320
attacctgta tcagcaacat taccggcctg ctgctgacaa gagacggggg aaagaacaat      1380
```

-continued

```
acagagactt ttaggcctgg cgggggaaac atgaaagata attggcgctc cgagctgtac    1440
aagtataaag tggtcaagat cgaaccactg ggagtggcac ctacccgatg taaacggaga    1500
gtggtcggaa ggcgccgacg gagaagggca gtgggaatcg gagccgtctt cctgggcttt    1560
ctgggagcag ctggcagcac aatgggagca gcctctatga ccctgacagt gcaggctcga    1620
aatctgctga gtgggatcgt gcagcagcag tcaaacctgc tgcgagcacc agaggcacag    1680
cagcatctgc tgaagctgac cgtgtggggc atcaagcagc tgcaggccag agtgctggct    1740
gtcgaacggt acctgagaga tcagcagctg ctgggaatct ggggatgcag cggaaagctg    1800
atttgctgta caaacgtgcc ctggaatagt tcatggtcaa acaggaatct gagcgagatc    1860
tgggacaata tgacctggct gcagtgggat aaggaaatca gtaactacac acagatcatc    1920
tatggcctgc tggaggaatc acagaaccag caggagaaaa atgaacagga cctgctggcc    1980
ctggattgat ga                                                        1992
```

<210> SEQ ID NO 41
<211> LENGTH: 1989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atgcccatgg gctccctgca gcccctggcc accctgtacc tgctgggcat gctggtggcc      60
tccgtgctgg ccggcggggg cggggccggc ggggcgggg gcggcggggg cggggccgcc     120
gagaacctgt gggtgaccgt gtactacggc gtgcccgtgt ggaaggaggc caagaccacc     180
ctgttctgcg cctccgacgc caaggcctac gagaagaagg tgcacaacgt gtgggccacc     240
cacgcctgcg tgcccaccga ccccaacccc caggagatgg tgctgaagaa cgtgaccgag     300
aacttcaaca tgtggaagaa cgacatggtg gaccagatgc acgaggacgt gatctccctg     360
tgggaccagt ccctgaagcc ctgcgtgaag ctgacccccc tgtgcgtgac cctgaactgc     420
accaacgcca ccgcctccaa ctcctccatc atcgagggca tgaagaactg ctccttcaac     480
atcaccaccg agctgcgcga caagcgcgag aagaagaacg ccctgttcta caagctggac     540
atcgtgcagc tggacggcaa ctcctcccag taccgcctga tcaactgcaa cacctccgtg     600
atcacccagg cctgccccaa ggtgtccttc gaccccatcc ccatccacta ctgcgccccc     660
gccggctacg ccatcctgaa gtgcaacaac aagaccttca ccggcaccgg ccctgcaac     720 aacgtgtcca ccgtgcagtg cacccacggc atcaagcccg tggtgtccac ccagctgctg     780
ctgaacggct ccctggccga gggcgagatc atcatccgct ccgagaacat caccaagaac     840
gtgaagacca tcatcgtgca cctgaacgag tccgtgaaga tcgagtgcac ccgccccaac     900
aacaagaccc gcacctccat ccgcatcggc cccggccagt ggttctacgc caccggccag     960
gtgatcggcg acatccgcga ggcctactgc aacatcaacg agtccaagtg gaacgagacc    1020
ctgcagcgcg tgtccaagaa gctgaaggag tacttccccc acaagaacat caccttccag    1080
ccctcctccg gcggcgacct ggagatcacc acccactcct tcaactgcgg cggcgagttc    1140
ttctactgca acacctcctc cctgttcaac cgcacctaca tggccaactc caccgacatg    1200
gccaactcca ccgagaccaa ctccaccccgc accatcacca tccactgccg catcaagcag    1260
atcatcaaca tgtggcagga ggtgggccgc gccatgtacg cccccccat cgccggcaac    1320 atcacctgca tctccaacat caccggcctg ctgctgaccc gcgacggcgg caagaacaac    1380
```

```
accgagacct tccgccccgg cggcggcaac atgaaggaca actggcgctc cgagctgtac      1440
aagtacaagg tggtgaagat cgagcccctg ggcgtggccc ccacccgctg caagcgccgc      1500
gtggtgggcc gccgccgccg ccgccgcgcc gtgggcatcg cgccgtgtt cctgggcttc      1560 ctgggcgccg ccggctccac catgggcgcc gcctccatga ccctgaccgt gcaggccgc       1620 aacctgctgt ccggcatcgt gcagcagcag tccaacctgc tgcgcgcccc cgaggcccag      1680
cagcacctgc tgaagctgac cgtgtgggc atcaagcagc tgcaggccg cgtgctggcc        1740 gtggagcgct acctgcgcga ccagcagctg ctgggcatct ggggctgctc cggcaagctg      1800
atctgctgca ccaacgtgcc ctggaactcc tcctggtcca accgcaacct gtccgagatc      1860
tgggacaaca tgacctggct gcagtgggac aaggagatct ccaactacac ccagatcatc      1920
tacggcctgc tggaggagtc ccagaaccag caggagaaga cgagcagga cctgctggcc       1980 ctggactag                                                            1989
```

<210> SEQ ID NO 42
<211> LENGTH: 662
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Met Pro Met Gly Ser Leu Gln Pro Leu Ala Thr Leu Tyr Leu Leu Gly
1               5                   10                  15

Met Leu Val Ala Ser Val Leu Ala Gly Gly Gly Gly Gly Gly Gly Gly
                20                  25                  30

Gly Gly Gly Gly Gly Gly Gly Ala Glu Asn Leu Trp Val Thr Val Tyr
            35                  40                  45

Tyr Gly Val Pro Val Trp Lys Glu Ala Lys Thr Thr Leu Phe Cys Ala
        50                  55                  60

Ser Asp Ala Lys Ala Tyr Glu Lys Lys Val His Asn Val Trp Ala Thr
65                  70                  75                  80

His Ala Cys Val Pro Thr Asp Pro Asn Pro Gln Glu Met Val Leu Lys
                85                  90                  95

Asn Val Thr Glu Asn Phe Asn Met Trp Lys Asn Asp Met Val Asp Gln
            100                 105                 110

Met His Glu Asp Val Ile Ser Leu Trp Asp Gln Ser Leu Lys Pro Cys
        115                 120                 125

Val Lys Leu Thr Pro Leu Cys Val Thr Leu Asn Cys Thr Asn Ala Thr
        130                 135                 140

Ala Ser Asn Ser Ser Ile Ile Glu Gly Met Lys Asn Cys Ser Phe Asn
145                 150                 155                 160

Ile Thr Thr Glu Leu Arg Asp Lys Arg Glu Lys Lys Asn Ala Leu Phe
                165                 170                 175

Tyr Lys Leu Asp Ile Val Gln Leu Asp Gly Asn Ser Ser Gln Tyr Arg
            180                 185                 190

Leu Ile Asn Cys Asn Thr Ser Val Ile Thr Gln Ala Cys Pro Lys Val
        195                 200                 205

Ser Phe Asp Pro Ile Pro Ile His Tyr Cys Ala Pro Ala Gly Tyr Ala
        210                 215                 220

Ile Leu Lys Cys Asn Asn Lys Thr Phe Thr Gly Thr Gly Pro Cys Asn
225                 230                 235                 240

Asn Val Ser Thr Val Gln Cys Thr His Gly Ile Lys Pro Val Val Ser
```

-continued

```
                    245                 250                 255

Thr Gln Leu Leu Leu Asn Gly Ser Leu Ala Glu Gly Glu Ile Ile Ile
        260                 265                 270

Arg Ser Glu Asn Ile Thr Lys Asn Val Lys Thr Ile Ile Val His Leu
        275                 280                 285

Asn Glu Ser Val Lys Ile Glu Cys Thr Arg Pro Asn Asn Lys Thr Arg
        290                 295                 300

Thr Ser Ile Arg Ile Gly Pro Gly Gln Trp Phe Tyr Ala Thr Gly Gln
305                 310                 315                 320

Val Ile Gly Asp Ile Arg Glu Ala Tyr Cys Asn Ile Asn Glu Ser Lys
                325                 330                 335

Trp Asn Glu Thr Leu Gln Arg Val Ser Lys Lys Leu Lys Glu Tyr Phe
                340                 345                 350

Pro His Lys Asn Ile Thr Phe Gln Pro Ser Ser Gly Gly Asp Leu Glu
                355                 360                 365

Ile Thr Thr His Ser Phe Asn Cys Gly Gly Glu Phe Phe Tyr Cys Asn
        370                 375                 380

Thr Ser Ser Leu Phe Asn Arg Thr Tyr Met Ala Asn Ser Thr Asp Met
385                 390                 395                 400

Ala Asn Ser Thr Glu Thr Asn Ser Thr Arg Thr Ile Thr Ile His Cys
                405                 410                 415

Arg Ile Lys Gln Ile Ile Asn Met Trp Gln Glu Val Gly Arg Ala Met
                420                 425                 430

Tyr Ala Pro Pro Ile Ala Gly Asn Ile Thr Cys Ile Ser Asn Ile Thr
                435                 440                 445

Gly Leu Leu Leu Thr Arg Asp Gly Gly Lys Asn Asn Thr Glu Thr Phe
        450                 455                 460

Arg Pro Gly Gly Gly Asn Met Lys Asp Asn Trp Arg Ser Glu Leu Tyr
465                 470                 475                 480

Lys Tyr Lys Val Val Lys Ile Glu Pro Leu Gly Val Ala Pro Thr Arg
                485                 490                 495

Cys Lys Arg Arg Val Val Gly Arg Arg Arg Arg Arg Ala Val Gly
                500                 505                 510

Ile Gly Ala Val Phe Leu Gly Phe Leu Gly Ala Ala Gly Ser Thr Met
        515                 520                 525

Gly Ala Ala Ser Met Thr Leu Thr Val Gln Ala Arg Asn Leu Leu Ser
        530                 535                 540

Gly Ile Val Gln Gln Gln Ser Asn Leu Leu Arg Ala Pro Glu Ala Gln
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
                580                 585                 590

Ile Trp Gly Cys Ser Gly Lys Leu Ile Cys Cys Thr Asn Val Pro Trp
        595                 600                 605

Asn Ser Ser Trp Ser Asn Arg Asn Leu Ser Glu Ile Trp Asp Asn Met
        610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp
                660
```

-continued

<210> SEQ ID NO 43
<211> LENGTH: 1959
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atgcccatgg gctccctgca gcccctggcc accctgtacc tgctgggcat gctggtggcc      60
tccgtgctgg ccgccgagaa cctgtgggtg accgtgtact acggcgtgcc cgtgtggaag     120
gaggccaaga ccaccctgtt ctgcgcctcc gacgccaagg cctacgagaa gaaggtgcac     180
aacgtgtggg ccacccacgc ctgcgtgccc accgacccca accccagga gatggtgctg      240 aagaacgtga ccgagaactt caacatgtgg aagaacgaca tggtggacca gatgcacgag     300
gacgtgatct ccctgtggga ccagtccctg aagccctgcg tgaagctgac ccccctgtgc     360
gtgaccctga actgcaccaa cgccaccgcc tccaactcct ccatcatcga gggcatgaag     420
aactgctcct tcaacatcac caccgagctg cgcgacaagc gcgagaagaa gaacgccctg     480
ttctacaagc tggacatcgt gcagctggac ggcaactcct cccagtaccg cctgatcaac     540
tgcaacacct ccgtgatcac ccaggcctgc cccaaggtgt ccttcgaccc catccccatc     600
cactactgcg cccccgccgg ctacgccatc ctgaagtgca caacaagac cttcaccggc      660 accggcccct gcaacaacgt gtccaccgtg cagtgcaccc acggcatcaa gcccgtggtg     720
tccacccagc tgctgctgaa cggctccctg gccgagggcg agatcatcat ccgctccgag     780
aacatcacca gaacgtgaa gaccatcatc gtgcacctga cgagtccgt gaagatcgag       840 tgcacccgcc ccaacaacaa gacccgcacc tccatccgca tcggccccgg ccagtggttc     900
tacgccaccg gccaggtgat cggcgacatc cgcgaggcct actgcaacat caacgagtcc     960
aagtggaacg agaccctgca gcgcgtgtcc aagaagctga aggagtactt cccccacaag    1020
aacatcacct ccagccctc ctccggcggc gacctggaga tcaccaccca ctccttcaac     1080
tgcggcggca gttcttcta ctgcaacacc tcctccctgt caaccgcac ctacatggcc      1140 aactccaccg acatggccaa ctccaccgag accaactcca cccgcaccat caccatccac    1200
tgccgcatca gcagatcat caacatgtgg caggaggtgg ccgcgccat gtacgccccc      1260 cccatcgccg gcaacatcac ctgcatctcc aacatcaccg gcctgctgct gacccgcgac    1320
ggcggcaaga acaacaccga gaccttccgc cccggcggcg gcaacatgaa ggacaactgg    1380
cgctccgagc tgtacaagta caaggtggtg aagatcgagc ccctgggcgt ggcccccacc    1440
cgctgcaagc gccgcgtggt gggccgccgc cgccgccgcc gcgccgtggg catcggcgcc    1500
gtgttcctgg gcttcctggg cgccgccggc tccaccatgg gcgccgcctc catgaccctg    1560
accgtgcagg cccgcaacct gctgtccggc atcgtgcagc agcagtccaa cctgctgcgc    1620
gcccccgagg cccagcagca cctgctgaag ctgaccgtgt ggggcatcaa gcagctgcag    1680
gcccgcgtgc tggccgtgga gcgctacctg cgcgaccagc agctgctggg catctggggc    1740
tgctccggca gctgatctg ctgcaccaac gtgccctgga ctcctcctg gtccaaccgc      1800 aacctgtccg agatctggga caacatgacc tggctgcagt gggacaagga gatctccaac    1860
tacacccaga tcatctacgg cctgctggag gagtcccaga accagcagga gaagaacgag    1920
caggacctgc tggccctgga cctgcctagc accggatag                          1959

-continued

```
<210> SEQ ID NO 44
<211> LENGTH: 652
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Val His Asn Val Trp Ala
        50                  55                  60

Thr His Ala Cys Val Pro Thr Asp Pro Asn Pro Gln Glu Met Val Leu
65                  70                  75                  80

Lys Asn Val Thr Glu Asn Phe Asn Met Trp Lys Asn Asp Met Val Asp
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Asn Cys Thr Asn Ala
            115                 120                 125

Thr Ala Ser Asn Ser Ser Ile Ile Glu Gly Met Lys Asn Cys Ser Phe
        130                 135                 140

Asn Ile Thr Thr Glu Leu Arg Asp Lys Arg Glu Lys Lys Asn Ala Leu
145                 150                 155                 160

Phe Tyr Lys Leu Asp Ile Val Gln Leu Asp Gly Asn Ser Ser Gln Tyr
                165                 170                 175

Arg Leu Ile Asn Cys Asn Thr Ser Val Ile Thr Gln Ala Cys Pro Lys
            180                 185                 190

Val Ser Phe Asp Pro Ile Pro Ile His Tyr Cys Ala Pro Ala Gly Tyr
            195                 200                 205

Ala Ile Leu Lys Cys Asn Asn Lys Thr Phe Thr Gly Thr Gly Pro Cys
        210                 215                 220

Asn Asn Val Ser Thr Val Gln Cys Thr His Gly Ile Lys Pro Val Val
225                 230                 235                 240

Ser Thr Gln Leu Leu Leu Asn Gly Ser Leu Ala Glu Gly Glu Ile Ile
                245                 250                 255

Ile Arg Ser Glu Asn Ile Thr Lys Asn Val Lys Thr Ile Ile Val His
            260                 265                 270

Leu Asn Glu Ser Val Lys Ile Glu Cys Thr Arg Pro Asn Asn Lys Thr
            275                 280                 285

Arg Thr Ser Ile Arg Ile Gly Pro Gly Gln Trp Phe Tyr Ala Thr Gly
        290                 295                 300

Gln Val Ile Gly Asp Ile Arg Glu Ala Tyr Cys Asn Ile Asn Glu Ser
305                 310                 315                 320

Lys Trp Asn Glu Thr Leu Gln Arg Val Ser Lys Lys Leu Lys Glu Tyr
                325                 330                 335

Phe Pro His Lys Asn Ile Thr Phe Gln Pro Ser Ser Gly Gly Asp Leu
            340                 345                 350

Glu Ile Thr Thr His Ser Phe Asn Cys Gly Gly Glu Phe Phe Tyr Cys
        355                 360                 365
```

-continued

```
Asn Thr Ser Ser Leu Phe Asn Arg Thr Tyr Met Ala Asn Ser Thr Asp
    370             375             380

Met Ala Asn Ser Thr Glu Thr Asn Ser Thr Arg Thr Ile Thr Ile His
385             390             395             400

Cys Arg Ile Lys Gln Ile Ile Asn Met Trp Gln Glu Val Gly Arg Ala
            405             410             415

Met Tyr Ala Pro Pro Ile Ala Gly Asn Ile Thr Cys Ile Ser Asn Ile
            420             425             430

Thr Gly Leu Leu Leu Thr Arg Asp Gly Gly Lys Asn Asn Thr Glu Thr
            435             440             445

Phe Arg Pro Gly Gly Gly Asn Met Lys Asp Asn Trp Arg Ser Glu Leu
    450             455             460

Tyr Lys Tyr Lys Val Val Lys Ile Glu Pro Leu Gly Val Ala Pro Thr
465             470             475             480

Arg Cys Lys Arg Arg Val Val Gly Arg Arg Arg Arg Arg Arg Ala Val
            485             490             495

Gly Ile Gly Ala Val Phe Leu Gly Phe Leu Gly Ala Ala Gly Ser Thr
            500             505             510

Met Gly Ala Ala Ser Met Thr Leu Thr Val Gln Ala Arg Asn Leu Leu
            515             520             525

Ser Gly Ile Val Gln Gln Gln Ser Asn Leu Leu Arg Ala Pro Glu Ala
    530             535             540

Gln Gln His Leu Leu Lys Leu Thr Val Trp Gly Ile Lys Gln Leu Gln
545             550             555             560

Ala Arg Val Leu Ala Val Glu Arg Tyr Leu Arg Asp Gln Gln Leu Leu
            565             570             575

Gly Ile Trp Gly Cys Ser Gly Lys Leu Ile Cys Cys Thr Asn Val Pro
            580             585             590

Trp Asn Ser Ser Trp Ser Asn Arg Asn Leu Ser Glu Ile Trp Asp Asn
    595             600             605

Met Thr Trp Leu Gln Trp Asp Lys Glu Ile Ser Asn Tyr Thr Gln Ile
    610             615             620

Ile Tyr Gly Leu Leu Glu Glu Ser Gln Asn Gln Gln Glu Lys Asn Glu
625             630             635             640

Gln Asp Leu Leu Ala Leu Asp Leu Pro Ser Thr Gly
            645             650
```

```
<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 45

Leu Pro Xaa Thr Gly Xaa Xaa
1               5
```

```
<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 46

Gly Gly Gly Gly Gly Xaa Xaa Xaa
1               5

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 47

Leu Pro Xaa Thr Gly Gly Gly Gly Gly Xaa Xaa Xaa
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
```

```
<222> LOCATION: (6)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 48

Xaa Xaa Xaa Leu Pro Xaa Thr Gly Xaa Xaa
1               5                   10

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Gly
1               5

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 50

Xaa Xaa Xaa Leu Pro Xaa Thr Gly Gly Gly Gly Gly
1               5                   10

<210> SEQ ID NO 51
<211> LENGTH: 815
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Glu Ala Lys Thr Thr Leu Phe Cys
        35                  40                  45
```

-continued

```
Ala Ser Asp Ala Lys Ala Tyr Glu Lys Lys Val His Asn Val Trp Ala
    50              55              60

Thr His Ala Cys Val Pro Thr Asp Pro Asn Pro Gln Glu Met Val Leu
65              70              75              80

Lys Asn Val Thr Glu Asn Phe Asn Met Trp Lys Asn Asp Met Val Asp
            85              90              95

Gln Met His Glu Asp Val Ile Ser Leu Trp Asp Gln Ser Leu Lys Pro
            100             105             110

Cys Val Lys Leu Thr Pro Leu Cys Val Thr Leu Asn Cys Thr Asn Ala
            115             120             125

Thr Ala Ser Asn Ser Ser Ile Ile Glu Gly Met Lys Asn Cys Ser Phe
    130             135             140

Asn Ile Thr Thr Glu Leu Arg Asp Lys Arg Glu Lys Lys Asn Ala Leu
145             150             155             160

Phe Tyr Lys Leu Asp Ile Val Gln Leu Asp Gly Asn Ser Ser Gln Tyr
            165             170             175

Arg Leu Ile Asn Cys Asn Thr Ser Val Ile Thr Gln Ala Cys Pro Lys
            180             185             190

Val Ser Phe Asp Pro Ile Pro Ile His Tyr Cys Ala Pro Ala Gly Tyr
            195             200             205

Ala Ile Leu Lys Cys Asn Asn Lys Thr Phe Thr Gly Thr Gly Pro Cys
    210             215             220

Asn Asn Val Ser Thr Val Gln Cys Thr His Gly Ile Lys Pro Val Val
225             230             235             240

Ser Thr Gln Leu Leu Leu Asn Gly Ser Leu Ala Glu Gly Glu Ile Ile
            245             250             255

Ile Arg Ser Glu Asn Ile Thr Asn Asn Val Lys Thr Ile Ile Val His
            260             265             270

Leu Asn Glu Ser Val Lys Ile Glu Cys Thr Arg Pro Asn Asn Lys Thr
            275             280             285

Arg Thr Ser Ile Arg Ile Gly Pro Gly Gln Trp Phe Tyr Ala Thr Gly
    290             295             300

Gln Val Ile Gly Asp Ile Arg Glu Ala Tyr Cys Asn Ile Asn Glu Ser
305             310             315             320

Lys Trp Asn Glu Thr Leu Gln Arg Val Ser Lys Lys Leu Lys Glu Tyr
            325             330             335

Phe Pro His Lys Asn Ile Thr Phe Gln Pro Ser Ser Gly Gly Asp Leu
            340             345             350

Glu Ile Thr Thr His Ser Phe Asn Cys Gly Gly Glu Phe Phe Tyr Cys
            355             360             365

Asn Thr Ser Ser Leu Phe Asn Arg Thr Tyr Met Ala Asn Ser Thr Asp
    370             375             380

Met Ala Asn Ser Thr Glu Thr Asn Ser Thr Arg Thr Ile Thr Ile His
385             390             395             400

Cys Arg Ile Lys Gln Ile Ile Asn Met Trp Gln Glu Val Gly Arg Ala
            405             410             415

Met Tyr Ala Pro Pro Ile Ala Gly Asn Ile Thr Cys Ile Ser Asn Ile
            420             425             430

Thr Gly Leu Leu Leu Thr Arg Asp Gly Gly Lys Asn Asn Thr Glu Thr
            435             440             445

Phe Arg Pro Gly Gly Gly Asn Met Lys Asp Asn Trp Arg Ser Glu Leu
    450             455             460
```

-continued

```
Tyr Lys Tyr Lys Val Val Lys Ile Glu Pro Leu Gly Val Ala Pro Thr
465             470              475             480

Arg Cys Lys Arg Arg Val Val Gly Arg Arg Arg Arg Arg Ala Val
            485          490              495

Gly Ile Gly Ala Val Phe Leu Gly Phe Leu Gly Ala Ala Gly Ser Thr
        500              505              510

Met Gly Ala Ala Ser Met Thr Leu Thr Val Gln Ala Arg Asn Leu Leu
        515              520              525

Ser Gly Ile Val Gln Gln Gln Ser Asn Leu Leu Arg Ala Pro Glu Ala
        530              535              540

Gln Gln His Leu Leu Lys Leu Thr Val Trp Gly Ile Lys Gln Leu Gln
545              550              555              560

Ala Arg Val Leu Ala Val Glu Arg Tyr Leu Arg Asp Gln Gln Leu Leu
            565              570              575

Gly Ile Trp Gly Cys Ser Gly Lys Leu Ile Cys Cys Thr Asn Val Pro
        580              585              590

Trp Asn Ser Ser Trp Ser Asn Arg Asn Leu Ser Glu Ile Trp Asp Asn
        595              600              605

Met Thr Trp Leu Gln Trp Asp Lys Glu Ile Ser Asn Tyr Thr Gln Ile
        610              615              620

Ile Tyr Gly Leu Leu Glu Glu Ser Gln Asn Gln Gln Glu Lys Asn Glu
625              630              635              640

Gln Asp Leu Leu Ala Leu Asp Gly Gly Gly Ser Gly Asp Ile Ile Lys
            645              650              655

Leu Leu Asn Glu Gln Val Asn Lys Glu Met Asn Ser Ser Asn Leu Tyr
            660              665              670

Met Ser Met Ser Ser Trp Cys Tyr Thr His Ser Leu Asp Gly Ala Gly
        675              680              685

Leu Phe Leu Phe Asp His Ala Ala Glu Glu Tyr Glu His Ala Lys Lys
        690              695              700

Leu Ile Ile Phe Leu Asn Glu Asn Asn Val Pro Val Gln Leu Thr Ser
705              710              715              720

Ile Ser Ala Pro Glu His Lys Phe Glu Gly Leu Thr Gln Ile Phe Gln
            725              730              735

Lys Ala Tyr Glu His Glu Gln His Ile Ser Glu Ser Ile Asn Asn Ile
            740              745              750

Val Asp His Ala Ile Lys Ser Lys Asp His Ala Thr Phe Asn Phe Leu
            755              760              765

Gln Trp Tyr Val Ala Glu Gln His Glu Glu Glu Val Leu Phe Lys Asp
        770              775              780

Ile Leu Asp Lys Ile Glu Leu Ile Gly Asn Glu Asn His Gly Leu Tyr
785              790              795              800

Leu Ala Asp Gln Tyr Val Lys Gly Ile Ala Lys Ser Arg Lys Ser
            805              810              815
```

<210> SEQ ID NO 52
<211> LENGTH: 2451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atgcccatgg gctccctgca gcccctggcc accctgtacc tgctgggcat gctggtggcc      60

```
tccgtgctgg ccgccgagaa cctgtgggtg accgtgtact acggcgtgcc cgtgtggaag      120
gaggccaaga ccaccctgtt ctgcgcctcc gacgccaagg cctacgagaa gaaggtgcac      180
aacgtgtggg ccacccacgc ctgcgtgccc accgacccca acccccagga gatggtgctg      240
aagaacgtga ccgagaactt caacatgtgg aagaacgaca tggtggacca gatgcacgag      300
gacgtgatct ccctgtggga ccagtccctg aagccctgcg tgaagctgac cccctgtgc      360 gtgaccctga actgcaccaa cgccaccgcc tccaactcct ccatcatcga gggcatgaag      420
aactgctcct tcaacatcac caccgagctg cgcgacaagc gcgagaagaa gaacgccctg      480
ttctacaagc tggacatcgt gcagctggac ggcaactcct cccagtaccg cctgatcaac      540
tgcaacacct ccgtgatcac ccaggcctgc cccaaggtgt ccttcgaccc catccccatc      600
cactactgcg cccccgccgg ctacgccatc ctgaagtgca caacaagac cttcaccggc      660 accggcccct gcaacaacgt gtccaccgtg cagtgcaccc acggcatcaa gcccgtggtg      720
tccacccagc tgctgctgaa cggctccctg gccgagggcg agatcatcat ccgctccgag      780
aacatcacca acaacgtgaa gaccatcatc gtgcacctga acgagtccgt gaagatcgag      840
tgcacccgcc ccaacaacaa gacccgcacc tccatccgca tcggccccgg ccagtggttc      900
tacgccaccg gccaggtgat cggcgacatc cgcgaggcct actgcaacat caacgagtcc      960
aagtggaacg agaccctgca gcgcgtgtcc aagaagctga aggagtactt cccccacaag     1020
aacatcacct tccagccctc ctccggcggc gacctggaga tcaccaccca ctccttcaac     1080
tgcggcggcg agttcttcta ctgcaacacc tcctccctgt tcaaccgcac ctacatggcc     1140
aactccaccg acatggccaa ctccaccgag accaactcca cccgcaccat caccatccac     1200
tgccgcatca agcagatcat caacatgtgg caggaggtgg gccgcgccat gtacgccccc     1260
cccatcgccg gcaacatcac ctgcatctcc aacatcaccg gcctgctgct gacccgcgac     1320
ggcggcaaga acaacaccga gaccttccgc cccggcggcg gcaacatgaa ggacaactgg     1380
cgctccgagc tgtacaagta caaggtggtg aagatcgagc ccctgggcgt ggcccccacc     1440
cgctgcaagc gccgcgtggt gggccgccgc cgccgccgcc gcgccgtggg catcggcgcc     1500
gtgttcctgg gcttcctggg cgccgccggc tccaccatgg gcgccgcctc catgaccctg     1560
accgtgcagg cccgcaacct gctgtccggc atcgtgcagc agcagtccaa cctgctgcgc     1620
gcccccgagg cccagcagca cctgctgaag ctgaccgtgt ggggcatcaa gcagctgcag     1680
gcccgcgtgc tggccgtgga gcgctacctg cgcgaccagc agctgctggg catctggggc     1740
tgctccggca gctgatctg ctgcaccaac gtgccctgga actcctcctg gtccaaccgc     1800
aacctgtccg agatctggga caacatgacc tggctgcagt gggacaagga gatctccaac     1860
tacacccaga tcatctacgg cctgctggag gagtcccaga accagcagga gaagaacgag     1920
caggacctgc tggccctgga cggcggcggc tccggcgaca tcatcaagct gctgaacgag     1980
caggtgaaca aggagatgaa ctcctccaac ctgtacatgt ccatgtcctc ctggtgctac     2040
acccactccc tggacggcgc cggcctgttc ctgttcgacc acgccgccga ggagtacgag     2100
cacgccaaga gctgatcat cttcctgaac gagaacaacg tgcccgtgca gctgacctcc     2160
atctccgccc ccgagcacaa gttcgagggc ctgacccaga tcttccagaa ggcctacgag     2220
cacgagcagc acatctccga gtccatcaac aacatcgtgg accacgccat caagtccaag     2280
gaccacgcca ccttcaactt cctgcagtgg tacgtggccg agcagcacga ggaggaggtg     2340
ctgttcaagg acatcctgga caagatcgag ctgatcggca cgagaaccca cggcctgtac     2400
ctggccgacc agtacgtgaa gggcatcgcc aagtcccgca agtcctgata a               2451
```

```
<210> SEQ ID NO 53
<211> LENGTH: 815
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asp Ala Lys Ala Tyr Glu Lys Lys Val His Asn Val Trp Ala
        50                  55                  60

Thr His Ala Cys Val Pro Thr Asp Pro Asn Pro Gln Glu Met Val Leu
65                  70                  75                  80

Lys Asn Val Thr Glu Asn Phe Asn Met Trp Lys Asn Asp Met Val Asp
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Asn Cys Thr Asn Ala
            115                 120                 125

Thr Ala Ser Asn Ser Ser Ile Ile Glu Gly Met Lys Asn Cys Ser Phe
        130                 135                 140

Asn Ile Thr Thr Glu Leu Arg Asp Lys Arg Glu Lys Lys Asn Ala Leu
145                 150                 155                 160

Phe Tyr Lys Leu Asp Ile Val Gln Leu Asp Gly Asn Ser Ser Gln Tyr
                165                 170                 175

Arg Leu Ile Asn Cys Asn Thr Ser Val Ile Thr Gln Ala Cys Pro Lys
            180                 185                 190

Val Ser Phe Asp Pro Ile Pro Ile His Tyr Cys Ala Pro Ala Gly Tyr
            195                 200                 205

Ala Ile Leu Lys Cys Asn Asn Lys Thr Phe Thr Gly Thr Gly Pro Cys
        210                 215                 220

Asn Asn Val Ser Thr Val Gln Cys Thr His Gly Ile Lys Pro Val Val
225                 230                 235                 240

Ser Thr Gln Leu Leu Leu Asn Gly Ser Leu Ala Glu Gly Glu Ile Ile
                245                 250                 255

Ile Arg Ser Glu Asn Ile Thr Lys Asn Val Lys Thr Ile Ile Val His
            260                 265                 270

Leu Asn Glu Ser Val Lys Ile Glu Cys Thr Arg Pro Asn Asn Lys Thr
            275                 280                 285

Arg Thr Ser Ile Arg Ile Gly Pro Gly Gln Trp Phe Tyr Ala Thr Gly
        290                 295                 300

Gln Val Ile Gly Asp Ile Arg Glu Ala Tyr Cys Asn Ile Asn Glu Ser
305                 310                 315                 320

Lys Trp Asn Glu Thr Leu Gln Arg Val Ser Lys Lys Leu Lys Glu Tyr
                325                 330                 335

Phe Pro His Lys Asn Ile Thr Phe Gln Pro Ser Ser Gly Gly Asp Leu
            340                 345                 350

Glu Ile Thr Thr His Ser Phe Asn Cys Gly Gly Glu Phe Phe Tyr Cys
```

-continued

```
             355                 360                 365

Asn Thr Ser Ser Leu Phe Asn Arg Thr Tyr Met Ala Asn Ser Thr Asp
    370                 375                 380

Met Ala Asn Ser Thr Glu Thr Asn Ser Thr Arg Thr Ile Thr Ile His
385                 390                 395                 400

Cys Arg Ile Lys Gln Ile Ile Asn Met Trp Gln Glu Val Gly Arg Ala
                405                 410                 415

Met Tyr Ala Pro Pro Ile Ala Gly Asn Ile Thr Cys Ile Ser Asn Ile
                420                 425                 430

Thr Gly Leu Leu Leu Thr Arg Asp Gly Gly Lys Asn Asn Thr Glu Thr
                435                 440                 445

Phe Arg Pro Gly Gly Gly Asn Met Lys Asp Asn Trp Arg Ser Glu Leu
    450                 455                 460

Tyr Lys Tyr Lys Val Val Lys Ile Glu Pro Leu Gly Val Ala Pro Thr
465                 470                 475                 480

Arg Cys Lys Arg Arg Val Val Gly Arg Arg Arg Arg Arg Ala Val
                485                 490                 495

Gly Ile Gly Ala Val Phe Leu Gly Phe Leu Gly Ala Ala Gly Ser Thr
                500                 505                 510

Met Gly Ala Ala Ser Met Thr Leu Thr Val Gln Ala Arg Asn Leu Leu
                515                 520                 525

Ser Gly Ile Val Gln Gln Gln Ser Asn Leu Leu Arg Ala Pro Glu Ala
    530                 535                 540

Gln Gln His Leu Leu Lys Leu Thr Val Trp Gly Ile Lys Gln Leu Gln
545                 550                 555                 560

Ala Arg Val Leu Ala Val Glu Arg Tyr Leu Arg Asp Gln Gln Leu Leu
                565                 570                 575

Gly Ile Trp Gly Cys Ser Gly Lys Leu Ile Cys Cys Thr Asn Val Pro
                580                 585                 590

Trp Asn Ser Ser Trp Ser Asn Arg Asn Leu Ser Glu Ile Trp Asp Asn
                595                 600                 605

Met Thr Trp Leu Gln Trp Asp Lys Glu Ile Ser Asn Tyr Thr Gln Ile
    610                 615                 620

Ile Tyr Gly Leu Leu Glu Glu Ser Gln Asn Gln Gln Glu Lys Asn Glu
625                 630                 635                 640

Gln Asp Leu Leu Ala Leu Asp Gly Gly Gly Ser Gly Asp Ile Ile Lys
                645                 650                 655

Leu Leu Asn Glu Gln Val Asn Lys Glu Met Asn Ser Ser Asn Leu Tyr
                660                 665                 670

Met Ser Met Ser Ser Trp Cys Tyr Thr His Ser Leu Asp Gly Ala Gly
                675                 680                 685

Leu Phe Leu Phe Asp His Ala Ala Glu Glu Tyr Glu His Ala Lys Lys
    690                 695                 700

Leu Ile Ile Phe Leu Asn Glu Asn Asn Val Pro Val Gln Leu Thr Ser
705                 710                 715                 720

Ile Ser Ala Pro Glu His Lys Phe Glu Gly Leu Thr Gln Ile Phe Gln
                725                 730                 735

Lys Ala Tyr Glu His Glu Gln His Ile Ser Glu Ser Ile Asn Asn Ile
                740                 745                 750

Val Asp His Ala Ile Lys Ser Lys Asp His Ala Thr Phe Asn Phe Leu
                755                 760                 765

Gln Trp Tyr Val Ala Glu Gln His Glu Glu Glu Val Leu Phe Lys Asp
    770                 775                 780
```

-continued

```
Ile Leu Asp Lys Ile Glu Leu Ile Gly Asn Glu Asn His Gly Leu Tyr
785                 790                 795                 800

Leu Ala Asp Gln Tyr Val Lys Gly Ile Ala Lys Ser Arg Lys Ser
                805                 810                 815

<210> SEQ ID NO 54
<211> LENGTH: 2451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgcccatgg gctccctgca gcccctggcc accctgtacc tgctgggcat gctggtggcc      60
tccgtgctgg ccgccgagaa cctgtgggtg accgtgtact acggcgtgcc cgtgtggaag     120
gaggccaaga ccaccctgtt ctgcgcctcc gacgccaagg cctacgagaa gaaggtgcac     180
aacgtgtggg ccacccacgc ctgcgtgccc accgacccca accccagga gatggtgctg     240 aagaacgtga ccgagaactt caacatgtgg aagaacgaca tggtggacca gatgcacgag     300
gacgtgatct ccctgtggga ccagtccctg aagccctgcg tgaagctgac ccccctgtgc     360
gtgaccctga actgcaccaa cgccaccgcc tccaactcct ccatcatcga gggcatgaag     420
aactgctcct tcaacatcac caccgagctg cgcgacaagc gcgagaagaa gaacgccctg     480
ttctacaagc tggacatcgt gcagctggac ggcaactcct cccagtaccg cctgatcaac     540
tgcaacacct ccgtgatcac ccaggcctgc cccaaggtgt ccttcgaccc catccccatc     600
cactactgcg cccccgccgg ctacgccatc ctgaagtgca acaacaagac cttcaccggc     660
accggcccct gcaacaacgt gtccaccgtg cagtgcaccc acggcatcaa gcccgtggtg     720
tccacccagc tgctgctgaa cggctccctg gccgagggcg agatcatcat ccgctccgag     780
aacatcacca gaacgtgaa gaccatcatc gtgcacctga cgagtccgt gaagatcgag     840 tgcacccgcc ccaacaacaa gacccgcacc tccatccgca tcggccccgg ccagtggttc     900
tacgccaccg gccaggtgat cggcgacatc cgcgaggcct actgcaacat caacgagtcc     960
aagtggaacg agaccctgca gcgcgtgtcc aagaagctga aggagtactt cccccacaag    1020
aacatcacct tccagccctc ctccggcggc gacctggaga tcaccaccca ctccttcaac    1080
tgcggcggcg agttcttcta ctgcaacacc tcctccctgt tcaaccgcac ctacatggcc    1140
aactccaccg acatggccaa ctccaccgag accaactcca cccgcaccat caccatccac    1200
tgccgcatca gcagatcat caacatgtgg caggaggtgg gccgcgccat gtacgccccc    1260
cccatcgccg gcaacatcac ctgcatctcc aacatcaccg gcctgctgct gacccgcgac    1320
ggcggcaaga acaacaccga gaccttccgc cccggcggcg gcaacatgaa ggacaactgg    1380
cgctccgagc tgtacaagta caaggtggtg aagatcgagc ccctgggcgt ggcccccacc    1440
cgctgcaagc gccgcgtggt gggccgccgc cgccgccgcc gcgccgtggg catcggcgcc    1500
gtgttcctgg gcttcctggg cgccgccggc tccaccatgg gcgccgcctc catgaccctg    1560
accgtgcagg cccgcaacct gctgtccggc atcgtgcagc agcagtccaa cctgctgcgc    1620 gccccccgagg cccagcagca cctgctgaag ctgaccgtgt ggggcatcaa gcagctgcag    1680
gcccgcgtgc tggccgtgga gcgctacctg cgcgaccagc agctgctggg catctggggc    1740
tgctccggca gctgatctg ctgcaccaac gtgccctgga actcctcctg gtccaaccgc    1800
aacctgtccg agatctggga caacatgacc tggctgcagt gggacaagga gatctccaac    1860
```

```
tacacccaga tcatctacgg cctgctggag gagtcccaga accagcagga gaagaacgag    1920
caggacctgc tggccctgga cggcggcggc tccggcgaca tcatcaagct gctgaacgag    1980
caggtgaaca aggagatgaa ctcctccaac ctgtacatgt ccatgtcctc ctggtgctac    2040
acccactccc tggacggcgc cggcctgttc ctgttcgacc acgccgccga ggagtacgag    2100
cacgccaaga agctgatcat cttcctgaac gagaacaacg tgcccgtgca gctgacctcc    2160
atctccgccc ccgagcacaa gttcgagggc ctgacccaga tcttccagaa ggcctacgag    2220
cacgagcagc acatctccga gtccatcaac aacatcgtgg accacgccat caagtccaag    2280
gaccacgcca ccttcaactt cctgcagtgg tacgtggccg agcagcacga ggaggaggtg    2340
ctgttcaagg acatcctgga caagatcgag ctgatcggca cgagaaccca cggcctgtac    2400
ctggccgacc agtacgtgaa gggcatcgcc aagtcccgca agtcctagta a           2451
```

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Asn Ala Thr Ala Ser Asn Ser Ser Ile Ile Glu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Thr Tyr Asn Asn Thr His Asn Ile Ser Lys
1               5                   10

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ala Phe Asn Ser Ser Ser His Thr Asn Ser Ser Ile Ala Met Gln
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Gly Asn Ser Ser Gln
1               5

<210> SEQ ID NO 59

-continued

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Asn Ser Ser Asn Thr Thr Asn
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Lys Asn Gly Arg Gln
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Gly Ser Gly
1               5
```

COMPOSITIONS COMPRISING V2 OPT HIV ENVELOPES

This application is a U.S. National Stage application under 35 U.S.C. § 371 of International Patent Application No. PCT/US2020/057205, filed on Oct. 23, 2020, which claims the benefit and priority of U.S. Application Ser. No. 62/925,173 filed Oct. 23, 2019. The contents of these applications are incorporated herein by reference in their entirety.

This invention was made with government support under Center for HIV/AIDS Vaccine Immunology-Immunogen Design grant UM1-AI100645 and UM1-AI144371 from the NIH, NIAID, Division of AIDS. The government has certain rights in the invention.

The United States government has rights in this invention pursuant to Contract No. 89233218CNA000001 between the United States Department of Energy and Triad National Security, LLC for the operation of Los Alamos National Laboratory.

The instant application contains a Sequence Listing which has been submitted electronically in ASCII format and is hereby incorporated by reference in its entirety. Said ASCII copy, created on Jan. 4, 2021, is named 1234300_00359WO1_SL.txt and is 221,348 bytes in size.

TECHNICAL FIELD

The present invention relates in general, to a composition suitable for use in inducing anti-HIV-1 antibodies, and, in particular, to immunogenic compositions comprising envelope proteins and nucleic acids to induce cross-reactive neutralizing antibodies and increase their breadth of coverage. The invention also relates to methods of inducing such broadly neutralizing anti-HIV-1 antibodies using such compositions.

BACKGROUND

The development of a safe and effective HIV-1 vaccine is one of the highest priorities of the scientific community working on the HIV-1 epidemic. While anti-retroviral treatment (ART) has dramatically prolonged the lives of HIV-1 infected patients, ART is not routinely available in developing countries.

SUMMARY OF THE INVENTION

In certain embodiments, the invention provides compositions and method for induction of immune response, for example cross-reactive (broadly) neutralizing Ab (bNAb) induction.

In certain aspects, the invention provides CH505 envelope immunogens comprising optimized V2 loop, for example but not limited to initiate V1V2, and/or CD4 binding site and/or Fusion Peptide unmutated common ancestor (UCA) broadly neutralizing antibody (bnAbs) precursors. In certain aspects the invention provides CH505 T/F envelope comprising optimized V2 loop.

In certain aspects the invention provides a recombinant HIV-1 envelope polypeptide optimized for V2 apex bnAb precursor targeting. In certain aspects the invention provides a recombinant HIV-1 envelope polypeptide optimized for V2 apex bnAb UCA/RUA (reverted unmutated ancestor) targeting. In non-limiting embodiments, the envelope is based on CH505 TF sequence. In non-limiting embodiments the envelope is any one of the envelopes from Table 1, FIGS.

3A-3C or FIGS. 4A-4B, wherein the polypeptide is a non-naturally occurring protomer designed to form an envelope trimer. In certain embodiments, the envelope is based on CH505 T/F envelope and comprises V2 binding antibody optimized sequence. In certain embodiments the envelope is designed to multimerize. In some embodiments the envelope sequence comprises a self-assembling protein, for example but not limited to ferritin. In other embodiments, the self-assembling protein is added via a sortase A reaction.

In certain embodiments, the optimized design has 11 mutations at positions 130, 161, 169, 170, 172, 316, 332, 335, 632, 644, and 717 as shown in FIG. 1. In certain embodiments, the optimized design has additional five mutations at positions 161, 200, 305, 322, and 732 as shown in FIG. 2.

In certain aspects, the invention provides a nucleic acid encoding the recombinant polypeptide of the invention. In non-limiting embodiments, the nucleic acid is mRNA. In non-limiting embodiments, the mRNA is modified. In non-limiting embodiments, the mRNA is administered as an LNP.

In certain aspects the invention provides a recombinant trimer comprising three identical protomers of an envelope of the invention, e.g. any envelope from Table 1, FIGS. 3A-3C or FIGS. 4A-4B.

In certain aspects, the invention provides an immunogenic composition comprising the recombinant trimer and a carrier, wherein the trimer comprises three identical protomers of an HIV-1 envelope listed in Table 1, FIGS. 3A-3C or FIGS. 4A-4B.

In certain aspects, the invention provides an immunogenic composition comprising nucleic acid encoding the recombinant HIV-1 envelope and a carrier.

In certain aspects, the immunogenic compositions of the invention are further comprise an adjuvant.

In certain embodiments, the nucleic acid of the invention is operably linked to a promoter, and wherein in certain embodiment the nucleic acid is inserted in an expression vector.

In certain aspects, the invention provides a method of inducing an immune response in a subject comprising administering a composition comprising any suitable form of a nucleic acid(s) of the invention or the recombinant polypeptide of the invention in an amount sufficient to induce an immune response.

In certain embodiments, the nucleic acid encodes a gp120 envelope, gp120D8 envelope, a gp140 envelope (gp140C, gp140CF, gp140CFI) as a soluble or stabilized protomer of a SOSIP trimer, a gp145 envelope, a gp150 envelope, a transmembrane bound envelope, or an envelope designed to multimerize.

In certain embodiments, the recombinant polypeptide is a gp120 envelope, gp120D8 envelope, a gp140 envelope (gp140C, gp140CF, gp140CFI) as a soluble or stabilized protomer of a SOSIP trimer, a gp145 envelope, a gp150 envelope, a transmembrane bound envelope, or an envelope designed to multimerize. In non-limiting embodiments, the envelope mutlimerizes via ferritin.

In certain embodiments, the composition further comprises an adjuvant.

In certain embodiments, the methods further comprise administering an agent which modulates host immune tolerance.

In certain embodiments, the recombinant polypeptide administered is multimerized in a liposome or nanoparticle.

In certain embodiments, the methods further comprise administering one or more additional HIV-1 immunogens to induce a T cell response.

In certain aspects, the invention provides a composition comprising a nanoparticle and a carrier, wherein the nanoparticle comprises any one of the envelopes of the invention.

In certain embodiments, the nanoparticle is ferritin self-assembling nanoparticle.

In certain aspects, the invention provides a composition comprising a nanoparticle and a carrier, wherein the nanoparticle comprises any one of the trimers of the invention.

In certain embodiments, the nanoparticle is a ferritin self-assembling nanoparticle.

In certain embodiments, the nanoparticle comprises multimers of trimers. In certain embodiments, the nanoparticle comprises 1-8 trimers.

In certain aspects, the invention provides methods of inducing an immune response in a subject comprising administering a sufficient amount to induce an immune response of an immunogenic composition comprising any one of the recombinant envelopes described herein or compositions described herein. In certain embodiments, the composition is administered as a prime. In certain embodiments, the composition is administered as a boost.

In certain embodiments, the invention provides a nucleic acid encoding any of the recombinant envelopes of the invention.

In certain embodiments, the invention provides a composition comprising the nucleic acid of the invention and a carrier.

In certain embodiments, the invention provides a method of inducing an immune response in a subject comprising administering an immunogenic composition comprising the nucleic acid or the composition comprising the nucleic acids of the invention.

In certain embodiments, the compositions contemplate nucleic acid, as DNA and/or RNA, or proteins immunogens either alone or in any combination. In certain embodiments, the methods contemplate genetic, as DNA and/or RNA, immunization either alone or in combination with envelope protein(s).

In certain embodiments the nucleic acid encoding an envelope is operably linked to a promoter inserted an expression vector. In certain aspects the compositions comprise a suitable carrier. In certain aspects the compositions comprise a suitable adjuvant.

In certain embodiments the induced immune response includes induction of antibodies, including but not limited to autologous and/or cross-reactive (broadly) neutralizing antibodies against HIV-1 envelope. Various assays that analyze whether an immunogenic composition induces an immune response, and the type of antibodies induced are known in the art and are also described herein.

In certain aspects the invention provides a nucleic acid sequence encoding any of the polypeptides of the invention, wherein the nucleic acid is operably linked to a promoter. In certain aspects the invention provides a nucleic acid consisting essentially of a nucleic acid sequence encoding any of the polypeptides of the invention, wherein the nucleic acid is operably linked to a promoter. In certain aspects the invention provides an expression vector comprising any of the nucleic acid sequences of the invention, wherein the nucleic acid is operably linked to a promoter. In certain aspects the invention provides an expression vector comprising a nucleic acid sequence encoding any of the polypeptides of the invention, wherein the nucleic acid is operably linked to a promoter. In certain aspects the invention provides an expression vector consisting essentially a nucleic acid sequence encoding any of the polypeptides of the invention, wherein the nucleic acid is operably linked to a promoter. In certain embodiments, the nucleic acids are codon optimized for expression in a mammalian cell, in vivo or in vitro. In certain aspects the invention provides nucleic acids comprising any one of the nucleic acid sequences of invention. In certain aspects the invention provides nucleic acids consisting essentially of any one of the nucleic acid sequences of invention. In certain aspects the invention provides nucleic acids consisting of any one of the nucleic acid sequences of invention. In certain embodiments the nucleic acid of the invention, is operably linked to a promoter and is inserted in an expression vector. In certain aspects the invention provides an immunogenic composition comprising the expression vector.

In certain aspects the invention provides a composition comprising at least one of the nucleic acid sequences of the invention. In certain aspects the invention provides a composition comprising any one of the nucleic acid sequences of invention. In certain aspects the invention provides a composition comprising at least one nucleic acid sequence encoding any one of the polypeptides of the invention.

In certain aspects the invention provides a composition comprising at least one nucleic acid encoding an HIV-1 envelope of the invention.

In certain embodiments, the compositions and methods employ an HIV-1 envelope as polypeptide instead of a nucleic acid sequence encoding the HIV-1 envelope. In certain embodiments, the compositions and methods employ an HIV-1 envelope as polypeptide, a nucleic acid sequence encoding the HIV-1 envelope, or a combination thereof. In certain embodiments, the polypeptides are recombinantly produced.

The envelope used in the compositions and methods of the invention can be a gp160, gp150, gp145, gp140, gp120, gp41, or N-terminal deletion variants thereof as described herein, cleavage resistant variants thereof as described herein, or codon optimized sequences thereof. In certain embodiments the composition comprises envelopes as trimers. In certain embodiments, envelope proteins are multimerized, for example trimers are attached to a particle such that multiple copies of the trimer are attached and the multimerized envelope is prepared and formulated for immunization in a human. In certain embodiments, the compositions comprise envelopes, including but not limited to trimers as particulate, high-density array on liposomes or other particles, for example but not limited to nanoparticles. In some embodiments, the trimers are in a well ordered, near native like or closed conformation. In some embodiments the trimer compositions comprise a homogenous mix of native like trimers. In some embodiments the trimer compositions comprise at least 65%, 70%, 75%, 80%, 85%, 90%, 95% native like trimers.

The polypeptide contemplated by the invention can be a polypeptide comprising any one of the polypeptides described herein. The polypeptide contemplated by the invention can be a polypeptide consisting essentially of any one of the polypeptides described herein. The polypeptide contemplated by the invention can be a polypeptide consisting of any one of the polypeptides described herein. In certain embodiments, the polypeptide is recombinantly produced. In certain embodiments, the polypeptides and nucleic acids of the invention are suitable for use as an immunogen, for example to be administered in a human subject.

In certain embodiments the envelope is any of the forms of HIV-1 envelope. In certain embodiments the envelope is a gp120, gp140, gp145 (i.e. with a transmembrane), gp150 envelope. In certain embodiments, gp140 is designed to form a stable trimer. In certain embodiments envelope protomers from a trimer which is not a SOSIP timer. In certain embodiment the trimer is a SOSIP based trimer wherein each protomer comprises additional modifications. In certain embodiments, envelope trimers are recombinantly produced. In certain embodiments, envelope trimers are purified from cellular recombinant fractions by antibody binding and reconstituted in lipid comprising formulations. See for example WO2015/127108 titled "Trimeric HIV-1 envelopes and uses thereof" which content is herein incorporated by reference in its entirety. In certain embodiments the envelopes of the invention are engineered and comprise non-naturally occurring modifications.

In certain embodiments, the envelope is in a liposome. In certain embodiments the envelope comprises a transmembrane domain with a cytoplasmic tail embedded in a liposome. In certain embodiments, the nucleic acid comprises a nucleic acid sequence which encodes a gp120, gp140, gp145, gp150, gp160.

In certain embodiments, where the nucleic acids are operably linked to a promoter and inserted in a vector, the vectors are any suitable vector. Non-limiting examples include, VSV, replicating rAdenovirus type 4, MVA, Chimp adenovirus vectors, pox vectors, and the like. In certain embodiments, the nucleic acids are administered in Nano-Taxi block polymer nanospheres. In certain embodiments, the composition and methods comprise an adjuvant. Non-limiting examples include, AS01 B, AS01 E, gla/SE, alum, Poly 1 poly C (poly IC), polyIC/long chain (LC) TLR agonists, TLR7/8 and 9 agonists, or a combination of TLR7/8 and TLR9 agonists (see Moody et al. (2014) J. Virol. March 2014 vol. 88 no. 6 3329-3339), or any other adjuvant. Non-limiting examples of TLR7/8 agonist include TLR7/8 ligands, Gardiquimod, Imiquimod and R848 (resiquimod). A non-limiting embodiment of a combination of TLR7/8 and TLR9 agonist comprises R848 and oCpG in STS (see Moody et al. (2014) J. Virol. March 2014 vol. 88 no. 6 3329-3339).

In certain aspects the invention provides a cell comprising a nucleic acid encoding any one of the envelopes of the invention suitable for recombinant expression. In certain aspects, the invention provides a clonally derived population of cells encoding any one of the envelopes of the invention suitable for recombinant expression. In certain aspects, the invention provides a stable pool of cells encoding any one of the envelopes of the invention suitable for recombinant expression.

In certain aspects, the invention provides a recombinant HIV-1 envelope polypeptide listed in Table 1. In certain embodiments, the polypeptide is a non-naturally occurring protomer designed to form an envelope trimer. The invention also provides nucleic acids encoding these recombinant polypeptides. Non-limiting examples of amino acids and nucleic acid of such protomers are shown in FIGS. 3A-5E.

In certain aspects the invention provides a recombinant trimer comprising three identical protomers of an envelope from Table 1. In certain aspects the invention provides an immunogenic composition comprising the recombinant trimer and a carrier, wherein the trimer comprises three identical protomers of an HIV-1 envelope listed in Table 1. In certain aspects the invention provides an immunogenic composition comprising a nucleic acid encoding these recombinant HIV-1 envelope and a carrier.

In certain aspects the invention provides nucleic acids encoding HIV-1 envelopes for immunization wherein the nucleic acid encodes a gp120 envelope, gp120D8 envelope, a gp140 envelope (gp140C, gp140CF, gp140CFI) as soluble or stabilized protomer of a SOSIP trimer, a gp145 envelope, a gp150 envelope, or a transmembrane bound envelope.

In certain aspects the invention provides a selection of HIV-1 envelopes for immunization wherein the HIV-1 envelope is a gp120 envelope or a gp120D8 variant. In certain embodiments a composition for immunization comprises protomers that form stabilized SOSIP trimers.

In certain embodiments, the compositions for use in immunization further comprise an adjuvant.

In certain embodiments, wherein the compositions comprise a nucleic acid, the nucleic acid is operably linked to a promoter, and could be inserted in an expression vector.

In one aspect the invention provides a composition for a prime boost immunization regimen comprising one or more envelopes from Table 1, wherein the polypeptide is a non-naturally occurring protomer designed to form an envelope trimer, wherein the envelope is a prime or boost immunogen. In one aspect the invention provides a composition for a prime boost immunization regimen comprising one or more envelopes of the invention.

In certain aspects the invention provides methods of inducing an immune response in a subject comprising administering a composition comprising a polypeptide and/or any suitable form of a nucleic acid(s) encoding an HIV-1 envelope(s) in an amount sufficient to induce an immune response.

In certain embodiments, the nucleic acid encodes a gp120 envelope, gp120D8 envelope, a gp140 envelope (gp140C, gp140CF, gp140CFI) as soluble or stabilized protomer of a SOSIP trimer, a gp145 envelope, a gp150 envelope, or a transmembrane bound envelope.

In certain embodiments, the polypeptide is gp120 envelope, gp120D8 envelope, a gp140 envelope (gp140C, gp140CF, gp140CFI) as soluble or stabilized protomer of a SOSIP trimer, a gp145 envelope, a gp150 envelope, or a transmembrane bound envelope.

In certain embodiments, the methods comprise administering an adjuvant. In certain embodiments, the methods comprise administering an agent which modulates host immune tolerance. In certain embodiments, the administered polypeptide is multimerized in a liposome or nanoparticle. In certain embodiments, the methods comprise administering one or more additional HIV-1 immunogens to induce a T cell response. Non-limiting examples include gag, nef, pol, etc.

In certain aspects, the invention provides a recombinant HIV-1 Env ectodomain timer, comprising three gp120-gp41 protomers comprising a gp120 polypeptide and a gp41 ectodomain, wherein each protomer is the same and each protomer comprises portions from envelope BG505 HIV-1 strain and gp120 polypeptide portions from a CH505 HIV-1 strain and stabilizing mutations A316W and E64K. In certain embodiments, the trimer is stabilized in a prefusion mature closed conformation, and wherein the trimer does not comprise non-natural disulfide bond between cysteine substitutions at positions 201 and 433 of the HXB2 reference sequence. Non-limited examples of envelopes contemplated as trimers are listed in Table 1. In some embodiments, the amino acid sequence of one monomer comprised in the trimer is shown in FIG. 3-5. In some embodiments, the trimer is immunogenic. In some embodiments the trimer binds to any one of the antibodies PGT145, PGT151, CH103UCA, CH103, VRC01, PGT128, or any combination thereof. In some embodiments the trimer does not bind to antibody 19B and/or 17B.

In certain aspects, the invention provides a pharmaceutical composition comprising any one of the recombinant trimers of the invention. In certain embodiments the compositions comprising trimers are immunogenic. The percent trimer in such immunogenic compositions could vary. In some embodiments the composition comprises 70%, 71%, 72%, 73%, 74%, 75%, 76%, 77%, 78%, 79%, 80%, 81%, 82%, 83%, 84%, 85%, 86%, 87%, 89%, 90%, 91%, 92%, 93%, 94%, 95%, 96%, 97%, 98%, or 99% stabilized trimer.

In certain embodiments, the envelope comprise ferritin. In certain embodiments, the inventive designs comprise modifications, including without limitation linkers between the envelope and ferritin designed to optimize ferritin nanoparticle assembly.

In certain aspects, the invention provides a composition comprising any one of the inventive envelopes or nucleic acid sequences encoding the same. In certain embodiments, the nucleic acid is mRNA. In certain embodiments, the m RNA is comprised in a lipid nanoparticle (LNP).

In certain aspects, the invention provides compositions comprising a nanoparticle which comprises any one of the envelopes of the invention.

In certain embodiments, the nanoparticle is ferritin self assembling nanoparticle.

In certain aspects, the invention provides a method of inducing an immune response in a subject comprising administering an immunogenic composition comprising any one of the stabilized envelopes of the invention. In certain embodiments, the composition is administered as a prime and/or a boost. In certain embodiments, the composition comprises nanoparticles. In certain embodiments, methods of the invention further comprise administering an adjuvant.

In certain aspects, the invention provides a composition comprising a plurality of nanoparticles comprising a plurality of the envelopes/trimers of the invention. In non-limiting embodiments, the envelopes/trimers of the invention are multimeric when comprised in a nanoparticle. The nanoparticle size is suitable for delivery. In non-liming embodiments the nanoparticles are ferritin based nanoparticles.

In certain aspects, the invention provides nucleic acids comprising sequences encoding polypeptides of the invention. In certain embodiments, the nucleic acids are DNAs. In certain embodiments, the nucleic acids are mRNAs. In certain aspects, the invention provides expression vectors comprising the nucleic acids of the invention.

In certain aspects, the invention provides a pharmaceutical composition comprising mRNAs encoding the inventive envelopes. In certain embodiments, these are optionally formulated in lipid nanoparticles (LNPs). In certain embodiments, the mRNAs are modified. Modifications include without limitations modified ribonucleotides, poly-A tail, 5' cap.

In certain aspects the invention provides nucleic acids encoding the inventive polypeptide designs. In non-limiting embodiments, the nucleic acids are mRNA, modified or unmodified, suitable for use any use, e.g but not limited to use as pharmaceutical compositions. In certain embodiments, the nucleic acids are formulated in lipid, such as but not limited to LNPs.

For 588, we suggest mutating to K (quite common aa, signature p-value=0.0005-0.026 depending on the V2 bnab, odd's ratio (OR)=2-5). For 644, we suggest mutating to R (most common sensitive aa, p=0.0006-0.007, OR=2.7-7.9).

To minimize the number of constructs, we propose adding these to UCA OPT1 SOSIP constructs (note: our UCA OPT1 carried all the sensitive signatures for mature bNAbs also in addition to most UCAs/intermediates). Gp41 mutations could also be added in some embodiments. The CH505 V2 Mature OPT design has 11 mutations as shown at positions 130, 161, 169, 170, 172, 316, 332, 335, 632, 644, and 717. These replaces 8 resistant or non-significant with sensitive signatures; One sensitive to more sensitive (R169K), one neutral to neutral (E170Q, remove charge), one resistance signature for completing glycan shield (NxST332; no impact on sensitivity).

Figure 2:
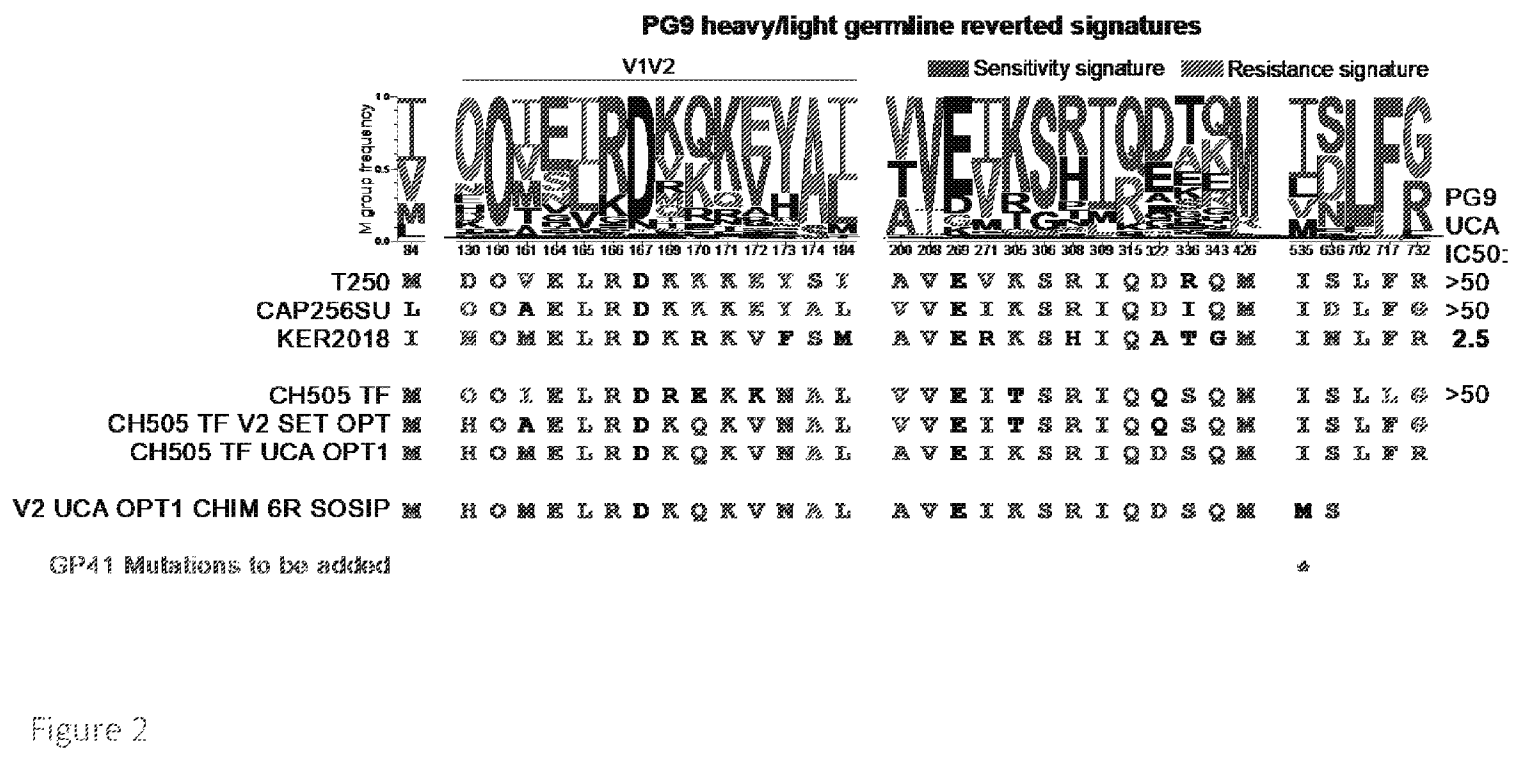

FIG. 2 shows additional signature amino acids associated with V2 bNAb unmutated common ancestor or early intermediate antibodies from early stages of V2 apex bNAb maturation. See FIG. 1 for details. UCA OPT1 SOSIP construct just has one sub-optimal aa at PG9 germline reverted Ab signature sites as compared to the full length UCA OPT1—it has an M-535 instead of I-535. We suggest using I-535 (fairly common aa, signature p=0.01, OR=3.3). Data not shown for other V2 UCAs/intermediates (CH04, PCT64) but the SOSIP UCA OPT1 construct carries all the favorable mutations for their signature sites as well. Gp41 mutations could also be added in some embodiments. The CH505 TF UCA OPT1 design includes mature V2 apex signatures, with 5 additional changes as shown at positions 161, 200, 305, 322, and 732 for UCAs.

FIGS. 3A-3C show non-limiting embodiments of amino acid sequences. FIG. 3A shows amino acid sequences of envelopes. These are continuous sequences where dashes represents gaps if these sequences were aligned. FIG. 3A discloses SEQ ID NOS 9-13, respectively, in order of appearance. FIG. 3B discloses SEQ ID NOS 14-20, respectively, in order of appearance. FIG. 3C discloses SEQ ID NOS 21-24 and 23-26, respectively, in order of appearance.

FIGS. 4A and 4B show non-limiting embodiments of amino acid and nucleic acid sequences. In FIG. 4B, VDAT (SEQ ID NO: 1)=cloning site and Kozak sequence. Underlined=signal peptide that is cleaved from mature protein. FIG. 4A discloses SEQ ID NOS 27-32, respectively, in order of appearance. FIG. 4B discloses SEQ ID NOS 33-38, respectively, in order of appearance.

Figure 5C:
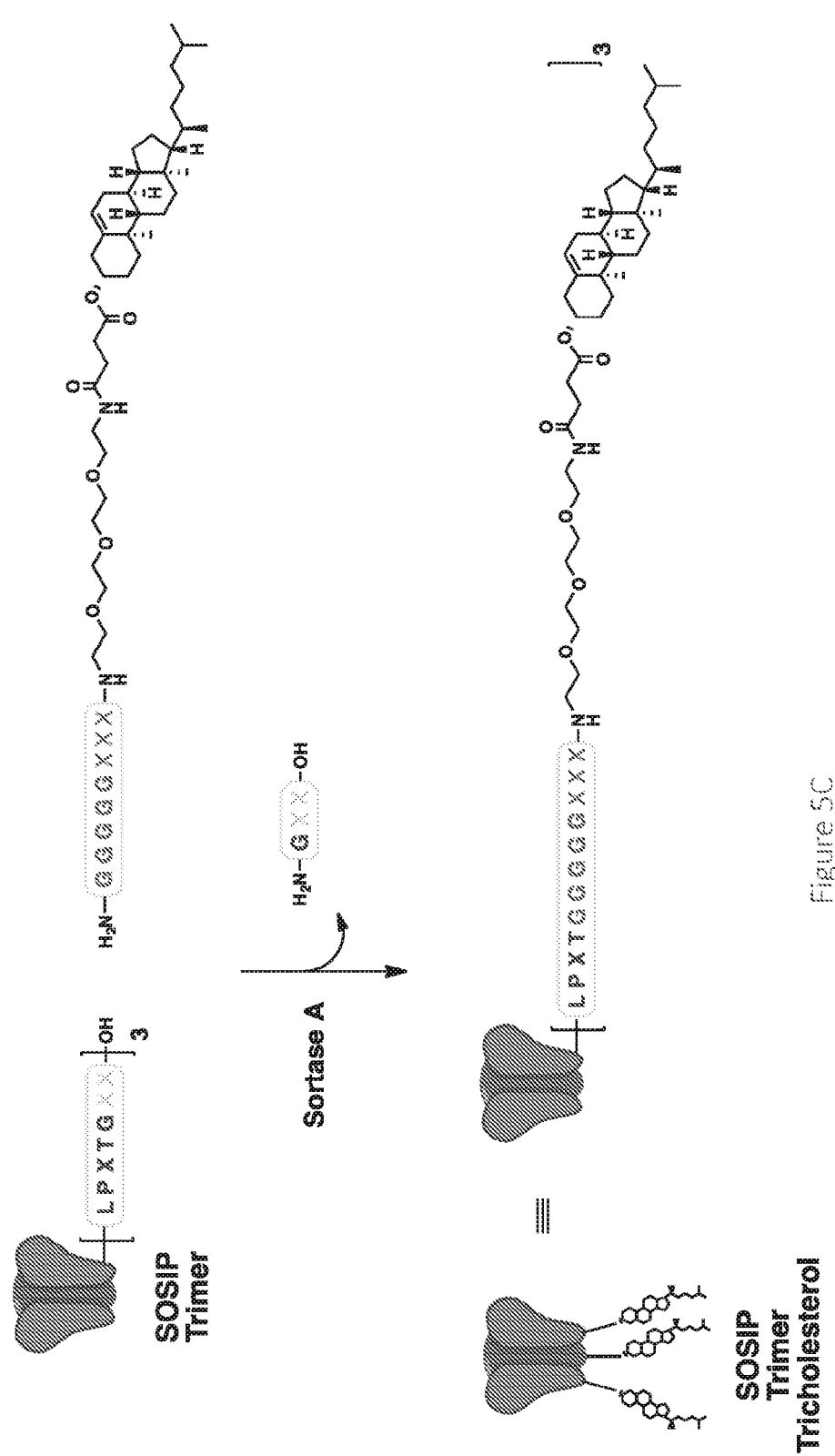
Figure 5D:
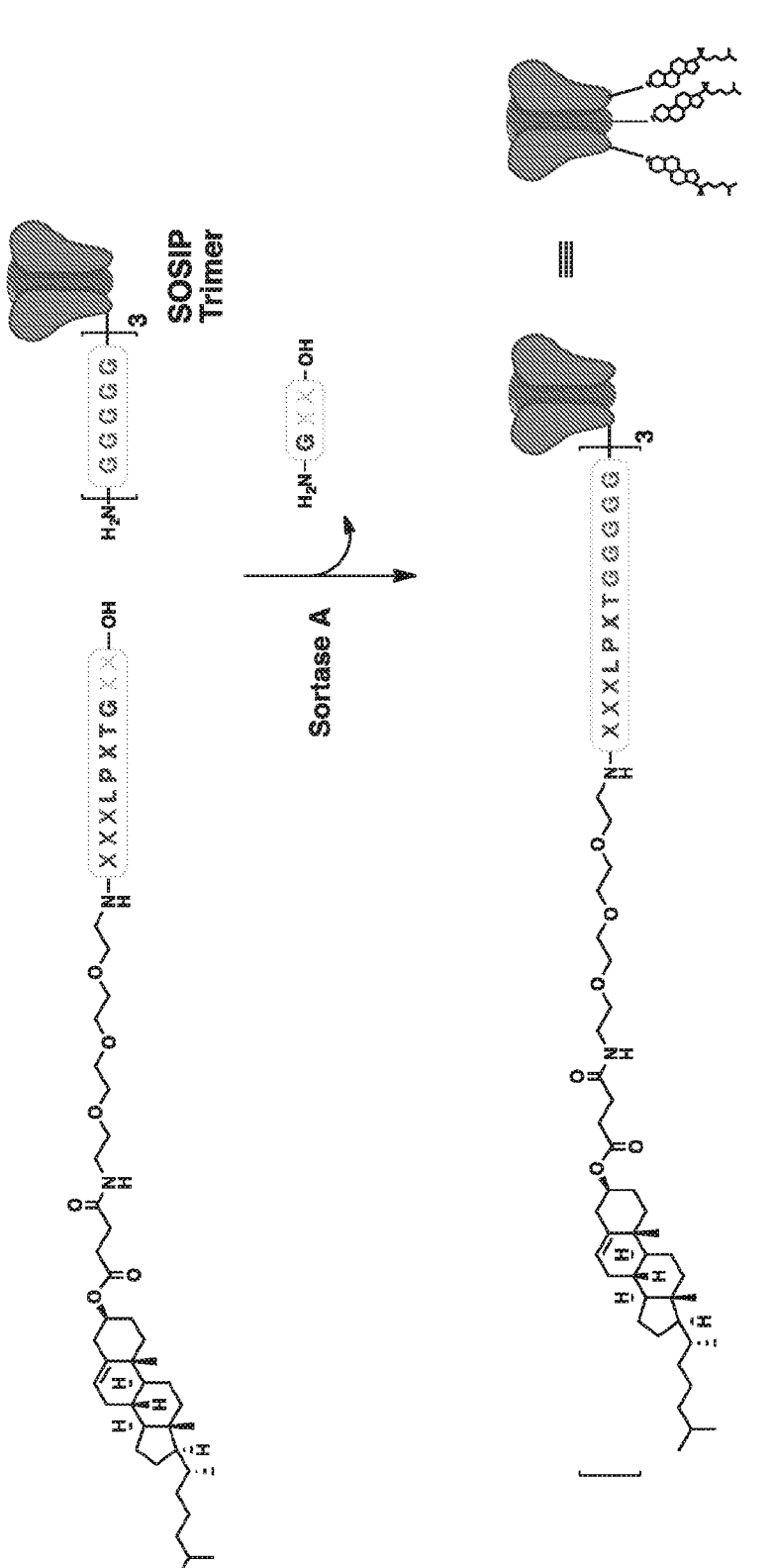

FIGS. 5A, 5B, 5C and 5D show non-limiting embodiment of sortase designs and nucleic acid and protein sequences. FIG. 5A discloses SEQ ID NO: 39. FIG. 5B discloses SEQ ID NOS 40-44, respectively, in order of appearance. FIG. 5C discloses SEQ ID NOS 45-47, respectively, in order of appearance. FIG. 5D discloses SEQ ID NOS 48-50, respectively, in order of appearance. FIG. 5E shows non-limiting embodiments of ferritin designs. FIG. 5E discloses SEQ ID NOS 61 and 51-54, respectively, in order of appearance. The linker between the envelope sequence and the ferritin protein sequence could be any suitable linker. The ferritin protein could be any suitable ferritin. See e.g. without limitation WO/2018/005558. The envelopes in these designs are CH505 T/F or CH505 M5. A skilled artisan can readily incorporate the V2 optimization into these envelopes.

FIG. 6 shows analyses for CAP256 IA4. For CAP256 IA4 weak signatures found due to low statistical power (3 out of 208 viruses neutralized). Only resistant signatures outside the epitope. Change to neutral at most sites would involve mutation to rare amino acid and/or removing glycans that could introduce vulnerable gaps in the glycan shield. Only two mutations introduce at 736 & 842. Designed UCA optimized constructs without (UCA OPT1) and with (UCA OPT2) these weak signatures.

Figure 7:
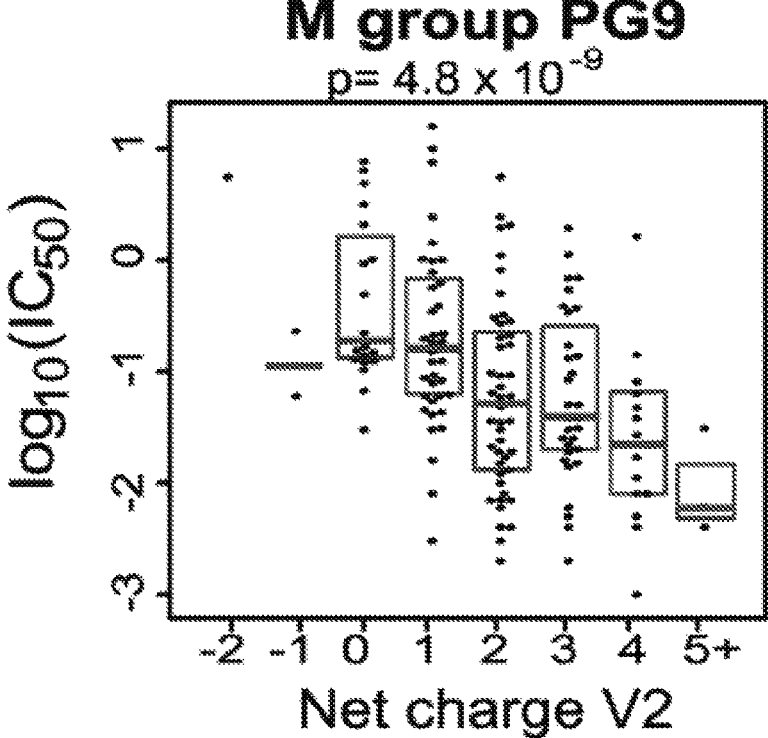

FIG. 7 shows Hypervariable Loop Characteristic. Hypervariable loops cannot be aligned due to extreme length & sequence variation. Tested for associations with net charge, length & number of glycans. Found two significant hypervariable loop associations with sensitivity to V2 apex bNAbs: Positively charged V2 loops; V2 apex bNAbs have long anionic CDRH3. Smaller hypervariable V1 & V2 combined: possible steric hindrance due to the dynamic loops.

Figure 8B:
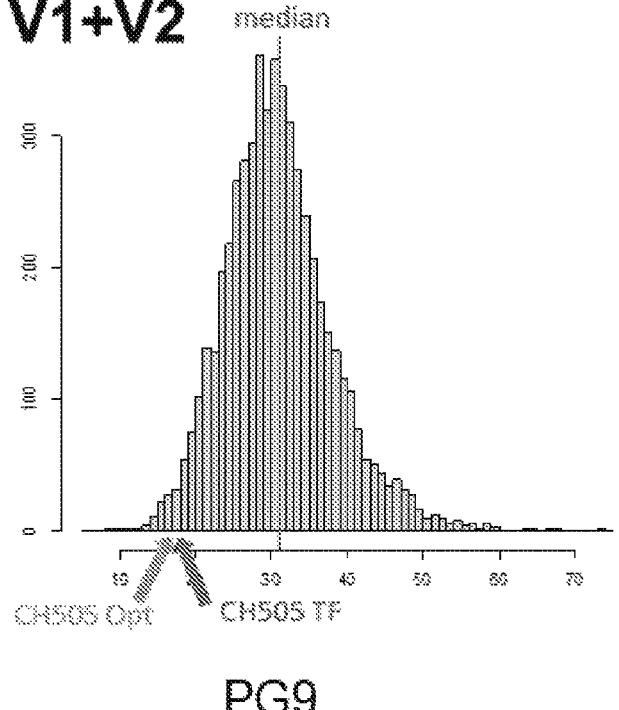
Figure 9A:
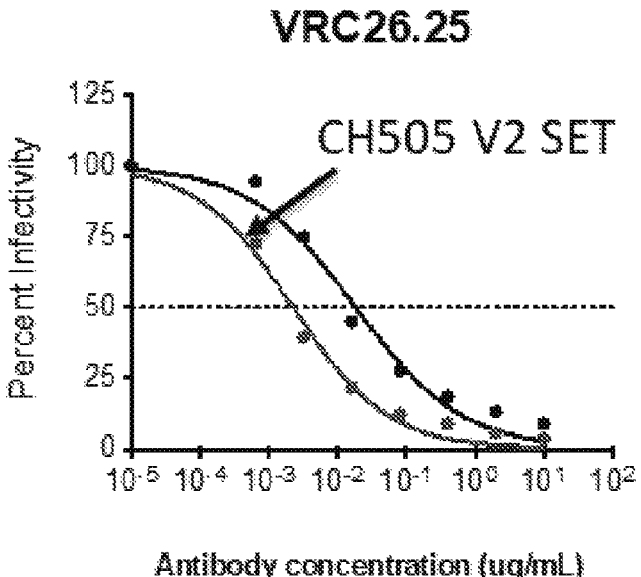
Figure 9B:
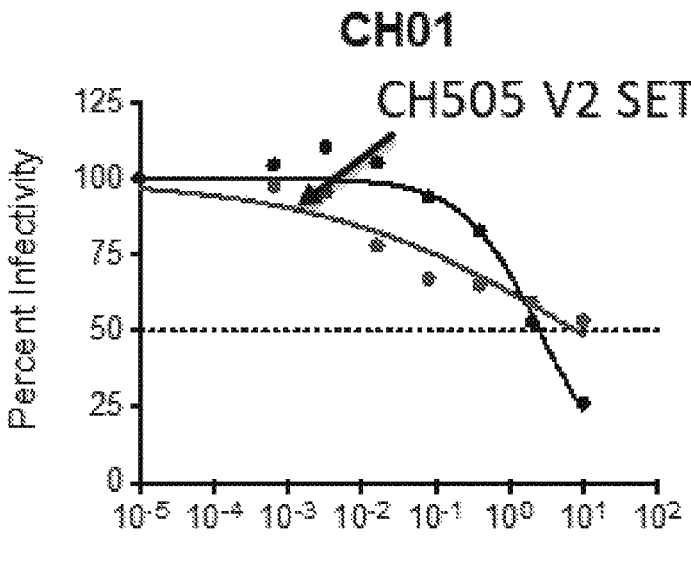
Figure 9C:
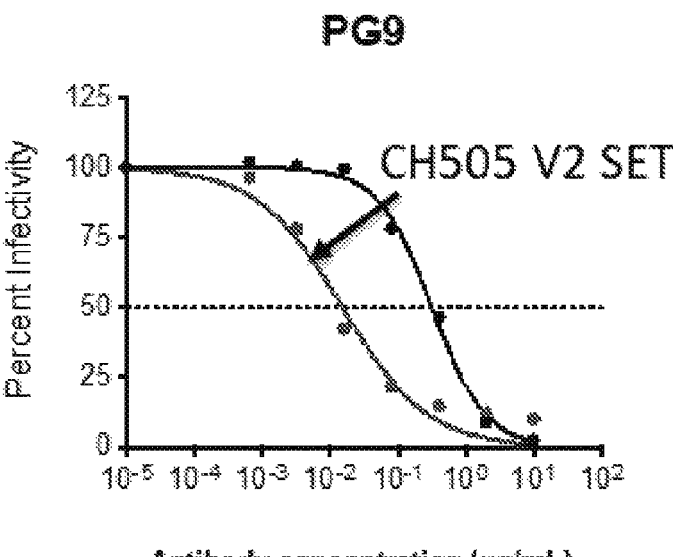
Figure 9D:
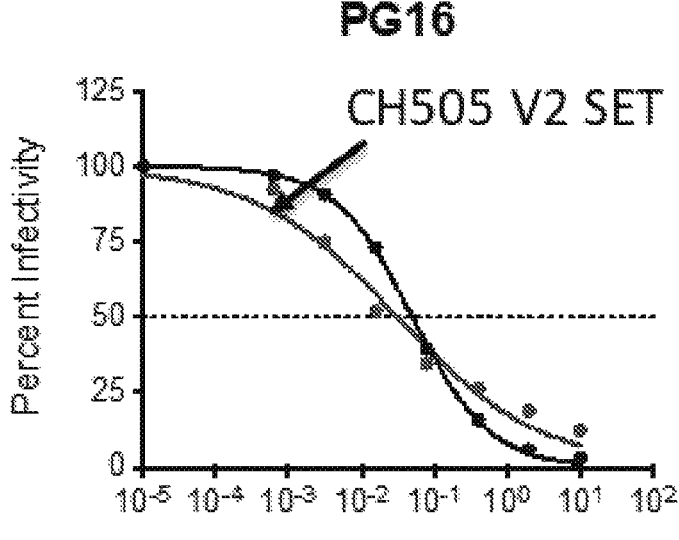
Figure 9E:
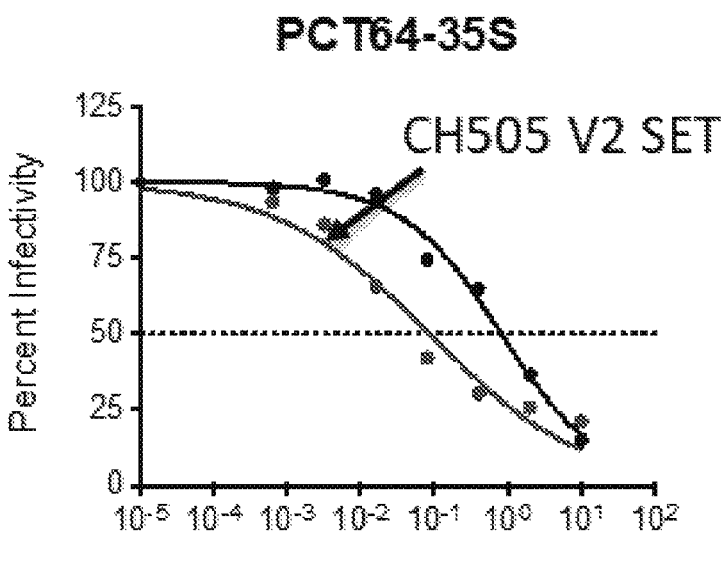
Figure 10A:
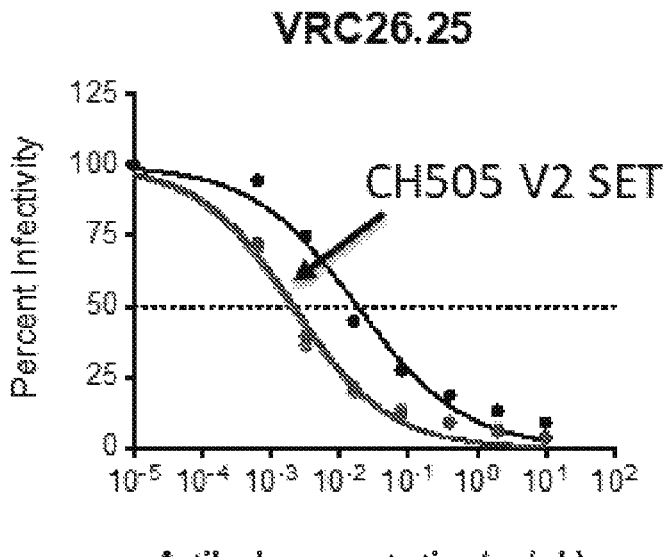
Figure 10B:
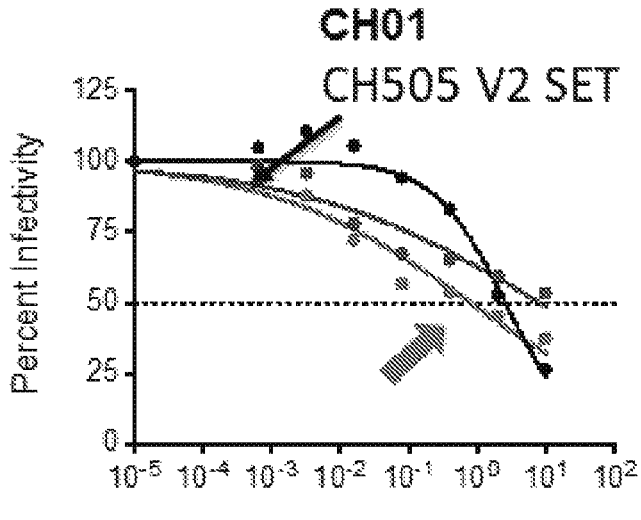
Figure 10C:
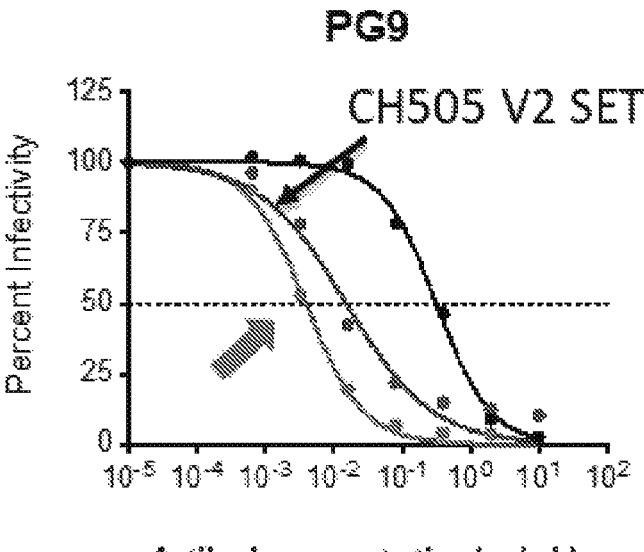
Figure 10D:
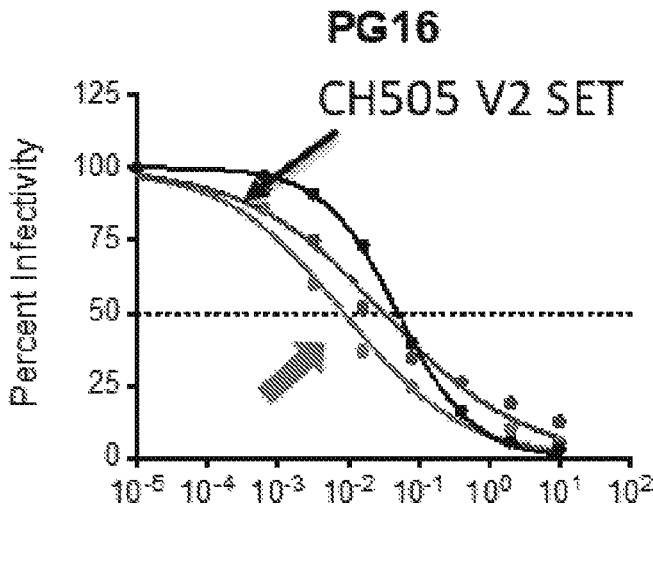
Figure 10E:
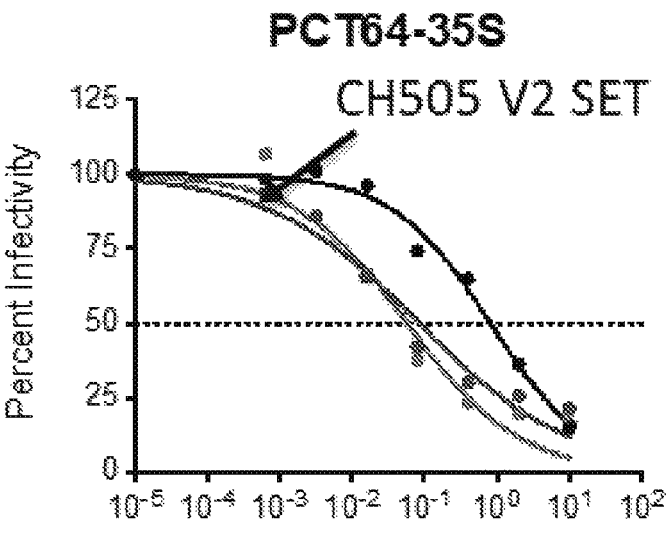
Figure 11A:
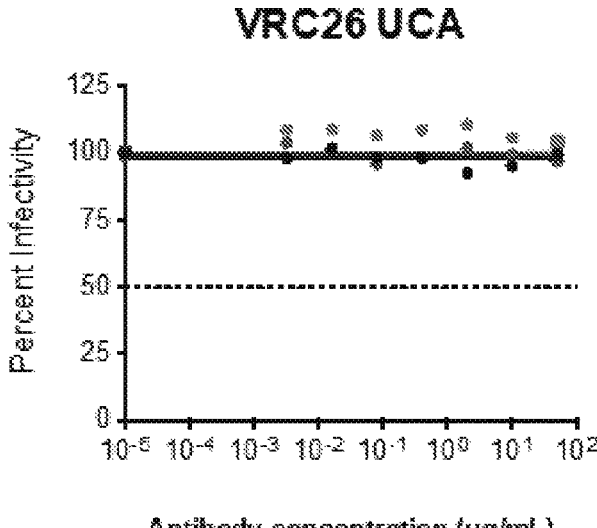
Figure 11B:
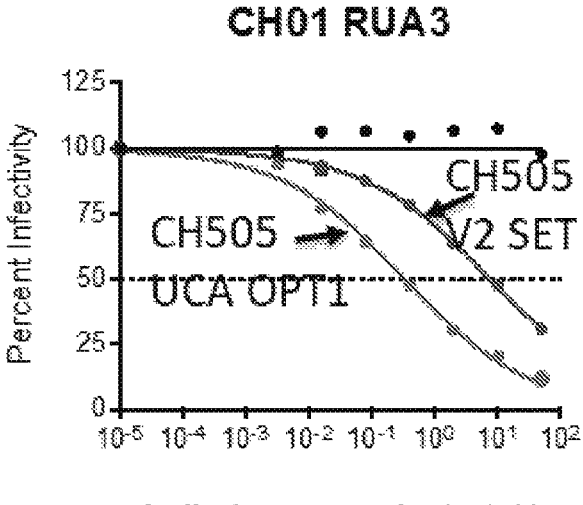
Figure 11C:
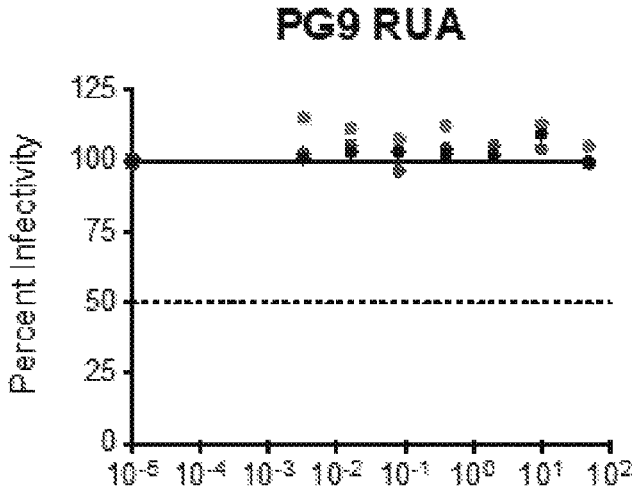
Figure 11D:
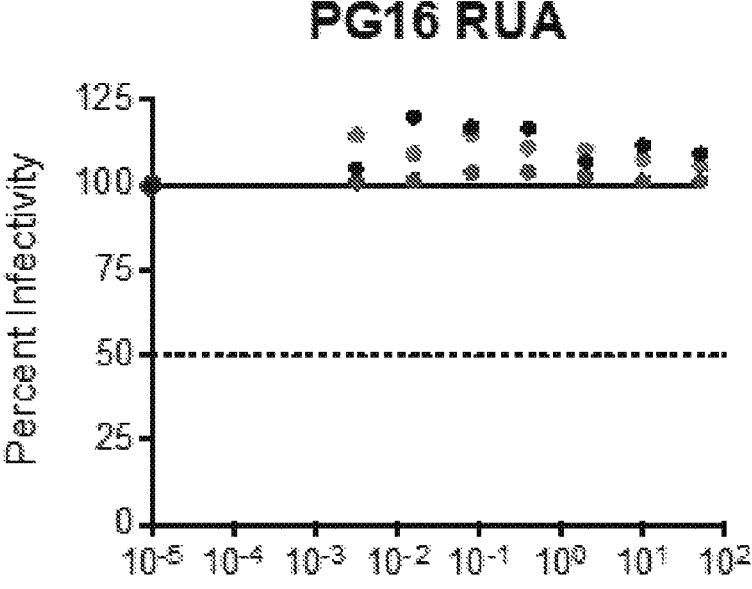

FIGS. 8A-B shows Hypervariable V1 & V2 substitutions: Optimizing for Positive Charge (FIG. 8A) and optimizing for smaller length based on M-group Hypervariable length distribution (FIG. 8B). In FIG. 8A, the HYP V1 column discloses SEQ ID NOS 55-57 and 56, and the HYP V2 column discloses SEQ ID NOS 58-60 and 60, respectively.

FIGS. 9A-9E show that mature signature introduction increases sensitivity to neutralization by mature V2 bNAbs. Shown are results for CH505 TF and CH505 V2 SET envelopes as gp160 constructs in a pseudovirus neutralization assay. The assay is a standard TZM-Bl cell neutralization assay as describer in Sarzotti-Kelsoe et al. J Immunol Methods. 2014 July; 409:131-46. doi: 10.1016/j.jim.2013.11.022. Epub 2013 Dec. 1. Antibody is shown in each panel.

FIGS. 10A-10E show that germline signatures further increase sensitivity to neutralization by mature V2 bNAbs. Shown are results for CH505 TF, CH505 V2 SET, and CH505 UCA OPT1 envelopes as gp160 constructs in a pseudovirus neutralization assay. Antibody is shown in each panel. The thick arrow shows CH505 UCA OPT1 curve, which in panels A and E overlaps with CH4505 V2 SET curve.

Figure 11E:
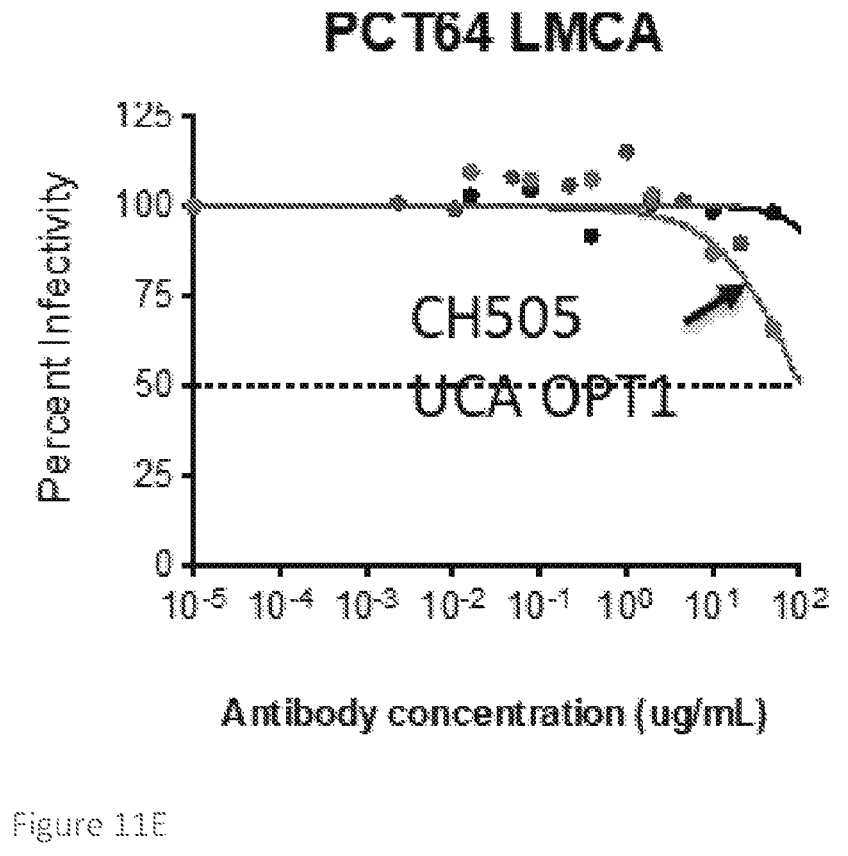

FIGS. 11A-11E show that UCA signatures increase neutralization sensitivity of CH505 envelopes by unmutated common ancestor (UCA) or reverted common ancestor (RUA) antibodies. Shown are results for CH505 TF, CH505 V2 SET, and CH505 UCA OPT1 envelopes as gp160 constructs in a pseudovirus neutralization assay. Antibody is shown in each panel. UCA signatures increased the sensitivity of CH505 to neutralization by both CH01 and the PCT64 V2 bNAb UCAs. V2 SET OPT also gains CH01 UCA sensitivity, likely due to H-130. UCA OPT2 that had CAP256 VRC26 UCA signatures did not confer sensitivity to this UCA.

Figure 15A:
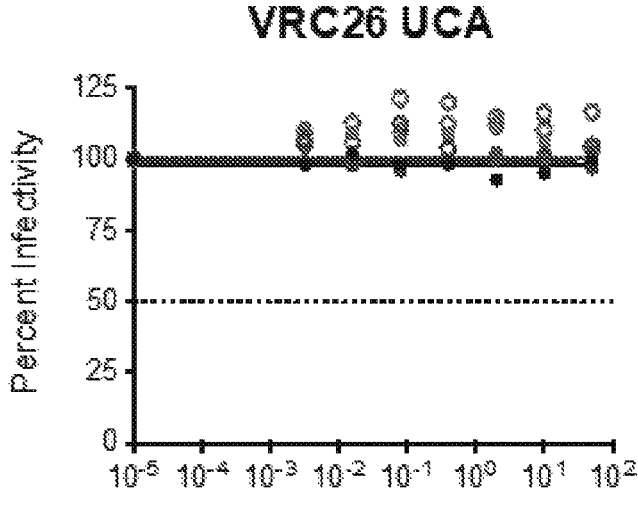
Figure 15B:
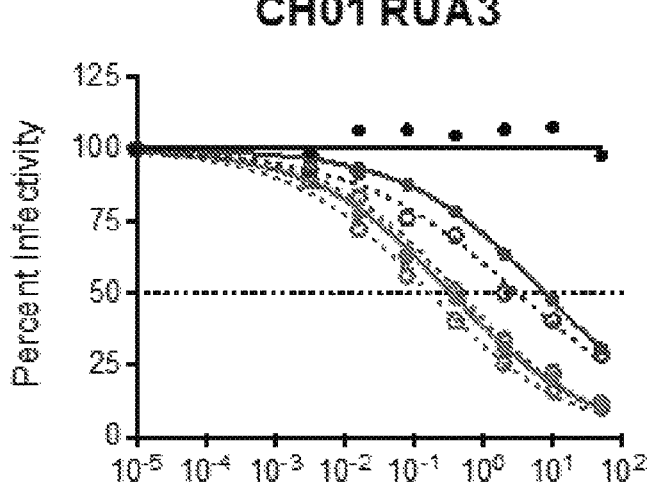
Figure 15C:
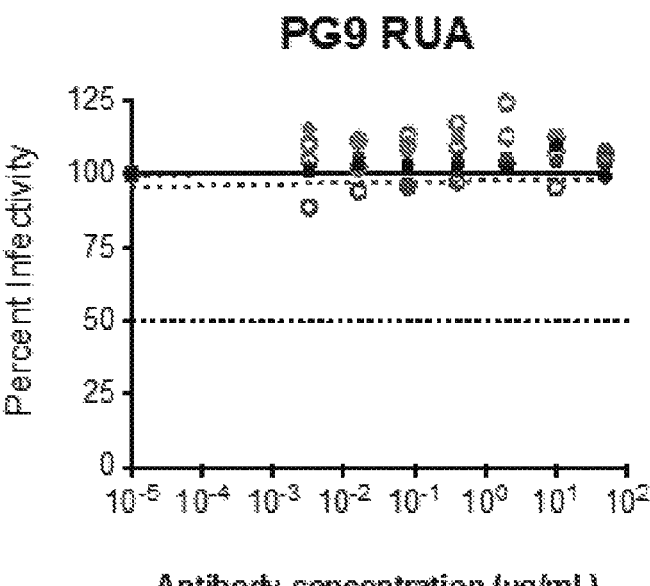
Figure 15D:
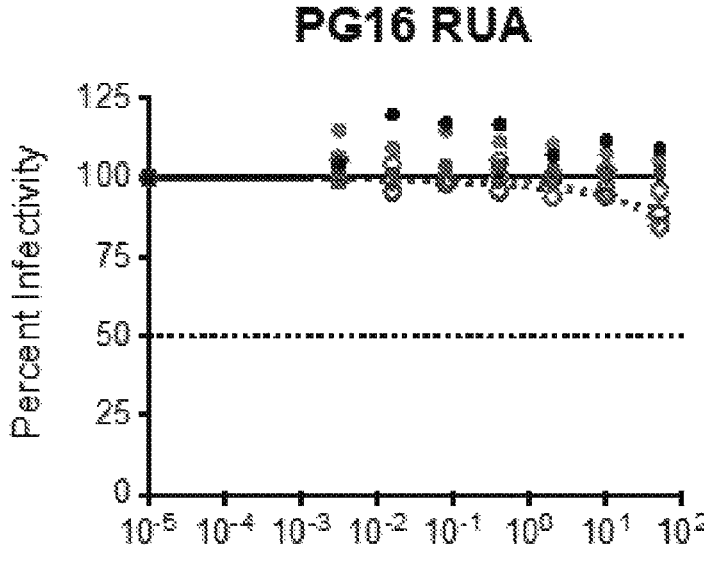
Figure 15E:
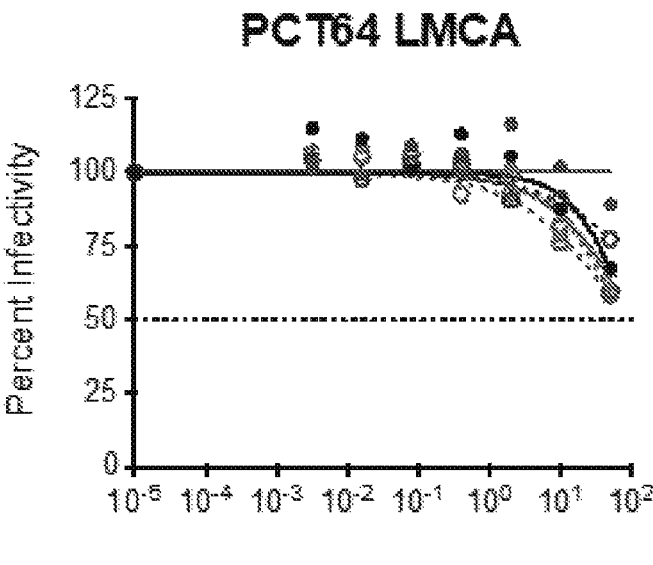

FIG. 12 shows a summary of the neutralization data. The table shows that introduction of V2 apex mature signatures in CH505 TF improved sensitivity to mature bNAbs, and gained sensitivity to CH01 UCA-SET OPT column. Introduction of UCA signatures further improved sensitivity to mature bNAbs, to CH01 UCA and gained sensitivity to PCT64 LMCA-UCA OPT column. In this figure the UCA OPT label shows UCA OPT2+N332—see the slope of the curve in FIG. 15E, where the curve for CH505 UCA OPT2+N332 is bending for the PCT64LMCA, whereas it is not for PG9RUA. This indicates that when measured the neutralization up to 250 ug/ml, 50% neutralization could be reached at 105 ug/ml. First column lists the antibody. "WT" refers to CH505 TF sequences without optimization signatures.

Figure 13A:
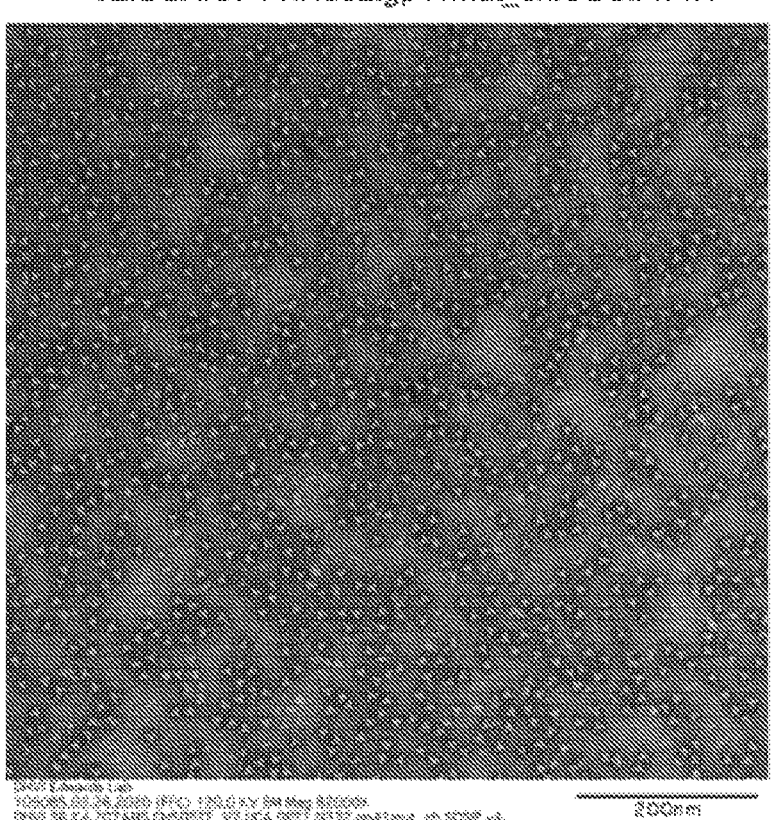
Figure 13B:
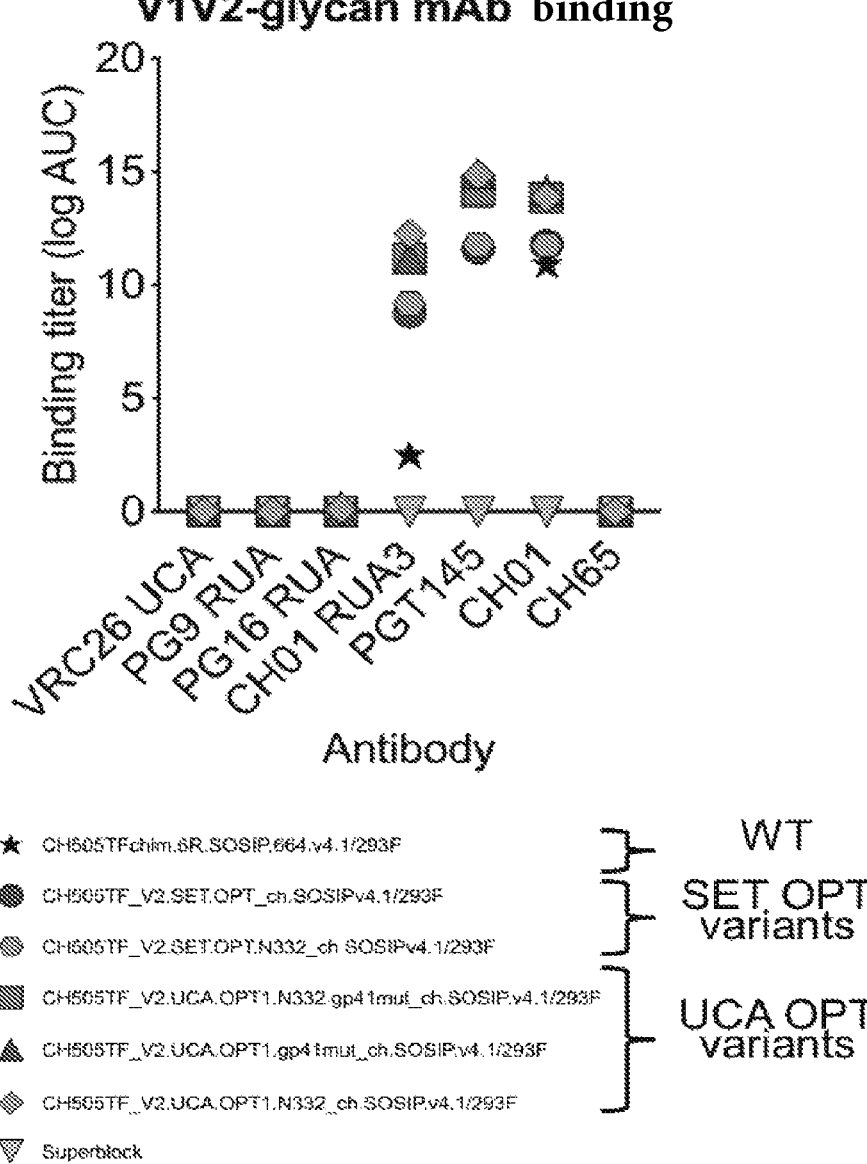

FIGS. 13A-13B shows summary of expression and binding data for various optimized designs expressed as SOSIP designs. Various non-limiting embodiments of SOSIP designs are shown in FIGS. 3 and 4. SET OPT & UCA OPT constructs expressed as chimeric CH505-BG505 SOSIPs. Different constructs tested with varying quality & expression. Expression of UCA OPT1 with NxST 332 and gp41 mutations resulted in highest level of trimer formation (88% versus 12% monomer) as shown in FIG. 13A. FIG. 13B shows antibody binding consistent with neutralization results. Binding data consistent with neutralization results.

Figure 14A:
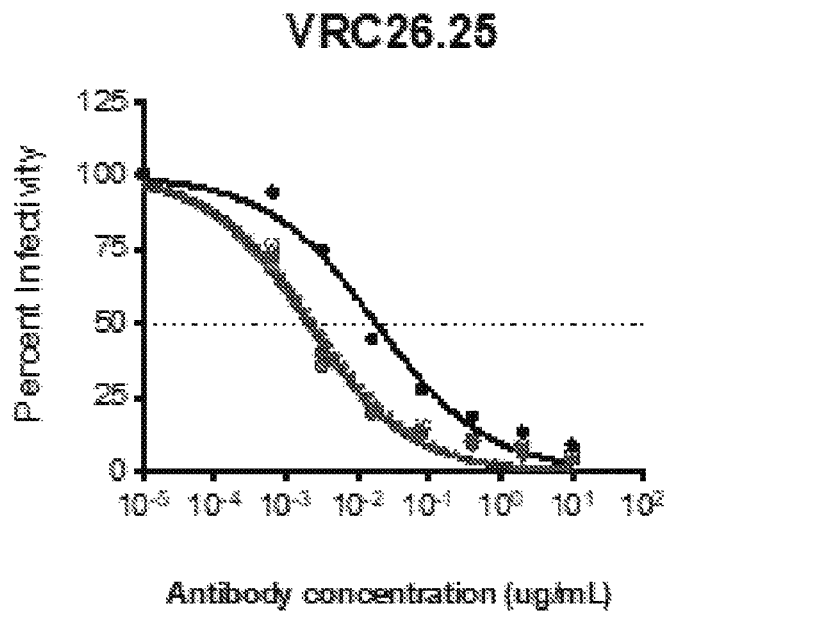
Figure 14B:
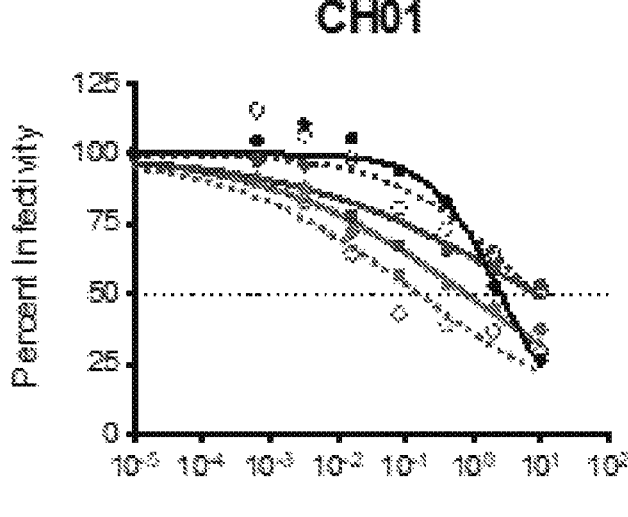
Figure 14C:
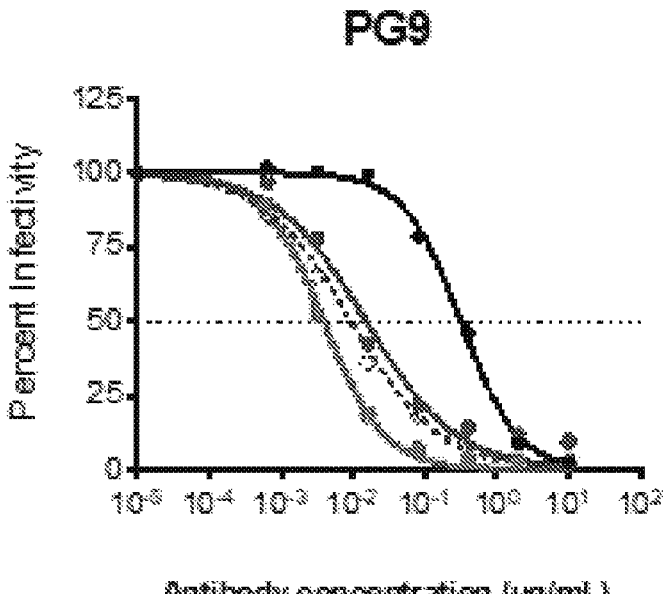
Figure 14D:
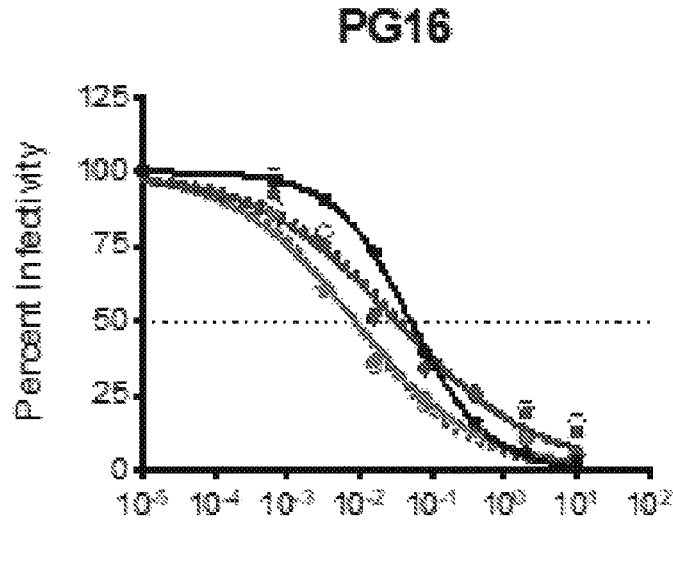
Figure 14E:
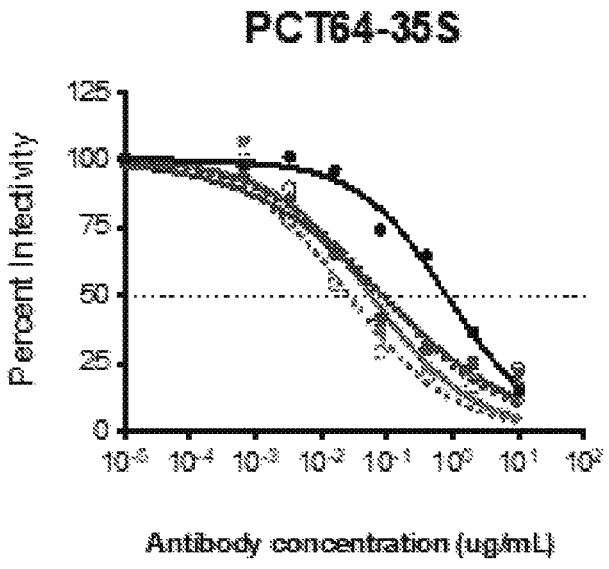
Figure 14F:
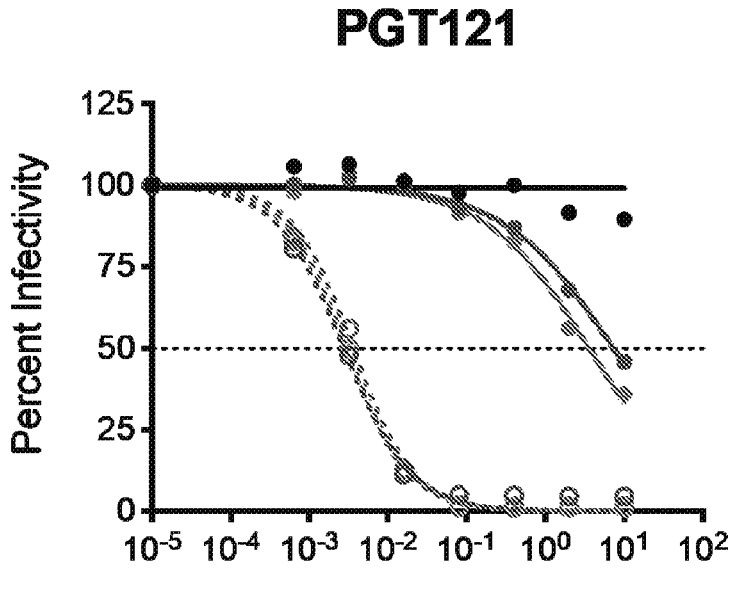

FIGS. 14A-14F show sensitivity to neutralization by mature V2 apex bnAbs. Respective antibodies are listed in each panel. N332 represents a predicted V2 apex bNab resistance signature, but is critical for V3 bNabs (CH505 Env has N334). Moving the N334 glycan to N332 did not reduce its sensitivity to mature V2 bNabs, and rendered it highly sensitive to PGT121. The legend listed in FIG. 14A is applicable to all panels in this figure.

FIGS. 15A-15E show sensitivity of UCA signatures optimized CH505 envelopes of to UCA antibodies neutralization. Respective antibodies are listed in each panel. UCA signatures increased the sensitivity of CH505 to neutralization by both CH01 and the PCT64 V2 bNab UCAs. The legend listed in FIG. 14A is applicable to all panels in this figure.

DETAILED DESCRIPTION OF THE INVENTION

The development of a safe, highly efficacious prophylactic HIV-1 vaccine is of paramount importance for the control and prevention of HIV-1 infection. A major goal of HIV-1 vaccine development is the induction of broadly neutralizing antibodies (bnAbs) (Immunol. Rev. 254: 225-244, 2013). BnAbs are protective in rhesus macaques against SHIV challenge, but as yet, are not induced by current vaccines.

For the past 25 years, the HIV vaccine development field has used single or prime boost heterologous Envs as immunogens, but to date has not found a regimen to induce high levels of bnAbs.

Recently, a new paradigm for design of strategies for induction of broadly neutralizing antibodies was introduced, that of B cell lineage immunogen design (Nature Biotech. 30: 423, 2012) in which the induction of bnAb lineages is recreated. It was recently demonstrated the power of mapping the co-evolution of bnAbs and founder virus for elucidating the Env evolution pathways that lead to bnAb induction (Nature 496: 469, 2013).

Sequences/Clones

Described herein are nucleic and amino acids sequences of HIV-1 envelopes. The sequences for use as immunogens are in any suitable form. In certain embodiments, the described HIV-1 envelope sequences are gp160s. In certain embodiments, the described HIV-1 envelope sequences are gp120s. Other sequences, for example but not limited to stable SOSIP trimer designs, gp145s, gp140s, both cleaved and uncleaved, gp140 Envs with the deletion of the cleavage (C) site, fusion (F) and immunodominant (I) region in gp41—named as gp140ΔCFI (gp140CFI), gp140 Envs with the deletion of only the cleavage (C) site and fusion (F) domain—named as gp140ΔCF (gp140CF), gp140 Envs with the deletion of only the cleavage (C)—named gp140ΔC (gp140C) (See e.g. Liao et al. Virology 2006, 353, 268-282), gp150s, gp41s, which are readily derived from the nucleic acid and amino acid gp160 sequences. In certain embodiments the nucleic acid sequences are codon optimized for optimal expression in a host cell, for example a mammalian cell, a rBCG cell or any other suitable expression system.

An HIV-1 envelope has various structurally defined fragments/forms: gp160; gp140—including cleaved gp140 and uncleaved gp140 (gp140C), gp140CF, or gp140CFI; gp120 and gp41. A skilled artisan appreciates that these fragments/forms are defined not necessarily by their crystal structure, but by their design and bounds within the full length of the gp160 envelope. While the specific consecutive amino acid sequences of envelopes from different strains are different, the bounds and design of these forms are well known and characterized in the art.

For example, it is well known in the art that during its transport to the cell surface, the gp160 polypeptide is processed and proteolytically cleaved to gp120 and gp41 proteins. Cleavages of gp160 to gp120 and gp41 occurs at a conserved cleavage site "REKR" (SEQ ID NO: 2). See Chakrabarti et al. Journal of Virology vol. 76, pp. 5357-5368 (2002) see for example FIG. 1, and Second paragraph in the Introduction on p. 5357; Binley et al. Journal of Virology vol. 76, pp. 2606-2616 (2002) for example at Abstract; Gao et al. Journal of Virology vol. 79, pp. 1154-1163 (2005); Liao et al. Virology vol. 353 (2): 268-282 (2006).

The role of the furin cleavage site was well understood both in terms of improving cleave efficiency, see Binley et al. supra, and eliminating cleavage, see Bosch and Pawlita, Virology 64 (5):2337-2344 (1990); Guo et al. Virology 174: 217-224 (1990); McCune et al. Cell 53:55-67 (1988); Liao et al. J Virol. April; 87(8):4185-201 (2013).

Likewise, the design of gp140 envelope forms is also well known in the art, along with the various specific changes which give rise to the gp140C (uncleaved envelope), gp140CF and gp140CFI forms. Envelope gp140 forms are designed by introducing a stop codon within the gp41 sequence. See Chakrabarti et al. at FIG. 1.

Envelope gp140C refers to a gp140 HIV-1 envelope design with a functional deletion of the cleavage (C) site, so that the gp140 envelope is not cleaved at the furin cleavage site. The specification describes cleaved and uncleaved forms, and various furin cleavage site modifications that prevent envelope cleavage are known in the art. In some embodiments of the gp140C form, two of the R residues in and near the furin cleavage site are changed to E, e.g., RRVVEREKR (SEQ ID NO: 3) is changed to ERVVEREKE (SEQ ID NO: 4), and is one example of an uncleaved gp140 form. Another example is the gp140C form which has the REKR (SEQ ID NO: 2) site changed to SEKS (SEQ ID NO: 5). See supra for references.

Envelope gp140CF refers to a gp140 HIV-1 envelope design with a deletion of the cleavage (C) site and fusion (F) region. Envelope gp140CFI refers to a gp140 HIV-1 envelope design with a deletion of the cleavage (C) site, fusion (F) and immunodominant (I) region in gp41. See Chakrabarti et al. Journal of Virology vol. 76, pp. 5357-5368 (2002) see for example FIG. 1, and Second paragraph in the Introduction on p. 5357; Binley et al. Journal of Virology vol. 76, pp. 2606-2616 (2002) for example at Abstract; Gao et al. Journal of Virology vol. 79, pp. 1154-1163 (2005); Liao et al. Virology vol 353(2): 268-282 (2006).

In certain embodiments, the envelope design in accordance with the present invention involves deletion of residues (e.g., 5-11, 5, 6, 7, 8, 9, 10, or 11 amino acids) at the N-terminus. For delta N-terminal design, amino acid residues ranging from 4 residues or even fewer to 14 residues or even more are deleted. These residues are between the maturation (signal peptide, usually ending with CX, X can be any amino acid) and "VPVXXXX . . . ". In case of CH505 T/F Env as an example, 8 amino acids (italicized and underlined in the below sequence) were deleted:

MRVMGIQRNYPQWWIWSMLGFWMLMICNG*MWVTVYYG*VPVWKEAKTTLFC

ASDAKAYEKEVHNVWATHACVPTDPNPQE . . .

(rest of envelop sequence is indicated as " ") (SEQ ID NO: 6). In other embodiments, the delta N-design described for CH505 T/F envelope can be used to make delta N-designs of other CH505 envelopes. In certain embodiments, the invention relates generally to an immunogen, gp160, gp120 or gp140, without an N-terminal Herpes Simplex gD tag substituted for amino acids of the N-terminus of gp120, with an HIV leader sequence (or other leader sequence), and without the original about 4 to about 25, for example 4, 5, 6, 7, 8, 9, 10, 11, 12, 13, 14, 15, 16, 17, 18, 19, 20, 21, 22, 23, 24, 25 amino acids of the N-terminus of the envelope (e.g. gp120). See WO2013/006688, e.g. at pages 10-12, the contents of which publication is hereby incorporated by reference in its entirety.

The general strategy of deletion of N-terminal amino acids of envelopes results in proteins, for example gp120s, expressed in mammalian cells that are primarily monomeric, as opposed to dimeric, and, therefore, solves the production and scalability problem of commercial gp120 Env vaccine production. In other embodiments, the amino acid deletions at the N-terminus result in increased immunogenicity of the envelopes.

In certain aspects, the invention provides composition and methods which CH505 Envs, as gp120s, gp140s cleaved and uncleaved, gp145s, gp150s and gp160s, stabilized and/or multimerized trimers, as proteins, DNAs, RNAs, or any combination thereof, administered as primes and boosts to elicit immune response. CH505 Envs as proteins would be co-administered with nucleic acid vectors containing Envs to amplify antibody induction. In certain embodiments, the compositions and methods include any immunogenic HIV-1 sequences to give the best coverage for T cell help and cytotoxic T cell induction. In certain embodiments, the compositions and methods include mosaic and/or consensus HIV-1 genes to give the best coverage for T cell help and cytotoxic T cell induction. In certain embodiments, the compositions and methods include mosaic group M and/or consensus genes to give the best coverage for T cell help and cytotoxic T cell induction. In some embodiments, the mosaic genes are any suitable gene from the HIV-1 genome. In some embodiments, the mosaic genes are Env genes, Gag genes, Pol genes, Nef genes, or any combination thereof. See e.g. U.S. Pat. No. 7,951,377. In some embodiments the mosaic genes are bivalent mosaics. In some embodiments the mosaic genes are trivalent. In some embodiments, the mosaic genes are administered in a suitable vector with each immunization with Env gene inserts in a suitable vector and/or as a protein. In some embodiments, the mosaic genes, for example as bivalent mosaic Gag group M consensus genes, are administered in a suitable vector, for example but not limited to HSV2, would be administered with each immunization with Env gene inserts in a suitable vector, for example but not limited to HSV-2.

Nucleic Acid Sequences

In certain aspects the invention provides compositions and methods of Env genetic immunization either alone or with Env proteins to recreate the swarms of evolved viruses that have led to bnAb induction. Nucleotide-based vaccines offer a flexible vector format to immunize against virtually any protein antigen. Currently, two types of genetic vaccination are available for testing—DNAs and mRNAs.

In certain aspects the invention contemplates using immunogenic compositions wherein immunogens are delivered as DNA. See Graham B S, Enama M E, Nason M C, Gordon I J, Peel S A, et al (2013) DNA Vaccine Delivered by a Needle-Free Injection Device Improves Potency of Priming for Antibody and CD8+ T-Cell Responses after rAd5 Boost in a Randomized Clinical Trial. PLoS ONE 8(4): e59340, page 9. Various technologies for delivery of nucleic acids, as DNA and/or RNA, so as to elicit immune response, both T-cell and humoral responses, are known in the art and are under developments. In certain embodiments, DNA can be delivered as naked DNA. In certain embodiments, DNA is formulated for delivery by a gene gun. In certain embodiments, DNA is administered by electroporation, or by a needle-free injection technologies, for example but not limited to Biojector® device. In certain embodiments, the DNA is inserted in vectors. The DNA is delivered using a suitable vector for expression in mammalian cells. In certain embodiments the nucleic acids encoding the envelopes are optimized for expression. In certain embodiments DNA is optimized, e.g. codon optimized, for expression. In certain embodiments the nucleic acids are optimized for expression in vectors and/or in mammalian cells. In non-limiting embodiments these are bacterially derived vectors, adenovirus based vectors, rAdenovirus (e.g. Barouch D H, et al. Nature Med. 16: 319-23, 2010), recombinant mycobacteria (e.g. rBCG or *M smegmatis*) (Yu, J S et al. Clinical Vaccine Immunol. 14: 886-093,2007; ibid 13: 1204-11,2006), and recombinant vaccinia type of vectors (Santra S. Nature Med. 16: 324-8, 2010), for example but not limited to ALVAC, replicating (Kibler K V et al., PLoS One 6: e25674, 2011 Nov. 9) and non-replicating (Perreau M et al. J. virology 85: 9854-62, 2011) NYVAC, modified vaccinia Ankara (MVA)), adeno-associated virus, Venezuelan equine encephalitis (VEE) replicons, Herpes Simplex Virus vectors, and other suitable vectors.

In certain aspects the invention contemplates using immunogenic compositions wherein immunogens are delivered as DNA or RNA in suitable formulations. Various technologies which contemplate using DNA or RNA or may use complexes of nucleic acid molecules and other entities to be used in immunization. In certain embodiments, DNA or RNA is administered as nanoparticles consisting of low dose antigen-encoding DNA formulated with a block copolymer (amphiphilic block copolymer 704). See Cany et al., Journal of Hepatology 2011 vol. 54 j 115-121; Arnaoty et al., Chapter 17 in Yves Bigot (ed.), Mobile Genetic Elements: Protocols and Genomic Applications, Methods in Molecular Biology, vol. 859, pp 293-305 (2012); Arnaoty et al. (2013) Mol Genet Genomics. 2013 August; 288(7-8):347-63. Nanocarrier technologies called Nanotaxi® for immunogenic macromolecules (DNA, RNA, Protein) delivery are under development. See for example technologies developed by incellart.

In certain aspects, the invention provides nucleic acids comprising sequences encoding envelopes of the invention. In certain embodiments, the nucleic acids are DNAs. In certain embodiments, the nucleic acids are mRNAs. In certain aspects, the invention provides expression vectors comprising the nucleic acids of the invention.

In certain aspects, the invention provides a pharmaceutical composition comprising mRNAs encoding the inventive antibodies. In certain embodiments, these are optionally formulated in lipid nanoparticles (LNPs). In certain embodiments, the mRNAs are modified. Modifications include without limitations modified ribonucleotides, poly-A tail, 5' cap.

In certain aspects the invention provides nucleic acids encoding the inventive envelopes. In non-limiting embodiments, the nucleic acids are mRNA, modified or unmodified, suitable for use any use, e.g. but not limited to use as pharmaceutical compositions. In certain embodiments, the nucleic acids are formulated in lipid, such as but not limited to LNPs.

In some embodiments the antibodies are administered as nucleic acids, including but not limited to mRNAs which could be modified and/or unmodified. See US Pub 20180028645A1, US Pub 20090286852, US Pub 20130111615, US Pub 20130197068, U.S. Pub 20130261172, US Pub 20150038558, US Pub 20160032316, US Pub 20170043037, U.S. Pub 20170327842, U.S. Pat. Nos. 10,006,007, 9,371,511, 9,012, 219, U.S. Pub 20180265848, US Pub 20170327842, US Pub 20180344838A1 at least at paragraphs [0260]-[0281], WO/2017/182524 for non-limiting embodiments of chemical modifications, wherein each content is incorporated by reference in its entirety.

mRNAs delivered in LNP formulations have advantages over non-LNPs formulations. See US Pub 20180028645A1, WO/2018/081638, WO/2016/176330, wherein each content is incorporated by reference in its entirety.

In certain embodiments the nucleic acid encoding an envelope is operably linked to a promoter inserted an expression vector. In certain aspects the compositions comprise a suitable carrier. In certain aspects the compositions comprise a suitable adjuvant.

In certain aspects the invention provides an expression vector comprising any of the nucleic acid sequences of the invention, wherein the nucleic acid is operably linked to a promoter. In certain aspects the invention provides an expression vector comprising a nucleic acid sequence encoding any of the polypeptides of the invention, wherein the nucleic acid is operably linked to a promoter. In certain embodiments, the nucleic acids are codon optimized for expression in a mammalian cell, in vivo or in vitro. In certain aspects the invention provides nucleic acids comprising any one of the nucleic acid sequences of invention. In certain aspects the invention provides nucleic acids consisting essentially of any one of the nucleic acid sequences of invention. In certain aspects the invention provides nucleic acids consisting of any one of the nucleic acid sequences of invention. In certain embodiments the nucleic acid of the invention, is operably linked to a promoter and is inserted in an expression vector. In certain aspects the invention provides an immunogenic composition comprising the expression vector.

In certain aspects the invention provides a composition comprising at least one of the nucleic acid sequences of the invention. In certain aspects the invention provides a composition comprising any one of the nucleic acid sequences of invention. In certain aspects the invention provides a composition comprising at least one nucleic acid sequence encoding any one of the polypeptides of the invention.

In one embodiment, the nucleic acid is an RNA molecule. In one embodiment, the RNA molecule is transcribed from a DNA sequence described herein. In some embodiments, the RNA molecule is encoded by one of the inventive sequences. In another embodiment, the nucleotide sequence comprises an RNA sequence transcribed by a DNA sequence encoding the polypeptide sequence of the sequences of the invention, or a variant thereof or a fragment thereof. Accordingly, in one embodiment, the invention provides an RNA molecule encoding one or more of inventive antibodies. The RNA may be plus-stranded. Accordingly, in some embodiments, the RNA molecule can be translated by cells without needing any intervening replication steps such as reverse transcription.

In some embodiments, a RNA molecule of the invention may have a 5' cap (e.g. but not limited to a 7-methylguanosine, 7 mG (5')ppp(5')NlmpNp). This cap can enhance in vivo translation of the RNA. The 5' nucleotide of an RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. In some embodiments, a RNA molecule useful with the invention may be single-stranded. In some embodiments, a RNA molecule useful with the invention may comprise synthetic RNA.

The recombinant nucleic acid sequence can be an optimized nucleic acid sequence. Such optimization can increase or alter the immunogenicity of the envelope. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; and eliminating to the extent possible cis-acting sequence motifs (i.e., internal TATA boxes).

Methods for in vitro transfection of mRNA and detection of envelope expression are known in the art.

Methods for expression and immunogenicity determination of nucleic acid encoded envelopes are known in the art.

In certain aspects the invention contemplates using immunogenic compositions wherein immunogens are delivered as recombinant proteins. Various methods for production and purification of recombinant proteins, including trimers such as but not limited to SOSIP based trimers, suitable for use in immunization are known in the art. In certain embodiments recombinant proteins are produced in CHO cells.

The immunogenic envelopes can also be administered as a protein boost in combination with a variety of nucleic acid envelope primes (e.g., HIV-1 Envs delivered as DNA expressed in viral or bacterial vectors).

Dosing of proteins and nucleic acids can be readily determined by a skilled artisan. A single dose of nucleic acid can range from a few nanograms (ng) to a few micrograms (μg) or milligram of a single immunogenic nucleic acid. Recombinant protein dose can range from a few μg micrograms to a few hundred micrograms, or milligrams of a single immunogenic polypeptide.

Administration: The compositions can be formulated with appropriate carriers using known techniques to yield compositions suitable for various routes of administration. In certain embodiments the compositions are delivered via intramuscular (IM), via subcutaneous, via intravenous, via nasal, via mucosal routes, or any other suitable route of immunization.

The compositions can be formulated with appropriate carriers and adjuvants using techniques to yield compositions suitable for immunization. The compositions can include an adjuvant, such as, for example but not limited to, alum, 3M052, poly IC, MF-59 or other squalene-based adjuvant, AS01B, or other liposomal based adjuvant suitable for protein or nucleic acid immunization. In certain embodiments, the adjuvant is GSK AS01E adjuvant containing MPL and QS21. This adjuvant has been shown by GSK to be as potent as the similar adjuvant AS01B but to be less reactogenic using HBsAg as vaccine antigen [Leroux-Roels et al., IABS Conference, April 2013]. In certain embodiments, TLR agonists are used as adjuvants. In other embodiment, adjuvants which break immune tolerance are included in the immunogenic compositions.

In certain embodiments, the compositions and methods comprise any suitable agent or immune modulation which could modulate mechanisms of host immune tolerance and release of the induced antibodies. In non-limiting embodiments modulation includes PD-1 blockade; T regulatory cell depletion; CD40L hyperstimulation; soluble antigen administration, wherein the soluble antigen is designed such that the soluble agent eliminates B cells targeting dominant epitopes, or a combination thereof. In certain embodiments, an immunomodulatory agent is administered in at time and in an amount sufficient for transient modulation of the subject's immune response so as to induce an immune response which comprises broad neutralizing antibodies against HIV-1 envelope. Non-limiting examples of such agents is any one of the agents described herein: e.g. chloroquine (CQ), PTP1B Inhibitor—CAS 765317-72-4—Calbiochem or MSI 1436 clodronate or any other bisphosphonate; a Foxo1 inhibitor, e.g. 344355|Foxo1 Inhibitor, AS1842856—Calbiochem; Gleevac, anti-CD25 antibody, anti-CCR4 Ab, an agent which binds to a B cell receptor for a dominant HIV-1 envelope epitope, or any combination thereof. In non-limiting embodiments, the modulation includes administering an anti-CTLA4 antibody. Non-limiting examples are ipilimumab and tremelimumab. In certain embodiments, the methods comprise administering a second immunomodulatory agent, wherein the second and first immunomodulatory agents are different.

There are various host mechanisms that control bnAbs. For example, highly somatically mutated antibodies become autoreactive and/or less fit (Immunity 8: 751, 1998; PloS Comp. Biol. 6 e1000800, 2010; J. Thoret. Biol. 164:37, 1993); Polyreactive/autoreactive naïve B cell receptors (unmutated common ancestors of clonal lineages) can lead to deletion of Ab precursors (Nature 373: 252, 1995; PNAS 107: 181, 2010; J. Immunol. 187: 3785, 2011); Abs with long HCDR3 can be limited by tolerance deletion (JI 162: 6060, 1999; JCI 108: 879, 2001). BnAb knock-in mouse models are providing insights into the various mechanisms of tolerance control of MPER BnAb induction (deletion, anergy, receptor editing). Other variations of tolerance control likely will be operative in limiting BnAbs with long HCDR3s, high levels of somatic hypermutations.

For a summary of CH505 sequences and designs see WO2017151801, e.g. but not limited to Table 1, FIGS. 22-24, and WO2014042669 (FIG. 17).

It is readily understood that the envelope glycoproteins referenced in various examples and figures comprise a signal/leader sequence. It is well known in the art that HIV-1 envelope glycoprotein is a secretory protein with a signal or leader peptide sequence that is removed during processing and recombinant expression (without removal of the signal peptide, the protein is not secreted). See for example Li et al. Control of expression, glycosylation, and secretion of HIV-1 gp120 by homologous and heterologous signal sequences. Virology 204 (1): 266-78 (1994) ("Li et al. 1994"), at first paragraph, and Li et al. Effects of inefficient cleavage of the signal sequence of HIV-1 gp120 on its association with calnexin, folding, and intracellular transport. PNAS 93:9606-9611 (1996) ("Li et al. 1996"), at 9609, Any suitable signal sequence could be used. In some embodiments the leader sequence is the endogenous leader sequence. Most of the gp120 and gp160 amino acid sequences include the endogenous leader sequence. In other non-limiting examples, the leader sequence is human Tissue Plasminogen Activator (TPA) sequence, human CD5 leader sequence (e.g. MPMGSLQPLATLYLLGMLVASVLA (SEQ ID NO: 7)). Most of the chimeric designs include CD5 leader sequence. A skilled artisan appreciates that when used as immunogens, and for example when recombinantly produced, the amino acid sequences of these proteins do not comprise the leader peptide sequences.

HIV-1 Envelope Trimers and Other Envelope Designs

This example shows that stabilized HIV-1 Env trimer immunogens show enhanced antigenicity for broadly neutralizing antibodies and are not recognized by non-neutralizing antibodies. The example also describes additional envelope modifications and designs. In some embodiments these envelopes, including but not limited to trimers are further multimerized, and/or used as particulate, high-density array in liposomes or other particles, for example but not limited to nanoparticles. Any one of the envelopes of the invention could be designed and expressed as described herein.

A stabilized chimeric SOSIP designs were used to generate CH505 trimers. This design was applicable to diverse viruses from multiple clades.

Elicitation of neutralizing antibodies is one goal for antibody-based vaccines. Neutralizing antibodies target the native trimeric HIV-1 Env on the surface virions. The trimeric HIV-1 envelope protein consists of three protomers each containing a gp120 and gp41 heterodimer. Recent immunogen design efforts have generated soluble near-native mimics of the Env trimer that bind to neutralizing antibodies but not non-neutralizing antibodies. The recapitulation of the native trimer could be a key component of vaccine induction of neutralizing antibodies. Neutralizing Abs target the native trimeric HIV-1 Env on the surface of viruses (Poignard et al. J Virol. 2003 January; 77(1):353-65; Parren et al. J Virol. 1998 December; 72(12):10270-4; Yang et al. J Virol. 2006 November; 80(22): 11404-8). The HIV-1 Env protein consists of three protomers of gp120 and gp41 heterodimers that are noncovalently linked together (Center et al. J Virol. 2002 August; 76(15):7863-7). Soluble near-native trimers preferentially bind neutralizing antibodies as opposed to non-neutralizing antibodies (Sanders et al. PLoS Pathog. 2013 September; 9(9): e1003618).

Sequential Env vaccination has elicited broad neutralization in the plasma of one macaque. The overall goal of our project is to increase the frequency of vaccine induction of bnabs in the plasma of primates with Env vaccination. We hypothesized that vaccination with immunogens that target bnAb B cell lineage and mimic native trimers will increase the frequency of broadly neutralizing plasma antibodies. One goal is increasing the frequency of vaccine induction of bnAb in the plasma of primates by Env vaccination. It is expected that vaccination with immunogens that target bnAb B cell lineages and mimic the native trimers on virions will increase the frequency of broadly neutralizing plasma antibodies.

Previous work has shown that CH505 derived soluble trimers are hard to produce. From a study published by Julien et al in 2015 (Proc Natl Acad Sci USA. 2015 Sep. 22; 112(38): 11947-11952) it was shown that while CH505 produced comparable amounts of protein by transient transfection, only 5% of the CH505 protein formed trimer which 5 times lower than the gold standard viral strain BG505. Provided here are non-limiting embodiments of well-folded trimers for Env immunizations.

Near-native soluble trimers using the 6R.SOSIP.664 design are capable of generating autologous tier 2 neutralizing plasma antibodies in the plasma (Sanders et al. 2015), which provides a starting point for designing immunogens to elicit broadly neutralizing antibodies. While these trimers are preferentially antigenic for neutralizing antibodies, they still possess the ability to expose the V3 loop, which generally results in strain-specific binding and neutralizing antibodies after vaccination. Using the unliganded structure the BG505.6R.SOSIP.664 has been stabilized by adding cysteines at position 201 and 433 to constrain the conformational flexibility such that the V3 loop is maintained unexposed (Kwon et al. Nat Struct Mol Biol. 2015 July; 22(7): 522-531).

Provided are engineered trimeric immunogens derived from multiple viruses from CH505. We generated chimeric 6R.SOSIP.664, chimeric disulfide stabilized (DS) 6R.SO-SIP.664 (Kwon et al Nat Struct Mol Biol. 2015 July; 22(7): 522-531), chimeric 6R.SOSIP.664v4.1 (DeTaeye et al. Cell. 2015 Dec. 17; 163(7):1702-15. doi: 10.1016/j.cell.2015.11.056), and chimeric 6R.SOSIP.664v4.2 (DeTaeye et al. Cell. 2015 Dec. 17; 163(7):1702-15. doi: 10.1016/j.cell.2015.11.056). The 6R.SOSIP.664 is the basis for all of these designs and is made as a chimera of C.CH0505 and A.BG505. The gp120 of C.CH505 was fused with the BG505 inner domain gp120 sequence within the alpha helix 5 (α5) to result in the chimeric protein. The chimeric gp120 is disulfide linked to the A.BG505 gp41 as outlined by Sanders et al. (PLoS Pathog. 2013 September; 9(9): e1003618). These immunogens were designed as chimeric proteins that possess the BG505 gp41 connected to the CH505 gp120, since the BG505 strain is particularly adept at forming well-folded, closed trimers. This envelope design retains the CH505 CD4 binding site that is targeted by the CH103 and CH235 broadly neutralizing antibody lineages that were isolated from CH505.

Based on the various designs, any other suitable envelope, for example but not limited to CH505 envelopes as described in WO2014042669 can be designed.

Recombinant envelopes as trimers could be produced and purified by any suitable method. For a non-limiting example of purification methods see Ringe R P, Yasmeen A, Ozorowski G, Go E P, Pritchard L K, Guttman M, Ketas T A, Cottrell C A, Wilson I A, Sanders R W, Cupo A, Crispin M, Lee K K, Desaire H, Ward A B, Klasse P J, Moore J P. 2015. Influences on the design and purification of soluble, recombinant native-like HIV-1 envelope glycoprotein trimers. J Virol 89:12189-12210. doi:10.1128/JVI.01768-15.

Multimeric Envelopes

Presentation of antigens as particulates reduces the B cell receptor affinity necessary for signal transduction and expansion (See Baptista et al. EMBO J. 2000 Feb. 15; 19(4): 513-520). Displaying multiple copies of the antigen on a particle provides an avidity effect that can overcome the low affinity between the antigen and B cell receptor. The initial B cell receptor specific for pathogens can be low affinity, which precludes vaccines from being able to stimulate and expand B cells of interest. In particular, very few naïve B cells from which HIV-1 broadly neutralizing antibodies arise can bind to soluble HIV-1 Envelope. Provided are envelopes, including but not limited to trimers as particulate, high-density array on liposomes or other particles, for example but not limited to nanoparticles. See e.g. He et al. Nature Communications 7, Article number: 12041 (2016), doi:10.1038/ncomms12041; Bamrungsap et al. Nanomedicine, 2012, 7 (8), 1253-1271.

To improve the interaction between the naïve B cell receptor and immunogens, envelope designed can be created to wherein the envelope is presented on particles, e.g. but not limited to nanoparticle. In some embodiments, the HIV-1 Envelope trimer could be fused to ferritin. Ferritin protein self assembles into a small nanoparticle with three fold axis of symmetry. At these axes the envelope protein is fused. Therefore, the assembly of the three-fold axis also clusters three HIV-1 envelope protomers together to form an envelope trimer. Each ferritin particle has 8 axes which equates to 8 trimers being displayed per particle. See e.g. Sliepen et al. Retrovirology 201512:82, DOI: 10.1186/s12977-015-0210-4.

Any suitable ferritin sequence could be used. In non-limiting embodiments, ferritin sequences are disclosed in WO/2018/005558.

Ferritin nanoparticle linkers: The ability to form HIV-1 envelope ferritin nanoparticles relies self-assembly of 24 ferritin subunits into a single ferritin nanoparticle. The addition of a ferritin subunit to the C-terminus of HIV-1 envelope may interfere with the ability of the ferritin subunit to fold properly and or associate with other ferritin subunits. When expressed alone ferritin readily forms 24-subunit nanoparticles, however appending it to envelope only yields nanoparticles for certain envelopes. Since the ferritin nanoparticle forms in the absence of envelope, the envelope could be sterically hindering the association of ferritin subunits. Thus, we designed ferritin with elongated glycine-serine linkers to further distance the envelope from the ferritin subunit. To make sure that the glycine linker is attached to ferritin at the correct position, we created constructs that attach at second amino acid position or the fifth amino acid position. The first four n-terminal amino acids of natural *Helicobacter pylori* ferritin are not needed for nanoparticle formation but may be critical for proper folding and oligomerization when appended to envelope. Thus, we designed constructs with and without the Leucine, serine, and lysine amino acids following the glycine-serine linker. The goal will be to find a linker length that is suitable for formation of envelope nanoparticles when ferritin is appended to most envelopes. Any suitable linker between the envelope and ferritin could be uses, so long as the fusion protein is expressed and the trimer is formed.

Another approach to multimerize expression constructs uses *Staphylococcus* Sortase A transpeptidase ligation to conjugate inventive envelope trimers, for e.g. but not limited to cholesterol. Non-limiting embodiments of envelope designs for use in Sortase A reaction are shown in FIGS. 5A-B. The trimers can then be embedded into liposomes via the conjugated cholesterol. To conjugate the trimer to cholesterol either a C-terminal LPXTG tag (SEQ ID NO: 8) or a N-terminal pentaglycine repeat tag (SEQ ID NO: 49) is added to the envelope trimer gene. Cholesterol is also synthesized with these two tags. Sortase A is then used to covalently bond the tagged envelope to the cholesterol. The sortase A-tagged trimer protein can also be used to conjugate the trimer to other peptides, proteins, or fluorescent labels. In non-limiting embodiments, the sortase A tagged trimers are conjugated to ferritin to form nanoparticles.

The invention provides design of envelopes and trimer designs wherein the envelope comprises a linker which permits addition of a lipid, such as but not limited to cholesterol, via a Sortase A reaction. See e.g. Tsukiji, S. and Nagamune, T. (2009), Sortase-Mediated Ligation: A Gift from Gram-Positive Bacteria to Protein Engineering. Chem-BioChem, 10: 787-798. doi:10.1002/cbic.200800724; Proft, T. Sortase-mediated protein ligation: an emerging biotechnology tool for protein modification and immobilisation. Biotechnol Lett (2010) 32: 1. doi:10.1007/s10529-009-0116-0; Lena Schmohl, Dirk Schwarzer, Sortase-mediated ligations for the site-specific modification of proteins, Current Opinion in Chemical Biology, Volume 22, October 2014, Pages 122-128, ISSN 1367-5931, dx.doi.org/10.1016/j.cbpa.2014.09.020; Tabata et al. Anticancer Res. 2015 August; 35(8):4411-7; Pritz et al. *J. Org. Chem.* 2007, 72, 3909-3912.

The lipid modified envelopes and trimers could be formulated as liposomes. Any suitable liposome composition is contemplated.

The lipid modified and multimerized envelopes and trimers could be formulated as liposomes. Any suitable liposome composition is contemplated.

Nomenclature for trimers: chim.6R.DS.SOSIP.664 is SOSIP.I; CHIM.6R.SOSIP.664 is SOSIP.II; CHIM.6R.SOSIP.664V4.1 is SOSIP.III.

V2 Optimization

V2 apex bNAbs are an attractive target for immunogen design. V2 apex bNAbs arise frequently in HIV-1 infected humans (12-15%) and in SHIV infected RMs (11%). V2 apex bNAbs have low levels of somatic hypermutation are required (Wiehe et al Cell Host Microbe 23(6):759 (2018)). V2 apex bNAbs have low levels of poly- and autoreactivity (Liu et al J Virol 89:784 (2015)). V2 apex bNAbs have long anionic CDRH3s (>24aa) encoded by germline. However, V2 apex bNAbs precursors are rare—germline targeting immunogens are critical. Also, no natural Envs that can target multiple V2 apex bNAb lineages. Described herein is immunogen design to design such immunogens.

The CH505 HIV-1 virus has been subject to intensive study as a vaccine reagent based on the observation that during the course of the natural CH505 HIV-1 infection, potent broadly neutralizing antibodies were generated by the host that targeted the CD4bs region. Here we have designed an immunogen based on the surprising finding that the HIV-1 CH505 transmitted-founder (TF) virus Envelopes, when used as vaccine, have the capacity to induce V2 apex directed heterologous neutralizing antibody responses. This has been observed in a knock-in mice, rabbits and rhesus macaques, and in one CH505 SHIV infected macaque. These results raise the prospect of ultimately creating a dual-targeting CH505-based immunogen design that can induce both V2 apex and CD4bs broadly neutralizing antibodies (bNAbs). The designs we propose focuses on enhancing both the initiation of appropriate V2 apex targeting neutralizing antibody and expand the breadth of the response.

Despite the fact the CH505 TF Envelope can elicit V2 apex neutralizing antibody responses, it is not particularly sensitive to mature V2 apex bNAbs and is not neutralized by putative V2 apex bNAb precursors. We hypothesized that these factors could be limit the successful V2 apex bNAb induction, and that CH505 TF variants with improved sensitivity to V2 apex mature and precursor antibodies might serve as better immunogens.

Figure 1A:
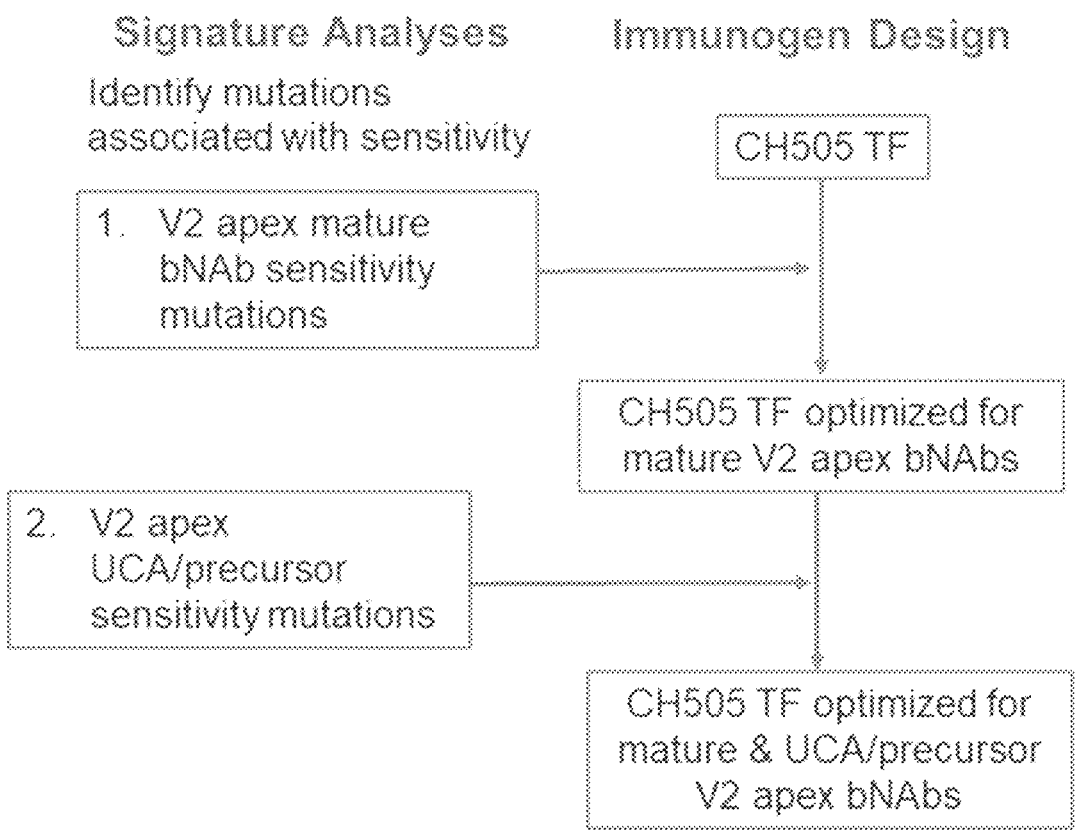
FIG. 1A shows schematic of signature based approach of immunogen design. See also Bricault et al. Cell Host Microbe 2019 25 (1) 59-72.
Figure 1B:
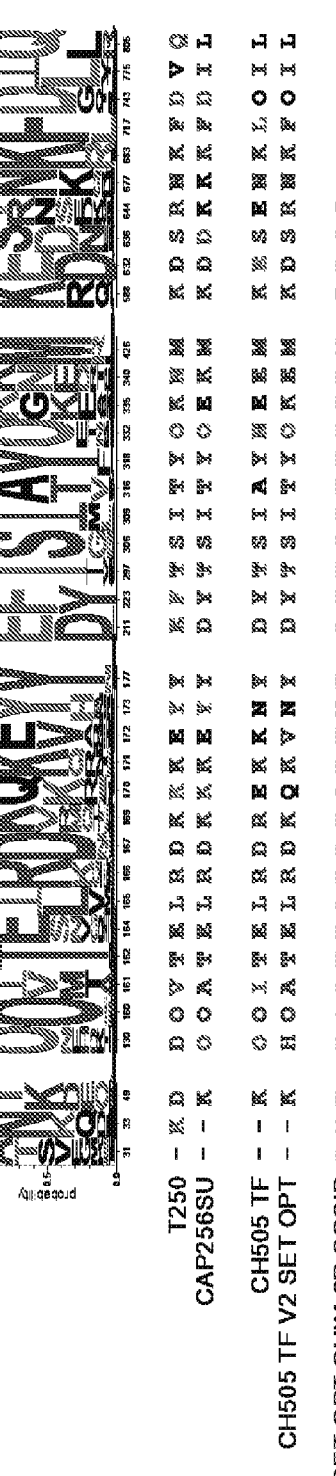
FIG. 1B shows CH505 V2 Mature Optimized Design. Shown are CH505 amino acid substitutions that are statistically associated with for V2 apex mature bNAb sensitivity. The letters represent single amino acids, and the height of the letter in the sequence LOGO indicates its frequency in the population. The numbers underneath the LOGO are HXB2 reference strain positions in the viral sequence. O stands for an N embedded in a N-linked glycosylation site. Blue are amino acids that are associated with sensitivity, red are amino acids associated with resistance, black are amino acids that were not associated with either sensitivity or resistance. The V2 SET OPT chimeric SOSIP (last row) carries all the design mutations from the full length CH505 TF V2 SET OPT except at 31, 33 and 588, 644. For the former, the SOSIP construct has the favorable mutations.

Thus, we used our previously published statistically robust and phylogenetically corrected strategy to compare the CH505 TF to amino acid and glycan signatures that associate with sensitivity to multiple V2 apex bNAbs (Bricault et al. *Cell Host-Microbe* (2019) 25:59-72). We found that CH505 TF carried resistance signatures at 10 sites, and by introducing favorable mutations at these sites, we designed a variant called V2 SET OPT (signature-based epitope targeted optimized) (FIG. 1). Shorter and more positively charged hypervariable V1 and V2 loops are significantly associated with neutralization sensitivity by mature V2 apex bNAbs, so we also introduced optimal V1 and V2 hypervariable loops from two natural Envs, ZM233.6 and T250-4, respectively, into our constructs.

For V2 Apex UCA analyses, neutralization data for 208 global viruses against CH04 & CAP256 UCAs, and heavy and/or light chain germline reverted PG9. See Gorman et al. NSMB 23 81-90 (2016). Unlike other bNAb classes, V2 apex precursors can neutralize heterologous strains. CH04 UCA shows 4% breadth. PG9 both heavy & light chain reverted=2% breadth. CAP256 UCA only neutralizes 1 autologous virus. Partial germline reverted PG9 (heavy or light) have higher breadth. These data were used these data to calculate signatures. The terms UCA and germline are used interchangeably.

We next applied signature analyses to neutralization data for 109-208 global viruses tested against unmutated or early ancestral antibodies that ultimately gave rise to antibody lineages that targeted the V2 apex and potent broadly neutralizing antibodies: CH04 UCA, CAP256-VRC26 and PCT64 early intermediates, and heavy and/or light chain germline reverted PG9 and PGT145. Using this strategy, we identified signatures associated with sensitivity to V2 apex precursors (FIG. 2). CH505 TF UCA OPT1 includes mature V2 apex signatures, with 5 additional for UCAs—additional positions are 161, 200, 305, 322, and 732.

The hypervariable loop characteristics associated with sensitivity to V2 apex precursors were similar to those of the mature, and hence, the hypervariable V1 and V2 loop modifications from V2 SET OPT were retained.

In non-limiting embodiments, these vaccines are being expressed as chimeric SOSIP proteins, and so have CH505 TF gp120s, with a BG505 gp41 that ends at HIV-1 HXB2 numbering position 664. SOSIP proteins are modified Env proteins that are stabilized for expression as native-like soluble trimers.

These sensitivity mutations in a CH505 TF background expressed as SOSIP proteins we propose will result in immunogens that are more susceptible to V2-apex antibodies, and thus may be better able to trigger and stimulate them.

The modified sequence we are suggesting trying as immunogens are enclosed. We start the alignment with CH505.TF as a reference, the natural transmitted founder virus that we are building mutations into. We follow with full length protein sequences that contain the amino acid modifications we believe may be advantageous. We include the natural strains ZM233.6 and T250-4 in the alignment, as we included their hypervariable regions.

Table 1 shows V2 Optimized CH505 TF immunogens

| Gene number | Protein name | Immunogen criteria |
|---|---|---|
| HV1301908 | CH505TF_V2.UCA.OPT1.gp41mut_ch.SOSIP.v4.1 | Optimized gp120 and gp41 based on V2-glycan bnAb UCA neutralization |
| HV1301909 | CH505TF_V2.UCA.OPT1.N332.gp41mut_ch.SOSIP.v4.1 | Optimized gp120 and gp41 based on V2-glycan bnAb UCA neutralization |
| HV1301910 | CH505TF_V2.SET.OPT_ch.SOSIPv4.1 | Optimized gp120 based on V2-glycan bnAb neutralization |
| HV1301911 | CH505TF_V2.SET.OPT.N332_ch.SOSIPv4.1 | Optimized gp120 based on V2-glycan bnAb neutralization with N332 glycan hole filled |
| HV1301912 | CH505TF_V2.UCA.OPT1_ch.SOSIPv4.1 | Optimized gp120 based on V2-glycan bnAb UCA neutralization |
| HV1301913 | CH505TF_V2.UCA.OPT1.N332_ch.SOSIP.v4.1 | Optimized gp120 based on V2-glycan bnAb UCA neutralization with N332 glycan hole filled |

Non-limiting embodiments of sequences of the envelopes in Table 1 are described in FIGS. 3A-C and 4A-B. FIGS. 5A-E shows non-limiting embodiments of multimerization designs, including ferritin and/or sortase, which could be used as guidance to design V2OPT CH505T/F designs. Non-limiting designs of envelope protomers include SOSIP designs, designs comprising F14 mutations (See WO/2020/072169), and so forth.

Throughout the application amino acid positions numbers refer to HXB2 numbering.

The invention is described in the following non-limiting examples.

EXAMPLES

Example 1

Saunders et al. have reported that vaccination with stabilized CH505 SOSIP trimers elicits V1V2-glycan bnAbs. See Cell Rep. 2017 Dec. 26; 21(13): 3681-3690, incorporated by reference in its entirety.

Example 2

CH505-BG505 Chimeric SOSIP Redesign for V2 UCA Constructs & for V5 Glycan Mutants Chimeric v4 6R SOSIP constructs have BG505 gp41 and end at HXB2 664. Thus, the SOSIP constructs have suboptimal amino acids at some of our mature and UCA signature sites in gp41.

Since the region encompassed by the SOSIP constructs ends at 664, the UCA OPT1 SOSIP and OPT2 SOSIP constructs are the same. Same for UCA OPT1 N332 and UCA OPT2 N332 SOSIPs. So, skip testing the OPT2 SOSIP constructs.

Instead, we suggest testing two other constructs: with and without gp41 optimized mutations in the backbones of UCA OPT1 and UCA OPT1 N332—these are UCA OPT1 gp41mut and UCA OPT1 N332 gp41mut.

The gp41mut constructs introduce favorable amino acids at 3 sites: 588 and 644 (signature sites for mature V2 apex bNAbs) and 535 (PG9 germline reverted signature).

List of SOSIP Constructs for Testing:

CH505TF_V2.SET.OPT_ch.SOSIPv4.1
CH505TF_V2.SET.OPT.N332_ch.SOSIPv4.1
CH505TF_V2.UCA.OPT1_ch.SOSIPv4.1
CH505TF_V2.UCA.OPT1.N332_ch.SOSIP.v4.1

But we propose testing the following two instead of the UCA OPT2 constructs (since they are same as UCA OPT1 for the SOSIP constructs):

CH505TF_V2.UCA.OPT1.gp41mut_ch.SOSIP.v4.1
CH505TF_V2.UCA.OPT1.N332.gp41mut_ch.SOSIP.v4.1

The gp41 mut constructs have 3 mutations in gp41: R→K at position 588; G→R at position 644; M→I at position 535.

Signatures are amino acids or glycan motifs statistically associated with one group of viruses vs others. We previously identified sequence patterns associated with sensitivity to mature V2 bNAbs. See Bricault et al. Cell Host Microbe 2019 25 (1) 59-72. These analyses were used for designing CH505 OPT sequences and consider phylogenetic and/or contact site, and robust across bNAbs and datasets.

Analyses and characterization of the optimized designs are shown in FIGS. 1, 2, 6-13.

Example 3 Animal Studies

In non-limiting embodiment these immunogens can be used as either single primes and boosts in humanized mice or bnAb UCA or intermediate antibody VH+VL knockin mice, non-human primates (NHPs) or humans, or used in combinations in animal models or in humans.

Immunogens to initiate V1V2, and/or CD4 binding site and/or Fusion Peptide unmutated common ancestor (UCA) broadly neutralizing antibody (bnAbs) precursors.

Non-Limiting Examples of Immunizations are Listed:

1. Prime×3 with either A, B, C, D, G or H (listed in FIGS. 3A-C, Table 1). In other embodiments, these immunogens could be in any suitable envelope form.
2. Take the optimal prime for bnAbs and after priming, boost with A, B, C, D, G or H.
3. Take the optimal prime for bnAbs, and after priming boost with a mixture of A, B, C, D, G or H.
4. Prime X3 with the mixture of A, B, C, D, G and H and the boost with one of A, B, C D, D or H to focus the response on bnAb epitopes.
5. Prime as in steps #1-4 above and then boost with the CH505 Transmitted/Founder (TF) gp140 SOSIP trimer that has induced autologous neutralizing antibodies against the CH505 tier 2 TF virus.
6. Prime as in steps #1-4 above and then boost with the forms of the MT145 SIV Env (see e.g. Andrabi et al., 2019, Cell Reports 27, 2426-244) or similar SIV envelope that has a V1V2 loop-glycan bnAb epitope that binds to V1 V2-glycan UCAs and bnAbs. 7. Prime as in steps #1-4 above and then boost with CM244, ZM233, WITO HIV-1 envelope or other WT Envs that have binding affinity for V1V2 bnAbs and their UCAs.

In non-limiting embodiments, these are administered as recombinant protein. Any suitable adjuvant could be use. In non-limiting embodiments, these are administered as nucleic acids, DNA and/or mRNAs. In non-limiting embodiments, the mRNAs are modified mRNAs administered as LNPs.

In non-limiting embodiments, the immunogens provide optimal prime for V1 V2, and/or CD4 binding site, and/or Fusion Peptide precursors. In some embodiments, an optimal prime is determined by measurement of the frequency of bnAb precursors before immunization and after each immunization to determine if the immunization has expanded the desired bnAb B cell precursor pool. This can be performed by initial B cell repertoire analysis by single cell sorting of memory or germinal center B cells (e.g. Bonsignori et al. Sci Transl Med. 2017 Mar. 15; 9 (381): eaai7514) and then followed by next generation sequencing of either lymph node, blood or other immune organ B cells to determine if the primed B cell bnAb clones were expanded and therefore boosted.

What is claimed is:

1. A recombinant HIV-1 envelope polypeptide comprising all consecutive amino acids immediately after the signal peptide MPMGSLOPLATLYLLGMLVASVLA in SEQ ID NO: 33, 34, 35, 36, 37 or 38.

2. A nucleic acid encoding the recombinant HIV-1 envelope polypeptide of claim 1.

3. A recombinant trimer comprising three identical protomers of an HIV-1 envelope polypeptide, wherein the HIV-1 envelope polypeptide comprises all consecutive amino acids immediately after the signal peptide MPMGSLOPLATLYLLGMLVASVLA in SEQ ID NO: 33, 34, 35, 36, 37 or 38.

4. An immunogenic composition comprising the recombinant trimer of claim 3 and a carrier.

5. An immunogenic composition comprising the nucleic acid of claim 2 and a carrier.

6. The immunogenic composition of claim 4, further comprising an adjuvant.

7. The nucleic acid of claim 2, wherein the nucleic acid is operably linked to a promoter, and wherein in certain embodiment the nucleic acid is inserted in an expression vector.

8. A method of inducing an immune response in a subject comprising administering an immunogenic composition comprising any suitable form of the nucleic acid(s) of claim 2 and a carrier in an amount sufficient to induce an immune response.

9. The method of claim 8 wherein the nucleic acid encodes a transmembrane.

10. The method of claim 8, wherein the immunogenic composition further comprises an adjuvant.

11. The method of claim 8, further comprising administering an agent which modulates host immune tolerance.

12. The method of claim 8, further comprising administering one or more additional HIV-1 immunogens to induce a T cell response.

13. A composition comprising a nanoparticle and a carrier, wherein the nanoparticle comprises any one of the recombinant HIV-1 envelope polypeptides of claim 1.

14. The composition of claim 13, wherein the nanoparticle is ferritin self-assembling nanoparticle.

15. A composition comprising a nanoparticle and a carrier, wherein the nanoparticle comprises any one of the trimers of claim 3.

16. The composition of claim 15 wherein the nanoparticle is ferritin self-assembling nanoparticle.

17. The composition of claim 15, wherein the nanoparticle comprises multimers of the trimers.

18. The composition of claim 15, wherein the nanoparticle comprises 1-8 trimers.

19. The method of claim 8, wherein the immunogenic composition is administered as a prime.

20. The method of claim 8, wherein the immunogenic composition is administered as a boost.

21. The immunogenic composition of claim 5 further comprising an adjuvant.

22. The recombinant HIV-1 envelope of claim 1, wherein the polypeptide is a protomer designed to form an envelope trimer.

23. The immunogenic composition of claim 5, wherein the nucleic acid is operably linked to a promoter, and wherein the nucleic acid is inserted in an expression vector.

24. A method of inducing an immune response in a subject comprising administering an immunogenic composition comprising any suitable form of any one of the recombinant HIV-1 envelope polypeptides of claim 1 and a carrier in an amount sufficient to induce an immune response.

25. The method of claim 24, wherein the recombinant HIV-1 envelope polypeptide forms a trimer, wherein the trimer comprises three identical protomers.

26. The method of claim 24, wherein the immunogenic composition further comprises an adjuvant.

27. The method of claim 24, further comprising administering an agent which modulates host immune tolerance.

28. The method of claim 24, wherein the recombinant HIV-1 envelope polypeptide administered is multimerized in a liposome or nanoparticle.

29. The method of claim 24, further comprising administering one or more additional HIV-1 immunogens to induce a T cell response.

30. The method of claim 24, wherein the immunogenic composition is administered as a prime.

31. The method of claim 24, wherein the immunogenic composition is administered as a boost.

32. The method of claim 28, wherein the nanoparticle is ferritin self-assembling nanoparticle.

33. The method of claim 25, wherein the trimer administered is in a nanoparticle.

34. The method of claim 33, wherein the nanoparticle is a ferritin self-assembling nanoparticle.

35. The method of claim 33, wherein the nanoparticle comprises multimers of the trimers.

36. The method of claim 33, wherein the nanoparticle comprises 1-8 trimers.

* * * * *